US007541367B2

(12) United States Patent
Chiu et al.

(10) Patent No.: US 7,541,367 B2
(45) Date of Patent: Jun. 2, 2009

(54) 3-BENZOIMIDAZOLYL-PYRAZOLOPYRIDINES USEFUL IN TREATING KINASE DISORDERS

(75) Inventors: George Chiu, Bridgewater, NJ (US); Peter J. Connolly, New Providence, NJ (US); Stuart Emanuel, Doylestown, PA (US); Shenlin Huang, San Diego, CA (US); Shengjian Li, Belle Mead, NJ (US); Ronghui Lin, East Brunswick, NJ (US); Yanhua Lu, Greenbrook, NJ (US); Steven A. Middleton, Flemington, NJ (US)

(73) Assignee: Janssen Pharmaceutica, N.V., Beerse (BE)

( * ) Notice: Subject to any disclaimer, the term of this patent is extended or adjusted under 35 U.S.C. 154(b) by 556 days.

(21) Appl. No.: 11/443,994

(22) Filed: May 31, 2006

(65) Prior Publication Data
US 2009/0048249 A1 Feb. 19, 2009

Related U.S. Application Data

(60) Provisional application No. 60/686,056, filed on May 31, 2005.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. .................................... 514/303; 546/119
(58) Field of Classification Search ................ 546/119; 514/303
See application file for complete search history.

(56) References Cited

U.S. PATENT DOCUMENTS

| 5,474,765 | A | 12/1995 | Thorpe |
| 5,762,918 | A | 6/1998 | Thorpe |
| 5,855,866 | A | 1/1999 | Thorpe et al. |
| 5,902,795 | A | 5/1999 | Toole et al. |
| 6,288,082 | B1 | 9/2001 | Wissner et al. |
| 6,335,344 | B1 | 1/2002 | Schnur et al. |
| 6,342,219 | B1 | 1/2002 | Thorpe et al. |
| 6,413,971 | B1 | 7/2002 | Arnold et al. |
| 2005/0009876 | A1 | 1/2005 | Bhagwat et al. |

FOREIGN PATENT DOCUMENTS

| WO | WO 01/02369 A2 | 1/2001 |
| WO | WO 01/53268 A2 | 7/2001 |
| WO | WO 03/004488 A1 | 1/2003 |
| WO | WO 03/045949 A1 | 6/2003 |
| WO | WO 2005/000303 A1 | 1/2005 |
| WO | WO 2005/009997 A1 | 2/2005 |

OTHER PUBLICATIONS

Straub et al., Bioorganic & Medicinal Chemistry Letters (2001),11(6), 781-784.*
International Search Report, PCT/US06/21097, Oct. 3, 2006.
Klijn J.G.M. et al, "The clinical significance of epidermal growth factor receptor (EGF-R) in human breast cancer: a review on 5232 patients", *Endocrine Reviews*, 1992, vol. 13, pp. 3-17.
Salomon D et al.; "The erbB family of receptors and their ligands: Multiple targets for therapy", *Signal*, 2001, vol. 2, pp. 4-11.
Ekstrand A.J. et al, "Amplified and rearranged epidermal growth factor receptor genes in human glioblastomas reveal deletions of sequences encoding portions of the N-and/or C-terminal tails", *Proc. Acad. Natl. Sci. USA*, 1992, vol. 89, pp. 4309-4313.
Wikstrand C.J., "Monoclonal antibodies against EGFRvIII are tumor specific and react with breast and lung carcinomas and malignant gliomas", *Cancer Res.*, 1995, vol. 55, pp. 3140-3148.
Koprivica V., et al, "EGFR activation mediates inhibition of axon regeneration by myelin and chondroitin sulfate proteoglycans", *Science*, 2005, vol. 310, pp. 106-110.
Horizons in Cancer Therapeutics: From Bench to Bedside, Signal Transduction Inhibitors, 2001, 2(2), ISSN 1532-3048.
Slamon D.J., "Human breast cancer: Correlation of relapse and survival with amplification of HER-2/neu oncogene", *Science*, 1987, vol. 235, pp. 177-182.
Slamon D.J et al; "Studies of the HER-2/neu proto-oncogene in human breast and ovarian cancer", *Science*, 1989, vol. 244, pp. 707-712.
Hetzel D.J., "HER-2/neu expression: A major prognostic factor in endometrial cancer", *Gynecologic Oncology*, 1992, vol. 47, pp. 179-185.
Kirsch D.G. et al.; "Targeting HER-2 in brain metastases from breast cancer", *Clinical Cancer Research*, 2003, vol. 9, pp. 5435-5436.
Grossi P.M., "Efficacy of intracerebral microinfusion of trastuzumab in an athymic rat model of intracerebral metastatic breast cancer", *Clinical Cancer Research*, 2003, vol. 9, pp. 5514-5520.
Wang X, et al., Nature, 2003, vol. 424, pp. 456-461.
Yeatman T.J., Nature Reviews Cancer, 2004, vol. 4(6), pp. 470-480.
Goldenberg-Furmanov M. et al., Cancer Research, 2004, vol. 64, pp. 1058-1064.

(Continued)

*Primary Examiner*—D. Margaret Seaman
*Assistant Examiner*—Niloofar Rahmani
(74) *Attorney, Agent, or Firm*—Laura A. Donnelly

(57) ABSTRACT

The present invention is directed to novel 3-benzoimidazolyl-pyrazolopyridine compounds of formula (I):

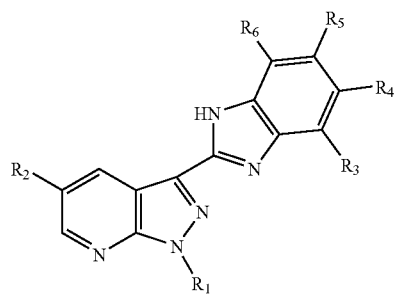

and pharmaceutically acceptable forms thereof and their synthesis and use as inhibitors of serine-threonine protein kinases and tyrosine protein kinases and interactions thereof.

38 Claims, No Drawings

OTHER PUBLICATIONS

Shah N.P. et al., Science, 2004, vol. 305, pp. 399-401.
Donato N.J. et al., Blood, 2003, vol. 101(2), pp. 690-698.
Pardee A.B., *Science*, 1989, vol. 246, pp. 603-608.
Nasmyth K., *Science*, 1996, vol. 274, pp. 1643-1677.
Morgan D.O., *Ann. Rev. Cell Dev. Biol*, 1997, vol. 13, pp. 261-291.
Draetta, G., *Trends in Biochem. Sci.*, 1990, vol. 15, pp. 378-382.
Sherr C.J., Cell, 1993, vol. 73, pp. 1059-1065.
Lee M. et al, *Trends Genet.*, 1988, vol. 4, pp. 289-290.
Dunphy W.G., *Cell*, 1988, vol. 54, pp. 423-431.
Gautier J., *Cell*, 1988, vol. 54, pp. 433-439.
Cross F. et al., *Ann. Rev. Cell Biol.*, 1989, vol. 5, pp. 341-395.
Hunt, T., *Current Opinion in Cell Biology*, 1989, vol. 1, pp. 268-274.
Nurse, P., *Nature*, 1990, vol. 344, pp. 503-508.
Davis S.T. et al., "Prevention of chemotherapy-induced alopecia in rats by CDK inhibitors", *Science*, 2001, vol. 291, pp. 134-137.
Jean Marx, *Science*, 2001, vol. 291, pp. 25-26.
Ross, R., *Nature*, 1993, vol. 362, pp. 801-809.
Brooks E. et al., "CVT-313, a Specific and Potent Inhibitor of CDK2 That Prevents Neointimal Proliferation", *J. Biol. Chem.*, 1997, vol. 272(46), pp. 29207-29211.
Arnon R. et al., "Monoclonal Antibodies For Immunotargeting Of Drugs In Cancer Therapy", *Monoclonal Antibodies And Cancer Therapy*, 1985, pp. 243-256.
Hellstrom K.E. et al., Antibodies For Drug Delivery, *Controlled Drug Delivery* (2nd Ed.), Robinson, et al. (eds.), pp. 623-653 (Marcel Dekker, Inc. 1987).
Thorpe P.E., "Antibody Carriers Of Cytotoxic Agents In Cancer Therapy: A Review", *Monoclonal Antibodies '84: Biological And Clinical Applications*, 1985, pp. 475-506.
Mickelson J.W., *J. Med. Chem.* 1996, vol. 39, pp. 4654-4666.

* cited by examiner

3-BENZOIMIDAZOLYL-PYRAZOLOPYRIDINES USEFUL IN TREATING KINASE DISORDERS

CROSS REFERENCE TO RELATED APPLICATIONS

This present application claims benefit of U.S. Provisional Patent Application Ser. No. 60/686,056, filed May 31, 2005, which is incorporated herein by reference in its entirety and for all purposes.

FIELD OF THE INVENTION

The present invention relates to a series of 3-benzoimidazolyl-pyrazolopyridine compounds, pharmaceutical compositions and methods for use thereof. In particular, the 3-benzoimidazolyl-pyrazolopyridine compounds of the present invention are protein kinase inhibitors useful in treating or ameliorating a kinase mediated disorder. More particularly, the 3-benzoimidazolyl-pyrazolopyridine compounds of the present invention are serine-threonine protein kinase and tyrosine protein kinase inhibitors useful in treating or ameliorating a serine-threonine protein kinase and tyrosine protein kinase mediated disorder.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR ($\alpha$ and $\beta$), Tie-1, Tie-2 (also Tek-1 or Tek), VEGFRl (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CKI, CK2, Erk, IKK-1 (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 ($\alpha$ and $\beta$), PKA, P38, Erk (1-3), PKB (including all PKB subtypes) (also AKT-1, AKT-2, AKT-3 or AKT3-1), IRAK1, FRK, SGK, TAK1 or Tpl-2 (also COT).

Protein kinases play very important roles in the normal regulation of cell growth. However, as a result of dysregulation of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohns disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, occular diseases, viral infections, heart disease, lung or pulmonary diseases or kidney or renal diseases. Therefore, kinase inhibitors have potential use as therapeutic agents.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-$\alpha$ (TGF-$\alpha$) and the HER-2 ligand heregulin are three of the ligands that bind to the EGFR receptors.

EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs, such as the lungs and gastrointestinal tract. The clinically prevalent cancers related to EGFR include lung, gastric and head and neck cancer (Klijn J G, Berns P M, Schmitz P I and Foekens J A; The clinical significance of epidermal growth factor receptor (EGF-R) in human breast cancer: a review on 5232 patients, *Endocr. Rev.*, 1992, 13, 3-17; Salomon D and Gullick W; The erbB family of receptors and their ligands: Multiple targets for therapy, *Signal*, 2001, 2, 4-11). Other diseases associated with increased EGFR expression include proliferative glomerulonephritis, diabetes-induced renal disease and chronic pancreatitis.

In treating cancers of the head such as brain cancers and the like, the ability of small molecule EGFR inhibitors to penetrate the blood brain barrier could have therapeutic advantages since EGFR is often overexpressed in primary brain tumors and also in breast and non-small cell lung carcinomas that frequently metastasize to the brain (Eckstrand A J, Sugawa N, James C D and Collins V P; Amplified and rearranged epidermal growth factor receptor genes in human glioblastomas reveal deletions of sequences encoding portions of the N- and/or C-terminal tails, *Proc. Acad. Natl. Sci. USA,* 1992, 89, 4309-4313; and, Wickstrand C J, Hale L P, Batra S K, Hill M L, Humphrey P A, Kurpad S N, McLendon R E, Moscatello D, Pegram C N, Reist C J, Traweek S T, Wong A J, Zalutsky M R and Bigner, D D; Monoclonal antibodies against Eggfruit are tumor specific and react with breast and lung carcinomas and malignant glooms, *Cancer Res.,* 1995, 55, 3140-3148).

EGFR inhibitors tested in neuritis outgrowth assays have activity in promoting neuritis outgrowth in both cerebella granule cells and dorsal root ganglion neurons, likely by acting directly on neurons to block neuronal inhibitory responses to myelin inhibitors, and thus an EGFR inhibitor may have potential use for promoting axon regeneration after brain and spinal cord injury (V. Koprivica, et al, EGFR activation mediates inhibition of axon regeneration by myelin and chondroitin sulfate proteoglycans, *Science,* 2005, 310, 106).

HER1 and HER2 overexpression has been implicated in a variety of cancers, such as bladder, breast, colorectal, endometrial, esophageal, gastric (stomach), glioma head and neck, lung (non-small cell lung cancer), ovarian, pancreatic, renal and prostate cancer.

Comparing the overexpression of HER1 and HER2 in tumors, according to order of prevalence, HER1 overexpression is found in breast, renal cell, lung, colorectal, head and neck, ovarian, pancreatic, glioma, bladder, esophageal, gastric, endometrial and cervical cancer tumors (such as cervical adenocarcinoma); in contrast, HER2 overexpression is found in esophageal, head and neck, lung, gastric, renal cell, breast, bladder, ovarian and colorectal, prostate and endometrial cancer tumors (Horizons in Cancer Therapeutics: From Bench to Bedside, Signal Transduction Inhibitors, 2001, 2(2), ISSN 1532-3048).

While the degree of HER2 overexpression in breast and ovarian cancer is not as great as in some other cancers, HER2 has been found to be responsible for these clinically prevalent cancers (Slamon D J, Clark G M, Wong S G, Levin W J, Ullrich A and McGuire W L; Human breast cancer: Correlation of relapse and survival with amplification of HER-2/neu oncogene, *Science,* 1987, 235, 177-82; Slamon D J, Godolphin W, Jones L A, Holt J A, Wong S G, Keith D E, et al; Studies of the HER-2/neu proto-oncogene in human breast and ovarian cancer, *Science,* 1989, 244, 707-712; Hetzel D J, Wilson T O, Keeney G L, Roche P C, Cha S S and Podrantz K C; HER-2/neu expression: A major prognostic factor in endometrial cancer, *Gynecol. Oncol.,* 1992, 47, 179-85).

Furthermore, patients with HER-2 overexpressing breast cancer frequently experience metastases to the brain (Kirsch D G and Hochberg F H; Targeting HER-2 in brain metastases from breast cancer, *Clin. Can. Res.,* 2003, 9, 5435-5436). These patients have an extremely poor prognosis and intracerebral tumors are often the cause of death. Autopsy revealed that 20-3.0% of patients who die of breast cancer have brain metastases (Grossi P M, Ochiai H, Archer G E, McLendon R E, Zalutsky M R, Friedman A H, Friedman H S, Bigner D D and Sampson J H; Efficacy of intracerebral microinfusion of trastuzumab in an athymic rat model of intracerebral metastatic breast cancer, *Clin. Can. Res.,* 2003, 9, 5514-5520).

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang X, et al., Nature, 24 Jul. 2003, Vol 424, 456-461). Accordingly, potent EGFR selective inhibitors may be useful in anti-CMV therapy.

The Src family of tyrosine-kinases includes the sub-family proteins c-Src, Lyn, Fyn, Lck, Syk, Hck, Yes, Blk, Fgr and Frk. While various members of the c-Src family are important for normal cellular proliferation, their overexpression and overactivation can promote development of cancer (Yeatman T J, Nature, June 2004, Vol. 4). For example, the Lyn kinase has been shown to be upregulated in hormone resistant prostate cancer. Tumor xenografts of hormone resistant prostate cancer cells showed delayed growth upon treatment with peptides that specifically block Lyn kinase activity (Goldenberg-Furmanov, et al., Cancer Research, 1 Feb. 2004, 64, 1058-1064).

The Lyn and Hck Src sub-family tyrosine-kinases have both been implicated in chronic myeloid leukemia (CML). CML is caused by the BCR-Abl fusion protein resulting from the t(9;22) chromosomal translocation that juxtaposes the c-Abl non-receptor tyrosine kinase gene on chromosome 9 with a breakpoint cluster region (bcr) gene on chromosome 22. The BCR-Abl fusion protein is a constitutively activated form of the Abl tyrosine kinase that drives uncontrolled growth leading to CML and many cases of adult acute lymphoblastic leukemia. Gleevec is an inhibitor of Abl that has been successfully used to treat CML. However, Gleevec does not help patients in blast crisis because they carry mutant forms of BCR-Abl that no longer bind Gleevec. Such Gleevec resistant CML cells are sensitive to a dual src/BCR-Abl inhibitor that binds and inhibits the mutant BCR-Abl and members of the src family (Shah, et al., Science, 16 Jul. 2004, Vol 305, 399-401). CML cells can also become resistant to treatment with the tyrosine kinase Abl inhibitor Gleevec in other ways. For example, CML K562 cells that become resistant to Gleevec minimize reliance on the BCR-Abl translocation for growth and instead upregulate the Lyn and Hck kinases, as demonstrated by expressing antisense Lyn in these cells, which reduced their rate of proliferation (Donato, et al., Blood, 15 Jan. 2003, 101(2)). c-Src and other Src family members are also involved in cellular adhesion, invasion and motility of tumor cells. Thus, small molecule inhibitors of the Src kinase family could offer new therapeutic opportunities for both leukemias and solid tumors.

Aurora kinases (Aurora-A, Aurora-B and Aurora-C) are highly conserved tyrosine kinases found in all organisms where they function to regulate microtubule dynamics during the M phase of the cell cycle and are essential for mitotic progression. Aurora-A kinase associates with the centrosome around the pericentriolar material, as well as the microtubules at the bipolar mitotic-spindle poles and the midbody microtubules and plays a role in spindle formation and organization of the centrosome. Aurora-B regulates chromosomal movement and cytokinesis and Aurora-C's biological function is not yet understood. The Aurora-A kinase is involved in centrosome separation, duplication and maturation as well as in bipolar spindle assembly and stability. Aurora-A is overexpressed in a number of different human cancers and tumor cell lines. Overexpression of Aurora is sufficient to induce growth in soft agar and transforms cells making them tumorigenic. Inhibition of Aurora activity results in centrosome/chromosome segregation defects leading to monopolar spindles and polyploidy which induces cell apoptosis in a variety of cancer cell lines and has suppressed tumor growth in vivo.

Angiogenesis plays a role in various processes including development of the vasculature, wound healing and maintenance of the female reproductive system. Pathological angiogenesis is associated with disease states such as cancer, diabetic retinopathy, rheumatoid arthritis, endometriosis and psoriasis. Solid-tumor cancers, in particular, are dependent on angiogenesis for their growth. The vascular endothelial growth factors (VEGFs) are mediators of both normal and pathologic angiogenesis. VEGF transmits signals into cells through their cognate receptors, which belong to the receptor tyrosine kinase (RTK) family of transmembrane receptors. These receptors are tripartite, consisting of an extracellular ligand-binding domain, a transmembrane domain, which anchors the receptor in the membrane of the cell, and an intracellular tyrosine kinase domain.

One subfamily of RTKs comprises the receptors Flt1/VEGF-R1 and KDR/Flk1/VEGF-R2, which bind VEGFs. Binding of the VEGF ligand to the receptor results in stimulation of the receptor tyrosine kinase activity and transduction of biological signals into the cell. The KDR/Flk1/VEGF-R2 receptor mediates the biological activities of mitogenesis and proliferation of endothelial cells while the Flt1/VEGF-R1 receptor mediates functions such as endothelial cell adhesion. Inhibition of KDR/Flk1/VEGF-R2 signalling has been shown to inhibit the process of angiogenesis. Inhibitors of this receptor are likely useful in controlling or limiting angiogenesis.

The cell division cycle is one of the most fundamental processes in biology which ensures the controlled proliferation of cells in multicellular organisms. Under normal growth conditions, cell proliferation is tightly regulated in response to diverse intracellular and extracellular signals. This is achieved by a complex network of proto-oncogenes and tumor-suppressor genes that are components of various signal transduction pathways. Activation of a proto-oncogene and/or a loss of a minor suppressor gene can lead to the unregulated activity of the cell cycle machinery. This, in turn, will lead to unregulated cell proliferation and to the accumulation of genetic errors which ultimately will result in the development of cancer (Pardee, A. B., Science, 1989, 246:603-608).

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

Cyclin dependent kinases (CDK) constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of DNA synthesis), or the progression from $G_2$ to M phase, in which active mitosis and cell-division occur. See, e.g., the articles compiled in Science, vol. 274 (1996), p. 1643-1677; and Ann. Rev. Cell Dev. Biol, vol. 13 (1997), pp. 261-291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The coordinated activation of these complexes drives the cells through the cell cycle and ensures the fidelity of the process (Draetta, G., Trends Biochem. Sci., 1990, 15:378-382; Sherr, C. J., Cell, 1993, 73:1059-1065). Each step in the cell cycle is regulated by a distinct and specific cyclin-dependent kinase. Regulation occurs at the boundaries of the G1/S and G2/M phases, two major transition points of the cell cycle.

A key regulator of these cell cycle transitions is CDK1 kinase, a universal intracellular factor which triggers the G2/M transition of the cell cycle in all organisms. Both biochemical and genetic evidence have shown that CDK1 is the primary activity required for a dell to enter mitosis in all eukaryotic cells. In late G2, it is present as an inactive complex of CDK1 and cyclin B. In M phase, it is activated and thereafter displays kinase, activity. CDK1 is known to phosphorylate a number of proteins including histone H1, DNA polymerase alpha, RNA polymerase II, retinoblastoma tumor suppressor protein (RB), p53, nucleolin, cAbl and lamin A.

The kinase activity of CDK1 is required for entry of cells into mitosis, i.e., for passage from the G2 phase of the cell cycle into the M phase (Lee M. and Nurse P., Trends Genet., 1988, 4:289-90; Dunphy W. G., Brizuela L., Beach D. and Newport J., Cell, 1988, 54:423-431; Gautier J., Norbury C., Lohka M., Nurse P. and Maller J., Cell, 1988, 54:433-439; Cross F., Roberts J. and Weintraub H., Ann. Rev. Cell Biol., 1989, 5:341-395; Hunt, T. and Sherr, C., Curr. Opinion Cell Biol., 1989, 1:268-274; and, Nurse, P., Nature, 1990, 344: 503-508). Therefore, using cyclin dependent kinase inhibitors for tumor therapy has the potential for inhibiting tumor growth or controlling unregulated cell proliferation.

A second protein target that can facilitate elimination of a tumor is the tyrosine kinase vascular endothelial growth factor (VEGF) receptor. This protein is associated with both normal and pathological angiogenesis. The VEGF receptors are tripartite, consisting of an extracellular ligand-binding domain, a transmembrane domain and an intracellular tyrosine kinase domain. Presently there are two known VEGF receptors: (1) VEGF-R2 (KDR/Flk1/VEGF-R2), a receptor that mediates the biological activities of mitogenesis and proliferation of endothelial cells; and (2) VEGF-R1 (Flt1/VEGF-R1), a receptor that mediates functions such as endothelial cell adhesion. Inhibition of VEGF-R2 signalling has been shown to inhibit the process of angiogenesis. Inhibitors of this receptor are likely useful in controlling or limiting angiogenesis.

Many conventional cytotoxic cancer therapies destroy the rapidly dividing epithelium of the hair follicle and induce alopecia (hair loss). Inhibition of cyclin dependent kinases during conventional chemotherapy may represent a therapeutic strategy for prevention of chemotherapy-induced alopecia by arresting the cell cycle and reducing the sensitivity of epithelial cells to antitumor agents (Davis S. T., et al., Prevention of chemotherapy-induced alopecia in rats by CDK inhibitors, Science, 2001, (January 5), 291, 5501, 25-6). Accordingly, to be useful for such an application, a CDK inhibitor compound would have to be cytostatic, rather than cytotoxic and be able to hold the cell in a stationary growth phase which would protect it from the cytotoxic activity of a conventional chemotherapeutic agent being administered at the same time. In this way, topical application of non-apoptotic CDK inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration and proliferation is largely responsible for restenosis following angioplasty (Ross, R., *Nature*, 1993, 362, 801-809). Therefore, antiproliferative therapies targeted to cyclin dependent kinases or other components of the cell cycle machinery may be a suitable approach to treat these disorders. One aspect for use of the compounds of the present invention is a method for the treatment or amelioration of restenosis wherein a CDK inhibitor is impregnated on the surface of an angioplasty balloon or stent, thus targeting drug delivery to the local environment where endothelial and smooth muscle cell proliferation are the leading cause of vascular occlusion following an initial angioplasty and restenosis in the area of a stent's implantation (Eric E. Brooks, Nathanael S. Gray, Alison Joly, Suresh S. Kerwar, Robert Lum, Richard L. Mackman, Thea C. Norman, Jose Rosete, Michael Rowe, Steven R. Schow, Peter G. Schultz, Xingbo Wang, Michael M. Wick and Dov Shiffman, CVT-313, a Specific and Potent Inhibitor of CDK2 That Prevents Neointimal Proliferation, *J. Biol. Chem.*, 1997, 272(46):29207-29211).

The receptor tyrosine kinase encoded by the RET (REarranged during Transformation) gene encodes several protein isoforms that are expressed as a result of alternative splicing of mRNA. Multiple ligands are able to bind and activate the RET receptor. These ligands belong to the family of glial-cell-line-derived neurotrophic factors which consists of four closely related homologues: glial derived neurotrophic factor, neurturin, artemin and persephin.

Thyroid tumors are the most common malignancies of the endocrine system and are frequently associated with specific alterations in the RET gene. The characterization of somatic rearrangements of RET have demonstrated that the gene is causally involved in the genesis of papillary thyroid carcinoma. The RET transforming gene results from a recombination event between two unlinked DNA sequences and causes papillary thyroid cancer. Point mutations in the RET gene are responsible for the inherited cancer syndrome medullary endocrine neoplasia and are also involved in development of sporadic medullary thyroid carcinomas.

Rearrangements of RET in papillary-thyroid carcinoma (called RET/PTC), juxtapose the region coding for the tyrosine kinase domain with the 5 prime-terminal regions of a variety of unrelated genes. This event deletes the extracellular ligand binding domain causing the fusion protein to localize to the cytoplasm. A unique RET/PTC chromosomal rearrangement has been identified in thyroid cancers in which a portion of a gene called Ele1 joins to RET. In these cases of thyroid cancer, it appears that exposure to radiation is responsible for inducing the chromosomal rearrangement. Germline mutations in the RET proto-oncogene are also responsible for multiple endocrine neoplasia type 2A and 2B, a dominantly inherited cancer syndrome and familial medullary thyroid carcinoma. The RET proto-oncogene is responsible for these cancers and is also involved in development of sporadic thyroid cancer.

PCT application WO 01/53268 describes 3,5-substituted indazole compounds as protein kinase inhibitors.

PCT application WO 01/02369 describes 3,6-substituted indazole compounds as protein kinase inhibitors.

PCT application WO 03/004488 describes 3-benzoimidazolyl-indazole compounds as protein kinase inhibitors.

PCT application WO 03/045949 describes substituted pyrazolopyridine compounds as GSK-3 inhibitors.

PCT application WO 2005/009997 describes 3-benzoimidazolyl-5-pyridinyl-indazole compounds as modulators or inhibitors of CDK mediated cell proliferation.

PCT application WO 2005/000303 describes the preparation of 2,7-dihydropyrazolopyridin-6-ones as GSK-3 inhibitors.

United States patent application US 2005/0009876 describes 3,5-substituted indazole compounds as modulators of protein kinase signal transduction.

There remains a need for small-molecule compounds that may be readily synthesized and are potent inhibitors of one or more serine-threonine protein kinases, tyrosine protein kinases inhibitors or complexes thereof useful in treating or ameliorating a serine-threonine protein kinase and tyrosine protein kinase mediated disorder.

SUMMARY OF THE INVENTION

Accordingly, one object of the invention is to attain compounds and drug compositions that inhibit the activity of one or more serine-threonine protein kinases, tyrosine protein kinases inhibitors or complexes thereof.

A further object is to provide an effective method of treating cancer indications by inhibiting the activity of one or more serine-threonine protein kinases, tyrosine protein kinases inhibitors or complexes thereof.

Another object is to achieve pharmaceutical compositions containing compounds effective to block the transition of cancer cells into their proliferative phase.

These and other objects and advantages provided by the present invention will become apparent in light of the detailed description below and are achieved through use of a series of 3-benzoimidazolyl-pyrazolopyridine compounds of formula (I):

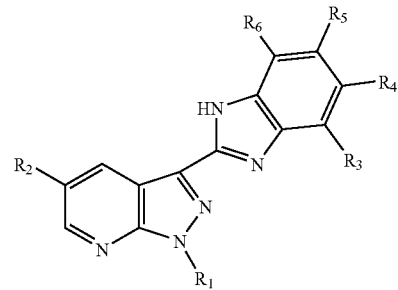

and forms thereof, wherein $R_1$, $R_2$, $R_3$, $R_4$, $R_5$ and $R_6$ are as defined herein.

An example of the present invention includes using a 3-benzoimidazolyl-pyrazolopyridine compound of formula (I) as a protein kinase inhibitor.

An example of the present invention includes using a 3-benzoimidazolyl-pyrazolopyridine compound of formula (I) as an inhibitor of a serine-threonine protein kinase, such as CDK-1.

An example of the present invention includes using a 3-benzoimidazolyl-pyrazolopyridine compound of formula (I) as an inhibitor of a tyrosine protein kinase such as VEGF-R2, human epidermal growth factor receptor-2 (HER-2), c-Src, Lyn, Aurora-A and RET.

An example of the present invention includes a method for using a 3-benzoimidazolyl-pyrazolopyridine compound of formula (I) in treating or ameliorating a kinase mediated disorder associated with cellular proliferation or angiogenesis and the like.

An example of the present invention includes a method for using a 3-benzoimidazolyl-pyrazolopyridine compound of formula (I) as a therapeutic agent for treating, preventing or ameliorating a chronic or acute protein kinase mediated disease, disorder or condition in a subject in need thereof comprising administering to the subject an effective amount of a compound of formula (I) or composition thereof.

DETAILED DESCRIPTION OF THE INVENTION

The present invention provides a compound of formula (I)

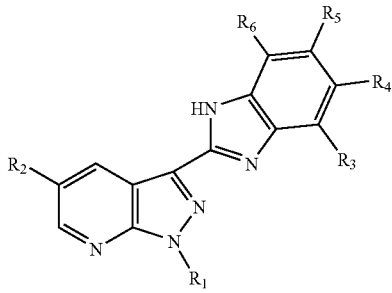

or a form thereof, wherein $R_1$ is hydrogen or $C_{1-8}$alkyl, $R_2$ is hydrogen, halogen, $C_{3-12}$cycloalkyl-$R_7$, heterocyclyl-$R_8$, aryl-$R_9$, heteroaryl-$R_{10}$, $C_{1-8}$alkyl-$C_{3-12}$cycloalkyl-$R_7$, $C_{1-8}$alkyl-heterocyclyl-$R_8$, $C_{1-8}$alkyl-aryl-$R_9$, $C_{1-8}$alkyl-heteroaryl-$R_{10}$, $C_{1-8}$alkyl-O—$C_{1-8}$alkyl-$C_{3-12}$cycloalkyl-$R_7$, $C_{1-8}$alkyl-O—$C_{1-8}$alkyl-heterocyclyl-$R_8$, $C_{1-8}$alkyl-O—$C_{1-8}$alkyl-aryl-$R_9$, $C_{1-8}$alkyl-O—$C_{1-8}$alkyl-heteroaryl-$R_{10}$, C(O)—$C_{3-12}$cycloalkyl-$R_7$, C(O)-heterocyclyl-$R_8$, C(O)-aryl-$R_9$, C(O)-heteroaryl-$R_{10}$, C(O)NH—$C_{3-12}$cycloalkyl-$R_7$, C(O)NH-heterocyclyl-$R_8$, C(O)NH-aryl-$R_9$ or C(O)NH-heteroaryl-$R_{10}$, $R_3$, $R_4$, $R_5$ and $R_6$ is each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, $C_{1-8}$alkyl-O—$C_{1-8}$alkyl, $C_{1-8}$alkyl-O—$C_{1-8}$alkyl-O—$C_{1-8}$alkyl, OH, OC(O)$C_{1-8}$alkyl, $C_{1-8}$alkyl-OH, $C_{1-8}$alkoxy-OH, C(O)H, C(O)$C_{1-8}$alkyl, C(O)OH, C(O)O—$C_{1-8}$alkyl, $NH_2$, NH—$C_{1-8}$ alkyl, N($C_{1-8}$alkyl)$_2$, NHC(O)$C_{1-8}$alkyl, NHC(O)NH$C_{1-8}$ alkyl, N($C_{1-8}$alkyl)C(O)$C_{1-8}$alkyl, $C_{1-8}$alkyl-$NH_2$, $C_{1-8}$alkyl-NH—$C_{1-8}$alkyl, $C_{1-8}$alkyl-N($C_{1-8}$alkyl)$_2$, $C_{1-8}$alkyl-NH(OH), $C_{1-8}$alkyl=N(OH), $C_{1-8}$alkyl-NH—$C_{1-8}$alkyl-$NH_2$, $C_{1-8}$alkyl-N($C_{1-8}$alkyl-$NH_2$)$_2$, $C_{1-8}$alkyl-N($C_{1-8}$alkyl)-$C_{1-8}$ alkyl-$NH_2$, C(O)$NH_2$, C(O)NH—$C_{1-8}$ alkyl, C(O)N($C_{1-8}$ alkyl)$_2$, C(O)NH—$C_{1-8}$alkyl-$NH_2$, C(O)NH—$C_{1-8}$alkyl-NH—$C_{1-8}$alkyl, C(O)NH—$C_{1-8}$ alkyl-N($C_{1-8}$alkyl)$_2$, C(O)N($C_{1-8}$alkyl-$NH_2$)$_2$, C(O)N($C_{1-8}$alkyl)-$C_{1-8}$alkyl-$NH_2$, C(O)N($C_{1-8}$alkyl)-$C_{1-8}$alkyl-NH—$C_{1-8}$alkyl, C(O)N($C_{1-8}$alkyl)-$C_{1-8}$alkyl-N($C_{1-8}$ alkyl)$_2$, $C_{3-12}$cycloalkyl-$R_{11}$, heterocyclyl-$R_{12}$, aryl-$R_{13}$, heteroaryl-$R_{14}$, $C_{1-8}$alkyl-$C_{3-12}$cycloalkyl-$R_{11}$, $C_{1-8}$alkyl-heterocyclyl-$R_{12}$, $C_{1-8}$alkyl-aryl-$R_{13}$, $C_{1-8}$alkyl-heteroaryl-$R_{14}$, $C_{1-8}$alkyl-O—$C_{1-8}$alkyl-$C_{3-12}$cycloalkyl-$R_{11}$, $C_{1-8}$alkyl-O—$C_{1-8}$ alkyl-heterocyclyl-$R_{12}$, $C_{1-8}$alkyl-O—$C_{1-8}$alkyl-aryl-$R_{13}$, $C_{1-8}$alkyl-O—$C_{1-8}$alkyl-heteroaryl-$R_{14}$, C(O)—$C_{3-12}$cycloalkyl-$R_{11}$, C(O)-heterocyclyl-$R_{12}$, C(O)-aryl-$R_{13}$, C(O)-heteroaryl-$R_{14}$, C(O)NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$, alternatively, one of each $R_3$ and $R_4$, $R_4$ and $R_5$ or $R_5$ and $R_6$ are taken together to form —O—$CH_2$—O— or —O—$(CH_2)_2$—O— which, together with the benzoimidazolyl ring of formula (I), form a 5H-[1,3]dioxolo[4',5':4,5]benzo[1,2-d]imidazol-6-yl, 6H-1,3-dioxa-6,8-diaza-as-indacen-7-yl, 8H-1,3-dioxa-6,8-diaza-as-indacen-7-yl, 6,7-dihydro-1H-5,8-dioxa-1,3-diaza-cyclopenta[b]naphthalen-2-yl, 7,8-dihydro-1H-6,9-dioxa-1,3-diaza-cyclopenta[a]naphthalen-2-yl or a 7,8-dihydro-3H-6,9-dioxa-1,3-diaza-cyclopenta[a]naphthalen-2-yl ring system, wherein the —O—$CH_2$—O— or —O—$(CH_2)_2$—O— portion is each optionally substituted on one or two carbon atoms with one or two substituents each selected from halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH or $C_{1-8}$alkyl-OH, $R_7$, $R_8$, $R_9$ and $R_{10}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-O—$C_{1-8}$alkyl, $C_{1-8}$alkoxy-OH, C(O)H, C(O)$C_{1-8}$alkyl, C(O)OH, C(O)O—$C_{1-8}$alkyl, $NH_2$, NH—$C_{1-8}$alkyl, N($C_{1-8}$ alkyl)$_2$, $C_{1-8}$alkyl-$NH_2$, $C_{1-8}$alkyl-NH—$C_{1-8}$alkyl, CH($C_{1-8}$alkyl)-NH—$C_{1-8}$alkyl, C($C_{1-8}$alkyl)$_2$-NH—$C_{1-8}$ alkyl, $C_{1-8}$alkyl-N($C_{1-8}$alkyl)$_2$, $C_{1-8}$alkyl-NH—$C_{1-8}$ alkyl-O—$C_{1-8}$alkyl, $C_{1-8}$alkyl-NH—$C_{1-8}$alkyl-$NH_2$, $C_{1-8}$alkyl-NH—C(O)$C_{1-8}$alkyl, $C_{1-8}$alkyl-NH—C(O)NH$C_{1-8}$alkyl, $C_{1-8}$alkyl-NH—$C_{1-8}$alkyl-NH—$C_{1-8}$alkyl, $C_{1-8}$alkyl-NH—$C_{1-8}$alkyl-N($C_{1-8}$alkyl)$_2$, $C_{1-8}$alkyl=N(OH), $C_{1-8}$alkyl-NH—$C_{1-8}$alkyl-OH, $SO_2NH_2$, $SO_2$NH—$C_{1-8}$ alkyl, $SO_2$N($C_{1-8}$alkyl)$_2$, $C_{3-12}$cycloalkyl-$R_{15}$, heterocyclyl-$R_{16}$, aryl-$R_{17}$, heteroaryl-$R_{18}$, $C_{1-8}$alkyl-$C_{3-12}$cycloalkyl-$R_{15}$, $C_{1-8}$alkyl-heterocyclyl-$R_{16}$, $C_{1-8}$alkyl-aryl-$R_{17}$, $C_{1-8}$alkyl-heteroaryl-$R_{18}$, $C_{1-8}$alkyl-NH—$C_{3-12}$cycloalkyl-$R_{15}$, $C_{1-8}$alkyl-NH-heterocyclyl-$R_{16}$, $C_{1-8}$alkyl-NH-aryl-$R_{17}$, $C_{1-8}$alkyl-NH-heteroaryl-$R_{18}$, $C_{1-8}$alkyl-NH—$C_{1-8}$alkyl-$C_{3-12}$cycloalkyl-$R_{15}$, $C_{1-8}$alkyl-NH—$C_{1-8}$alkyl-heterocyclyl-$R_{16}$, $C_{1-8}$alkyl-NH—$C_{1-8}$alkyl-aryl-$R_{17}$, $C_{1-8}$alkyl-NH—$C_{1-8}$alkyl-heteroaryl-$R_{18}$, $SO_2$—$C_{3-12}$cycloalkyl-$R_{15}$, $SO_2$-heterocyclyl-$R_{16}$, $SO_2$-aryl-$R_{17}$ or $SO_2$-heteroaryl-$R_{18}$, $R_{11}$, $R_{12}$, $R_{13}$ and $R_{14}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-OH, $NH_2$, NH—$C_{1-8}$alkyl or N($C_{1-8}$alkyl)$_2$, and $R_{15}$, $R_{16}$, $R_{17}$ and $R_{18}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-OH, C(O)H, C(O)$C_{1-8}$alkyl, C(O)OH, C(O)O—$C_{1-8}$alkyl, $NH_2$, NH—$C_{1-8}$alkyl or N($C_{1-8}$alkyl)$_2$.

An example of the present invention is a compound of formula (I) or a form thereof, wherein $R_1$ is hydrogen.

An example of the present invention is a compound of formula (I) or a form thereof, wherein $R_2$ is hydrogen, halogen, $C_{3-12}$cycloalkyl-$R_7$, heterocyclyl-$R_8$, aryl-$R_9$ or heteroaryl-$R_{10}$.

An example of the present invention is a compound of formula (I) or a form thereof, wherein $R_2$ is hydrogen, halogen, aryl-$R_9$ or heteroaryl-$R_{10}$.

An example of the present invention is a compound of formula (I) or a form thereof, wherein $R_3$, $R_4$, $R_5$ and $R_6$ is each selected from hydrogen, halogen, cyano, $C_{1-4}$alkyl, $C_{1-4}$alkoxy, $C_{1-4}$alkyl(halogen)$_{1-3}$, $C_{1-4}$alkoxy(halogen)$_{1-3}$, $C_{1-4}$alkyl-O—$C_{1-4}$alkyl, $C_{1-4}$alkyl-O—$C_{1-4}$alkyl-O—$C_{1-4}$alkyl, OH, $C_{1-4}$alkyl-OH, $C_{1-4}$alkoxy-OH, C(O)OH, C(O)O—$C_{1-4}$alkyl, $NH_2$, NH—$C_{1-4}$alkyl, N($C_{1-4}$alkyl)$_2$, NHC(O)$C_{1-4}$alkyl, NHC(O)NH$C_{1-4}$alkyl, N($C_{1-4}$alkyl)C(O)$C_{1-4}$alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, C(O)$NH_2$, C(O)NH—$C_{1-4}$alkyl, C(O)N($C_{1-4}$alkyl)$_2$, C(O)NH—$C_{1-4}$alkyl-$NH_2$, C(O)NH—$C_{1-4}$alkyl-NH—$C_{1-4}$alkyl, C(O)NH—$C_{1-4}$alkyl-N($C_{1-4}$alkyl)$_2$, C(O)N($C_{1-4}$alkyl)-$C_{1-4}$alkyl-$NH_2$, C(O)N($C_{1-4}$alkyl)-$C_{1-4}$alkyl-NH—$C_{1-4}$alkyl, C(O)N($C_{1-4}$alkyl)-$C_{1-4}$alkyl-N($C_{1-4}$alkyl)$_2$, $C_{3-12}$cycloalkyl-$R_{11}$, heterocyclyl-$R_{12}$, aryl-$R_{13}$, heteroaryl-$R_{14}$, $C_{1-4}$alkyl-$C_{3-12}$cycloalkyl-$R_{11}$, $C_{1-4}$alkyl-heterocyclyl-$R_{12}$, $C_{1-4}$alkyl-aryl-$R_{13}$, $C_{1-4}$alkyl-heteroaryl-$R_{14}$, $C_{1-4}$alkyl-O—$C_{1-4}$alkyl-$C_{3-12}$cycloalkyl-$R_{11}$, $C_{1-4}$alkyl-O—$C_{1-4}$alkyl-heterocyclyl-$R_{12}$, $C_{1-4}$alkyl-O—$C_{1-4}$alkyl-aryl-$R_{13}$, $C_{1-4}$alkyl-O—$C_{1-4}$alkyl-heteroaryl-$R_{14}$, C(O)—$C_{3-12}$cycloalkyl-$R_{11}$, C(O)-heterocyclyl-$R_{12}$, C(O)-aryl-$R_{13}$, C(O)-heteroaryl-$R_{14}$, C(O)NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$.

An example of the present invention is a compound of formula (I) or a form thereof, wherein $R_3$, $R_4$, $R_5$ and $R_6$ is each selected from hydrogen, halogen, cyano, $C_{1-4}$alkyl, $C_{1-4}$alkoxy, $C_{1-4}$alkoxy(halogen)$_{1-3}$ $C_{1-4}$alkyl-O—$C_{1-4}$alkyl, $C_{1-4}$alkyl-O—$C_{1-4}$alkyl-O—$C_{1-4}$alkyl, $C_{1-4}$alkyl-OH, $C_{1-4}$alkoxy-OH, C(O)OH, C(O)O—$C_{1-4}$alkyl, $C_{1-4}$alkyl-NH—$C_{1-4}$alkyl, $C_{1-4}$alkyl-N($C_{1-4}$alkyl)$_2$, C(O)NH—$C_{1-4}$alkyl, C(O)N($C_{1-4}$alkyl)$_2$, C(O)NH—$C_{1-4}$alkyl-N($C_{1-4}$alkyl)$_2$, C(O)N($C_{1-4}$alkyl)-$C_{1-4}$alkyl-N($C_{1-4}$alkyl)$_2$, heterocyclyl-$R_{12}$, $C_{1-4}$alkyl-heterocyclyl-$R_{12}$, $C_{1-4}$alkyl-O—$C_{1-4}$alkyl-heterocyclyl-$R_{12}$, C(O)-heterocyclyl-$R_{12}$, C(O)NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$.

An example of the present invention is a compound of formula (I) or a form thereof, wherein $R_4$ and $R_5$ are taken together to form —O—$CH_2$—O— or —O—$(CH_2)_2$—O— which, together with the benzoimidazolyl ring of formula (I), form a 5H-[1,3]dioxolo[4',5':4,5]benzo[1,2-d]imidazol-6-yl or a 6,7-dihydro-1H-5,8-dioxa-1,3-diaza-cyclopenta[b]naphthalen-2-yl ring system, wherein the —O—$CH_2$—O— or —O—$(CH_2)_2$—O— portion is each optionally substituted on one or two carbon atoms with one or two substituents each selected from halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH or $C_{1-4}$alkyl-OH.

An example of the present invention is a compound of formula (I) or a form thereof, wherein $R_4$ and $R_5$ are taken together to form —O—$CH_2$—O— which, together with the benzoimidazolyl ring of formula (I), form a 5H-[1,3]dioxolo[4',5':4,5]benzo[1,2-d]imidazol-6-yl ring system, wherein the —O—$CH_2$—O— portion is optionally substituted on the carbon atom with one or two substituents each selected from halogen, $C_{1-4}$alkyl, $C_{1-4}$alkoxy, $C_{1-4}$alkyl(halogen)$_{1-3}$, $C_{1-4}$alkoxy(halogen)$_{1-3}$, OH or $C_{1-4}$alkyl-OH.

An example of the present invention is a compound of formula (I) or a form thereof, wherein $R_7$, $R_8$, $R_9$ and $R_{10}$ is each one, two, three, four or five substituents each selected from hydrogen, halogen, nitro, cyano, $C_{1-4}$alkyl, $C_{1-4}$alkoxy, OH, $C_{1-4}$alkyl-OH, $C_{1-4}$alkoxy-O—$C_{1-4}$alkyl, $C_{1-4}$alkoxy-OH, C(O)H, C(O)$C_{1-4}$alkyl, C(O)OH, C(O)O—$C_{1-4}$alkyl, $C_{1-4}$alkyl-$NH_2$, $C_{1-4}$alkyl-NH—$C_{1-4}$alkyl, CH($C_{1-4}$alkyl)-NH—$C_{1-4}$alkyl, C($C_{1-4}$alkyl)$_2$-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-$NH_2$, $C_{1-4}$alkyl-NH—C(O)$C_{1-4}$alkyl, $C_{1-4}$alkyl-NH—C(O)NH$C_{1-4}$alkyl, $C_{1-4}$alkyl-NH—$C_{1-4}$alkyl-NH—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, $SO_2NH_2$, $C_{3-12}$cycloalkyl-$R_{15}$, heterocyclyl-$R_{16}$, aryl-$R_{17}$, heteroaryl-$R_{18}$, $C_{1-4}$alkyl-$C_{3-12}$cycloalkyl-$R_{15}$, $C_{1-4}$alkyl-heterocyclyl-$R_{16}$, $C_{1-4}$alkyl-aryl-$R_{17}$, $C_{1-4}$alkyl-heteroaryl-$R_{18}$, $C_{1-4}$alkyl-NH—$C_{3-12}$cycloalkyl-$R_{15}$, $C_{1-4}$alkyl-NH-heterocyclyl-$R_{16}$, $C_{1-4}$alkyl-NH-aryl-$R_{17}$, $C_{1-4}$alkyl-NH-heteroaryl-$R_{18}$, $C_{1-4}$alkyl-NH—$C_{1-4}$alkyl-$C_{3-12}$cycloalkyl-$R_{15}$, $C_{1-4}$alkyl-NH—$C_{1-4}$alkyl-heterocyclyl-$R_{16}$, $C_{1-4}$alkyl-NH—$C_{1-4}$alkyl-aryl-$R_{17}$, $C_{1-4}$alkyl-NH—$C_{1-4}$alkyl-heteroaryl-$R_{18}$, $SO_2$—$C_{3-12}$cycloalkyl-$R_{15}$, $SO_2$-heterocyclyl-$R_{16}$, $SO_2$-aryl-$R_{17}$ or $SO_2$-heteroaryl-$R_{18}$.

An example of the present invention is a compound of formula (I) or a form thereof, wherein $R_7$ and $R_8$ is each hydrogen.

An example of the present invention is a compound of formula (I) or a form thereof, wherein $R_9$ and $R_{10}$ is each one, two, three, four or five substituents each selected from hydrogen, halogen, $C_{1-4}$alkyl, $C_{1-4}$alkoxy, $C_{1-4}$alkyl-OH, C(O)H, C(O)O—$C_{1-4}$alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, $SO_2NH_2$, heterocyclyl-$R_{16}$, $C_{1-4}$alkyl-heterocyclyl-$R_{16}$, $C_{1-4}$alkyl-NH-heterocyclyl-$R_{16}$, $C_{1-4}$alkyl-NH—$C_{1-4}$alkyl-heterocyclyl-$R_{16}$ or $SO_2$-aryl-$R_{17}$.

An example of the present invention is a compound of formula (I) or a form thereof, wherein $R_9$ is selected from hydrogen or $SO_2NH_2$.

An example of the present invention is a compound of formula (I) or a form thereof, wherein $R_{10}$ is one, two, three, four or five substituents each selected from hydrogen, halogen, $C_{1-4}$alkyl, $C_{1-4}$alkoxy, $C_{1-4}$alkyl-OH, C(O)H, C(O)O—$C_{1-4}$alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, heterocyclyl-$R_{16}$, $C_{1-4}$alkyl-heterocyclyl-$R_{16}$, $C_{1-4}$alkyl-NH-heterocyclyl-$R_{16}$, $C_{1-4}$alkyl-NH—$C_{1-4}$alkyl-heterocyclyl-$R_{16}$ or $SO_2$-aryl-$R_{17}$.

An example of the present invention is a compound of formula (I) or a form thereof, wherein $R_{11}$, $R_{12}$, $R_{13}$ and $R_{14}$ is each one, two, three, four or five substituents each selected from hydrogen, $C_{1-4}$alkyl, OH, $NH_2$ or N($C_{1-4}$alkyl)$_2$.

An example of the present invention is a compound of formula (I) or a form thereof, wherein $R_{11}$ is one, two, three, four or five substituents each selected from hydrogen, halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or N($C_{1-4}$alkyl)$_2$.

An example of the present invention is a compound of formula (I) or a form thereof, wherein $R_{11}$ is one, two, three, four or five substituents each selected from hydrogen, OH or $NH_2$.

An example of the present invention is a compound of formula (I) or a form thereof, wherein $R_{12}$ is one, two, three, four or five substituents each selected from hydrogen, halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or N($C_{1-4}$alkyl)$_2$.

An example of the present invention is a compound of formula (I) or a form thereof, wherein $R_{12}$ is one, two, three, four or five substituents each selected from hydrogen or $C_{1-4}$alkyl.

An example of the present invention is a compound of formula (I) or a form thereof, wherein $R_{13}$ is one, two, three, four or five substituents each selected from hydrogen, halogen, nitro, cyano; $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or $N(C_{1-4}$alkyl)$_2$.

An example of the present invention is a compound of formula (I) or a form thereof, wherein $R_{13}$ is one, two, three, four or five substituents each selected from hydrogen, $C_{1-4}$alkyl or $N(C_{1-4}$alkyl)$_2$.

An example of the present invention is a compound of formula (I) or a form thereof, wherein $R_{14}$ is hydrogen.

An example of the present invention is a compound of formula (I) or a form thereof, wherein $R_{15}$, $R_{16}$, $R_{17}$ and $R_{18}$ is each one, two, three, four or five substituents each selected from hydrogen, halogen, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, C(O)OH, C(O)O—$C_{1-4}$alkyl, $NH_2$, NH—$C_{1-4}$alkyl or $N(C_{1-4}$ alkyl)$_2$.

An example of the present invention is a compound of formula (I) or a form thereof, wherein $R_{15}$ and $R_{16}$ is each hydrogen.

An example of the present invention is a compound of formula (I) or a form thereof, wherein $R_{17}$ and $R_{18}$ is each one, two, three, four or five substituents each selected from hydrogen, halogen, $C_{1-4}$alkyl or C(O)O—$C_{1-4}$alkyl.

An example of the present invention is a compound of formula (Ia):

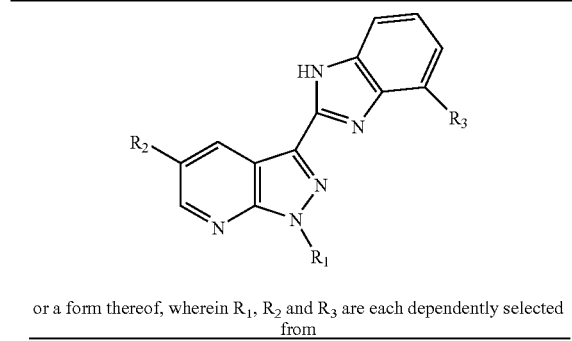

or a form thereof, wherein $R_1$, $R_2$ and $R_3$ are each dependently selected from

| Cpd | $R_1$ | $R_2$ | $R_3$ |
|---|---|---|---|
| 1 | H | isoquinolin-4-yl | H |
| 2 | H | isoquinolin-4-yl | $CH_3$ |
| 3 | H | isoquinolin-4-yl | $CH_2OH$ |
| 4 | H | isoquinolin-4-yl | $CH_2OCH_3$ |
| 5 | H | isoquinolin-4-yl | $CH_2N(CH_2CH_3)_2$ |
| 6 | H | Br | $CH_2N(CH_2CH_3)_2$ |
| 7 | H | isoquinolin-4-yl | $CH_2$-pyrrolidin-1-yl |
| 8 | H | isoquinolin-4-yl | $CH_2$-piperidin-1-yl |
| 9 | H | isoquinolin-4-yl | $CH_2$-morpholin-4-yl |
| 10 | H | isoquinolin-4-yl | $CH_2$-(4-$CH_2CH_3$-piperazin-1-yl) |
| 11 | H | Br | $CH_2OCH_3$ |
| 12 | H | isoquinolin-4-yl | $CH_2$-imidazol-1-yl |
| 13 | H | isoquinolin-4-yl | $CH_2NHCH(CH_3)_2$ |
| 14 | H | isoquinolin-4-yl | $CH_2O(CH_2)_2OCH_3$ |
| 15 | H | isoquinolin-4-yl | $CH_2O(CH_2)_2$-morpholin-4-yl |
| 16 | H | isoquinolin-4-yl | $CH_2O(CH_2)_2OCH_2CH_3$ |
| 17 | H | isoquinolin-4-yl | C(O)OH |
| 18 | H | isoquinolin-4-yl | $C(O)NHCH(CH_3)_2$ |
| 19 | H | isoquinolin-4-yl | $C(O)N(CH_2CH_3)_2$ |
| 20 | H | isoquinolin-4-yl | $C(O)NHC(CH_3)_3$ |
| 21 | H | isoquinolin-4-yl | C(O)-pyrrolidin-1-yl |
| 22 | H | isoquinolin-4-yl | C(O)-piperidin-1-yl |
| 23 | H | isoquinolin-4-yl | C(O)-(4-$CH_3$-piperazin-1-yl) |
| 24 | H | isoquinolin-4-yl | C(O)-morpholin-4-yl |
| 25 | H | isoquinolin-4-yl | $C(O)NH(CH_2)_2N(CH_3)_2$ |
| 26 | H | isoquinolin-4-yl | $C(O)N(CH_3)(CH_2)_2N(CH_3)_2$ |
| 27 | H | isoquinolin-4-yl | C(O)NH-cyclopentyl |

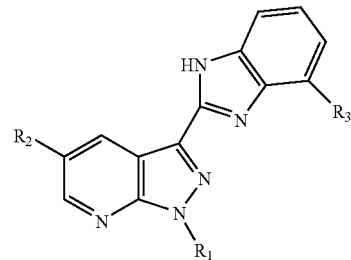

or a form thereof, wherein $R_1$, $R_2$ and $R_3$ are each dependently selected from

| Cpd | $R_1$ | $R_2$ | $R_3$ |
|---|---|---|---|
| 28 | H | isoquinolin-4-yl | C(O)NH-(1-$CH_3$-piperidin-4-yl) |
| 29 | H | isoquinolin-4-yl | C(O)NH-(4-OH-cyclohexyl) |
| 32 | H | isoquinolin-4-yl | $CH_2OCH(CH_3)_2$ |
| 33 | $CH_3$ | isoquinolin-4-yl | $CH_2OCH_3$ |
| 34 | H | isoquinolin-4-yl | $CH_2OCH_3$ |
| 35 | H | pyridin-3-yl | $CH_2OCH_3$ |
| 36 | H | 4-$SO_2NH_2$-phenyl | $CH_2OCH_3$ |
| 37 | H | 7-aza-indol-3-yl | $CH_2OCH_3$ |
| 38 | H | (1-$SO_2$-phenyl)-indol-3-yl | $CH_2OCH_3$ |
| 39 | H | indol-3-yl | $CH_2OCH_3$ |
| 40 | H | 1H-pyrrol-3-yl | $CH_2OCH_3$ |
| 41 | H | 5-C(O)H-pyridin-3-yl | $CH_2OCH_3$ |
| 42 | H | 5-$CH_2NHCH_2CH_3$-pyridin-3-yl | $CH_2OCH_3$ |
| 43 | H | 5-$CH_2NHCH(CH_3)_2$-pyridin-3-yl | $CH_2OCH_3$ |
| 44 | H | 5-$CH_2OH$-pyridin-3-yl | $CH_2OCH_3$ |
| 45 | H | isoquinolin-4-yl | C(O)NH-(4-$NH_2$-cyclohexyl) |
| 46 | H | isoquinolin-4-yl | C(O)NH-(2-$CH_3$-phenyl) |
| 47 | H | isoquinolin-4-yl | C(O)NH-cyclopropyl |
| 48 | H | isoquinolin-4-yl | C(O)NH-pyridin-3-yl |
| 49 | H | isoquinolin-4-yl | C(O)NH-[4-$N(CH_3)_2$-phenyl] |
| 50 | H | isoquinolin-4-yl | C(O)NH-[2-$CH_3$-4-$N(CH_2CH_3)_2$-phenyl] |
| 52 | H | pyridin-3-yl | $CH_2N(CH_2CH_3)_2$ |
| 53 | H | 5-$CH_2NHC(CH_3)_3$-pyridin-3-yl | $CH_2OCH_3$ |
| 54 | H | 5-$CH_2$-morpholin-4-yl-pyridin-3-yl | $CH_2OCH_3$ |
| 55 | H | 5-$CH_2N(CH_3)_2$-pyridin-3-yl | $CH_2OCH_3$ |
| 56 | H | 5-$CH_2NHCH_3$-pyridin-3-yl | $CH_2OCH_3$ |
| 57 | H | 4-$CH_3$-pyridin-3-yl | $CH_2OCH_3$ |
| 58 | H | 4-$CH_3$-5-$CH_2NH$—$CH(CH_3)_2$-pyridin-3-yl | $CH_2OCH_3$ |
| 59 | H | 4-$CH_3$-5-$CH_2NHCH_2CH_3$-pyridin-3-yl | $CH_2OCH_3$ |
| 60 | H | 4-$CH_3$-5-$CH_2$-morpholin-4-yl-pyridin-3-yl | $CH_2OCH_3$ |
| 61 | H | 4-$CH_3$-5-$CH_2N(CH_3)_2$-pyridin-3-yl | $CH_2OCH_3$ |
| 62 | H | 4-$CH_3$-5-$CH_2NHCH_3$-pyridin-3-yl | $CH_2OCH_3$ |
| 63 | H | 6-$OCH_3$-pyridin-3-yl | $CH_2OCH_3$ |
| 64 | H | 5-$OCH_3$-pyridin-3-yl | $CH_2OCH_3$ |
| 65 | H | pyridin-4-yl | $CH_2OCH_3$ |
| 66 | H | 6-morpholin-4-yl-pyridin-3-yl | $CH_2OCH_3$ |
| 67 | H | 6-[4-$C(O)OC(CH_3)_3$-piperazin-1-yl]-pyridin-3-yl | $CH_2OCH_3$ |
| 68 | H | pyrimidin-5-yl | $CH_2OCH_3$ |
| 69 | H | 6-piperazin-1-yl-pyridin-3-yl | $CH_2OCH_3$ |
| 70 | H | 5-$C(O)OCH_2CH_3$-pyridin-3-yl | $CH_2OCH_3$ |
| 71 | H | 6-F-pyridin-3-yl | $CH_2OCH_3$ |
| 72 | H | 5-CH═N(OH)-pyridin-3-yl | $CH_2OCH_3$ |
| 73 | H | 5-$CH_2NH_2$-pyridin-3-yl | $CH_2OCH_3$ |
| 74 | H | 5-$CH_2NH(CH_2)_2$-morpholin-4-yl-pyridin-3-yl | $CH_2OCH_3$ |

-continued

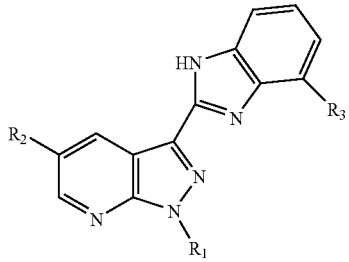

or a form thereof, wherein $R_1$, $R_2$ and $R_3$ are each dependently selected from

| Cpd | $R_1$ | $R_2$ | $R_3$ |
|---|---|---|---|
| 75 | H | 5-CH$_2$NH(CH$_2$)$_2$OCH$_3$-pyridin-3-yl | CH$_2$OCH$_3$ |
| 76 | H | 5-CH$_2$NH(CH$_2$)$_2$N(CH$_3$)$_2$-pyridin-3-yl | CH$_2$OCH$_3$ |
| 77 | H | 5-CH$_2$NH(CH$_2$)$_2$OH-pyridin-3-yl | CH$_2$OCH$_3$ |
| 78 | H | 5-CH$_2$NH(CH$_2$)$_2$CH$_3$-pyridin-3-yl | CH$_2$OCH$_3$ |
| 79 | H | 5-CH$_2$NH(CH$_2$)$_3$CH$_3$-pyridin-3-yl | CH$_2$OCH$_3$ |
| 80 | H | 5-CH$_2$NH-(1-CH$_3$-piperidin-4-yl)-pyridin-3-yl | CH$_2$OCH$_3$ |
| 93 | H | pyridin-3-yl | C(O)OCH$_3$ |
| 108 | H | isoquinolin-4-yl | C(O)OCH$_3$ |

An example of the present invention is a compound of formula (Ia) or a form thereof, wherein $R_1$ is selected from hydrogen or CH$_3$;

$R_2$ is selected from Br, isoquinolin-4-yl, pyridin-3-yl, 4-SO$_2$NH$_2$-phenyl, 7-aza-indol-3-yl, (1-SO$_2$-phenyl)-indol-3-yl, indol-3-yl, 1H-pyrrol-3-yl, 5-C(O)H-pyridin-3-yl, 5-CH$_2$NHCH$_2$CH$_3$-pyridin-3-yl, 5-CH$_2$NHCH(CH$_3$)$_2$-pyridin-3-yl, 5-CH$_2$OH-pyridin-3-yl, 5-CH$_2$NHC(CH$_3$)$_3$-pyridin-3-yl, 5-CH$_2$-morpholin-4-yl-pyridin-3-yl, 5-CH$_2$N(CH$_3$)$_2$-pyridin-3-yl, 5-CH$_2$NHCH$_3$-pyridin-3-yl, 4-CH$_3$-pyridin-3-yl, 4-CH$_3$-5-CH$_2$NH—CH(CH$_3$)$_2$-pyridin-3-yl, 4-CH$_3$-5-CH$_2$NHCH$_2$CH$_3$-pyridin-3-yl, 4-CH$_3$-5-CH$_2$-morpholin-4-yl-pyridin-3-yl, 4-CH$_3$-5-CH$_2$N(CH$_3$)$_2$-pyridin-3-yl, 4-CH$_3$-5-CH$_2$NHCH$_3$-pyridin-3-yl, 6-OCH$_3$-pyridin-3-yl, 5-OCH$_3$-pyridin-3-yl, pyridin-4-yl, 6-morpholin-4-yl-pyridin-3-yl, 6-[4-C(O)OC(CH$_3$)$_3$-piperazin-1-yl]-pyridin-3-yl, pyrimidin-5-yl, 6-piperazin-1-yl-pyridin-3-yl, 5-C(O)OCH$_2$CH$_3$-pyridin-3-yl, 6-F-pyridin-3-yl, 5-CH═N(OH)-pyridin-3-yl, 5-CH$_2$NH$_2$-pyridin-3-yl, 5-CH$_2$NH(CH$_2$)$_2$-morpholin-4-yl-pyridin-3-yl, 5-CH$_2$NH(CH$_2$)$_2$OCH$_3$-pyridin-3-yl, 5-CH$_2$NH(CH$_2$)$_2$N(CH$_3$)$_2$-pyridin-3-yl, 5-CH$_2$NH(CH$_2$)$_2$OH-pyridin-3-yl, 5-CH$_2$NH(CH$_2$)$_2$CH$_3$-pyridin-3-yl, 5-CH$_2$NH(CH$_2$)$_3$CH$_3$-pyridin-3-yl or 5-CH$_2$NH-(1-CH$_3$-piperidin-4-yl)-pyridin-3-yl; and $R_3$ is selected from hydrogen, CH$_3$, CH$_2$OH, CH$_2$OCH$_3$, CH$_2$N(CH$_2$CH$_3$)$_2$, CH$_2$-pyrrolidin-1-yl, CH$_2$-piperidin-1-yl, CH$_2$-morpholin-4-yl, CH$_2$-(4-CH$_2$CH$_3$-piperazin-1-yl), CH$_2$-imidazol-1-yl, CH$_2$NHCH(CH$_3$)$_2$, CH$_2$O(CH$_2$)$_2$OCH$_3$, CH$_2$O(CH$_2$)$_2$-morpholin-4-yl, CH$_2$O(CH$_2$)$_2$OCH$_2$CH$_3$, C(O)OH, C(O)NHCH(CH$_3$)$_2$, C(O)N(CH$_2$CH$_3$)$_2$, C(O)NHC(CH$_3$)$_3$, C(O)-pyrrolidin-1-yl, C(O)-piperidin-1-yl, C(O)-(4-CH$_3$-piperazin-1-yl), C(O)-morpholin-4-yl, C(O)NH(CH$_2$)$_2$N(CH$_3$)$_2$, C(O)N(CH$_3$)(CH$_2$)$_2$N(CH$_3$)$_2$, C(O)NH-cyclopentyl, C(O)NH-(1-CH$_3$-piperidin-4-yl), C(O)NH-(4-OH-cyclohexyl), CH$_2$OCH(CH$_3$)$_2$, C(O)NH-(4-NH$_2$-cyclohexyl), C(O)NH-(2-CH$_3$-phenyl), C(O)NH-cyclopropyl, C(O)NH-pyridin-3-yl, C(O)NH-[4-N(CH$_3$)$_2$-phenyl], C(O)NH-[2-CH$_3$-4-N(CH$_2$CH$_3$)$_2$-phenyl], CH$_2$N(CH$_2$CH$_3$)$_2$ or C(O)OCH$_3$.

An example of the present invention is a compound of formula (Ib):

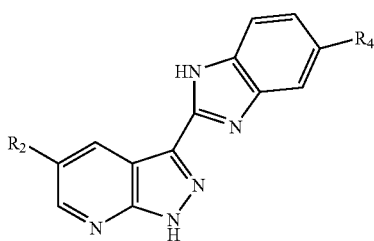

or a form thereof, wherein $R_2$ and $R_4$ are each dependently selected from

| Cpd | $R_2$ | $R_4$ |
|---|---|---|
| 30 | Br | 4-CH$_3$-piperazin-1-yl |
| 31 | isoquinolin-4-yl | 4-CH$_3$-piperazin-1-yl |
| 51 | isoquinolin-4-yl | morpholin-4-yl |
| 81 | 5-CH$_2$NHCH$_3$-pyridin-3-yl | 4-CH$_3$-piperazin-1-yl |
| 82 | 5-CH$_2$NHCH$_2$CH$_3$-pyridin-3-yl | 4-CH$_3$-piperazin-1-yl |
| 83 | 5-CH$_2$NHCH(CH$_3$)$_2$-pyridin-3-yl | 4-CH$_3$-piperazin-1-yl |
| 84 | 5-CH$_2$-morpholin-4-yl-pyridin-3-yl | 4-CH$_3$-piperazin-1-yl |
| 85 | 5-CH$_2$NH(CH$_2$)$_2$CH$_3$-pyridin-3-yl | 4-CH$_3$-piperazin-1-yl |
| 86 | 5-CH$_2$NH(CH$_2$)$_2$OCH$_3$-pyridin-3-yl | 4-CH$_3$-piperazin-1-yl |
| 87 | 5-CH$_2$-pyrrolidin-1-yl-pyridin-3-yl | 4-CH$_3$-piperazin-1-yl |
| 88 | 5-CH$_2$N(CH$_3$)$_2$-pyridin-3-yl | 4-CH$_3$-piperazin-1-yl |
| 89 | pyridin-3-yl | 4-CH$_3$-piperazin-1-yl |
| 91 | pyridin-3-yl | C(O)OCH$_3$ |
| 92 | pyridin-3-yl | F |
| 94 | pyridin-3-yl | OCF$_3$ |
| 95 | pyridin-3-yl | O(CH$_2$)$_2$OH |
| 96 | 5-CH$_2$NHCH$_3$-pyridin-3-yl | OCF$_3$ |
| 97 | 5-CH$_2$NHCH$_3$-pyridin-3-yl | OCH$_3$ |
| 101 | 5-CH$_2$NHCH$_2$CH$_3$-pyridin-3-yl | OCH$_3$ |
| 102 | 5-CH$_2$NHCH(CH$_3$)$_2$-pyridin-3-yl | OCH$_3$ |
| 103 | 5-CH$_2$NH(CH$_2$)$_2$CH$_3$-pyridin-3-yl | OCH$_3$ |
| 104 | 5-CH$_2$NH(CH$_2$)$_3$CH$_3$-pyridin-3-yl | OCH$_3$ |
| 105 | 5-CH$_2$NHCH$_3$-pyridin-3-yl | CN |
| 106 | 5-CH$_2$NHCH$_2$CH$_3$-pyridin-3-yl | F |

An example of the present invention is a compound of formula (Ia) or a form thereof, wherein $R_2$ is selected from Br, isoquinolin-4-yl, 5-CH$_2$NHCH$_3$-pyridin-3-yl, 5-CH$_2$NHCH$_2$CH$_3$-pyridin-3-yl, 5-CH$_2$NHCH(CH$_3$)$_2$-pyridin-3-yl, 5-CH$_2$-morpholin-4-yl-pyridin-3-yl, 5-CH$_2$NH(CH$_2$)$_2$CH$_3$-pyridin-3-yl, 5-CH$_2$NH(CH$_2$)$_2$OCH$_3$-pyridin-3-yl, 5-CH$_2$-pyrrolidin-1-yl-pyridin-3-yl, 5-CH$_2$N(CH$_3$)$_2$-pyridin-3-yl, pyridin-3-yl or 5-CH$_2$NH(CH$_2$)$_3$CH$_3$-pyridin-3-yl; and $R_4$ is selected from 4-CH$_3$-piperazin-1-yl, morpholin-4-yl, C(O)OCH$_3$, F, OCF$_3$, O(CH$_2$)$_2$OH, OCH$_3$ or CN.

An example of the present invention is a compound of formula (Ic):

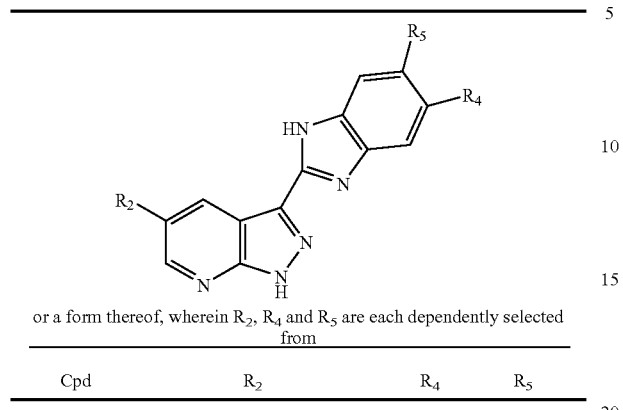

or a form thereof, wherein $R_2$, $R_4$ and $R_5$ are each dependently selected from

| Cpd | $R_2$ | $R_4$ | $R_5$ |
|-----|-------|-------|-------|
| 90 | pyridin-3-yl | H | OCH$_3$ |
| 98 | pyridin-3-yl | —O—C(F)$_2$—O— | |
| 99 | pyridin-3-yl | —O—CH$_2$—O— | |
| 100 | 5-CH$_2$NHCH$_3$-pyridin-3-yl | —O—C(F)$_2$—O— | |
| 107 | 5-CH$_2$NHCH$_2$CH$_3$-pyridin-3-yl | F | F |

An example of the present invention is a compound of formula (Ib) or a form thereof, wherein $R_2$ is selected from pyridin-3-yl, 5-CH$_2$NHCH$_3$-pyridin-3-yl or 5-CH$_2$NHCH$_2$CH$_3$-pyridin-3-yl; and $R_4$ is selected from hydrogen or F; and $R_5$ is selected from OCH$_3$ or F; or alternatively, $R_4$ and $R_5$ are taken together to form —O—CH$_2$—O— which, together with the benzoimidazolyl ring of formula (I), form a 5H-[1,3]dioxolo[4',5':4,5]benzo[1,2-d]imidazol-6-yl ring system, wherein the —O—CH$_2$—O— portion is optionally substituted on the carbon atom with one or two substituents selected from F.

An example of the present invention is a compound of formula (I) or a form thereof represented by a compound selected from:

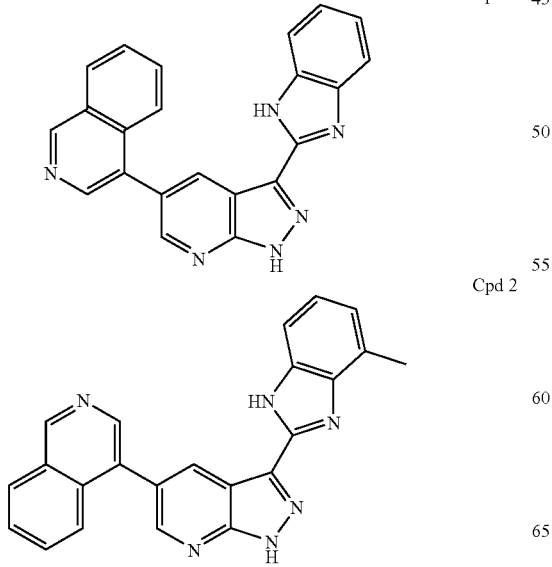

Cpd 1

Cpd 2

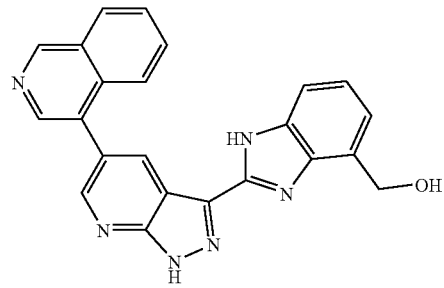

Cpd 3

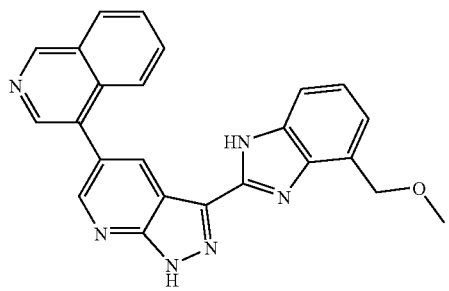

Cpd 4

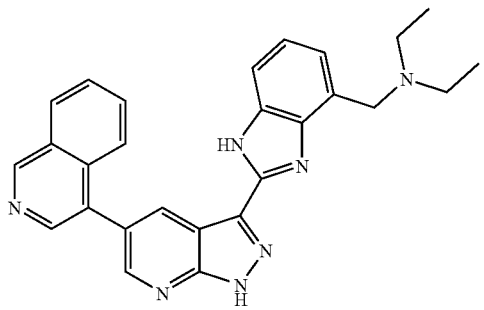

Cpd 5

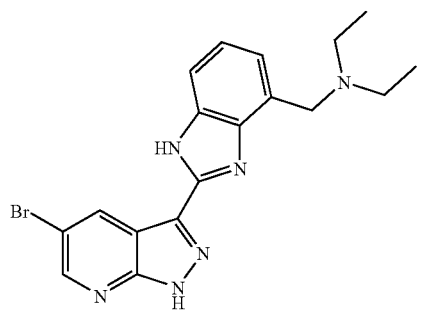

Cpd 6

-continued
Cpd 7
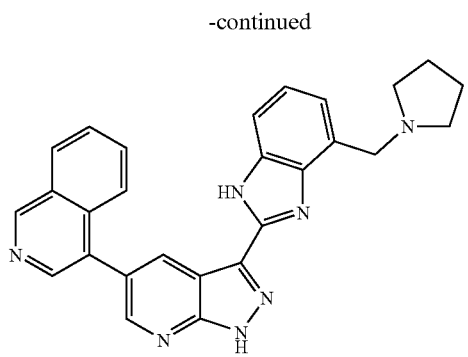
Cpd 8
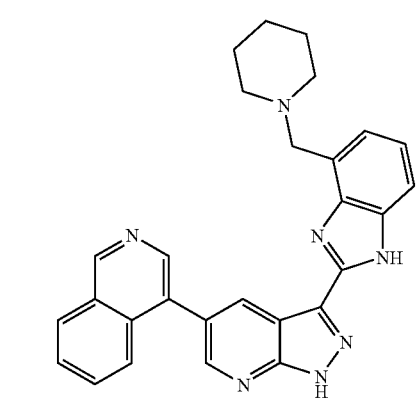
Cpd 9
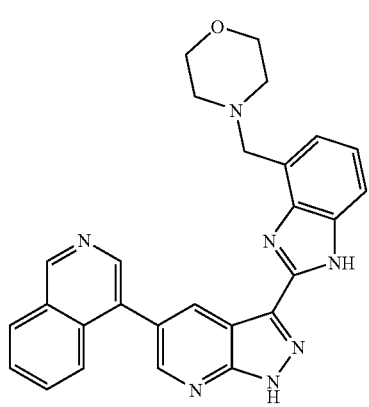
Cpd 10
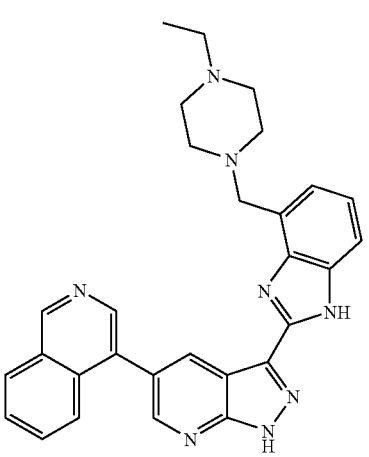
-continued
Cpd 11
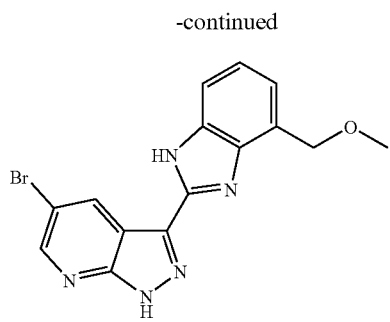
Cpd 12
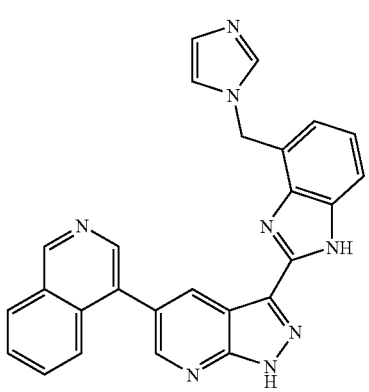
Cpd 13
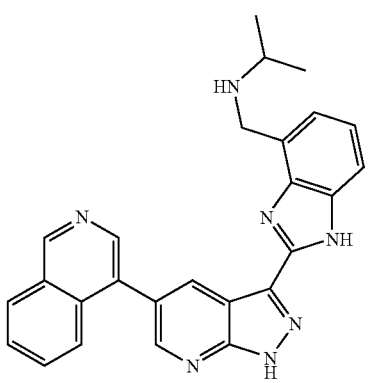
Cpd 14
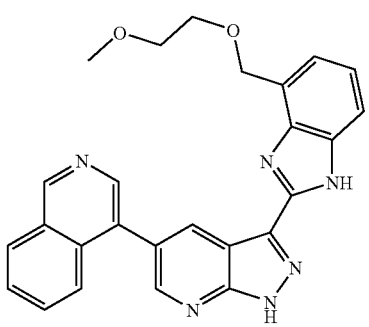

-continued
Cpd 15
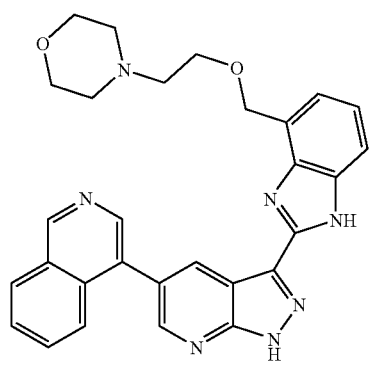
Cpd 16
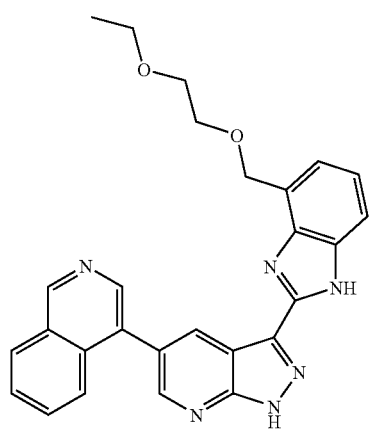
Cpd 17
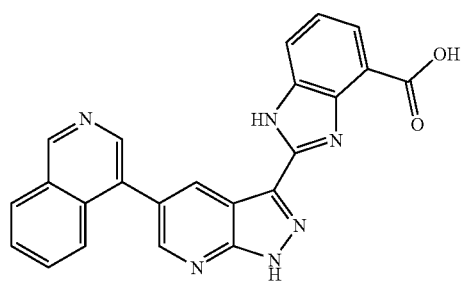
Cpd 18
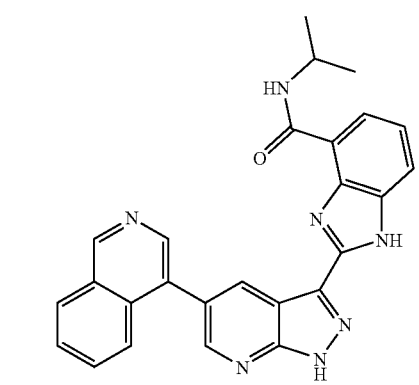
-continued
Cpd 19
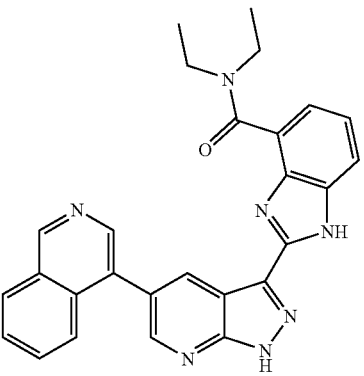
Cpd 20
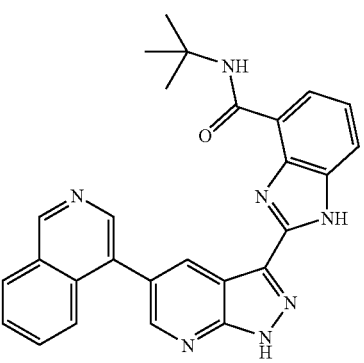
Cpd 21
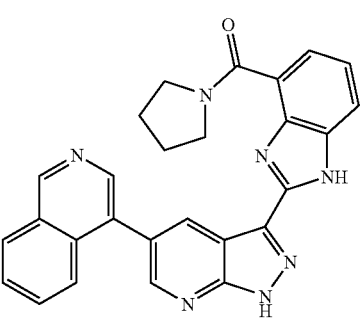
Cpd 22
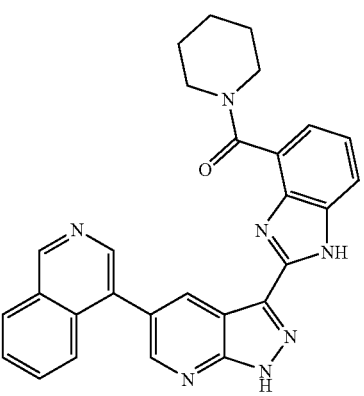

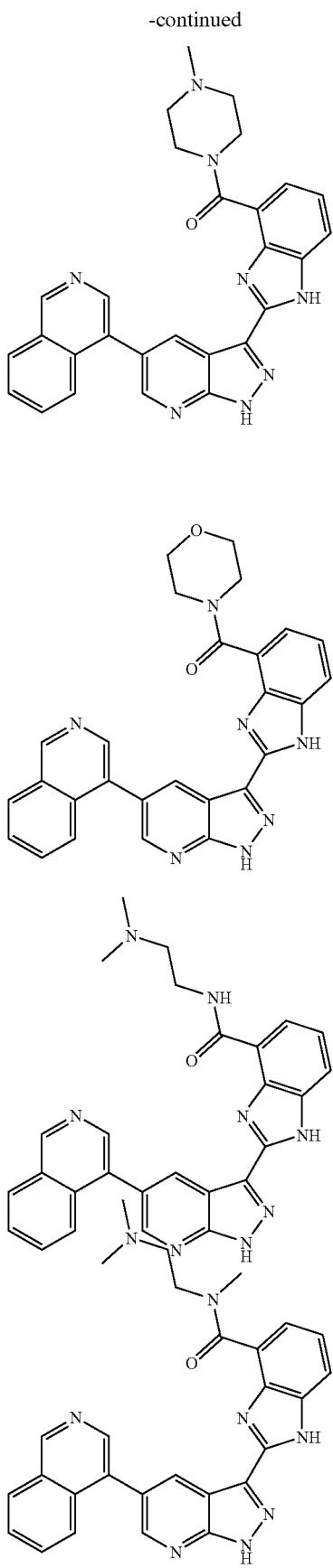

Cpd 31
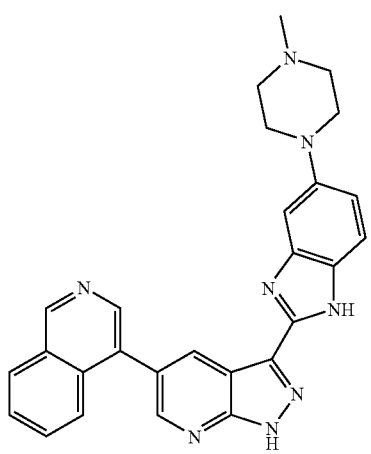
Cpd 32
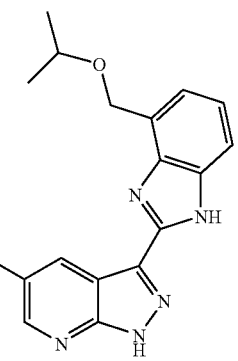
Cpd 33
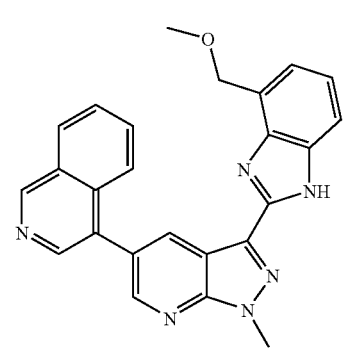
Cpd 34
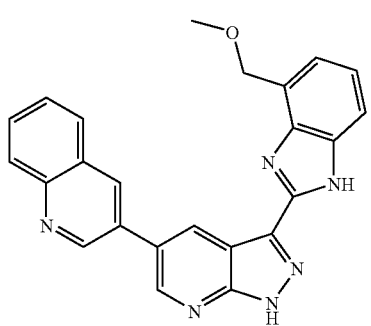
Cpd 35
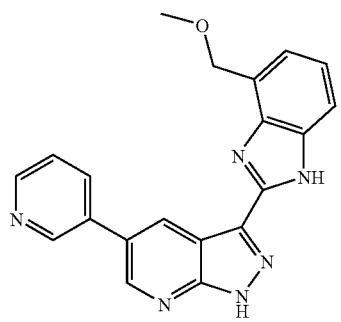
Cpd 36
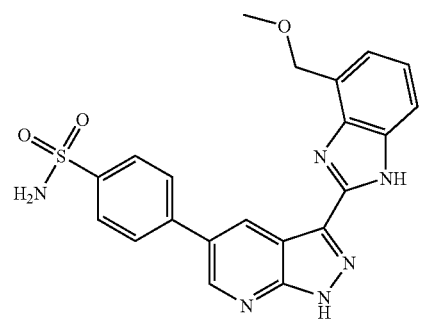
Cpd 37
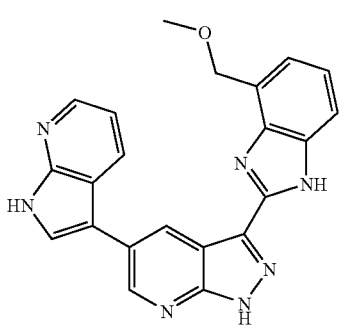
Cpd 38
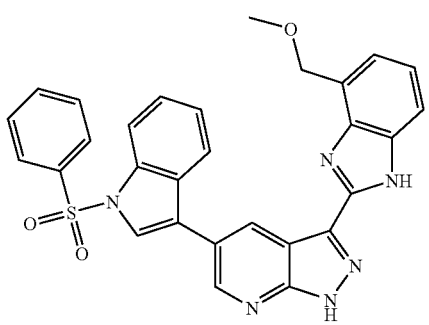
Cpd 39
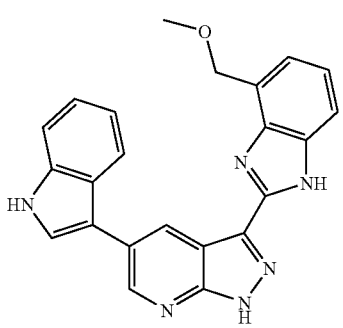

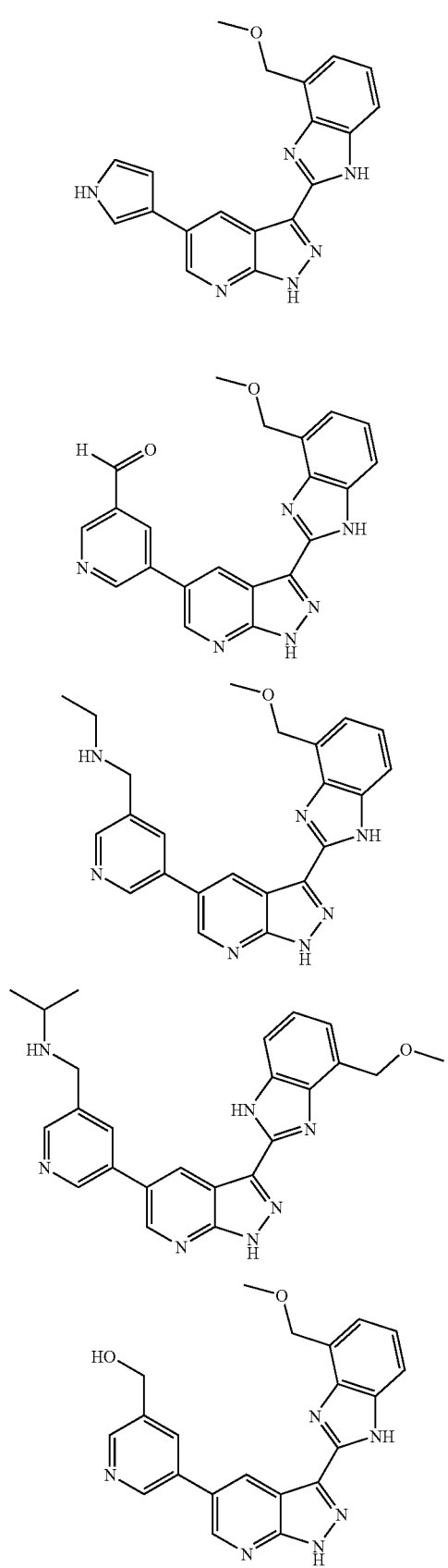
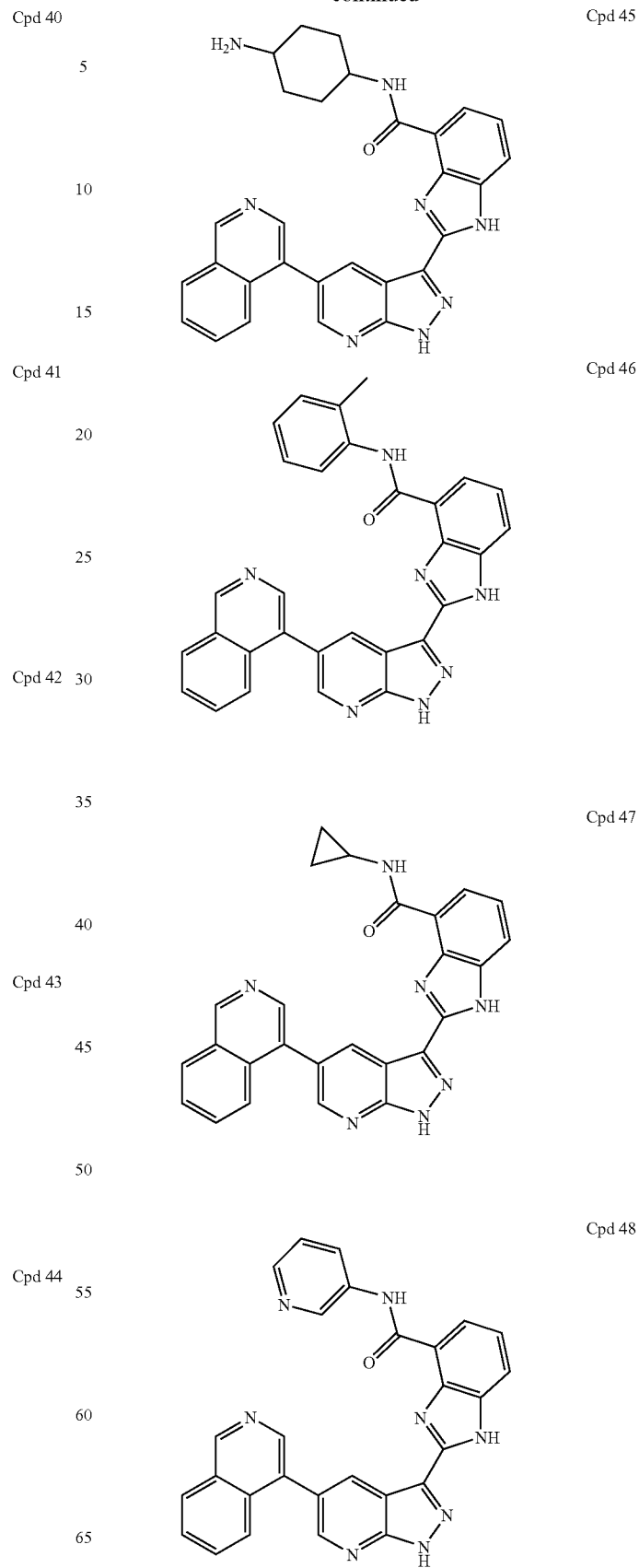

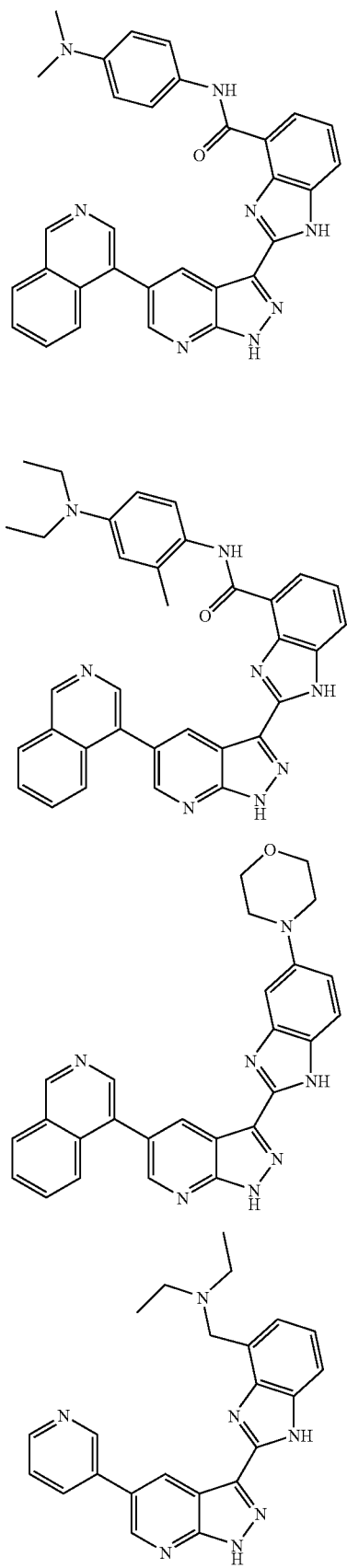
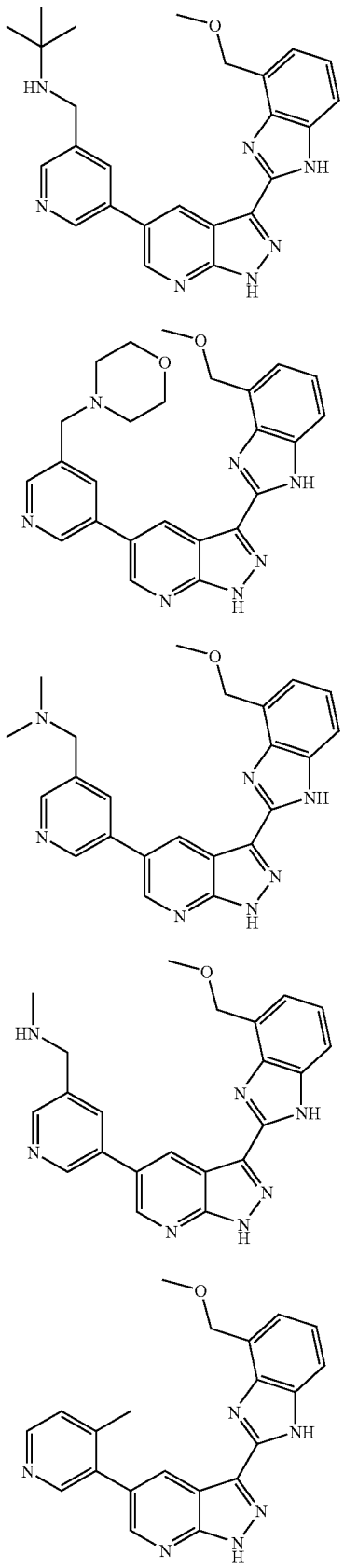

-continued
Cpd 58
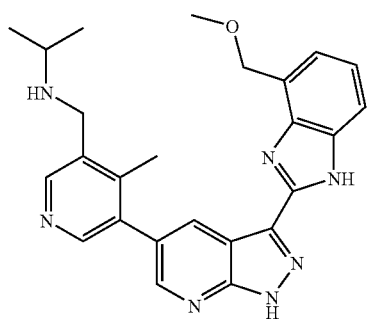
Cpd 59
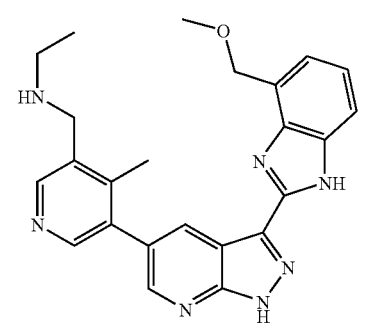
Cpd 60
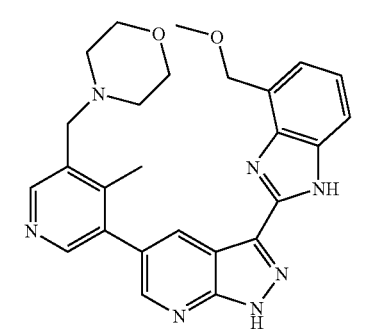
Cpd 61
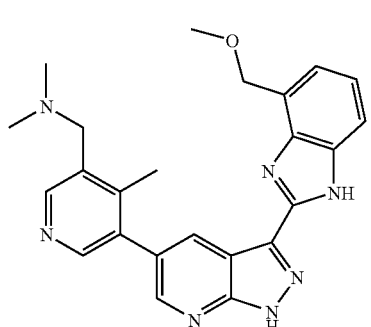
Cpd 62
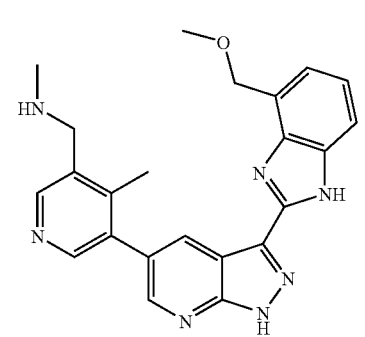
-continued
Cpd 63
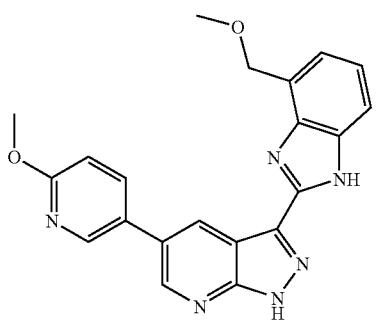
Cpd 64
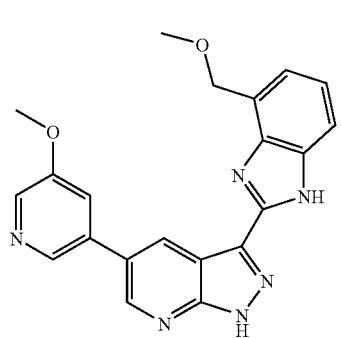
Cpd 65
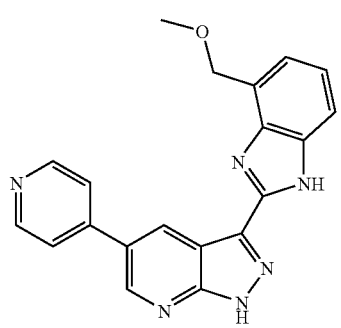
Cpd 66
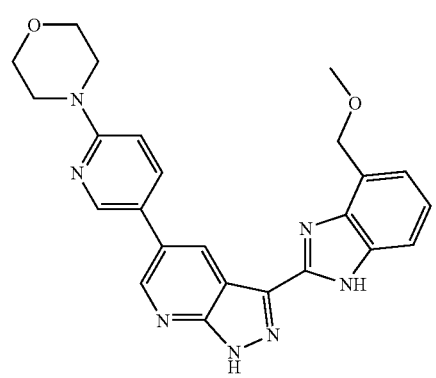

-continued
Cpd 67
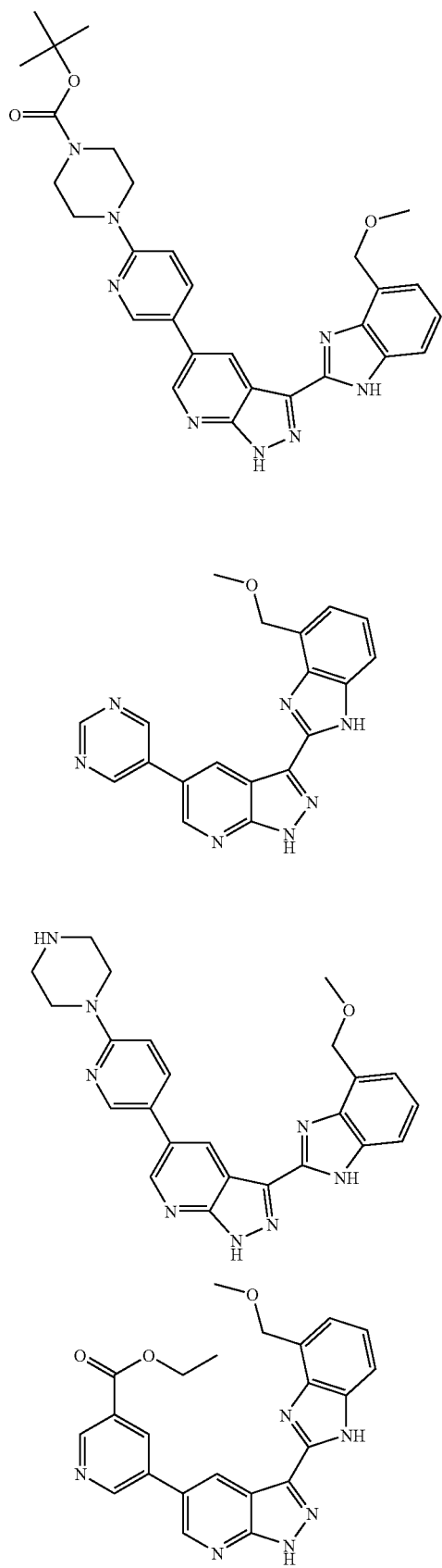
Cpd 68
Cpd 69
Cpd 70
-continued
Cpd 71
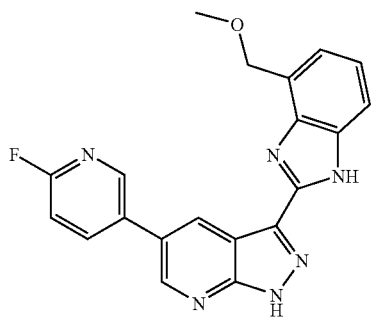
Cpd 72
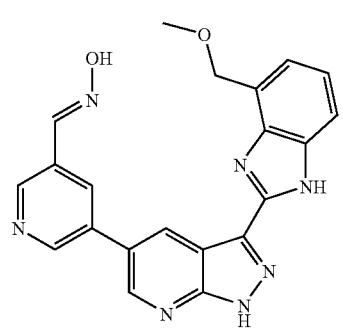
Cpd 73
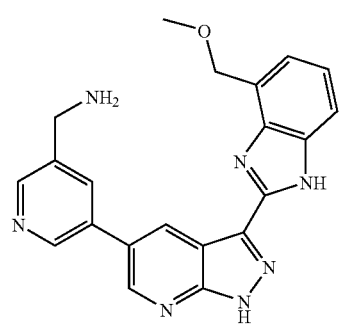
Cpd 74
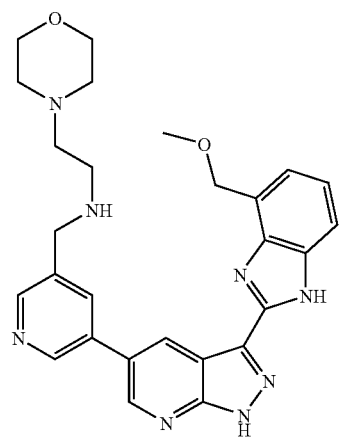

-continued
Cpd 75
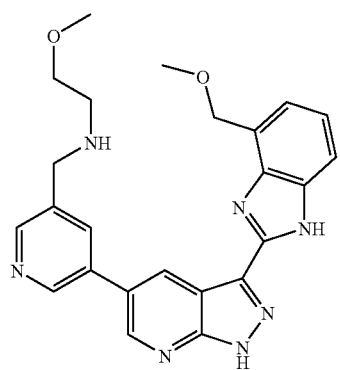
Cpd 76
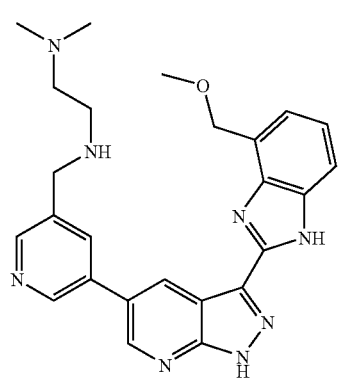
Cpd 77
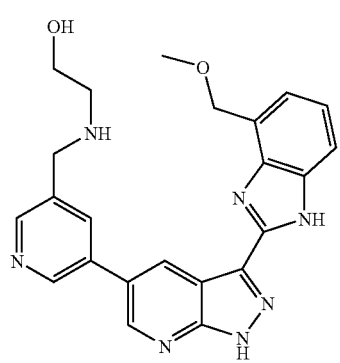
Cpd 78
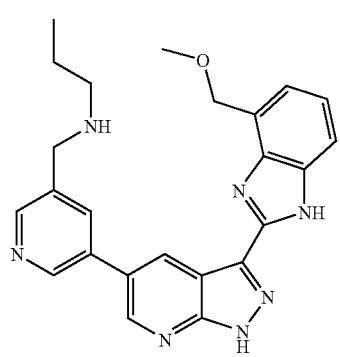
-continued
Cpd 79
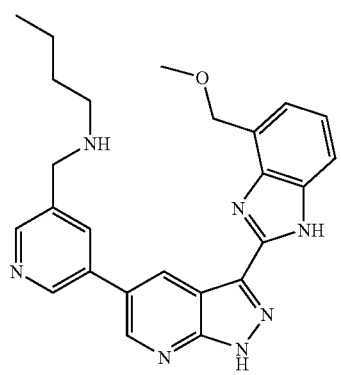
Cpd 80
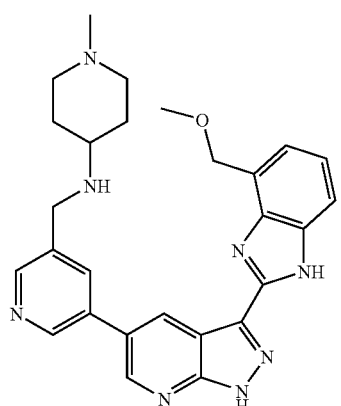
Cpd 81
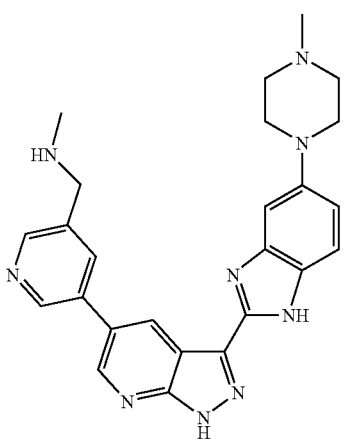
Cpd 82
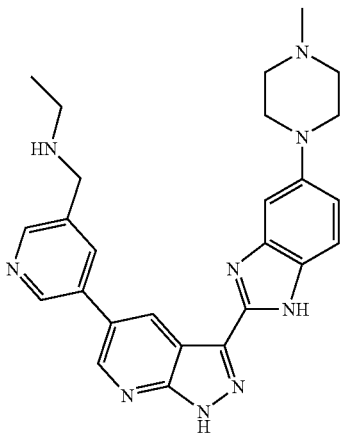

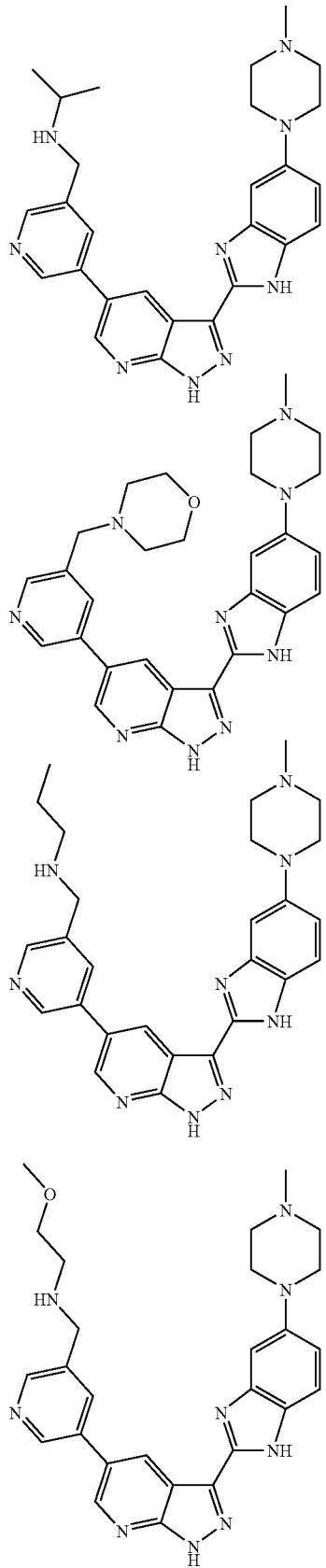
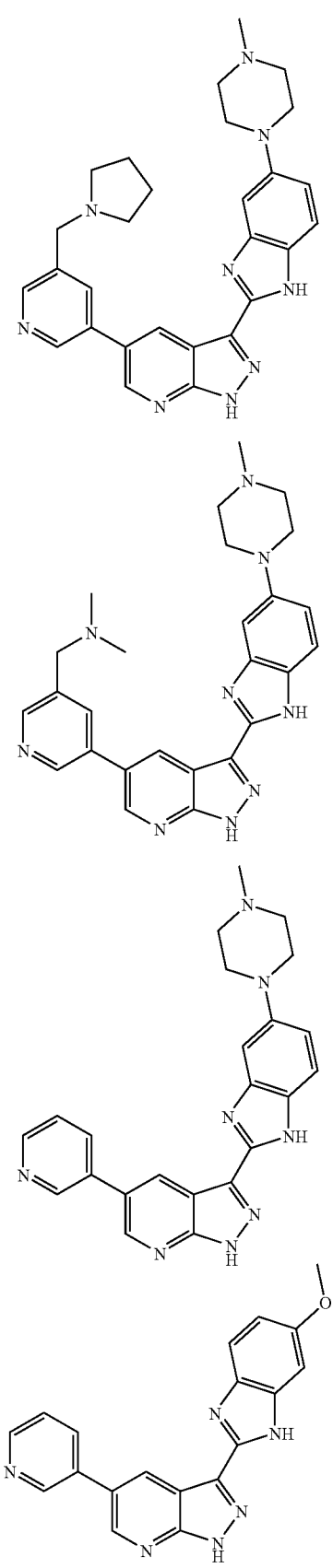

Cpd 91
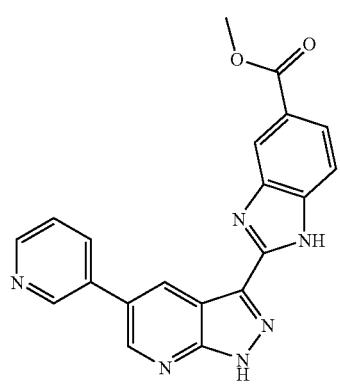
Cpd 92
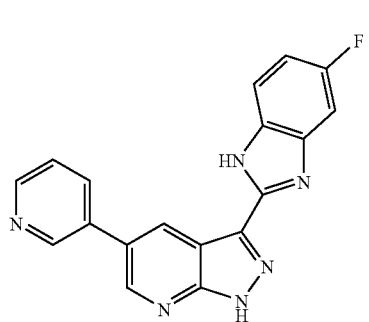
Cpd 93
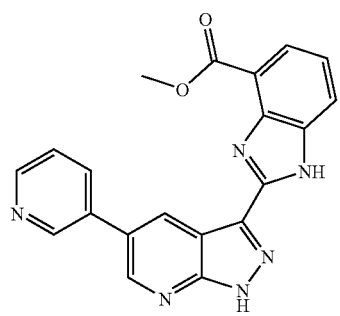
Cpd 94
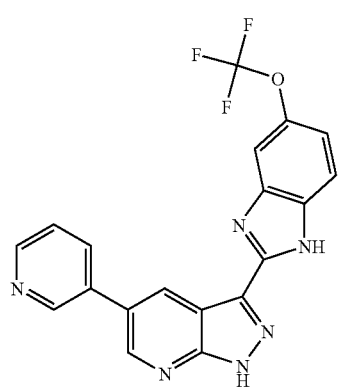
Cpd 95
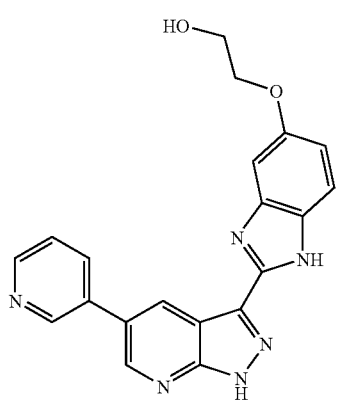
Cpd 96
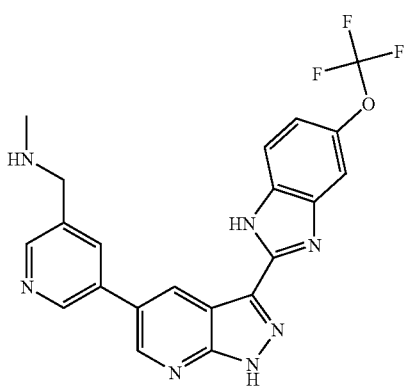
Cpd 97
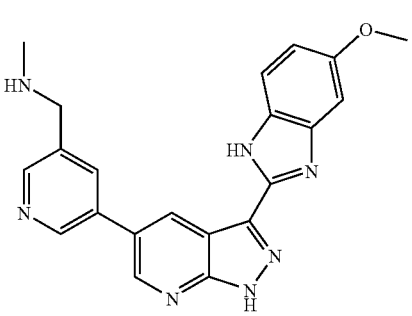
Cpd 98
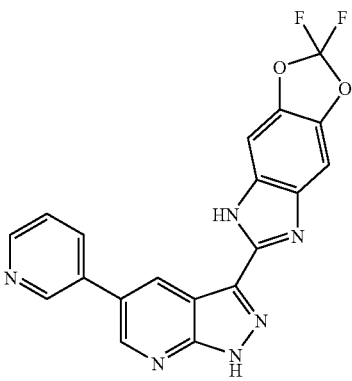

-continued
Cpd 99
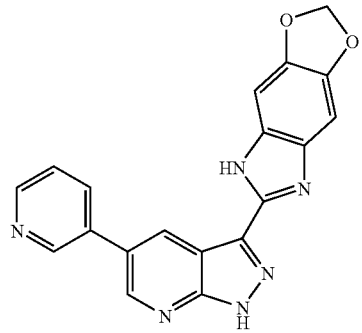
Cpd 100
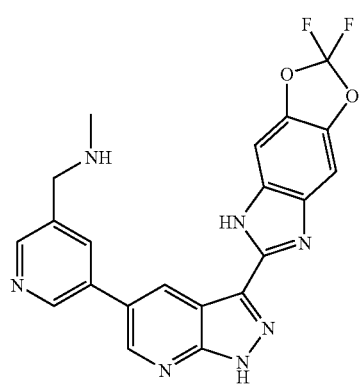
Cpd 101
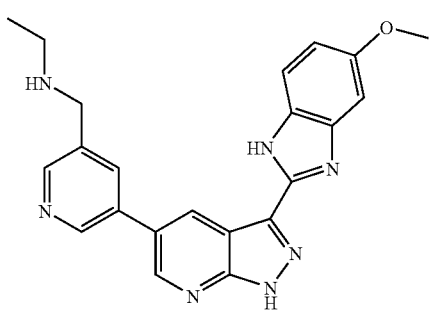
Cpd 102
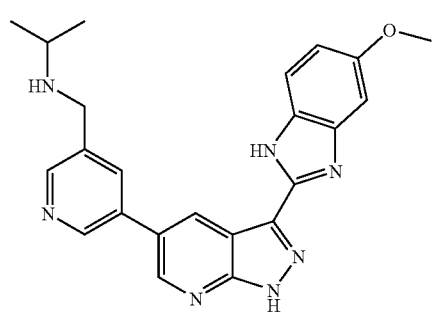
-continued
Cpd 103
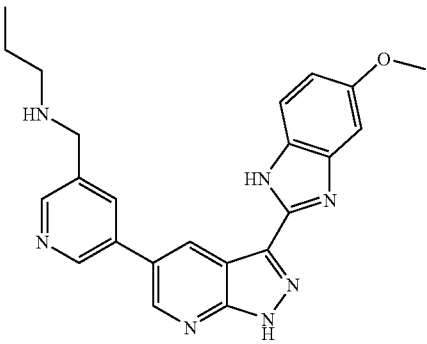
Cpd 104
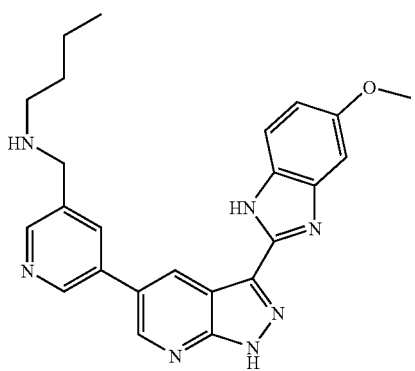
Cpd 105
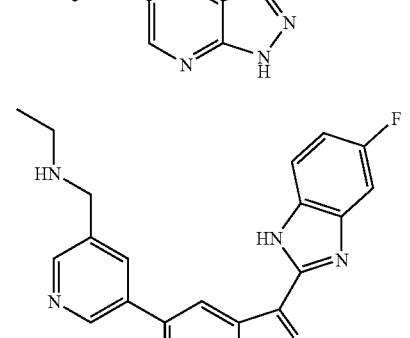
Cpd 106
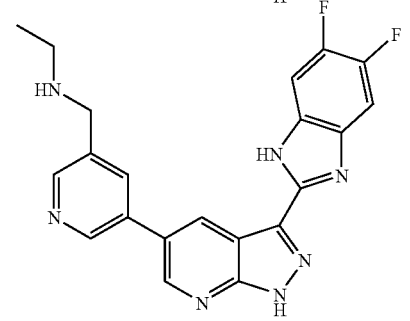
Cpd 107

-continued

Cpd 108

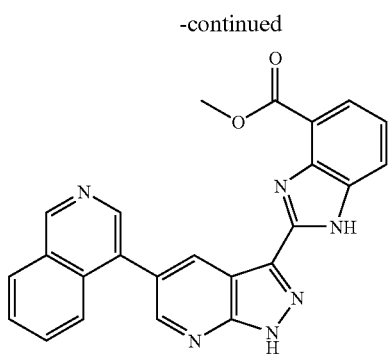

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl" means a saturated aliphatic branched or straight-chain hydrocarbon radical or linking group having from 1-8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" includes a "$C_{1-4}$alkyl" radical or linking group having from 1-4 carbon atoms wherein such radicals or linking groups are further referred to by methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule and further substituted on any atom when allowed by available valences.

The term "$C_{1-8}$alkoxy" means an alkyl radical or linking group having from 1-8 carbon atoms in a linear or branched arrangement, wherein the radical or linking group is attached through an oxygen linking atom, as in the formula: —O—$C_{1-8}$ alkyl. The term "$C_{1-8}$alkoxy" includes a "$C_{1-4}$alkoxy" radical or linking group having from 1-4 carbon atoms wherein such radicals or linking groups are further referred to by methoxy, ethoxy, propoxy, butoxy and the like. $C_{1-8}$alkoxy may also be represented by the formula —O—$C_{1-4}$ alkyl. An alkoxy radical may be attached to a core molecule and further substituted on any atom when allowed by available valences.

The term "$C_{3-12}$cycloalkyl" means a saturated or partially unsaturated monocyclic or polycyclic hydrocarbon ring system radical. Cycloalkyl ring systems include cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like. Examples include $C_{3-8}$cycloalkyl, $C_{5-6}$cycloalkyl, $C_{5-8}$cycloalkyl, $C_{3-10}$cycloalkyl, $C_{5-12}$cycloalkyl, $C_{9-13}$cycloalkyl, benzofused-$C_{3-12}$cycloalkyl and the like.

The term "benzofused-$C_{3-12}$cycloalkyl" means a $C_{3-12}$cycloalkyl ring system radical having a benzene ring fused on the ring system on adjacent carbons. A benzofused-$C_{3-12}$cycloalkyl radical may be attached to a core molecule and further substituted on any atom when allowed by available valences.

The term "Aryl" means an aromatic, unsaturated monocyclic or polycyclic cycloalkyl radical. Aryl ring systems include phenyl, naphthalenyl, azulenyl, anthracenyl and the like. An aryl radical may be attached to a core molecule and further substituted on any atom when allowed by available valences.

The term "Hetero," when used as a prefix for a ring system, refers to the replacement of at least one carbon atom member in the ring system with a heteroatom selected from N, O, S, S(O) or SO$_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S or O.

The term "Heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl, 5H-[1,3]dioxolo[4',5':4,5]benzo[1,2-d]imidazol-6-yl, 6H-1,3-dioxa-6,8-diaza-as-indacen-7-yl, 8H-1,3-dioxa-6,8-diaza-as-indacen-7-yl, 6,7-dihydro-1H-5,8-dioxa-1,3-diaza-cyclopenta[b]naphthalen-2-yl, 7,8-dihydro-1H-6,9-dioxa-1,3-diaza-cyclopenta[a]naphthalen-2-yl, 7,8-dihydro-3H-6,9-dioxa-1,3-diaza-cyclopenta[a]naphthalen-2-yl and the like. A heterocyclyl radical may be attached to a core molecule and further substituted on any atom when allowed by available valences.

The term "Heteroaryl" means an aromatic monocyclic or polycyclic unsaturated heterocyclyl radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, azaindolyl, isoindolyl, benzo[b]furyl, benzo[b]thienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. A heteroaryl radical may be attached to a core molecule and further substituted on any atom when allowed by available valences.

The term "halogen" includes fluoro, chloro, bromo, and iodo.

The term "substituted," refers to a core molecule on which one or more hydrogen atoms have been replaced with one or more functional radical moieties. The number that is allowed by available valences limits the amount of substituents. Substitution is hot limited to the core molecule, but may also occur on a substituent radical, whereby the substituent radical becomes a linking group.

"Dependently selected" means that one or more substituents are specified in an indicated combination of structure variables.

In general, IUPAC nomenclature-rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Furthermore, certain compounds of formula (I) may exist as tautomeric mixtures in equilibrium, represented by the tautomeric forms of formula (I) and formula (II) shown below. The present invention further encompasses all such kinase inhibiting compounds of formula (I) and formula (II) or forms thereof.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromide, hydrochloride, iodide, isothionate, lactate, malate, maleate, malonate, mandelate,

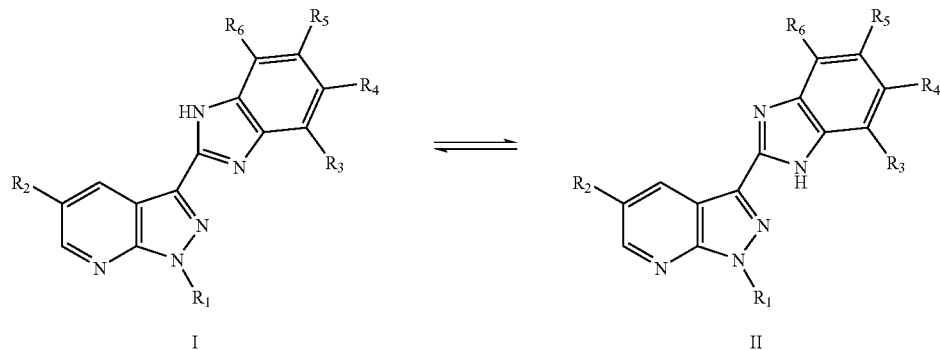

I  II

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

mesylate, nitrate, oleate, pamoate, palmitate, phosphate/diphosphate, saccharinate, salicylate, stearate, succinate, sulfate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, $3^{rd}$ Edition, John Wiley & Sons, 1999. The protecting groups may be removed at a convenient subsequent stage using methods known in the art.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An isolated form of a achiral mixture means those forms that are substantially free of one mirror image molecule. Such substantially pure forms include those wherein one mirror image is present in a range of less than 25% in the mixture, of less than 10%, of less than 5%, of less than 2% or less than 1%.

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms. Said forms are included in the scope of the invention. In addition, some of the compounds may form solvates with water (i.e., hydrates) or common organic solvents (e.g., organic esters such as ethanolate and the like). Said solvates are encompassed within the scope of this invention.

Methods of Use

The compounds of formula (I) are inhibitors of a protein kinase such as CDK-1, VEGF-R2, HER-2, c-Src, Lyn, Aurora-A, RET and the like, having an $IC_{50}$ (50% inhibition concentration) or an $EC_{50}$ (50% effective concentration) in a range of about 50 µM or less, of about 25 µM or less, of about 15 µM or less, of about 10 µM or less, of about 5 µM or less, of about 1 µM or less, of about 0.5 µM or less, of about 0.25 µM or less or of about 0.1 µM or less.

The present invention includes a compound of formula (I) and forms thereof as a protein kinase inhibitor, wherein the protein kinase is selected from CDK-1, VEGF-R2, HER-2, c-Src, Lyn, Aurora-A and RET.

The present invention includes a prodrug form of a compound of formula (I) and forms thereof as a protein kinase inhibitor.

The present invention includes a metabolite form of a compound of formula (I) and forms thereof as a protein kinase inhibitor.

The present invention includes an isolated form of a compound of formula (I) and forms thereof as a protein kinase inhibitor.

The present invention includes a compound of formula (I) or a form thereof, wherein the compound is labeled with a ligand for use as a marker, and wherein the ligand is a radioligand selected from deuterium, tritium and the like.

The present invention includes a first method for inhibiting unregulated protein kinase activity comprising contacting a protein kinase domain with one or more compounds of formula (I).

The first method also includes inhibiting unregulated serine-threonine and tyrosine protein kinase activity.

The first method also includes inhibiting increased or unregulated protein kinase expression or signaling leading to unregulated cell proliferation.

The first method further comprises inhibiting the unregulated expression of a protein kinase such as CDK-1, VEGF-R2, HER-2, c-Src, Lyn, Aurora-A, RET and the like.

The present invention includes a second method for use of one or more compounds of formula (I) as a therapeutic agent for treating, preventing or ameliorating a chronic or acute protein kinase mediated disease, disorder or condition in a subject in need thereof comprising administering to the subject an effective amount of one or more compounds of formula (I) or a pharmaceutical composition thereof.

The second method includes use as a therapeutic agent for inhibiting the effects of unregulated kinase activity in the subject.

The second method includes use as a therapeutic agent for treating, preventing or ameliorating a chronic or acute kinase mediated disease, disorder or condition associated with cellular proliferation or angiogenesis and the like in the subject.

The second method includes use as a therapeutic agent for treating, preventing or ameliorating a chronic or acute kinase mediated cancer in the subject.

The second method includes use as a therapeutic agent for suppressing a chronic or acute tumor associated with non-small-cell lung cancers, colon cancers, breast cancers and the like.

The second method also includes treating, preventing or ameliorating chronic unregulated cell proliferation whereby cancer remission is induced in the subject.

The second method includes treating, preventing or ameliorating a chronic or acute serine-threonine or tyrosine protein kinase mediated disease, disorder or condition in the subject.

The second method includes treating, preventing or ameliorating a chronic or acute CDK-1, VEGF-R2, HER-2, c-Src, Lyn, Aurora-A, RET and the like protein kinase mediated disease, disorder or condition in the subject.

The second method includes treating or preventing a chronic or acute kinase mediated disease, disorder or condition characterized by unregulated cell proliferation or metastatic cancer cell invasion and migration in the subject.

The second method includes administering to the subject an effective amount of a compound of formula (I) or composition thereof in the form of a medicament. Consequently, the invention encompasses the use of the compound of formula (I) as a medicament.

The present invention includes a third method for use of a compound of formula (I) as a marker, wherein the compound is labeled with a ligand such as a radioligand (selected from deuterium, tritium and the like).

The present invention includes a fourth method for treating or ameliorating chemotherapy induced alopecia in a subject in need thereof comprising topically administering to the subject an effective amount of a compound of formula (I) or pharmaceutical composition thereof.

An aspect of this method includes treating or ameliorating a melanoma cancer in a subject in need thereof comprising topically administering to the subject an effective amount of a compound of formula (I) or pharmaceutical composition thereof.

The present invention includes the use of a compound of formula (I) for the manufacture of a medicament for treating any of the diseases, disorders or conditions mentioned in any of the foregoing methods.

The term "chronic or acute kinase mediated disease, disorder or condition" as used herein, includes, and is not limited to diseases, disorders or conditions associated with unregulated kinase activity and conditions that accompany such activity.

The term "unregulated kinase activity" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The term "treating, preventing or ameliorating" includes, and is not limited to, facilitating the eradication of, inhibiting the progression of or promoting stasis of a malignancy.

The foregoing methods contemplate that the compounds of the present invention are therapeutically useful for treating, preventing or ameliorating kinase mediated diseases, disorders or conditions such as, without limitation, the kinase mediated disorder is selected from osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea, chemotherapy-induced alopecia), central nervous system diseases (such as neuronal apoptosis, Alzheimer's disease, Parkinson's disease or depression), mycotic infection, cancer (such as glioma cancers, epidermoid cancers, head and neck cancers, lung cancers, breast cancers, cervical cancers (such as cervical adenocarcinoma), colorectal cancers, colon cancers (such as colon carcinoma), prostate cancers, gastric cancers, esophageal cancers, papillocarcinomas, malignant melanomas, associated pathologies such as unregulated cell proliferation, tumor growth, tumor vascularization, angiopathy, angiogenesis, metastatic cancer cell invasion and migration, leukemias or lymphomas), occular diseases (such as macular degeneration, diseases of the cornea, glaucoma or neovascular glaucoma), viral infections (such as cytomegalovirus), heart disease (such as atherosclerosis, neointima formation or transplantation-induced vasculopathies (such as restenosis), lung or pulmonary diseases (such as allergic-asthma, lung fibrosis or complications resulting from chronic obstructive pulmonary disorder) or kidney or renal diseases (such as acute, subacute or chronic forms of glomerulonephritis or membranoproliferative glomerulonephritis, glomerulosclerosis, congenital multicystic renal dysplasia or kidney fibrosis).

An embodiment of the method of the present invention includes kinase mediated disorders selected from mycotic infection, cancer, tumor growth, tumor vascularization, angiopathy, angiogenesis, chemotherapy-induced alopecia or restenosis.

The term "administering," with respect to the methods of the present invention, refers to a means for treating, ameliorating or preventing a disease, disorder or condition as described herein with a compound specifically disclosed or a compound or prodrug thereof, which would obviously be included within the scope of the invention albeit not specifically disclosed for certain of the instant compounds.

Such methods include prophylactically or therapeutically administering an effective amount of one or more compounds of formula (I) or a composition or medicament thereof at different times during the course of a therapy or concurrently in a combination form. Prophylactic administration can occur prior to the manifestation of symptoms characteristic of a kinase associated disease or disorder such that the disease or disorder is prevented or, alternatively, delayed in its progression. The instant invention is therefore to be understood as embracing all such regimes of simultaneous or alternating treatment and the term "administering" is to be interpreted accordingly.

The term "prodrug" refers to a metabolic precursor of a compound of formula (I) or pharmaceutically acceptable form thereof. In general, a prodrug is a functional derivative of a compound which may be inactive when administered to a subject but is readily convertible in vivo into an active metabolite compound.

The term "active metabolite" refers to a metabolic product of a compound that is pharmaceutically acceptable and effective. Conventional procedures for the selection and preparation of suitable prodrug derivatives are described, for example, in "Design of Prodrugs", ed. H. Bundgaard, Elsevier, 1985.

The term "subject" as used herein, refers to a patient, such as an animal, preferably a mammal, most preferably a human, who has been the object of treatment, observation or experiment and is at risk of (or susceptible to) developing a disease or disorder or having a disease or disorder related to unregulated kinase activity.

The term "effective amount" refers to that amount of active compound or pharmaceutical agent that elicits a non-toxic biological or medicinal response (such as inhibiting activation of unregulated kinase activity) in a tissue system, animal or human, that is being sought by a researcher, veterinarian, medical doctor, or other clinician, which includes treating, preventing or ameliorating the symptoms of the disease, disorder or condition being treated.

The effective amount of a compound of formula (I) exemplified in such a method is from about 0.001 mg/kg/day to about 300 mg/kg/day.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating, preventing or ameliorating a kinase mediated disease, disorder or condition.

The term "pharmaceutically acceptable" refers to molecular entities and compositions that are of sufficient purity and quality for use in the formulation of a composition or medicament of the present invention and that, when appropriately administered to an animal or a human, do not produce a toxic, adverse, allergic or other untoward reaction. Since both human use (prescriptive and over-the-counter) and veterinary use are equally included within the scope of the present invention, a pharmaceutically acceptable formulation would include a composition or medicament for either human or veterinary use.

The methods of the present invention further include therapeutically administering an effective amount of one or more compounds of formula (I) or a composition or medicament thereof with one or more therapeutic agents at different times during the course of a therapy or concurrently in a combination therapy.

Such a combination therapy may advantageously facilitate the use of a reduced effective dose of the compound of formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agents" includes, and is not limited to, chemotherapeutic agents such as anti-angiogenic agents, anti-tumor agents, cytotoxic agents, inhibitors of cell proliferation and the like.

The term "combination therapy" refers to the use of one or more compounds of formula (I) or composition or medicament thereof advantageously administered in one or more cell anti-proliferation therapies including chemotherapy, radiation therapy, gene therapy or immunotherapy for treating, preventing or ameliorating a chronic or acute protein kinase mediated disease, disorder or condition. The combination therapy comprises 1. coadministration of a compound of formula (I) or pharmaceutical composition thereof and a chemotherapeutic agent for treating, preventing or ameliorating a chronic or acute protein kinase mediated disease, disorder or condition,
2. sequential administration of a compound of formula (I) or pharmaceutical composition thereof and a chemotherapeutic agent for treating, preventing or ameliorating a chronic or acute protein kinase mediated disease, disorder or condition,
3. administration of a pharmaceutical composition containing a compound of formula (I) or pharmaceutical composition thereof and a chemotherapeutic agent for treating, preventing or ameliorating a chronic or acute protein kinase mediated disease, disorder or condition, or,
4. simultaneous administration of a separate pharmaceutical composition containing a compound of formula (I) or pharmaceutical composition thereof and a separate pharmaceutical composition containing a chemotherapeutic agent for treating, preventing or ameliorating a chronic or acute protein kinase mediated disease, disorder or condition.

For example, an inhibitor compound of the present invention, acting as an anti-angiogenic agent can be administered in a dosing regimen with at least one other cytotoxic compound, such as a DNA alkylating agent.

Preferred anti-tumor agents are selected from the group consisting of cladribine (2-chloro-2'-deoxy-(beta)-D-adenosine), chlorambucil (4-(bis(2-chlorethyl)amino)benzenebutanoic acid), DTIC-Dome (5-(3,3-dimethyl-1-triazeno)-imidazole-4-carboxamide), platinum chemotherapeutics and nonplatinum chemotherapeutics.

Platinum containing anti-tumor agents include, and are not limited to, cisplatin (CDDP) (cis-dichlorodiamineplatinum).

Non-platinum containing anti-tumor agents include, and are not limited to, adriamycin (doxorubicin), aminopterin, bleomycin, camptothecin, caminomycin, combretastatin(s), cyclophosphamide, cytosine arabinoside, dactinomycin, daunomycin, epirubicin, etoposide (VP-16), 5-fluorouracil (5FU), herceptin actinomycin-D, methotrexate, mitomycin C, tamoxifen, taxol, taxotere, thiotepa, vinblastine, vincristine, vinorelbine and derivatives and prodrugs thereof.

Each anti-tumor agent is administered in an effective amount, which varies based on the agent used, the type of malignancy to be treated or ameliorated and other conditions according to methods well known in the art.

As will be understood by those of ordinary skill in the art, the appropriate doses of chemotherapeutic agents will be generally around those already employed in clinical therapies wherein the chemotherapeutics are administered alone or in combination with other chemotherapeutics.

By way of example only, agents such as cisplatin, and other DNA alkylating are used widely to treat cancer. The efficacious dose of cisplatin used in clinical applications is about 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic agents include adriamycin (doxorubicin), etoposide, verapamil or podophyllotoxin and the like and are widely used in clinical settings for tumor treatment.

These compounds are administered through bolus injections intravenously at doses ranging from about 25 to about 75 mg/m$^2$ at 21 day intervals (for adriamycin) or from about 35 to about 50 mg/m$^2$ (for etoposide) intravenously or at double the intravenous dose orally.

Agents that disrupt the synthesis and fidelity of polynucleotide precursors such as 5-fluorouracil (5-FU) are preferentially used to target tumors. Although quite toxic, 5-FU is commonly used via intravenous administration with doses ranging from about 3 to about 15 mg/kg/day.

The method of the present invention further includes a method for administering a compound of the present invention in combination with radiation therapy. As used herein, "radiation therapy" refers to a therapy comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

The method of the present invention further includes a method for administering a compound of the present invention in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, or with the so-called 'suicide genes'.

The method of the present invention further includes a method for administering a compound of the present invention in combination with an immunotherapy. As used herein, "immunotherapy" refers to a therapy targeted to a particular protein involved in tumor development via antibodies specific to such protein. For example, monoclonal antibodies against vascular endothelial growth factor have been used in treating cancers.

An example of the present invention includes a method for treating, preventing or ameliorating a chronic or acute protein kinase mediated disease, disorder or condition, particularly a tumor, in a subject in need thereof comprising administering to the subject an effective amount of a compound of formula (I) or pharmaceutical composition thereof conjugated to a targeting agent and delivered or "seeded" directly or indirectly into tissues with unregulated kinase activity.

The term "delivered or "seeded" directly or indirectly into tissues" includes conjugating a compound of formula (I) to a targeting agent which then directs the conjugate to its intended site of action (i.e., to vascular endothelial cells or to tumor cells). The term "targeting agent" includes the use of both antibody and non-antibody agents. Because of the specific interaction between the targeting agent and its corresponding binding partner, a compound of this invention can be administered with high local concentrations at or near a target site and thus treats the disorder at the target site more effectively.

An antibody targeting agent includes antibodies or antigen-binding fragments thereof, that bind to a targetable or accessible component of a tumor cell, tumor vasculature or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies or antigen-binding fragments thereof that bind to insoluble intracellular antigen(s) present in cells that may be induced to be permeable or in cell ghosts of substantially all tumor or normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No. 5,855,866 (Thorpe, et al). Methods are known to those skilled in the art to produce and isolate antibodies to be used as targeting agents against tumors (U.S. Pat. No. 5,855,866 (Thorpe); and, U.S. Pat. No. 6,342,219 (Thorpe)).

Non-antibody targeting agents include growth factors, such as PDGF, VEGF and FGF; peptides containing the tripeptide R-G-D, that bind specifically to the tumor vasculature and other targeting components such as annexins and related ligands. In addition, a variety of other organic molecules can also be used as targeting agents for tumors, examples are hyaluronan oligosaccharides which specifically recognize Hyaluronan-binding protein, a cell surface protein expressed during tumor cell and endothelial cell migration and during capillary-like tubule formation (U.S. Pat. No. 5,902,795 (Toole, et al.)) and polyanionic compounds, particularly polysulphated or polysulphonated compounds such as N- and O-sulfated polyanionic polysaccharides, polystyrene sulfonate and other polyanionic compounds (as described in U.S. Pat. No. 5,762,918 (Thorpe) which selectively bind to vascular endothelial cells.

Techniques for conjugating therapeutic moiety to antibodies are well known (Amon, et al., Monoclonal Antibodies For Immunotargeting Of Drugs In Cancer Therapy, *Monoclonal Antibodies And Cancer Therapy*, Reisfeld, et al. (eds.), pp. 243-56 (Alan R. Liss, Inc. 1985); Hellstrom, et al., Antibodies For Drug Delivery, *Controlled Drug Delivery* (*2nd Ed.*), Robinson, et al. (eds.), pp. 623-53 (Marcel Dekker, Inc. 1987); Thorpe, Antibody Carriers Of Cytotoxic Agents In Cancer Therapy: A Review, *Monoclonal Antibodies '84: Biological And Clinical Applications*, Pinchera, et al. (eds.), pp. 475-506 (1985). Similar techniques can also be applied to attach compounds of the invention to non-antibody targeting agents. Those skilled in the art will know or be able to determine methods of forming conjugates with non-antibody targeting agents, such as oligopeptides, polysaccharides or other polyanionic compounds.

Although any linking moiety that is reasonably stable in blood can be used to link the compound of the invention to the targeting agent, those with biologically-releasable bonds and/or selectively cleavable spacers or linkers are preferred. "Biologically-releasable bonds" and "selectively cleavable spacers or linkers" refers to those linking moieties which have reasonable stability in the circulation and are releasable, cleavable or hydrolyzable only or preferentially under certain conditions, (i.e., within a certain environment or in contact with a particular agent). Such bonds include, for example, disulfide and trisulfide bonds and acid-labile bonds (as described in U.S. Pat. Nos. 5,474,765 and 5,762,918) and enzyme-sensitive bonds, including peptide bonds, esters, amides, phosphodiesters and glycosides (as described in U.S. Pat. Nos. 5,474,765 and 5,762,918). Such selective-release design features facilitate sustained release of the compounds from the conjugates at the intended target site.

The effective amount of a compound of the invention conjugated to a targeting agent depends on the individual, the disease type, the disease state, the method of administration and other clinical variables. The effective amount is readily determinable using data from an animal model. Experimental animals bearing solid tumors are frequently used to optimize appropriate therapeutically effective amount prior to translating to a clinical environment. Such models are known to be very reliable in predicting effective anti-cancer strategies. For example, mice bearing solid tumors are widely used in preclinical testing to determine working ranges of therapeutic agents that give beneficial anti-tumor effects with minimal toxicity.

The present invention further provides a pharmaceutical composition that comprises an effective amount of the compound of the invention conjugated to a targeting agent and a pharmaceutically acceptable carrier. When proteins such as antibodies or growth factors, or polysaccharides are used as targeting agents, they are preferably administered in the form of injectable compositions. The injectable antibody solution will, be administered into a vein, artery or into the spinal fluid over the course of from about 2 minutes to about 45 minutes, preferably from about 10 to about 20 minutes. In certain cases, intradermal and intracavitary administration are advantageous for tumors restricted to areas close to particular regions of the skin and/or to particular body cavities. In addition, intrathecal administrations may be used for tumors located in the brain.

Another aspect of the present invention includes a method for treating or disorders related to unregulated kinase activity (in particular, restenosis, intimal hyperplasia or inflammation in vessel walls) in a subject in need thereof comprising administering to the subject by controlled delivery an effective amount of a compound of formula (I) or pharmaceutical composition thereof coated onto a intraluminal medical device (in particular, a balloon-catheter or stent). Such devices are useful to prevent the occurrence of restenosis by inhibiting upregulated kinase activity and thus preventing hyperproliferation of the endothelium.

The term "intraluminal medical device" refers to any delivery device, such as intravascular drug delivery catheters, wires, pharmacological stents and endoluminal paving. It is preferred that the delivery device comprises a stent that includes a coating or sheath which elutes or releases the compounds. The term "controlled delivery" refers to the release of active ingredient in a site-directed and time dependent manner. Alternatively, the delivery system for such a device may comprise a local infusion catheter that delivers the compound at a variably controlled rate.

The term "stent" refers to any device capable of being delivered by a catheter. A stent is routinely used to prevent vascular closure due to physical anomalies such as unwanted inward growth of vascular tissue due to surgical trauma. A stent often has a tubular, expanding lattice-type structure appropriate to be left inside the lumen of a duct to relieve an obstruction. The stent, has a lumen wall-contacting surface and a lumen-exposed surface. The lumen-wall contacting surface is the outside surface of the tube and the lumen-exposed surface is the inner surface of the tube. The stent material may be a polymeric, metallic or a combination polymeric-metallic material and can be optionally biodegradable.

The compounds of the present invention can also be administered in the form of liposome delivery systems, such as small unilamellar vesicles, large unilamellar vesicles and muluilamellar vesicles. Liposomes containing delivery systems as well known in the art are formed from a variety of phospholipids, such as cholesterol, stearylamine of phosphatidylcholines.

Pharmaceutical Compositions

An example of the present invention includes a pharmaceutical composition comprising an admixture of one or more compounds of formula (I) and/or one or more pharmaceutically acceptable forms thereof and one or more pharmaceutically acceptable excipients.

The pharmaceutically acceptable forms for a compound of formula (I) include a pharmaceutically acceptable salt, ester, prodrug or active metabolite of a compound of formula (I).

Pharmaceutical compositions according to the invention may, alternatively or in addition to a compound of formula I, comprise as an active ingredient a pharmaceutically acceptable salt of a compound of formula I or a prodrug or pharmaceutically active metabolite of such a compound or salt.

The present invention further includes the use of a process for making the composition or medicament comprising mixing one or more of the instant compounds and an optional pharmaceutically acceptable carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Furthermore, compositions or medicaments can be administered in intranasal form via topical use of suitable intranasal vehicles, or via transdermal routes, using, e.g., those forms of transdermal skin patches well known to those of ordinary skill in that art.

Advantageously, a compound of formula (I) may be administered in a single daily dose, or the total daily dosage may be administered in divided doses of two, three or four times daily. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the composition or medicament contains an effective amount of the active ingredient necessary to be therapeutically or prophylactically effective as described above.

The composition or medicament may contain from about 0.001 mg to about 5000 mg (preferably, from about 0.001 to about 500 mg) of the active compound or prodrug thereof and may be constituted into any form suitable for the mode of administration selected for a subject in need. A contemplated effective amount may range from about 0.001 mg to about 300 mg/kg of body weight per day. Preferably, the range is from about 0.003 to about 100 mg/kg of body weight per day. Most preferably, the range is from about 0.005 to about 15 mg/kg of body weight per day. The composition or medicament may be administered according to a dosage regimen of from about 1 to about 5 times per day.

For oral administration, the composition or medicament is preferably in the form of a tablet or capsule containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated.

Optimal dosages will vary depending on factors associated with the particular patient being treated (e.g., age, weight, diet and time of administration), the severity of the condition being treated, the compound being employed, the amount of compound dosed to achieve a non-toxic, therapeutic effect, the mode of administration and the strength of the preparation. The use of either daily administration or post-periodic dosing may be employed.

A representative compound of formula (I) or a form thereof for use in the therapeutic methods and pharmaceutical compositions, medicines or medicaments described herein includes a compound selected from the group consisting of:
4-[3-(1H-benzoimidazol-2-yl)-1H-pyrazolo[3,4-b]pyridin-5-yl]-isoquinoline,
4-[3-(4-methyl-1H-benzoimidazol-2-yl)-1H-pyrazolo[3,4-b]pyridin-5-yl]-isoquinoline,
[2-(5-isoquinolin-4-yl-1H-pyrazolo[3,4-b]pyridin-3-yl)-1H-benzoimidazol-4-yl]-methanol,
4-[3-(4-methoxymethyl-1H-benzoimidazol-2-yl)-1H-pyrazolo[3,4-b]pyridin-5-yl]-isoquinoline,
diethyl-[2-(5-isoquinolin-4-yl-1H-pyrazolo[3,4-b]pyridin-3-yl)-1H-benzoimidazol-4-ylmethyl]-amine,
[2-(5-bromo-1H-pyrazolo[3,4-b]pyridin-3-yl)-1H-benzoimidazol-4-ylmethyl]-diethyl-amine,
4-[3-(4-pyrrolidin-1-ylmethyl-1H-benzoimidazol-2-yl)-1H-pyrazolo[3,4-b]pyridin-5-yl]-isoquinoline,
4-[3-(4-piperidin-1-ylmethyl-1H-benzoimidazol-2-yl)-1H-pyrazolo[3,4-b]pyridin-5-yl]-isoquinoline,
4-[3-(4-morpholin-4-ylmethyl-1H-benzoimidazol-2-yl)-1H-pyrazolo[3,4-b]pyridin-5-yl]-isoquinoline,
4-{3-[4-(4-ethyl-piperazin-1-ylmethyl)-1H-benzoimidazol-2-yl]-1H-pyrazolo[3,4-b]pyridin-5-yl}-isoquinoline,
4-[3-(4-imidazol-1-ylmethyl-1H-benzoimidazol-2-yl)-1H-pyrazolo[3,4-b]pyridin-5-yl]-isoquinoline,
isopropyl-[2-(5-isoquinolin-4-yl-1H-pyrazolo[3,4-b]pyridin-3-yl)-1H-benzoimidazol-4-ylmethyl]-amine,
4-{3-[4-(2-methoxy-ethoxymethyl)-1H-benzoimidazol-2-yl]-1H-pyrazolo[3,4-b]pyridin-5-yl}-isoquinoline,
4-{3-[4-(2-morpholin-4-yl-ethoxymethyl)-1H-benzoimidazol-2-yl]-1H-pyrazolo[3,4-b]pyridin-5-yl}-isoquinoline,
4-{3-[4-(2-ethoxy-ethoxymethyl)-1H-benzoimidazol-2-yl]-1H-pyrazolo[3,4-b]pyridin-5-yl}-isoquinoline,
2-(5-isoquinolin-4-yl-1H-pyrazolo[3,4-b]pyridin-3-yl)-1H-benzoimidazole-4-carboxylic acid isopropylamide,
2-(5-isoquinolin-4-yl-1H-pyrazolo[3,4-b]pyridin-3-yl)-1H-benzoimidazole-4-carboxylic acid diethylamide,
2-(5-isoquinolin-4-yl-1H-pyrazolo[3,4-b]pyridin-3-yl)-1H-benzoimidazole-4-carboxylic acid tert-butylamide,
[2-(5-isoquinolin-4-yl-1H-pyrazolo[3,4-b]pyridin-3-yl)-1H-benzoimidazole-4-yl]-morpholin-4-yl-methanone,
2-(5-isoquinolin-4-yl-1H-pyrazolo[3,4-b]pyridin-3-yl)-1H-benzoimidazole-4-carboxylic acid cyclopentylamide,
2-(5-isoquinolin-4-yl-1H-pyrazolo[3,4-b]pyridin-3-yl)-1H-benzoimidazole-4-carboxylic acid (4-hydroxy-cyclohexyl)-amide,
4-{3-[5-(4-methyl-piperazin-1-yl)-1H-benzoimidazol-2-yl]-1H-pyrazolo[3,4-b]pyridin-5-yl}-isoquinoline,
4-[3-(4-isopropoxymethyl-1H-benzoimidazol-2-yl)-1H-pyrazolo[3,4-b]pyridin-5-yl]-isoquinoline,
3-[3-(4-methoxymethyl-1H-benzoimidazol-2-yl)-1H-pyrazolo[3,4-b]pyridin-5-yl]-quinoline,
3-(4-methoxymethyl-1H-benzoimidazol-2-yl)-5-pyridin-3-yl-1H-pyrazolo[3,4-b]pyridine,
4-[3-(4-methoxymethyl-1H-benzoimidazol-2-yl)-1H-pyrazolo[3,4-b]pyridin-5-yl]benzenesulfonamide,
3-(4-methoxymethyl-1H-benzoimidazol-2-yl)-5-(1H-pyrrolo[2,3-b]pyridin-3-yl)-1H-pyrazolo[3,4-b]pyridine,
5-(1-benzenesulfonyl-1H-indol-3-yl)-3-(4-methoxymethyl-1H-benzoimidazol-2-yl)-1H-pyrazolo[3,4-b]pyridine,
5-(1H-indol-3-yl)-3-(4-methoxymethyl-1H-benzoimidazol-2-yl)-1H-pyrazolo[3,4-b]pyridine,
3-(4-methoxymethyl-1H-benzoimidazol-2-yl)-5-(1H-pyrrol-3-yl)-1H-pyrazolo[3,4-b]pyridine,
5-[3-(4-methoxymethyl-1H-benzoimidazol-2-yl)-1H-pyrazolo[3,4-b]pyridin-5-yl]-pyridine-3-carbaldehyde,
ethyl-{5-[3-(4-methoxymethyl-1H-benzoimidazol-2-yl)-1H-pyrazolo[3,4-b]pyridin-5-yl]-pyridin-3-ylmethyl}-amine,
isopropyl-{5-[3-(4-methoxymethyl-1H-benzoimidazol-2-yl)-1H-pyrazolo[3,4-b]pyridin-5-yl]-pyridin-3-ylmethyl}-amine,
{5-[3-(4-methoxymethyl-1H-benzoimidazol-2-yl)-1H-pyrazolo[3,4-b]pyridin-5-yl]-pyridin-3-yl}-methanol,
2-(5-isoquinolin-4-yl-1H-pyrazolo[3,4-b]pyridin-3-yl)-1H-benzoimidazole-4-carboxylic acid (4-amino-cyclohexyl)-amide,
2-(5-isoquinolin-4-yl-1H-pyrazolo[3,4-b]pyridin-3-yl)-1H-benzoimidazole-4-carboxylic acid o-tolylamide,
2-(5-isoquinolin-4-yl-1H-pyrazolo[3,4-b]pyridin-3-yl)-1H-benzoimidazole-4-carboxylic acid cyclopropylamide,
2-(5-isoquinolin-4-yl-1H-pyrazolo[3,4-b]pyridin-3-yl)-1H-benzoimidazole-4-carboxylic acid pyridin-3-ylamide,
2-(5-isoquinolin-4-yl-1H-pyrazolo[3,4-b]pyridin-3-yl)-1H-benzoimidazole-4-carboxylic acid (4-dimethylamino-phenyl)-amide,
2-(5-isoquinolin-4-yl-1H-pyrazolo[3,4-b]pyridin-3-yl)-1H-benzoimidazole-4-carboxylic acid (4-diethylamino-2-methyl-phenyl)-amide,
4-[3-(5-morpholin-4-yl-1H-benzoimidazol-2-yl)-1H-pyrazolo[3,4-b]pyridin-5-yl]-isoquinoline,
diethyl-[2-(5-pyridin-3-yl-1H-pyrazolo[3,4-b]pyridin-3-yl)-1H-benzoimidazol-4-ylmethyl]-amine,
3-(4-methoxymethyl-1H-benzoimidazol-2-yl)-5-(5-morpholin-4-ylmethyl-pyridin-3-yl)-1H-pyrazolo[3,4-b]pyridine,
{5-[3-(4-methoxymethyl-1H-benzoimidazol-2-yl)-1H-pyrazolo[3,4-b]pyridin-5-yl]-pyridin-3-ylmethyl}-methyl-amine,
3-(4-methoxymethyl-1H-benzoimidazol-2-yl)-5-(4-methyl-pyridin-3-yl)-1H-pyrazolo[3,4-b]pyridine,
isopropyl-{5-[3-(4-methoxymethyl-1H-benzoimidazol-2-yl)-1H-pyrazolo[3,4-b]pyridin-5-yl]-4-methyl-pyridin-3-ylmethyl}-amine,
ethyl-{5-[3-(4-methoxymethyl-1H-benzoimidazol-2-yl)-1H-pyrazolo[3,4-b]pyridin-5-yl]-4-methyl-pyridin-3-ylmethyl}-amine,
3-(4-methoxymethyl-1H-benzoimidazol-2-yl)-5-(4-methyl-5-morpholin-4-ylmethyl-pyridin-3-yl)-1H-pyrazolo[3,4-b]pyridine,
{5-[3-(4-methoxymethyl-1H-benzoimidazol-2-yl)-1H-pyrazolo[3,4-b]pyridin-5-yl]-4-methyl-pyridin-3-ylmethyl}-dimethyl-amine,
{5-[3-(4-methoxymethyl-1H-benzoimidazol-2-yl)-1H-pyrazolo[3,4-b]pyridin-5-yl]-4-methyl-pyridin-3-ylmethyl}-methyl-amine,
3-(4-methoxymethyl-1H-benzoimidazol-2-yl)-5-(6-methoxy-pyridin-3-yl)-1H-pyrazolo[3,4-b]pyridine,
3-(4-methoxymethyl-1H-benzoimidazol-2-yl)-5-(5-methoxy-pyridin-3-yl)-1H-pyrazolo[3,4-b]pyridine,
3-(4-methoxymethyl-1H-benzoimidazol-2-yl)-5-pyridin-4-yl-1H-pyrazolo[3,4-b]pyridine,
3-(4-methoxymethyl-1H-benzoimidazol-2-yl)-5-(6-morpholin-4-yl-pyridin-3-yl)-1H-pyrazolo[3,4-b]pyridine,
4-{5-[3-(4-methoxymethyl-1H-benzoimidazol-2-yl)-1H-pyrazolo[3,4-b]pyridin-5-yl]-pyridin-2-yl}-piperazine-1-carboxylic acid tert-butyl ester,
3-(4-methoxymethyl-1H-benzoimidazol-2-yl)-5-(6-piperazin-1-yl-pyridin-3-yl)-1H-pyrazolo[3,4-b]pyridine,
5-[3-(4-methoxymethyl-1H-benzoimidazol-2-yl)-1H-pyrazolo[3,4-b]pyridin-5-yl]-nicotinic acid ethyl ester,
5-(6-fluoro-pyridin-3-yl)-3-(4-methoxymethyl-1H-benzoimidazol-2-yl)-1H-pyrazolo[3,4-b]pyridine, 5-[3-(4-methoxymethyl-1H-benzoimidazol-2-yl)-1H-pyrazolo[3,4-b]pyridin-5-yl]-pyridine-3-carbaldehyde oxime,
C-{5-[3-(4-methoxymethyl-1H-benzoimidazol-2-yl)-1H-pyrazolo[3,4-b]pyridin-5-yl]-pyridin-3-yl}-methylamine,
(2-methoxy-ethyl)-{5-[3-(4-methoxymethyl-1H-benzoimidazol-2-yl)-1H-pyrazolo[3,4-b]pyridin-5-yl]-pyridin-3-ylmethyl}-amine,
N'-{5-[3-(4-methoxymethyl-1H-benzoimidazol-2-yl)-1H-pyrazolo[3,4-b]pyridin-5-yl]-pyridin-3-ylmethyl}-N,N-dimethyl-ethane-1,2-diamine,
2-({5-[3-(4-methoxymethyl-1H-benzoimidazol-2-yl)-1H-pyrazolo[3,4-b]pyridin-5-yl]-pyridin-3-ylmethyl}-amino)-ethanol,
{5-[3-(4-methoxymethyl-1H-benzoimidazol-2-yl)-1H-pyrazolo[3,4-b]pyridin-5-yl]-pyridin-3-ylmethyl}-propyl-amine,
butyl-{5-[3-(4-methoxymethyl-1H-benzoimidazol-2-yl)-1H-pyrazolo[3,4-b]pyridin-5-yl]-pyridin-3-ylmethyl}-amine,
{5-[3-(4-methoxymethyl-1H-benzoimidazol-2-yl)-1H-pyrazolo[3,4-b]pyridin-5-yl]-pyridin-3-ylmethyl}-(1-methyl-piperidin-4-yl)-amine,
methyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
ethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
isopropyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-(5-morpholin-4-ylmethyl-pyridin-3-yl)-1H-pyrazolo[3,4-b]pyridine,
(5-{3-[5-(4-methyl-piperazin-1-yl)-1H-benzoimidazol-2-yl]-1H-pyrazolo[3,4-b]pyridin-5-yl}-pyridin-3-ylmethyl)-propyl-amine,
(2-methoxy-ethyl)-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-(5-pyrrolidin-1-ylmethyl-pyridin-3-yl)-1H-pyrazolo[3,4-b]pyridine,
dimethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-pyridin-3-yl-1H-pyrazolo[3,4-b]pyridine,
3-(6-methoxy-1H-benzoimidazol-2-yl)-5-pyridin-3-yl-1H-pyrazolo[3,4-b]pyridine,
2-(5-pyridin-3-yl-1H-pyrazolo[3,4-b]pyridin-3-yl)-3H-benzoimidazole-5-carboxylic acid methyl ester,
3-(6-fluoro-1H-benzoimidazol-2-yl)-5-pyridin-3-yl-1H-pyrazolo[3,4-b]pyridine,
5-pyridin-3-yl-3-(5-trifluoromethoxy-1H-benzoimidazol-2-yl)-1H-pyrazolo[3,4-b]pyridine,
2-[2-(5-pyridin-3-yl-1H-pyrazolo[3,4-b]pyridine-3-yl)-1H-benzoimidazol-5-yloxy]-ethanol,
methyl-{5-[3-(5-trifluoromethoxy-1H-benzoimidazol-2-yl)-1H-pyrazolo[3,4-b]pyridin-5-yl]-pyridin-3-ylmethyl}-amine,
{5-[3-(6-methoxy-1H-benzoimidazol-2-yl)-1H-pyrazolo[3,4-b]pyridin-5-yl]-pyridin-3-ylmethyl}-methyl-amine,
2,2-difluoro-6-(5-pyridin-3-yl-1H-pyrazolo[3,4-b]pyridin-3-yl)-5H-[1,3]dioxolo[4',5':4,5]benzo[1,2-d]imidazole,
6-(5-pyridin-3-yl-1H-pyrazolo[3,4-b]pyridin-3-yl)-5H-[1,3]dioxolo[4',5':4,5]benzo[1,2-d]imidazole,
{5-[3-(2,2-difluoro-5H-[1,3]dioxolo[4',5':4,5]benzo[1,2-d]imidazol-6-yl)-1H-pyrazolo[3,4-b]pyridin-5-yl]-pyridin-3-ylmethyl}-methyl-amine,
ethyl-{5-[3-(5-methoxy-1H-benzoimidazol-2-yl)-1H-pyrazolo[3,4-b]pyridin-5-yl]-pyridin-3-ylmethyl}-amine,
isopropyl-{5-[3-(5-methoxy-1H-benzoimidazol-2-yl)-1H-pyrazolo[3,4-b]pyridin-5-yl]-pyridin-3-ylmethyl}-amine,
{5-[3-(5-methoxy-1H-benzoimidazol-2-yl)-1H-pyrazolo[3,4-b]pyridin-5-yl]-pyridin-3-ylmethyl}-propyl-amine,
butyl-{5-[3-(5-methoxy-1H-benzoimidazol-2-yl)-1H-pyrazolo[3,4-b]pyridin-5-yl]-pyridin-3-ylmethyl}-amine,
2-[5-(5-methylaminomethyl-pyridin-3-yl)-1H-pyrazolo[3,4-b]pyridin-3-yl]-3H-benzoimidazole-5-carbonitrile,
ethyl-{5-[3-(6-fluoro-1H-benzoimidazol-2-yl)-1H-pyrazolo[3,4-b]pyridin-5-yl]-pyridin-3-ylmethyl}-amine, and
{5-[3-(5,6-difluoro-1H-benzoimidazol-2-yl)-1H-pyrazolo[3,4-b]pyridin-5-yl]-pyridin-3-methyl}-ethyl-amine.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. Except where indicated, starting materials and intermediates used in the schemes and examples are prepared by known methodologies well within the ordinary skill of persons versed in the art. No attempt has been made to optimize the yields obtained in any of the example reactions. One skilled in the art would also know how to increase such yields through routine variations in materials, solvents, reagents, reaction conditions and the like. All commercially available chemicals were used without further purification. Particular equipment components used in the examples such as reaction vessels and the like are also commercially available.

The terms used in describing the invention are commonly used and known to those skilled in the art. When used herein, the following abbreviations have the indicated meanings:

(BOC)$_2$O di-tert-butyl dicarbonate
Boc t-butoxycarbonyl
Cpd compound
DCM dichloromethane
DIPEA diisopropylethylamine
DMAP 4-(dimethylamino)pyridine
DMF N,N-dimethylformamide
DMSO dimethyl sulfoxide
EtOAc ethyl acetate
HATU O-(7-azabenzotriazol-1-yl)-N,N,N',N'-tetramethyluronium hexafluorophosphate
HOAc acetic acid
hr(s)/min(s) hour(s)/min(s)
MeOH methanol
NaBH$_3$CN sodium cyanoborohydride
NaBH$_4$ sodium borohydride
NaHCO$_3$ sodium bicarbonate
NH$_4$Cl ammonium chloride
NH$_4$OH ammonium hydroxide
NaH sodium hydride
NaOAc sodium acetate
NaOH sodium hydroxide
MgSO$_4$ magnesium sulfate
Pd(PPh$_3$)$_4$ tetrakis(triphenylphosphine)palladium(0)

Pd(PPh₃)₂Cl₂ dichlorobis(triphenylphosphine)palladium(II)
PSI pounds per square inch
RT/rt/r.t. room temperature
sat'd saturated
SEM (trimethylsilyl)ethoxymethyl
TBAF tetrabutylammonium fluoride
TEA or Et₃N triethylamine
TFA trifluoroacetic acid
THF tetrahydrofuran General Synthetic Methods Representative compounds of the present invention can be synthesized in accordance with the general synthetic methods described below, which are illustrated more particularly in the schemes that follow. The invention should not be construed as being limited by the chemical reactions and conditions expressed.

Scheme A

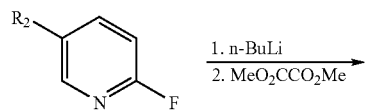

A1

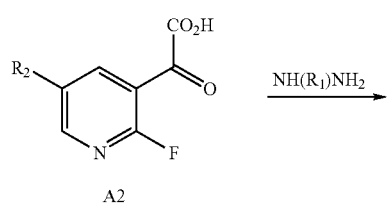

A2

A solution of a commercially available Compound A1 (in a solvent such as anhydrous THF and the like; wherein R₂ is appropriately selected from the definition given above) is reacted with a reagent (such as dimethyl oxylate and the like) to give Compound A2.

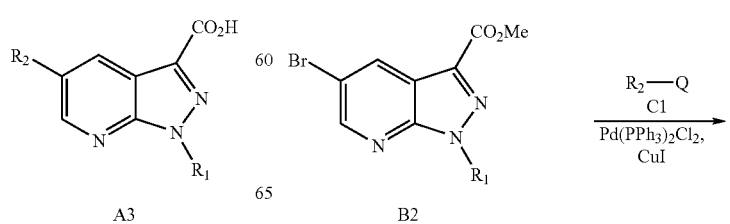

A3

Compound A2 is then reacted with an R₁ substituted hydrazine to give Compound A3.

Scheme B

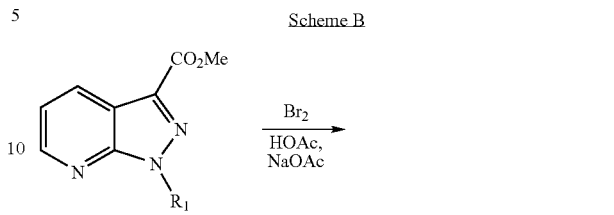

B1

B2

Alternatively to Scheme A, a mixture of a commercially available Compound B1, sodium acetate and bromine in glacial acetic is reacted to give Compound B2.

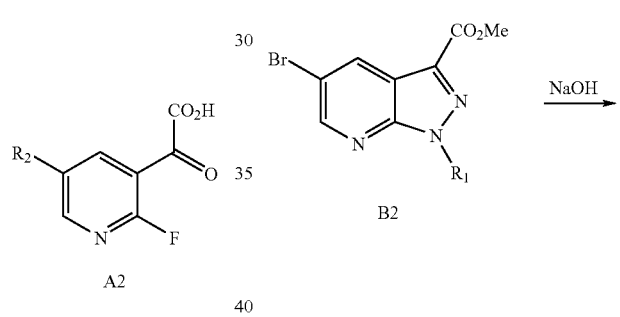

B2

B3

A solution of Compound B2 (in a solvent such as MeOH and the like) is hydrolyzed with a suitable acid or a base (such as aqueous NaOH and the like), then acidified (with an acid such as hydrochloric acid and the like) to give Compound B3.

Scheme C

B2

-continued

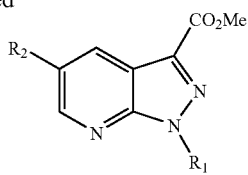

C2

Using a Stille coupling reaction, Compound B2 is coupled with Compound C1 (wherein $R_2$ is other than halogen and Q is an organometallic agent such as an alkylated tin and the like) in the presence of a suitable catalyst (such as dichlorobis (triphenylphosphine) palladium(II) of the formula: $Pd(PPh_3)Cl_2$ and the like) and copper (I) iodide to give Compound C2.

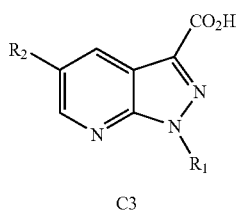

C2

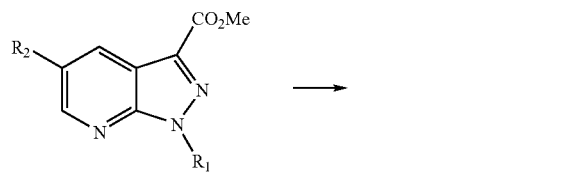

C3

Using the procedure of Scheme B, Compound C2 is carried forward in place of Compound B2 to give Compound C3.

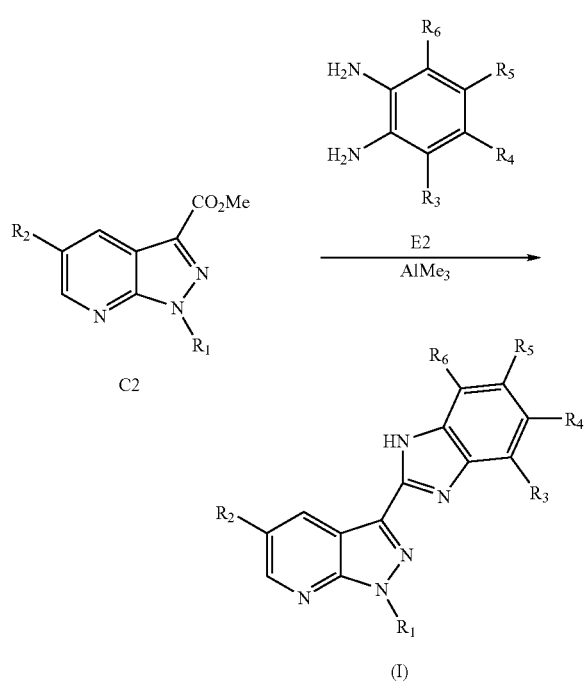

Scheme C1

(I)

Alternatively, a solution of Compound C2 (in a solvent such as toluene and the like) is reacted with a Compound E2 in the presence of a reagent (such as trimethyl aluminum and the like in a solvent such as toluene and the like) to provide a compound of formula (I) directly.

Scheme D

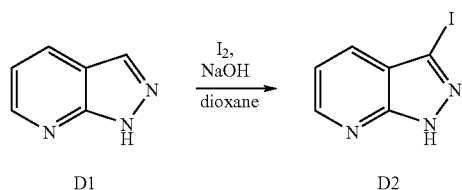

D1            D2

A solution of a commercially available Compound D1 (in a solvent such as 1,4-dioxane and the like) is reacted with an iodine solution (in a mixture with aqueous NaOH and the like) to afford Compound D2.

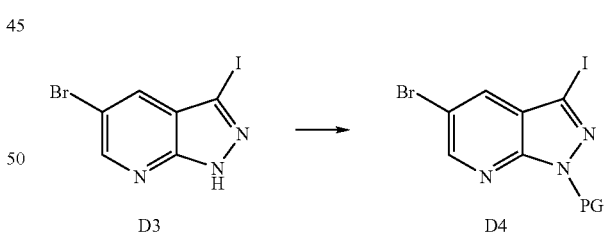

D2            D3

A solution of Compound D2 (in a solvent such as acetic acid and the like) is reacted with a halogenating agent (such as bromine and the like) to provide Compound D3.

D3            D4

Compound D3 is reacted with one equivalent of a protecting group in solution to give Compound D4 (wherein PG is the protecting group).

When the protecting group is Boc and the like, a solution of $Boc_2O$ (Boc anhydride) in DMAP and TEA (in a solvent such as methylene chloride and the like) is reacted with Compound D3 to give Compound D4.

When the protecting group is (trimethylsilyl)ethoxymethyl (SEM) and the like, a solution of SEM-chloride (in solution with a base such as sodium hydride and the like) is reacted with Compound D3 to give Compound D4.

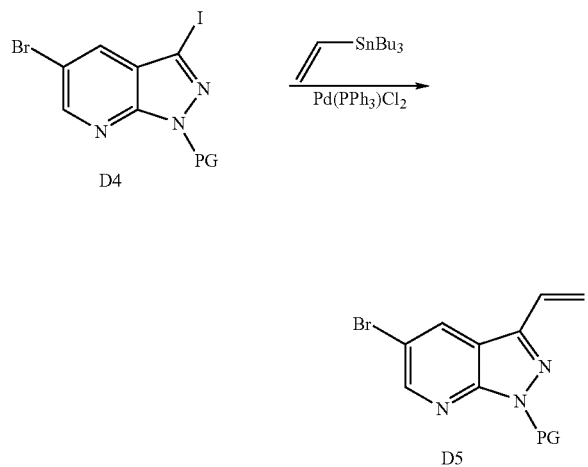

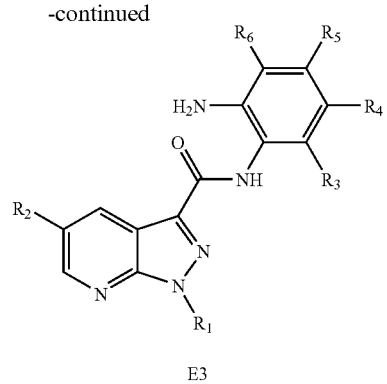

A solution of Compound D4 (in a solvent such as THF) is reacted overnight with tributyl-vinyl-stannane (also referred to as tributyl vinyl tin) in the presence of a suitable catalyst (such as dichlorobis(triphenylphosphine) palladium(II) of the formula: Pd(PPh₃)Cl₂ and the like) to afford Compound D5.

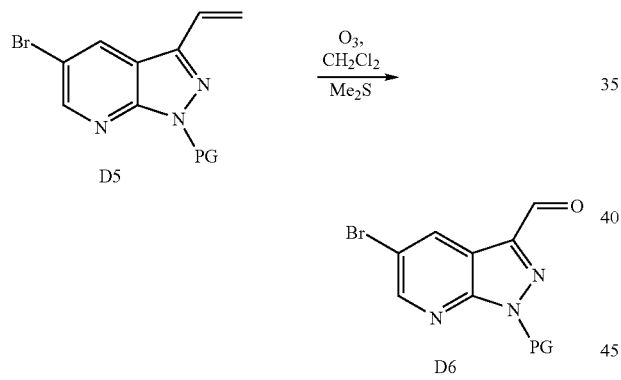

A solution of Compound D5 (in a solvent such as CH₂Cl₂ and the like) is reacted with an oxidizing agent (such as ozone and the like) to provide a Compound D6.

Scheme E

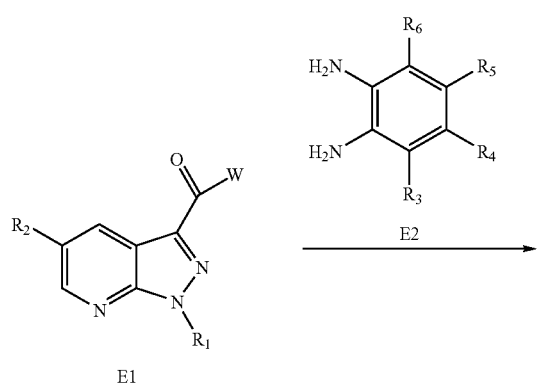

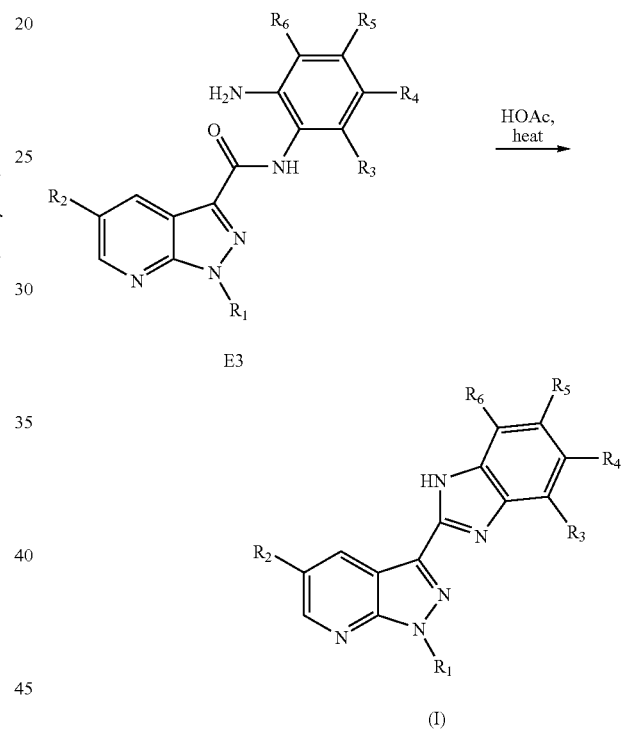

Compound E1 is reacted with Compound E2. The mixture is evaporated in vacuo and purified (via chromatography on silica gel with a suitable solvent) to give Compound E3.

A solution of Compound E3 (in an acid such as glacial acetic acid and the like) is reacted to provide a compound of formula (I).

Scheme E1

When W is OH (as in Compound A3, Compound B3 and Compound C3), Compound E1 is reacted with Compound E2 using a coupling reagent (such as HATU or DIPEA in DMF and the like) to give Compound E3.

Scheme E2

When W is $C_{1-4}$alkoxy (as in Compound B2 in Scheme C1), a solution of Compound E1 (in a solvent such as toluene and the like) is condensed with Compound E2 using a reagent (such as trimethyl aluminum, phosphorus pentoxide, triflic anhydride and the like) to provide a compound of formula (I) directly.

Scheme E3

When W is hydrogen (as in Compound D6), a solution of Compound E31 (in a solvent such as toluene and the like) is condensed with Compound E2 using a sulfur solution (in a solvent such as DMF and the like) to obtain a compound of formula (I) directly.

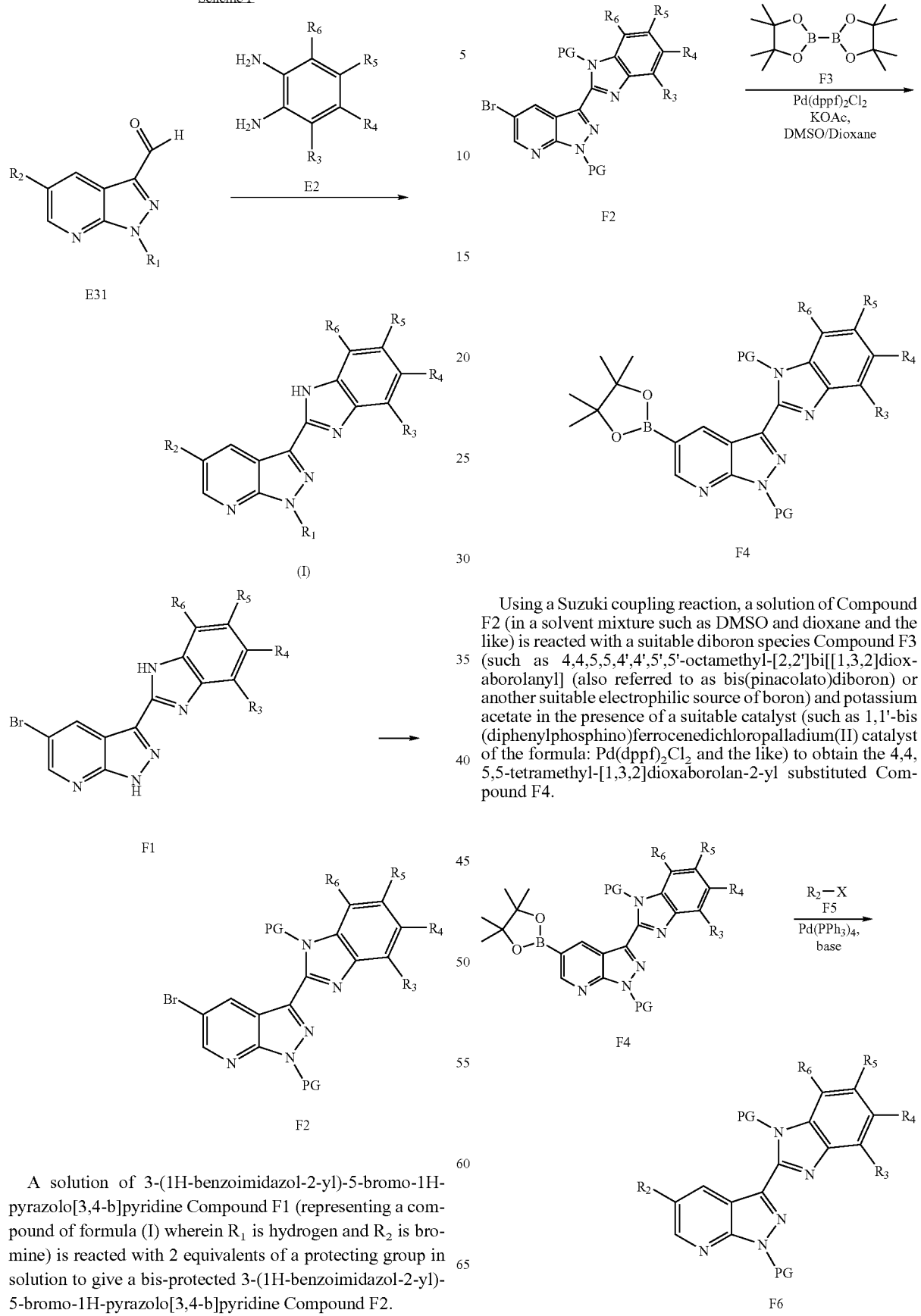

Using a Suzuki coupling reaction, a solution of Compound F2 (in a solvent mixture such as DMSO and dioxane and the like) is reacted with a suitable diboron species Compound F3 (such as 4,4,5,5,4',4',5',5'-octamethyl-[2,2']bi[[1,3,2]dioxaborolanyl] (also referred to as bis(pinacolato)diboron) or another suitable electrophilic source of boron) and potassium acetate in the presence of a suitable catalyst (such as 1,1'-bis(diphenylphosphino)ferrocenedichloropalladium(II) catalyst of the formula: Pd(dppf)$_2$Cl$_2$ and the like) to obtain the 4,4,5,5-tetramethyl-[1,3,2]dioxaborolan-2-yl substituted Compound F4.

A solution of 3-(1H-benzoimidazol-2-yl)-5-bromo-1H-pyrazolo[3,4-b]pyridine Compound F1 (representing a compound of formula (I) wherein R$_1$ is hydrogen and R$_2$ is bromine) is reacted with 2 equivalents of a protecting group in solution to give a bis-protected 3-(1H-benzoimidazol-2-yl)-5-bromo-1H-pyrazolo[3,4-b]pyridine Compound F2.

Compound F4 is coupled with a $R_2$—X Compound F5 (wherein $R_2$ is other than halogen and X is a halogen leaving group such as Cl, Br or I or a triflate leaving group such as OTf) in the presence of a suitable catalyst (such as tetrakis(triphenylphosphine)palladium(0) of the formula: Pd(PPh$_3$)$_4$) and a base (such as sodium carbonate and the like) to obtain the $R_2$ substituted 3-(1H-benzoimidazol-2-yl)-1H-pyrazolo[3,4-b]pyridine Compound F6.

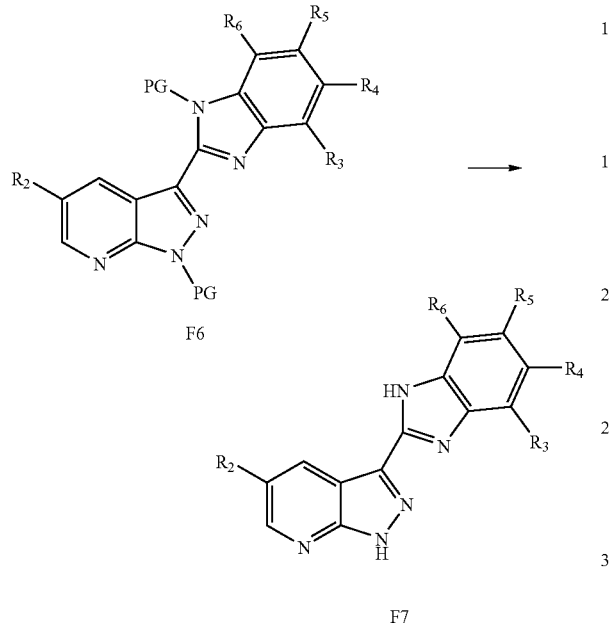

Compound F6 is deprotected using a suitable reagent (such as TFA or hydrochloric acid) and the mixture is purified to give Compound F7.

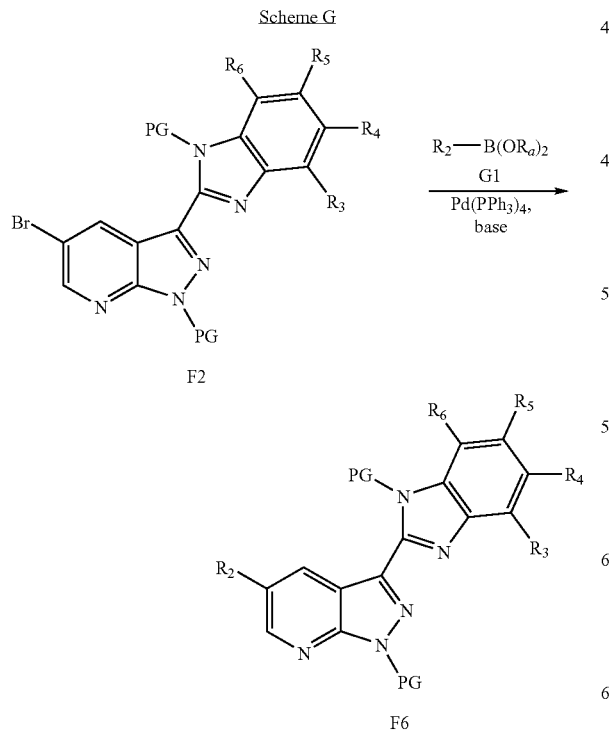

As an alternative to Scheme F, a solution of Compound F2 (in a solvent such as dioxane and the like) is reacted with a suitable $R_2$ substituted boron Compound G1 (wherein $R_2$ is other than halogen and $R_a$ is hydrogen or $C_{1-4}$alkyl) in the presence of a suitable catalyst (such as tetrakis(triphenylphosphine)palladium(0) of the formula: Pd(PPh$_3$)$_4$ and the like) and a base (such as sodium carbonate and the like) to obtain Compound F6. Compound F6 is then carried forward according to the procedure of Scheme F.

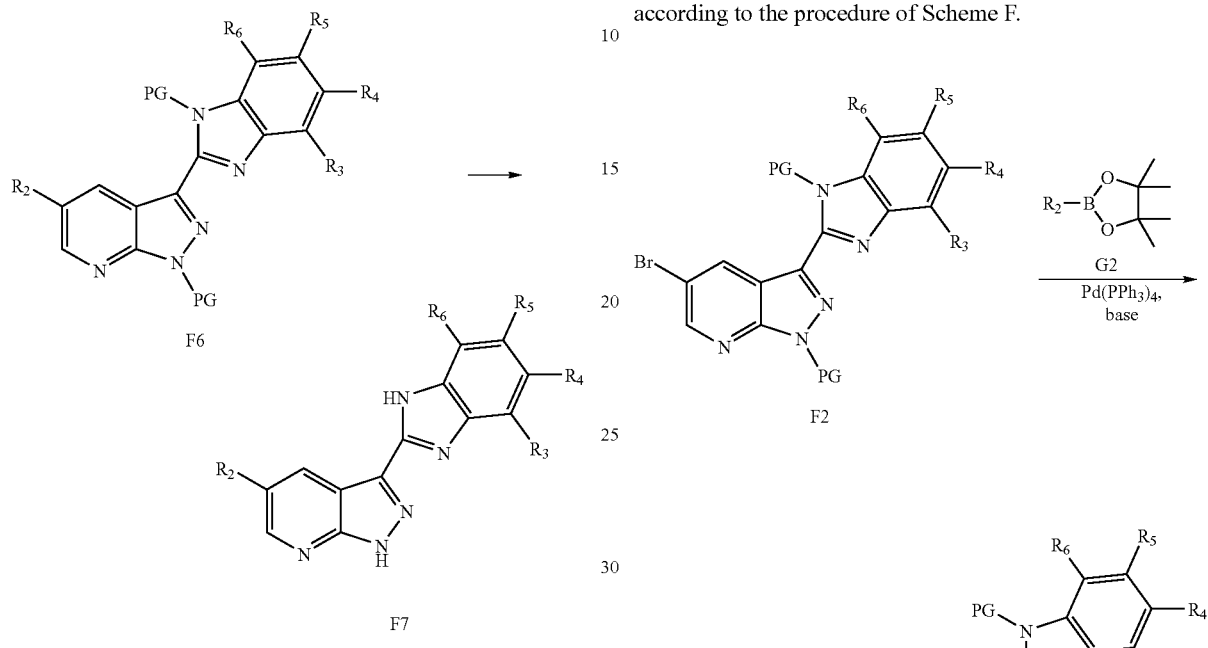

As an alternative to Scheme F, a solution of Compound F2 (in a solvent such as dioxane) is reacted with a $R_2$ substituted 4,4,5,5-tetramethyl-[1,3,2]dioxaborolanyl Compound G2 (wherein $R_2$ is other than halogen) in the presence of a suitable catalyst (such as Pd(PPh$_3$)$_4$ and the like) and a base (such as sodium carbonate and the like) to obtain Compound F6. Compound F6 is then carried forward according to the procedure of Scheme F.

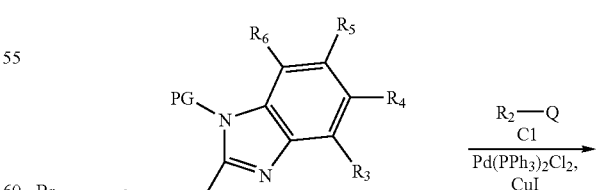

-continued

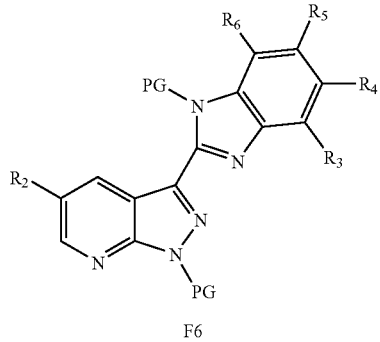

F6

Using the procedure of Scheme C, is coupled with Compound C1 (wherein $R_2$ is other than halogen and Q is a suitable organometallic agent such as an alkylated tin) in the presence of a suitable catalyst (such as $Pd(PPh_3)Cl_2$) and copper (I) iodide to give Compound F6. Compound F6 is then carried forward according to the procedure of Scheme F.

Scheme H

Included within the scope of the present invention are art known functional group transformations wherein, for any of the foregoing intermediates or compounds described in the present invention, when any one of a $R_3$, $R_4$, $R_5$ or $R_6$ substitutent on a compound of formula (I), any one of a $R_7$, $R_8$, $R_9$ or $R_{10}$ substituent on $R_2$ (when $R_2$ is other than halogen), any one of a $R_{11}$, $R_{13}$, $R_{14}$ or $R_{15}$ substituent on any one of $R_3$, $R_4$, $R_5$ or $R_6$ or any one of a $R_{15}$, $R_{16}$, $R_{17}$ or $R_{18}$ substituent on any one of $R_7$, $R_8$, $R_9$ or $R_{10}$ is $C_{1-4}$alkyl-OH, the corresponding amine may be obtained by converting the OH group of said intermediates or compounds to a leaving group (such as a mesylate, triflate, tosylate and the like), then displacing the leaving group with a nucleophile (such as a mono or disubstituted amine, a monosubstituted alcohol and the like).

The scope of this invention includes functional group transformations wherein, when any one of the foregoing substitutents on any one of the instant intermediates or compounds is C(O)OH, the corresponding amide may be obtained by coupling a mono or disubstituted amine in the presence of an amide coupling reagent (such as HATU, DIC, EDCI, DCC, and the like).

The scope of this invention includes functional group transformations wherein, when any one of the foregoing substitutents on any one of the instant intermediates or compounds is C(O)H, the corresponding amine may be obtained by coupling a mono or disubstituted amine in the presence of a reducing agent (such as sodium triacetoxyborohydride or $NaBH_3CN$), the corresponding alcohol may be obtained in the presence of a reducing agent (such as sodium borohydride) or the corresponding oxime may be obtained by reaction with hydroxylamine hydrochloride.

The scope of this invention includes functional group transformations wherein, when any one of the foregoing substitutents on any one of the instant intermediates or compounds is a monosubstituted amine, the disubstituted amine may be obtained by coupling a monosubstituted aldehyde in the presence of a reducing agent (such as sodium triacetoxyborohydride or $NaBH_3CN$).

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

General: 1H and $C^{13}$ NMR spectra were obtained at 400 MHz and 300 MHz on a Brucker AVANCE300 and AVANCE400 spectrometer. Chemical shifts are reported in ppm downfield from TMS as an internal standard. Magnesium sulfate was employed to dry organic extracts prior to concentration by rotary evaporation. Flash chromatography was done using EM science silica gel 60 (230-400 mesh).

Standard solvents from J. T. Baker were used as received. Anhydrous solvents from Aldrich or J.T. Baker and all other commercially available reagents were used without further purification.

Silica gel (E. Merck, 230-400 mesh) was used for all flash chromatography. Thin-layer chromatography was performed on precoated plates with silica gel 60 F254 from EM Science. Yields were not optimized.

Mass electrospray positive or negative spectra (MS) was performed on Hewlett Packard 1100 series or Agilent 1100 series spectrometer with a Zorbax stablebond $C^{18}$ narrow bore column, using gradient 0.05% acetic acid in MeOH and 0.05% acetic acid in water as mobile phase for MS analysis, and using gradient 0.05% TFA in acetonitrile and 0.05% acetic acid in water as mobile phase for LCMS analysis.

HPLC quantitative purity analysis were additionally carried on Agilent 1100 Series LC/MSD equipment on a Agilent 4.6×50 mm Zorbax 3.5 uM column (Elips XDB-phenyl) using gradient 0.05% TFA acetonitrile and 0.05% TFA in water as solvent system and based on the absorption at 254 nM.

Example 1

5-bromo-3-(4-methoxymethyl-1H-benzoimidazol-2-yl)-1H-pyrazolo[3,4-b]pyridine (Compound 11)

3-(4-methoxymethyl-1H-benzoimidazol-2-yl)-5-pyridin-3-yl-1H-pyrazolo[3,4-b]pyridine (Compound 35)

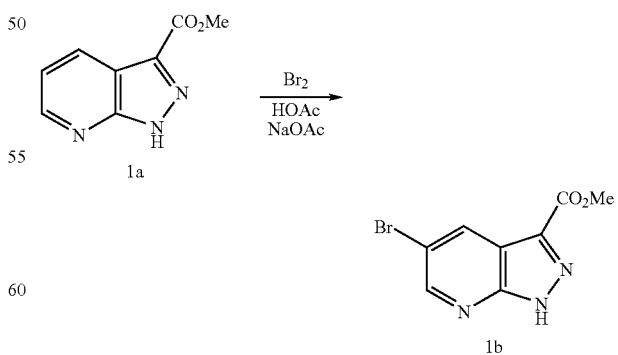

Commercially available Compound 1a (7.45 g, 35 mmol), sodium acetate (17.2 g, 210 mmol), and bromine (5.3 mL, 105 mmol) in glacial acetic acid (140 mL) were stirred in a sealed reaction tube in an oil-bath at 115° C. overnight. The mixture was evaporated in vacuo and purified via chromatography on silica gel with an ethyl acetate/hexanes gradient to give Compound 1b (3.87 g, 43%). ¹H NMR (300 MHz, (CD₃)₂SO) δ 14.8 (s, br, 1H), 8.75 (s, 1H), 8.65 (s, 1H), 3.98 (s, 3H); MS (ESI) m/z: 257 (M+H⁺).

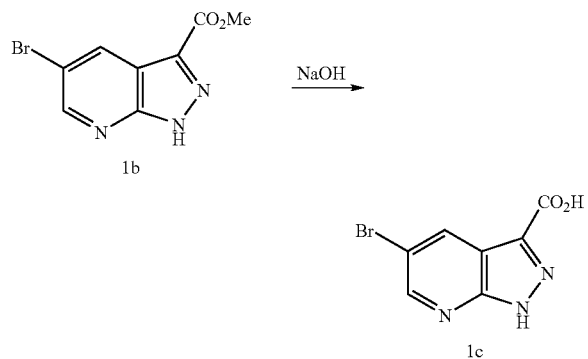

Compound 1b (3.4 g, 13.2 mmol) in MeOH (50 mL) was refluxed with 2M NaOH (10 mL) for 4 hrs. The mixture was cooled to room temperature and acidified with hydrochloric acid to give Compound 1c (3.22 g, 100%). ¹H NMR (300 MHz, CD₃OD) δ 8.62 (s, 1H), 8.58 (s, 1H); MS (ESI) m/z: 359 (M+H⁺).

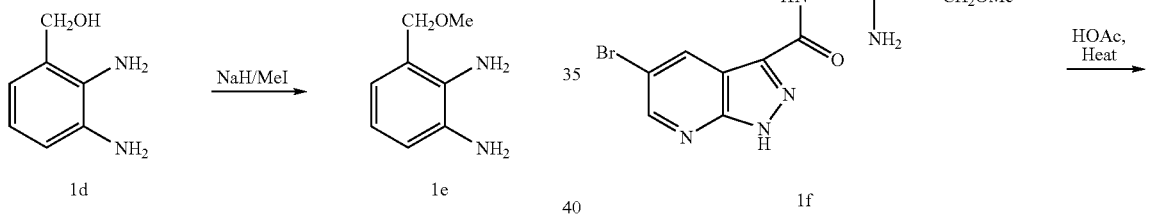

Commercially available Compound 1d (0.896 g, 5.89 mmol) was dissolved in THF (500 mL). NaH (1.68 g, 70 mmol) was added to the solution at 0° C. The resultant suspension was stirred at 0° C. for 30 mins. Methyl iodide (4.6 mL, 73.2 mmol) was added and the reaction mixture was stirred overnight. The mixture was concentrated and separated by column chromatography on silica gel with 1:1 ethyl acetate:hexanes to give Compound 1e (3.46 g, 34%). ¹H NMR (300 MHz, CDCl₃) δ 6.72 (m, 1H), 6.65 (m, 1H), 4.50 (s, 2H), 4.0-3.5 (br, 4H), 3.32 (3, 3H); MS (ESI) m/z: 153 (M+H⁺).

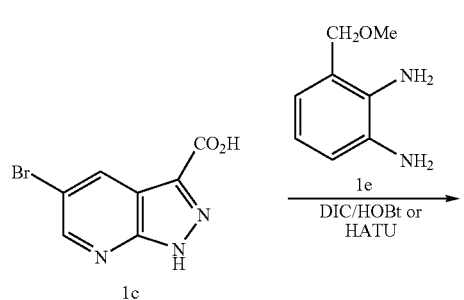

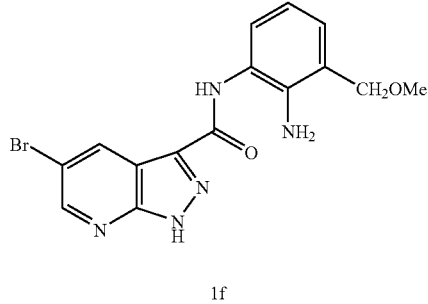

Compound 1c (1.425 g, 5.89 mmol), Compound 1e (0.896 g, 5.89 mmol), HATU (2.686 g, 7.07 mmol) and DIPEA (3.69 mL, 21.2 mmol) in DMF (15 mL) was stirred at room temperature overnight. The mixture was then evaporated in vacuo and purified via chromatography on silica gel with a 10-20% MeOH/methylene chloride gradient to give Compound 1f 1.265 g (57%). ¹H NMR (300 MHz, (CD₃)₂SO) δ 9.9 (s, br, 1H), 8.72 (s, 1H), 8.65 (s, 1H), 7.25 (d, 1H), 7.0 (d, 1H), 6.62 (t, 1H), 4.7 (s, br, 2H), 4.40 (s, 2H), 3.30 (s, 3H); MS (ESI) m/z: 377 (M+H⁺), 399 (M+Na⁺).

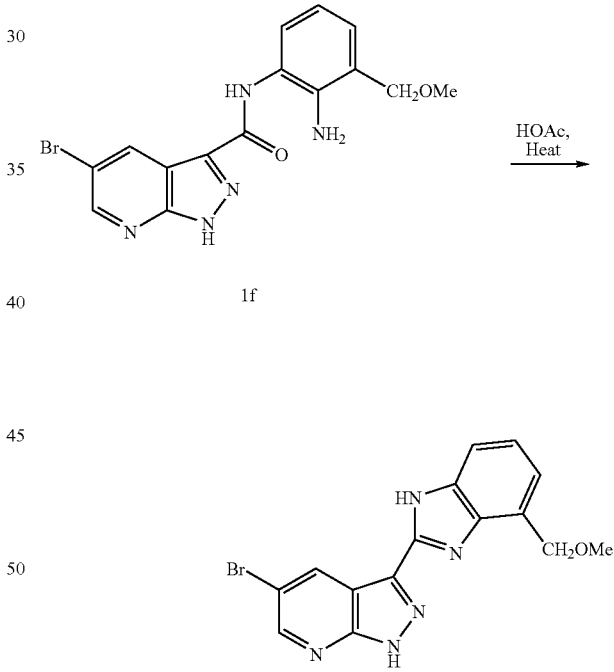

A solution of Compound 1f (1.195 g, 3.18 mmol) in glacial acetic acid (20 mL) was heated in an oil-bath at 120° C. for 3.5 hrs and evaporated to dryness in vacuo. The resultant solid was rinsed with methylene chloride to give Compound 11 as an acetic acid salt (yellowish powder, 1.162 g, 87%). ¹H NMR (300 MHz, CD₃OD) δ 9.08 (s, 1H), 8.72 (s, 1H), 8.55 (s, 1H), 7.62 (m, 1H), 7.30 (m, 2H), 4.90 (s, 2H), 3.50 (s, 3H), 2.00 (3, 3H); MS (ESI) m/z: 359 (M+H⁺).

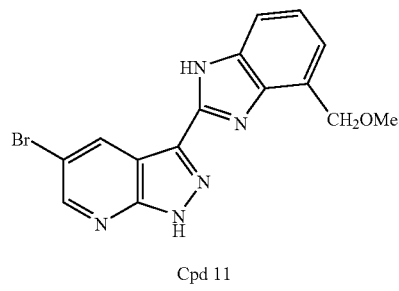

Cpd 11

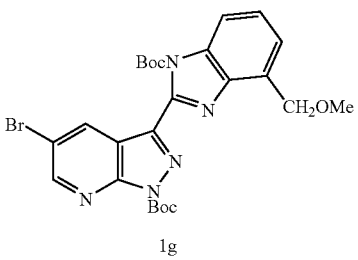

1g

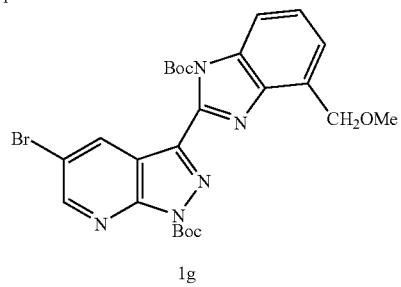

1g

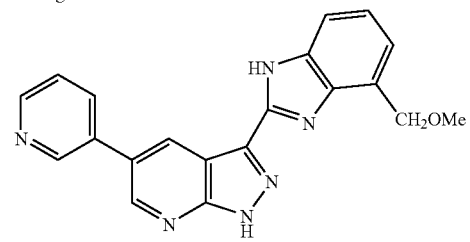

Cpd 35

Compound 11 (1.16 g, 5.89 mmol) was stirred with Boc$_2$O (1.555 g, 7.12 mmoL), DMAP (0.32 mmol, 39.6 mg) and Et$_3$N (994 uL, 7.72 mmoL) in methylene chloride (50 mL) at room temperature overnight. The resultant solution was then evaporated in vacuo. The residue was re-dissolved in methylene chloride and washed with 5% aqueous NaHCO$_3$. The organic phase was dried (MgSO$_4$), filtrated and evaporated to give the bis-Boc-protected Compound 1h as a brown foam (1.55 g, 100%). $^1$H NMR (300 MHz, CDCl$_3$) δ 8.82 (s, 1H), 8.52 (s, 1H), 8.02 (m, 1H), 7.25 (d, 1H), 7.50 (m, 2H), 5.02 (s, 2H), 3.52 (s, 3H), 1.72 (s, 9H), 1.49 (s, 9H); MS (ESI) m/z: 559 (M+H$^+$).

Compound 1h (55.8 mg, 0.1 mmol) in dioxane (2 mL) was stirred with 3-pyridineboronic acid Compound 1i (24.4 mg, 0.2 mmol), Pd (PPh$_3$)$_4$ (23 mg, 0.02 mmol) and 2M sodium carbonate (0.2 mL) in a sealed reaction tube at 90° C. overnight. The resultant mixture was cooled to room temperature and rinsed with dioxane, then concentrated and purified via chromatography to give Compound 35 as a white powder (5 mg, 11%). $^1$H NMR (300 MHz, CD$_3$OD) δ 9.30 (s, 1H), 9.28 (s, 1H), 9.10 (s, 1H), 8.85 (m, 2H), 8.10 (m, 1H), 7.80 (m, 1H), 7.52 (m, 2H), 4.90 (s, 2H), 3.50 (s, 3H); MS (ESI) m/z: 357 (M+H$^+$).

Using the procedure of Example 1, other compounds of the present invention were prepared:

| Cpd | Data |
|---|---|
| 4 | 4-[3-(4-methoxymethyl-1H-benzoimidazol-2-yl)-1H-pyrazolo[3,4-b]pyridin-5-yl]-isoquinoline<br>4-isoquinoline boronic acid was used in place of Compound 1h (50%).<br>$^1$H NMR (300 MHz, CD$_3$OD) δ 9.34 (s, 1H), 9.14 (d, 1H, J = 2.1 Hz), 8.76 (d, 1H, J = 2.1 Hz), 8.57 (s, 1H), 8.24 (d, 1H, J = 8.4 Hz), 8.00 (d, 1H, J = 8.4 Hz), 7.86 (m, 2H), 7.66 (m, 1H), 7.02 (m, 2H), 4.92 (s, 2H), 3.49 (s, 3H); MS (ESI) m/z: 407 (M + H$^+$). |
| 34 | 3-[3-(4-methoxymethyl-1H-benzoimidazol-2-yl)-1H-pyrazolo[3,4-b]pyridin-5-yl]-quinoline<br>3-quinoline boronic acid was used in place of Compound 1h (25%).<br>$^1$H NMR (300 MHz, CD$_3$OD) δ 9.48 (s, 1H), 9.30 (s, 1H), 9.20 (s, 1H), 9.05 (s, 1H), 8.20 (m, 2H), 8.10 (m, 1H), 7.95 (m, 1H), 7.80 (m, 2H), 7.50 (m, 2H), 4.90 (s, 2H), 3.50 (s, 3H); MS (ESI) m/z: 407 (M + H$^+$). |
| 36 | 4-[3-(4-methoxymethyl-1H-benzoimidazol-2-yl)-1H-pyrazolo[3,4-b]pyridin-5-yl]benzenesulfonamide<br>4-(4,4,5,5-tetramethyl-[1,3,2]dioxaborolan-2-yl)-benzenesulfonamide was used in place of Compound 1h (9%).<br>$^1$H NMR (300 MHz, (CD$_3$)$_2$CO) δ 9.25 (s, 1H), 9.02 (s, 1H), 8.20-8.00 (m, 4H), 7.68 (m, 1H), 7.40 (m, 2H), 6.7 (s, br, 2H), 4.95 (s, 2H), 3.50 (s, 3H); MS (ESI) m/z: 435 (M + H$^+$). |
| 37 | 3-(4-methoxymethyl-1H-benzoimidazol-2-yl)-5-(1H-pyrrolo[2,3-b]pyridin-3-yl)-1H-pyrazolo[3,4-b]pyridine<br>1-benzenesulfonyl-3-(4,4,5,5-tetramethyl-[1,3,2]dioxaborolan-2-yl)-1H-pyrrolo[2,3-b]pyridine was used in place of Compound 1h then deprotected with NaOH (26%).<br>$^1$H NMR (300 MHz, CD$_3$OD) δ 9.15 (s, 1H), 8.95 (s, 1H), 8.02 (m, 1H), 7.75 (m, 1H), 7.70 (s, 1H), 7.60-7.48 (m, 2H), 7.32-7.18 (m, 3H), 4.60 (s, 2H), 3.55 (s, 3H); MS (ESI) m/z: 395 (M + H$^+$). |

-continued

| Cpd | Data |
|---|---|
| 38 | 5-(1-benzenesulfonyl-1H-indol-3-yl)-3-(4-methoxymethyl-1H-benzoimidazol-2-yl)-1H-pyrazolo[3,4-b]pyridine<br>1-(phenylsulfonyl)-3-indole boronic acid was used in place of Compound 1h. |
| 39 | 5-(1H-indol-3-yl)-3-(4-methoxymethyl-1H-benzoimidazol-2-yl)-1H-pyrazolo[3,4-b]pyridine<br>Compound 38 was deprotected with NaOH (10%).<br>$^1$H NMR (300 MHz, CD$_3$OD) δ 9.15 (s, 1H), 8.95 (s, 1H), 8.55 (m, 1H), 8.30 (m, 1H), 7.90 (s, 1H), 7.75 (m, 1H), 7.30 (m, 3H), 4.90 (s, 2H), 3.50 (s, 3H); MS (ESI) m/z: 396 (M + H$^+$). |
| 40 | 3-(4-methoxymethyl-1H-benzoimidazol-2-yl)-5-(1H-pyrrol-3-yl)-1H-pyrazolo[3,4-b]pyridine<br>1-(triisopropylsilyl)pyrrol-3-yl boronic acid was used in place of Compound 1h then deprotected with TBAF in THF (43%).<br>$^1$H NMR (300 MHz, CD$_3$OD) δ 10.4 (s, br, 1H), 9.05 (s, 1H), 8.95 (s, 1H), 7.75 (m, 1H), 7.45-7.30 (m, 3H), 6.95 (m, 1H), 6.70 (s, 1H), 5.00 (s, 2H), 3.48 (s, 3H); MS (ESI) m/z: 335 (M + H$^+$). |
| 41 | 5-[3-(4-methoxymethyl-1H-benzoimidazol-2-yl)-1H-pyrazolo[3,4-b]pyridin-5-yl]-pyridine-3-carbaldehyde<br>5-(4,4,5,5-tetramethyl-[1,3,2]dioxaborolan-2-yl)-pyridine-3-carbaldehyde Compound 15b was used in place of Compound 1h (62%).<br>MS (ESI) m/z: 385 (M + H$^+$). |
| 42 | ethyl-{5-[3-(4-methoxymethyl-1H-benzoimidazol-2-yl)-1H-pyrazolo[3,4-b]pyridin-5-yl]-pyridin-3-ylmethyl}-amine<br>Compound 41 was aminated with ethyl amine via NaBH$_4$ (73%).<br>$^1$H NMR (300 MHz, CD$_3$OD) δ 9.25 (s, 1H), 9.20 (s, 1H), 9.10 (s, 1H), 8.83 (s, 1H), 8.58 (s, 1H), 7.85 (m, 1H), 7.58 (m, 1H), 4.92 (s, 2H), 4.48 (s, 2H), 3.50 (s, 3H), 3.22 (q, 2H), 1.42 (t, 3H); MS (ESI) m/z: 414 (M + H$^+$). |
| 43 | isopropyl-{5-[3-(4-methoxymethyl-1H-benzoimidazol-2-yl)-1H-pyrazolo[3,4-b]pyridin-5-yl]-pyridin-3-ylmethyl}-amine<br>Compound 41 was aminated with isopropyl amine via NaBH$_4$ (83%).<br>$^1$H NMR (300 MHz, CD$_3$OD) δ 9.22 (s, 1H), 9.20 (s, 1H), 9.10 (s, 1H), 8.85 (s, 1H), 8.60 (s, 1H), 7.85 (m, 1H), 7.60 (m, 2H), 4.92 (s, 2H), 4.48 (s, 2H), 3.60 (m, 1H), 3.50 (s, 3H), 1.50 (d, 6H); MS (ESI) m/z: 428 (M + H$^+$). |
| 44 | {5-[3-(4-methoxymethyl-1H-benzoimidazol-2-yl)-1H-pyrazolo[3,4-b]pyridin-5-yl]-pyridin-3-yl}-methanol<br>Compound 41 was hydroxylated via NaBH$_4$ (92%).<br>$^1$H NMR (300 MHz, CD$_3$OD) δ 9.22 (s, 1H), 9.18 (s, 1H), 9.08 (s, 1H), 8.78 (s, 1H), 8.72 (s, 1H), 7.78 (m, 1H), 7.48 (m, 2H), 4.85 (s, 2H), 4.45 (s, 2H), 3.50 (s, 3H); MS (ESI) m/z: 387 (M + H$^+$). |
| 52 | diethyl-[2-(5-pyridin-3-yl-1H-pyrazolo[3,4-b]pyridin-3-yl)-1H-benzoimidazol-4-ylmethyl]-amine<br>Compound 6 was used in place of Compound 1h (11%).<br>$^1$H NMR (300 MHz, (CD$_3$)$_2$CO) δ 9.30 (m, 2H), 9.15 (s, 1H), 8.95 (m, 1H), 8.75 (m, 1H), 8.02 (m, 1H), 7.80 (d, 1H), 7.55 (d, 1H), 7.40 (t, 1H), 5.10 (s, 2H), 3.50 (m, 2H), 1.60 (t, 3H); MS (ESI) m/z: 398 (M + H$^+$). |
| 53 | tert-butyl-{5-[3-(4-methoxymethyl-1H-benzoimidazol-2-yl)-1H-pyrazolo[3,4-b]pyridin-5-yl]-pyridin-3-ylmethyl}-amine<br>Compound 41 was aminated with tert-butyl amine via NaBH$_4$ (34%).<br>$^1$H NMR (300 MHz, CD$_3$OD) δ 9.22 (s, 1H), 9.18 (s, 1H), 9.08 (s, 1H), 8.80 (s, 1H), 8.50 (s, 1H), 7.80 (m, 1H), 7.50 (m, 2H), 4.85 (s, 2H), 4.45 (s, 2H), 3.50 (s, 3H); MS (ESI) m/z: 442 (M + H$^+$). |
| 54 | 3-(4-methoxymethyl-1H-benzoimidazol-2-yl)-5-(5-morpholin-4-ylmethyl-pyridin-3-yl)-1H-pyrazolo[3,4-b]pyridine<br>Compound 41 was aminated with morpholine via NaBH(OAc)$_3$ (41%).<br>$^1$H NMR (300 MHz, CD$_3$OD) δ 9.15 (s, 1H), 8.92 (m, 2H), 8.55 (s, 1H), 8.22 (s, 1H), 7.65 (m, 1H), 7.25 (m, 2H), 4.92 (s, 2H), 3.72 (m, 4H), 3.68 (s, 2H), 3.48 (s, 3H), 2.52 (m, 4H); MS (ESI) m/z: 456 (M + H$^+$). |
| 55 | {5-[3-(4-methoxymethyl-1H-benzoimidazol-2-yl)-1H-pyrazolo[3,4-b]pyridin-5-yl]-pyridin-3-ylmethyl}-dimethyl-amine<br>Compound 41 was aminated with dimethyl amine via NaBH(OAc)$_3$ (38%).<br>$^1$H NMR (300 MHz, CD$_3$OD) δ 9.22 (s, 1H), 8.98 (m, 2H), 8.60 (s, 1H), 8.30 (s, 1H), 7.70 (m, 1H), 7.30 (m, 2H), 4.92 (s, 2H), 3.75 (s, 2H), 3.50 (s, 3H), 2.40 (s, 6H); MS (ESI) m/z: 414 (M + H$^+$). |
| 56 | {5-[3-(4-methoxymethyl-1H-benzoimidazol-2-yl)-1H-pyrazolo[3,4-b]pyridin-5-yl]-pyridin-3-ylmethyl}-methyl-amine<br>Compound 41 was aminated with methyl amine via NaBH$_4$ (73%).<br>$^1$H NMR (300 MHz, MeOD) δ 8.97 (d, 1H, J = 2.1 Hz), 8.78 (s, 1H), 8.73 (d, 1H, J = 2.1 Hz), 8.70 (d, 1H, J = 5.7 Hz), 7.92 (d, 1H, J = 5.7 Hz), 7.68 (dd, 1H, J = 4.2 Hz), 7.37 (m, 2H), 4.88 (s, 2H), 3.46 (s, 2H), 2.63 (s, 3H); MS (ESI) m/z: 400 (M + H$^+$). |
| 63 | 3-(4-methoxymethyl-1H-benzoimidazol-2-yl)-5-(6-methoxy-pyridin-3-yl)-1H-pyrazolo[3,4-b]pyridine<br>6-methoxy-3-pyridine-boronic acid was used in place of Compound 1h (76%). |

| Cpd | Data |
|---|---|
|  | $^1$H NMR (300 MHz, CD$_3$OD) δ 9.08 (s, 1H), 8.87 (s, 1H), 8.57 (s, 1H), 8.15 (m, 1H), 7.72 (m, 1H), 7.30 (d, 2H), 6.98 (d, 1H), 4.95 (s, 2H), 3.99 (s, 3H), 3.50 (s, 3H); MS (ESI) m/z: 435 (M + H$^+$). |
| 64 | 3-(4-methoxymethyl-1H-benzoimidazol-2-yl)-5-(5-methoxy-pyridin-3-yl)-1H-pyrazolo[3,4-b]pyridine<br>3-methoxy-5-(4,4,5,5-tetramethyl-[1,3,2]dioxaborolan-2-yl)-pyridine was used in place of Compound 1h (68%).<br>$^1$H NMR (300 MHz, CD$_3$OD) δ 9.02 (m, 2H), 8.60 (s, 1H), 8.88 (s, 1H), 7.82 (s, 1H), 7.48 (m, 1H), 7.22 (m, 2H), 4.98 (s, 2H), 3.98 (s, 3H), 3.42 (s, 3H); MS (ESI) m/z: 387 (M + H$^+$). |
| 65 | 3-(4-methoxymethyl-1H-benzoimidazol-2-yl)-5-pyridin-4-yl-1H-pyrazolo[3,4-b]pyridine<br>4-(4,4,5,5-tetramethyl-[1,3,2]dioxaborolan-2-yl)-pyridine was used in place of Compound 1h (45%).<br>$^1$H NMR (300 MHz, CD$_3$OD) δ 9.28 (s, 1H), 9.02 (s, 1H), 8.68 (d, 2H), 7.95 (d, 2H), 7.75 (m, 1H), 7.30 (d, 2H), 4.92 (s, 2H), 3.50 (s, 3H); MS (ESI) m/z: 357 (M + H$^+$). |
| 66 | 3-(4-methoxymethyl-1H-benzoimidazol-2-yl)-5-(6-morpholin-4-yl-pyridin-3-yl)-1H-pyrazolo[3,4-b]pyridine<br>4-[5-(4,4,5,5-tetramethyl-[1,3,2]dioxaborolan-2-yl)-pyridin-2-yl]-morpholine was used in place of Compound 1h (51%).<br>$^1$H NMR (300 MHz, CD$_3$OD) δ 9.05 (s, 1H), 8.88 (s, 1H), 8.60 (s, 1H), 8.05 (m, 1H), 7.68 (m, 1H), 7.30 (d, 2H), 7.00 (d, 1H), 4.90 (s, 2H), 3.88 (t, 4H), 3.60 (t, 4H), 3.50 (s, 3H); MS (ESI) m/z: 442 (M + H$^+$). |
| 67 | 4-{5-[3-(4-methoxymethyl-1H-benzoimidazol-2-yl)-1H-pyrazolo[3,4-b]pyridin-5-yl]-pyridin-2-yl}-piperazine-1-carboxylic acid tert-butyl ester<br>4-[5-(4,4,5,5-tetramethyl-[1,3,2]dioxaborolan-2-yl)-pyridin-2-yl]-piperazine-1-carboxylic acid tert-butyl ester was used in place of Compound 1h. |
| 68 | 3-(4-methoxymethyl-1H-benzoimidazol-2-yl)-5-pyrimidin-5-yl-1H-pyrazolo[3,4-b]pyridine<br>pyrimidine-5-boronic acid was used in place of Compound 1h (91%).<br>$^1$H NMR (300 MHz, CD$_3$OD) δ 9.29 (s, 1H), 9.25 (s, 1H), 9.22 (s, 1H), 8.99 (s, 1H), 8.33 (s, 1H), 7.75 (m, 1H), 7.29 (d, 2H), 5.02 (s, 2H), 3.50 (s, 3H); MS (ESI) m/z: 358 (M + H$^+$). |
| 69 | 3-(4-methoxymethyl-1H-benzoimidazol-2-yl)-5-(6-piperazin-1-yl-pyridin-3-yl)-1H-pyrazolo[3,4-b]pyridine<br>Compound 67 was deprotected (100%).<br>$^1$H NMR (300 MHz, CD$_3$OD) δ 9.05 (d, 1H), 9.00 (d, 1H), 8.65 (d, 1H), 8.15 (dd, 1H), 7.75 (m, 1H), 7.82 (m, 1H), 7.60 (m, 2H), 7.15 (d, 1H), 4.48 (s, 2H), 3.95 (t, 4H), 3.55 (s, 3H), 3.40 (t, 4H); MS (ESI) m/z: 441 (M + H$^+$). |
| 70 | 5-[3-(4-methoxymethyl-1H-benzoimidazol-2-yl)-1H-pyrazolo[3,4-b]pyridin-5-yl]-nicotinic acid ethyl ester<br>5-(4,4,5,5-tetramethyl-[1,3,2]dioxaborolan-2-yl)-nicotinic acid ethyl ester was used in place of Compound 1h (92%).<br>$^1$H NMR (300 MHz, CD$_3$OD) δ 15 (dd, 2H, J = 1.0, 2.2 Hz), 9.11 (d, 1H, J = 1.9 Hz), 8.91 (d, 1H, J = 2.2 Hz), 8.20 (s, 1H), 7.60 (m, 1H), 7.25 (d, 2H, J = 5.2 Hz), 4.90 (s, 2H), 4.48 (q, 2H, J = 7.1 Hz), 3.50 (s, 3H), 1.45 (t, 3H J = 7.1 Hz); MS (ESI) m/z: 429 (M + H$^+$). |
| 71 | 5-(6-fluoro-pyridin-3-yl)-3-(4-methoxymethyl-1H-benzoimidazol-2-yl)-1H-pyrazolo[3,4-b]pyridine<br>2-fluoropyridine-5-boronic acid was used in place of Compound 1h (47%).<br>$^1$H NMR (300 MHz, CD$_3$OD) δ 9.10 (s, 1H), 8.85 (s, 1H), 8.62 (s, 1H), 8.35 (m, 1H), 7.62 (m, 1H), 7.20-7.30 (m, 2H), 4.95 (s, 2H), 3.48 (s, 3H); MS (ESI) m/z: 375 (M + H$^+$). |
| 72 | 5-[3-(4-methoxymethyl-1H-benzoimidazol-2-yl)-1H-pyrazolo[3,4-b]pyridin-5-yl]-pyridine-3-carbaldehyde oxime<br>Compound 41 was aminated with hydroxylamine hydrochloride (93%).<br>$^1$H NMR (300 MHz, CD$_3$OD) δ 9.10 (m, 3H), 8.90 (s, 1H), 8.40 (m, 2H), 7.60 (m, 2H), 7.20 (d, 2H), 3.40 (s, 3H); MS (ESI) m/z: 400 (M + H$^+$). |
| 73 | C-{5-[3-(4-methoxymethyl-1H-benzoimidazol-2-yl)-1H-pyrazolo[3,4-b]pyridin-5-yl]-pyridin-3-yl}-methylamine<br>Compound 41 was aminated with ammonium acetate via NaBH$_3$CN (6%).<br>$^1$H NMR (300 MHz, CD$_3$OD) δ 9.22 (s, 1H), 9.12 (s, 1H), 9.05 (s, 1H), 8.78 (s, 1H), 8.52 (s, 1H), 7.80 (m, 1H), 7.55 (m, 2H), 4.90 (s, 2H), 4.38 (s, 2H), 3.50 (s, 3H); MS (ESI) m/z: 386 (M + H$^+$). |

-continued

| Cpd | Data |
|---|---|
| 74 | {5-[3-(4-methoxymethyl-1H-benzoimidazol-2-yl)-1H-pyrazolo[3,4-b]pyridin-5-yl]-pyridin-3-ylmethyl}-(2-morpholin-4-yl-ethyl)-amine<br>Compound 41 was aminated with 4-(2-aminoethyl)-morpholine via NaBH$_4$ (70%).<br>$^1$H NMR (300 MHz, CD$_3$OD) δ 9.25 (s, 1H), 9.20 (s, 1H), 9.18 (s, 1H), 9.08 (s, 1H), 8.83 (s, 1H), 8.55 (s, 1H), 7.82 (m, 1H), 7.60 (m, 2H), 4.95 (s, 2H), 4.58 (s, 2H), 3.95 (m, 4H), 3.75 (t, 2H), 3.60 (t, 2H), 3.50 (s, 3H), 3.40 (s, 4H); MS (ESI) m/z: 498 (M + H$^+$). |
| 75 | (2-methoxy-ethyl)-{5-[3-(4-methoxymethyl-1H-benzoimidazol-2-yl)-1H-pyrazolo[3,4-b]pyridin-5-yl]-pyridin-3-ylmethyl}-amine<br>Compound 41 was aminated with 2-methoxyethyl amine via NaBH$_4$ (30%).<br>$^1$H NMR (300 MHz, CD$_3$OD) δ 9.20 (s, 1H), 9.15 (s, 1H), 9.10 (s, 1H), 8.82 (s, 1H), 8.55 (s, 1H), 7.80 (m, 1H), 7.58 (m, 2H), 4.90 (s, 2H), 4.48 (s, 2H), 3.72 (m, 2H), 3.50 (m, 3H), 3.40 (m, 3H), 3.35 (m, 2H); MS (ESI) m/z: 443 (M + H$^+$). |
| 76 | N'-{5-[3-(4-methoxymethyl-1H-benzoimidazol-2-yl)-1H-pyrazolo[3,4-b]pyridin-5-yl]-pyridin-3-ylmethyl}-N,N-dimethyl-ethane-1,2-diamine<br>Compound 41 was aminated with N,N-dimethyl ethylene diamine via NaBH$_4$ (37%).<br>$^1$H NMR (300 MHz, CD$_3$OD) δ 9.22 (s, 1H), 9.18 (s, 1H), 9.10 (s, 1H), 8.83 (s, 1H), 8.62 (s, 1H), 7.82 (m, 1H), 7.58 (m, 2H), 4.92 (s, 2H), 4.52 (s, 2H), 3.3.70-3.60 (m, 4H), 3.500 (s, 3H), 3.00 (s, 6H); MS (ESI) m/z: 457 (M + H$^+$). |
| 77 | 2-({5-[3-(4-methoxymethyl-1H-benzoimidazol-2-yl)-1H-pyrazolo[3,4-b]pyridin-5-yl]-pyridin-3-ylmethyl}-amino)-ethanol<br>Compound 41 was aminated with ethanol amine via NaBH$_4$ (97%).<br>$^1$H NMR (300 MHz, CD$_3$OD) δ 9.22 (s, 1H), 9.15 (s, 1H), 9.10 (s, 1H), 8.80 (s, 1H), 8.50 (s, 1H), 7.80 (m, 1H), 7.52 (m, 2H), 4.95 (s, 2H), 4.50 (s, 2H), 3.88 (m, 2H), 3.50 (s, 3H); MS (ESI) m/z: 430 (M + H$^+$). |
| 78 | {5-[3-(4-methoxymethyl-1H-benzoimidazol-2-yl)-1H-pyrazolo[3,4-b]pyridin-5-yl]-pyridin-3-ylmethyl}-propyl-amine<br>Compound 41 was aminated with propyl amine via NaBH$_4$ (99%).<br>$^1$H NMR (300 MHz, CD$_3$OD) δ 9.20 (s, 1H), 9.15 (s, 1H), 9.10 (s, 1H), 8.80 (s, 1H), 8.50 (s, 1H), 7.80 (m, 1H), 7.58 (m, 2H), 4.95 (s, 2H), 4.45 (s, 2H), 3.50 (s, 3H), 3.15 (t, 2H), 1.80 (m, 2H), 1.05 (t, 3H); MS (ESI) m/z: 428 (M + H$^+$). |
| 79 | butyl-{5-[3-(4-methoxymethyl-1H-benzoimidazol-2-yl)-1H-pyrazolo[3,4-b]pyridin-5-yl]-pyridin-3-ylmethyl}-amine<br>Compound 41 was aminated with n-butyl amine via NaBH$_4$ (95%).<br>$^1$H NMR (300 MHz, CD$_3$OD) δ 9.20 (s, 1H), 9.15 (s, 1H), 9.08 (s, 1H), 8.80 (s, 1H), 8.50 (s, 1H), 7.80 (m, 1H), 7.55 (m, 2H), 4.90 (s, 2H), 4.45 (s, 2H), 3.48 (s, 3H), 3.20 (t, 2H), 1.75 (m, 2H), 1.48 (m, 2H), 1.02 (t, 3H); MS (ESI) m/z: 428 (M + H$^+$). |
| 80 | {5-[3-(4-methoxymethyl-1H-benzoimidazol-2-yl)-1H-pyrazolo[3,4-b]pyridin-5-yl]-pyridin-3-ylmethyl}-(1-methyl-piperidin-4-yl)-amine<br>Compound 41 was aminated with 1-methyl-piperidin-4-ylamine via NaBH$_4$ (99%).<br>$^1$H NMR (300 MHz, CD$_3$OD) δ 9.22 (s, 1H), 9.18 (s, 1H), 9.10 (s, 1H), 8.85 (s, 1H), 8.65 (s, 1H), 7.82 (m, 1H), 7.60 (m, 2H), 4.95 (s, 2H), 4.55 (s, 2H), 3.80-3.60 (m, 3H), 3.50 (s, 3H), 3.20 (m, 2H), 2.92 (s, 3H), 2.60-2.50 (m, 2H), 2.22-2.00 (m, 2H); MS (ESI) m/z: 483 (M + H$^+$). |

Example 2

[2-(5-bromo-1H-pyrazolo[3,4-b]pyridin-3-yl)-1H-benzoimidazol-4-ylmethyl]-diethyl-amine (Compound 6)

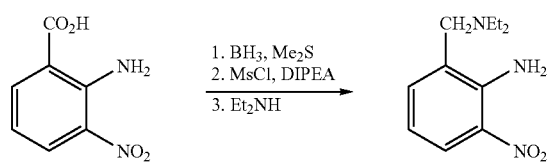

Commercially available 2-amino-3-nitro-benzoic acid Compound 2a, was used to prepare Compound 2b according to a literature procedure (*J. Med. Chem.* 1996, 39, 4654). $^1$H NMR (300 MHz, CDCl$_3$) δ 8.05 (d, 1H), 7.80 (br, 2H), 7.20 (d, 1H), 6.55 (t, 1H), 3.68 (s, 2H), 2.55 (q, 4H), 1.12 (t, 6H); MS (ESI) m/z: 224 (M+H$^+$).

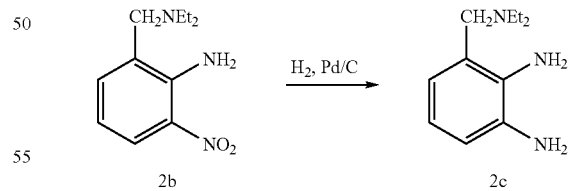

Compound 2b (0.5 g, 2.2 mmol) was dissolved in MeOH (15 mL) and hydrogenated with a hydrogen balloon with 10% palladium on charcoal (119 mg). The reaction mixture was filtrated, rinsed with MeOH, then concentrated and separated by column chromatography on silica gel with 5% MeOH/methylene chloride to give Compound 2c (94 mg, 22%). $^1$H NMR (300 MHz, CDCl$_3$) δ 6.65-6.55 (m, 3H), 4.80-3.70 (br, 4H), 4.0-3.5 (br, 4H), 3.60 (s, 2H), 2.50 (q, 4H), 1.02 (t, 6H); MS (ESI) m/z: 194 (M+H$^+$).

83

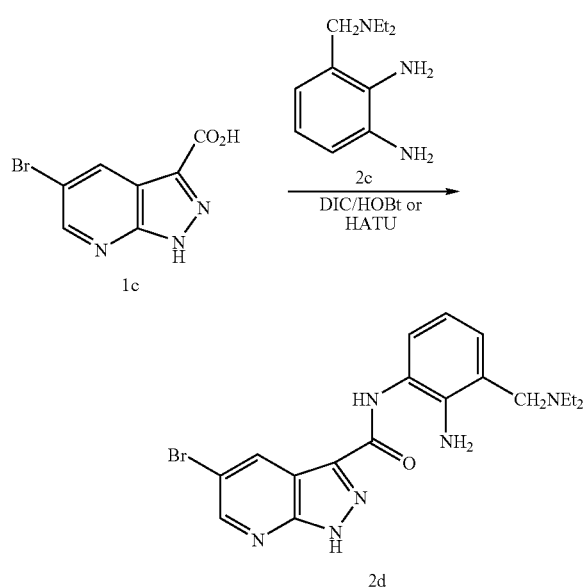

Using the procedure of Example 1, Compound 2c was used in place of Compound 1d to provide Compound 2d. 1H NMR (300 MHz, CD3OD) δ 8.85 (s, 1H), 8.65 (s, 1H), 7.40 (t, 1H), 7.25 (d, 1H), 7.18 (d, 1H), 4.35 (s, 2H), 3.35 (m, 4H), 1.30 (s, 3H); MS (ESI) m/z: 418 (M+H$^+$).

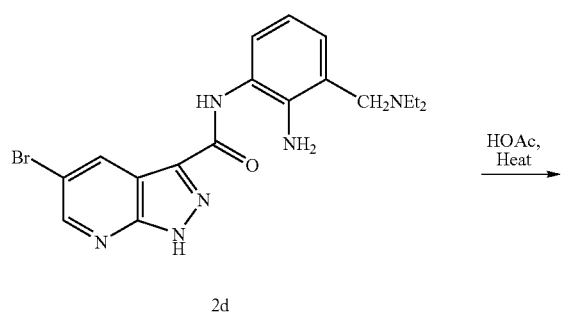

Using the procedure of Example 1, Compound 2d was carried forward to provide Compound 6. $^1$H NMR (300 MHz, CD$_3$OD) δ 9.08 (s, 1H), 8.65 (s, 1H), 7.75 (m, 1H), 7.40 (m, 2H), 4.85 (s, 2H), 3.40 (m, 4H), 1.50 (t, 6H); MS (ESI) m/z: 400 (M+H$^+$).

84

Example 3 diethyl-[2-(5-isoquinolin-4-yl-1H-pyrazolo[3,4-b]pyridin-3-yl)-1H-benzoimidazol-4-ylmethyl]-amine (Compound 5)

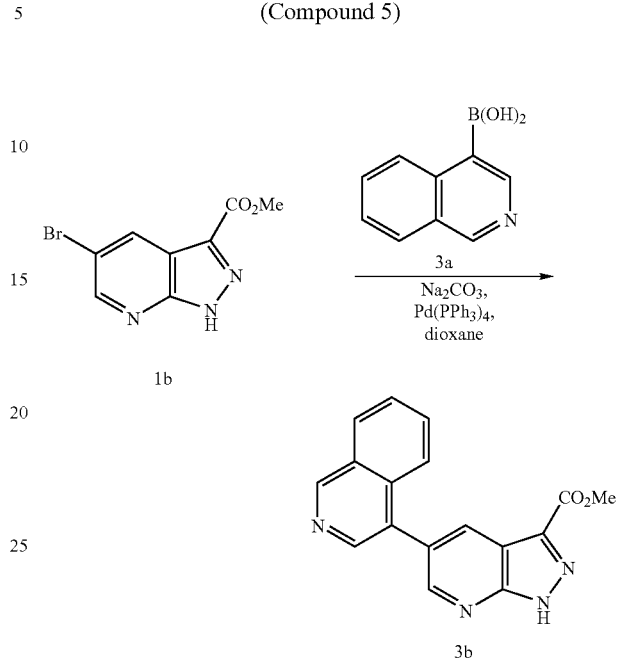

Compound 1b (256 mg, 1.0 mmol) in DME (12 mL) and MeOH (3 mL) was stirred with 4-isoquinoline boronic acid Compound 3a (260 mg, 1.5 mmol), Pd (PPh$_3$)$_4$ (231 mg, 0.2 mmol), and cesium carbonate (456 mg, 3 mmol) in a sealed reaction tube at 100° C. overnight. The mixture was cooled to room temperature; rinsed with MeOH, then concentrated and purified via chromatography on silica gel with 1:1 ethyl acetate:hexanes to give Compound 3b as a pale yellow powder (125 mg, 41%). $^1$H NMR (300 MHz, CD$_3$OD) δ 9.42 (s, 1H), 8.78 (s, 1H), 8.65 (s, 1H), 8.10 (m, 2H), 8.25 (m, 2H), 7.60 (m, 1H), 3.95 (s, 3H); MS (ESI) m/z: 305 (M+H$^+$).

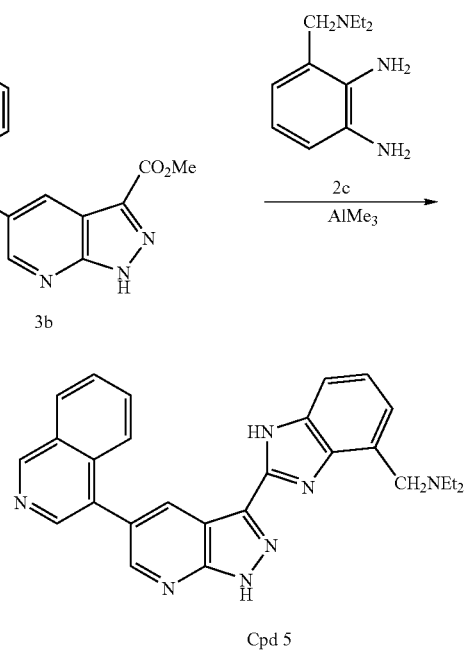

Trimethyl aluminum in toluene (0.34 mL of 2M solution, 0.68 mmol) was added to a solution of Compound 3b (38.6 mg, 0.2 mmol) in toluene (1.3 mL) at 0° C. The mixture was stirred while warming to room temperature for 30 mins. Compound 2c was added and the mixture was refluxed overnight. The reaction mixture was concentrated and purified via chromatography to give Compound 5 as a light brown powder (9.7 mg, 17%). $^1$H NMR (300 MHz, CD$_3$OD) δ 9.42 (s, 1H), 8.78 (s, 1H), 8.65 (s, 1H), 8.10 (m, 2H), 8.25 (m, 2H), 7.60 (m, 1H), 3.95 (s, 3H); MS (ESI) m/z: 305 (M+H$^+$).

Example 4

4-[3-(1H-benzoimidazol-2-yl)-1H-pyrazolo[3,4-b]pyridin-5-yl]-isoquinoline (Compound 1)

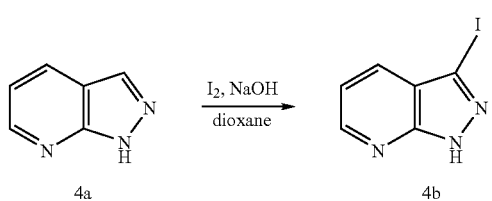

1H-pyrazolo[3,4-b]pyridine Compound 4a (0.50 g, 4.2 mmol), iodine (2.1 g, 8.3 mmol), 3M aqueous NaOH (20 mL) and 1,4-dioxane (20 mL) were added to a flask and the mixture was heated to 55° C. overnight. The organic solvent was removed in vacuo and acetic acid was added dropwise to adjust the solution pH to 5. A yellow solid was precipitated, collected by filtration and air-dried to afford Compound 4b (0.93 g, 90%). $^1$H NMR (400 MHz, CDCl$_3$) δ 13.80 (br, s, 1H), 8.66 (d, J=4.8 Hz, 1H), 7.88 (d, J=7.2 Hz, 1H), 7.26 (dd, J=7.2, 4.8 Hz, 1H); MS (ESI) m/z: 246 (M+H$^+$).

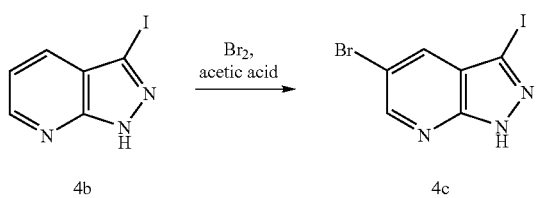

Compound 4b (8 mg, 0.033, mmol), bromine (20 μL, 0.39 mmol) and acetic acid (1 mL) were added to a flask and the mixture was heated to reflux overnight. The reaction mixture was concentrated in vacuo, the residue was dissolved in EtOAc and sequentially washed with aqueous NaHCO$_3$ and Na$_2$S$_2$O$_3$. The organic layer was dried over MgSO$_4$ then concentrated. The residue was purified by flash chromatography (silica gel, CH$_2$Cl$_2$:EtOAc 8:2) to afford Compound 4c (5.5 mg, 52%) as a yellow solid. $^1$H NMR (300 MHz, CDCl$_3$) δ 11.02 (br s, 1H), 8.62 (s, 1H), 8.16 (s, 1H); MS (ESI) m/z: 322 (M+H$^+$).

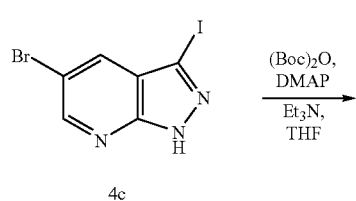

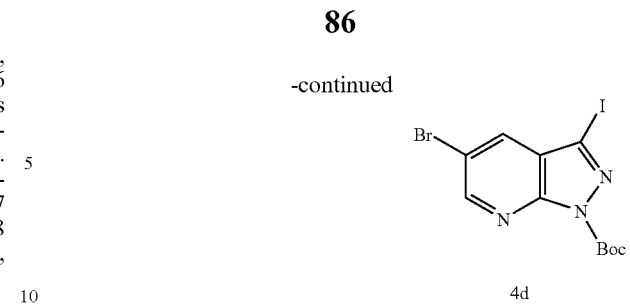

Compound 4c (0.90 g, 2.78 mmol), (BOC)$_2$O (0.73 g, 4.19 mmol), DMAP (40 mg, 0.33 mmol), Et$_3$N (0.78 mL, 5.5 mmol), and THF (50 mL) were added to a flask and the mixture was stirred at room temperature for 1 hr, then concentrated and the residue purified by flash chromatography (silica gel; CH$_2$Cl$_2$) to afford Compound 4d (1.1 g, 94%) as a white-solid. $^1$H NMR (300 MHz, CDCl$_3$) δ 8.78 (s, 1H), 8.13 (s, 1H), 1.72 (s, 9H); MS (ESI) m/z: 425 (M+H$^+$).

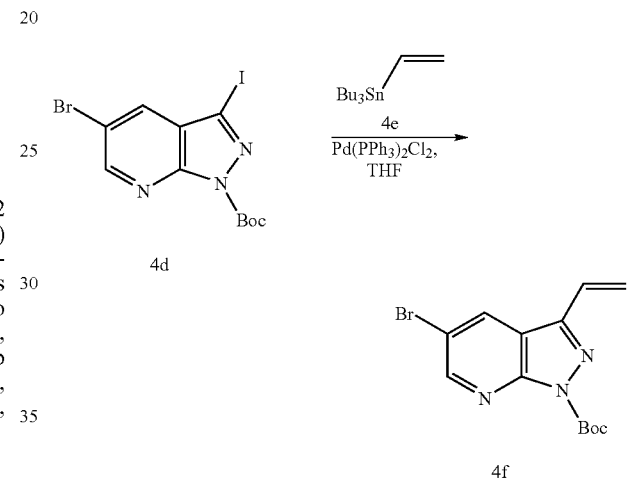

Compound 4d (1.0 g, 2.36 mmol), trimethyl vinyl tin Compound 4e (0.9 g, 2.84 mmol), dichlorobis(triphenylphosphine)palladium(II) (0.16 g, 0.23 mmol) and THF (10 mL) were added to a screw cap tube. The mixture was flushed with nitrogen, then heated to 80° C. overnight. The solvent was removed in vacuo and the residue was purified by flash chromatography (silica gel, CH$_2$Cl$_2$) to afford Compound 4f (0.54 g, 70%) as a white solid. $^1$H NMR (400 MHz, CDCl$_3$) δ 8.76 (s, 1H), 8.38 (s, 1H), 6.96 (dd, J=13.2, 10.6 Hz, 1 H), 6.19 (d, J=13.2 Hz, 1 H), 5.78 (d, J=10.6 Hz, 1 H), 1.76 (s, 9 H); MS (ESI) m/z: 325 (M+H$^+$).

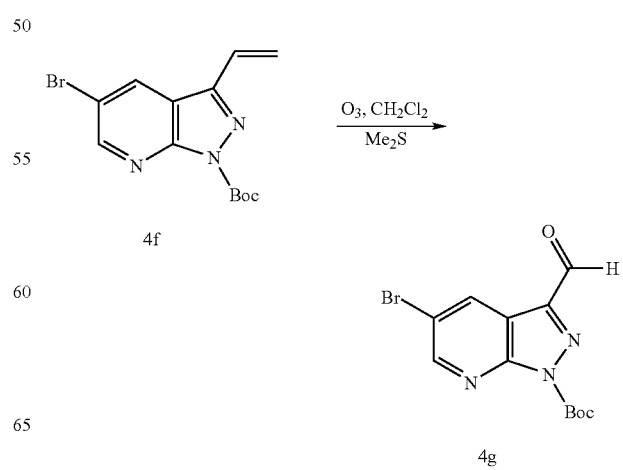

Compound 4f (100 mg, 0.31 mmol) was dissolved in CH$_2$Cl$_2$ (15 mL) and cooled to −78° C. Ozone was bubbled into the solution until the solution turned blue. The solution was purged with N$_2$ and a drop of dimethyl sulfide was added. The temperature of the mixture was maintained at −78° C. for 10 minutes. The mixture was warmed to room temperature and stirred for 30 minutes. The solvent was removed in vacuo and the residue was purified by flash chromatography (silica gel, CH$_2$Cl$_2$) to afford Compound 4g (50 mg, 50%) as a white solid. $^1$H NMR (400 MHz, CDCl$_3$) δ 10.24 (s, 1H), 8.84 (s, 1H), 8.78 (s, 1 H), 1.78 (s, 9 H); MS (ESI) m/z: 327 (M+H)$^+$.

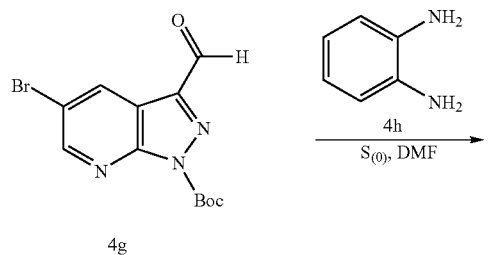

4g    4h

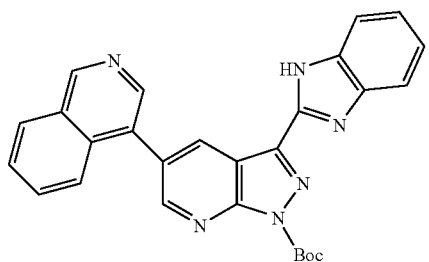

4k

Compound 4i (7.0 mg, 0.017 mmol), 4-trimethylstannyl-isoquinoline Compound 4j (5.4 mg, 0.018 mmol), dichlorobis(triphenylphosphine)palladium(II) (3.0 mg, 0.0043 mmol), copper (I) iodide (3.0 mg, 0.016 mmol) and THF (3 mL) were added to a screw cap tube. The mixture was purged with nitrogen at 0° C. for a few minutes, then heated to 95° C. overnight. The solvent was removed in vacuo and the residue was purified by flash chromatography (silica gel, CH$_2$Cl$_2$: EtOAc 1:1) to afford Compound 4k (6.3 mg, 81%). $^1$H NMR (400 MHz, CDCl$_3$) δ 10.66 (s, 1 H), 9.36 (s, 1 H), 9.24 (s, 1 H), 8.94 (s, 1 H), 8.56 (s, 1 H), 8.08 (d, J=7.2 Hz, 1 H), 7.79 (m, 1 H), 7.62 (m 3 H), 7.52 (t, J=7.2 Hz, 1 H), 7.44 (t, J=7.2 Hz, 1 H), 7.30 (m, 1 H), 1.80 (s, 9 H); MS (ESI) m/z: 463 (M+H)$^+$.

Compound 4g (10.0 mg, 0.03 mmol), 1,2-benzenediamine Compound 4h (3.3 mg, 0.03 mmol), sulfur (1.2 mg, 0.038 mmol) and N,N-dimethyl formamide (2 mL) were added to a nitrogen-purged flask. The mixture was heated to 90° C. for 2 hrs, then poured into water and extracted with EtOAc. The organic layer was separated, dried with MgSO$_4$, then concentrated and the residue was purified by flash chromatography (silica gel, CH$_2$Cl$_2$:EtOAc/9:1) to afford Compound 4i (8.9 mg, 70%). $^1$H NMR (400 MHz, CDCl$_3$) δ 10.55 (s, 1H), 9.22 (s, 1H), 8.81 (s, 1 H), 7.88 (d, J=8.0 Hz, 1 H), 7.52 (d, J=8.0 Hz, 1 H), 7.35 (m, 2 H), 1.76 (s, 9 H); MS (ESI) m/z: 327 (M+H)$^+$.

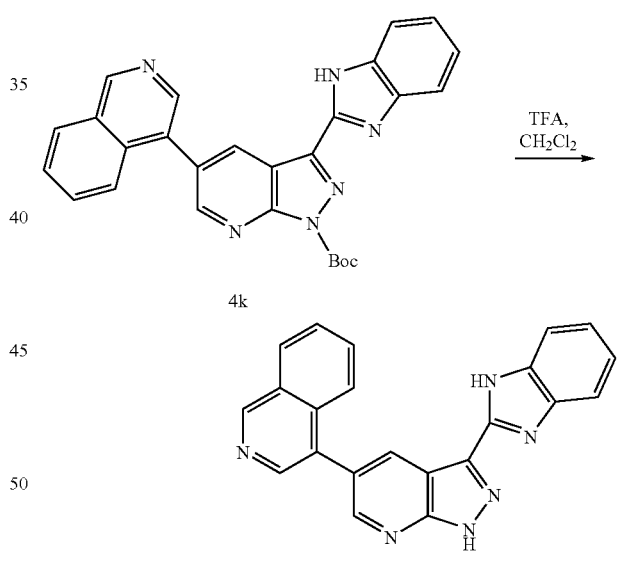

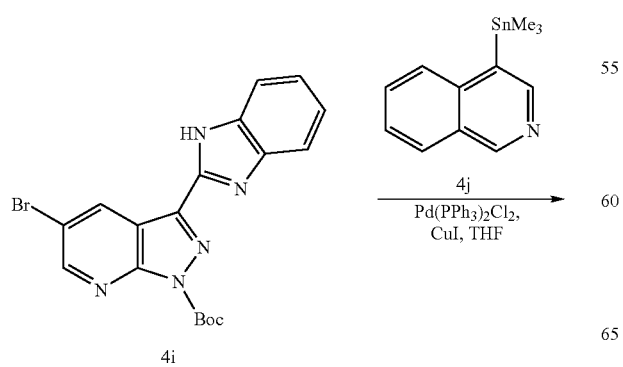

4i

Compound 4k (5.0 mg, 0.011 mmol), TFA (0.5 mL) and CH$_2$Cl$_2$ (2 mL) were added to a flask. The mixture was stirred for 3 hrs, then concentrated. The residue was dissolved in EtOAc, then washed with aqueous sodium bicarbonate. The organic layer was separated, dried with MgSO$_4$, then concentrated. The residue was purified by flash chromatography to afford Compound 1 (1.5 mg, 38%) as a white solid. $^1$H NMR (400 MHz, CDCl$_3$) δ 10.28 (s, 1 H), 9.36 (s, 1 H), 9.37 (s, 1

H), 9.18 (s, 1 H), 8.83 (s, 1 H), 8.13 (d, J=7.2 Hz, 1 H), 7.88 (d, J=7.2 Hz, 1 H), 7.73 (m, 4 H), 7.58 (m, 1 H), 7.31 (m, 1 H); MS (ESI) m/z: 367 (M+H)+.

Example 5

4-[3-(4-methyl-1H-benzoimidazol-2-yl)-1H-pyrazolo[3,4-b]pyridin-5-yl]-isoquinoline (Compound 2)

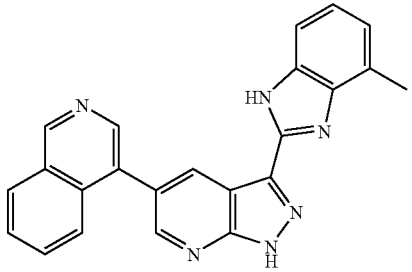

A mixture of 5-bromo-1H-pyrazolo[3,4-b]pyridine-3-carbaldehyde Compound 5a (50 mg, 0.22 mmol) and 3-methylbenzene-1,2-diamine Compound 5b (27 mg, 0.22 mmol) and sulfur (9 mg, 0.28 mmol) in DMF (1 mL) was heated to 100° C. overnight. The solvent was removed and the residue was purified by silica gel chromatography (10% to 50% of ethyl acetate in hexanes) to yield 5-bromo-3-(4-methyl-1H-benzoimidazol-2-yl)-1H-pyrazolo[3,4-b]pyridine Compound 5c (50 mg, 69% yield) as a grey powder. $^1$H NMR (400 MHz, MeOD) δ 9.03 (s, 1H), 8.68 (s, 1H), 7.18 (t, 1H, J=8.4 Hz), 7.09 (m, 2H), 2.69 (s, 3H); MS (ESI) m/z: 329 (M+H+).

Compound 5c (15 mg, 0.05 mmol) was stirred with (BOC)$_2$O (23 μL, 0.11 mmol), DMAP (1 mg, 0.005 mmol), TEA (19 μl, 0.15 mmol) in DCM (2 mL) at room temperature for one hour. The solution was diluted with addition DCM (30 mL) and washed with saturated aqueous sodium bicarbonate solution. The organic phase was dried (MgSO$_4$) and evaporated to give the bis-Boc-protected 5-bromo-3-(4-methyl-1H-benzoimidazol-2-yl)-1H-pyrazolo[3,4-b]pyridine Compound 5d (24 mg, 98%) as brown foam. $^1$H NMR (400 MHz, CDCl$_3$) δ 8.85 (s, 1H), 8.54 (s, 1H), 7.89 (d, 1H, J=8.4 Hz), 7.33 (t, 1H, J=8.4 Hz), 7.20 (d, 1H, J=8.4 Hz), 2.72 (s, 3H), 1.72 (s, 9H), 1.44 (s, 9H); MS (ESI) m/z: 529 (M+H+).

Compound 5d (30 mg, 0.06 mmol), 4-trimethylstannylisoquinoline Compound 4j (18.3 mg, 0.06 mmol), dichlorobis(triphenylphosphine)palladium(II) (12.0 mg, 0.002 mmol), copper (I) iodide (11.0 mg, 0.06 mmol) and THF (3 mL) were added to a screw cap tube. The mixture was purged with nitrogen for a few minutes and then heated to 95° C. overnight. The solvent was removed in vacuo and the residue was purified by flash chromatography (silica gel, CH$_2$Cl$_2$:EtOAc 1:1). The fractions were concentrated and the residue was dissolved in TFA (0.4 mL) and CH$_2$Cl$_2$ (1.2 mL). The mixture was stirred at room temperature for 10 minutes then the solvent was removed. The crude product was purified by semi-prep Gilson HPLC (10% to 90% of 0.1% TFA in ACN/0.1% TFA in H$_2$O) to yield Compound 2 (3 mg, 14%) as a white powder. $^1$H NMR (300 MHz, MeOD) δ 9.08 (s, 2H), 8.89 (s, 2H), 8.45 (d, 1H, J=7.5 Hz), 8.02 (m, 3H), 7.60 (m, 1H), 7.41 (t, 1H, J=7.5 Hz), 7.31 (d, 1H, J=7.5 Hz), 2.69 (s, 3H); MS (ESI) m/z: 377 (M+H+).

Example 6

[2-(5-isoquinolin-4-yl-1H-pyrazolo[3,4-b]pyridin-3-yl)-1H-benzoimidazol-4-yl]-methanol (Compound 3)

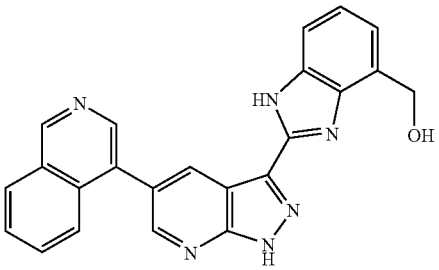

A mixture of 5-bromo-1H-pyrazolo[3,4-b]pyridine-3-carboxylic acid Compound 1c (1.0 g, 4.13 mmol) and 3-(tert-butyl-dimethyl-silanyloxymethyl)-benzene-1,2-diamine Compound 6a (1.05 g, 4.17 mmol), HATU (1.58 g, 4.16 mmol) and DIPEA (2.5 mL, 35.9 mmol) in DMF (50 mL) was stirred at room temperature overnight. The solvent was removed and the residue was dissolved in ethyl acetate (100 mL), then sequentially washed with hydrochloric acid 20 mL, 1M), water (30 mL×3) and brine (20 mL). The organic solution was evaporated to dryness in vacuo and purified by silica gel chromatography (10% to 50% of ethyl acetate in hexanes) to yield 5-bromo-1H-pyrazolo[3,4-b]pyridine-3-carboxylic acid [2-amino-3-(tert-butyl-dimethyl-silanyloxymethyl)-phenyl]-amide Compound 6b (1.21 g, 61% yield) as a yellow powder. $^1$H NMR (300 MHz, CDCl$_3$) δ 8.91 (d, 1H, J=2.1 Hz), 8.73 (s, 1H), 8.67 (d, 1H, J=2.1 Hz), 7.47 (d, 1H, J=7.2 Hz), 7.01 (d, 1H, J=7.2 Hz), 6.83 (t, 1H, J=7.2 Hz), 4.78 (s, 2H), 0.95 (s; 9H), 0.11 (s, 6H); MS (ESI) m/z: 477 (M+H+).

A solution of Compound 6b (1.1 g, 2.31 mmol) in glacial acetic acid (12 mL) was heated in an oil-bath at 80° C. for 3.5 hrs, then evaporated to dryness in vacuo. The residue was purified by silica gel column chromatography (10% to 50% of ethyl acetate in hexanes) to give 5-bromo-3-[4-(tert-butyl-dimethyl-silanyloxymethyl)-1H-benzoimidazol-2-yl]-1H-pyrazolo[3,4-b]pyridine Compound 6c (0.936 g, 88%) as a white powder. $^1$H NMR (300 MHz, MeOD) δ 9.06 (d, 1H, J=2.1 Hz), 8.66 (d, 1H, J=2.1 Hz), 7.31 (m, 3H), 5.49 (s, 2H), 0.99 (s, 9H), 0.18 (s, 6H); MS (ESI) m/z: 459 (M+H+).

A mixture of Compound 6c (0.936 g, 2.04 mmol), (BOC)$_2$O (1.03 mL, 4.48 mmoL), DMAP (20 mg, 0.16 mmol), TEA (994 uL, 7.72 mmol) in DCM (50 mL) were stirred at room temperature for one hour. The solution was diluted with additional DCM (50 mL) and washed with a saturated aqueous sodium bicarbonate solution. The organic phase was dried (MgSO$_4$) and evaporated to give the bis-Boc-protected 5-bromo-3-[4-(tert-butyl-dimethyl-silanyloxymethyl)-1H-benzoimidazol-2-yl]-1H-pyrazolo[3,4-b]pyridine Compound 6d (1.55 g, 100%) as a brown foam. $^1$H NMR (300 MHz, CDCl$_3$) δ 8.33 (d, 1H, J=2.4 Hz), 8.49 (d, 1H, J=2.4 Hz), 7.96 (d, 1H, J=8.4 Hz), 7.58 (d, 1H, J=8.4 Hz), 7.49 (t, 1H, J=8.4 Hz), 5.30 (s, 2H), 1.76 (s, 9H), 1.53 (s, 9H), 0.99 (s, 9H), 0.17 (s, 6H); MS (ESI) m/z: 659 (M+H+).

A mixture of Compound 6d (0.936 mg, 1.42 mmol), 4-isoquinoline boronic acid Compound 3a (0.3 g, 1.73 mmol), tetrakis(triphenylphosphine)palladium(0) (0.25 g, 0.22 mmol) and aqueous sodium carbonate solution (1.8 mL, 2M, 3.6 mmol) in dioxane (40 mL) and MeOH (12 mL) was flushed with nitrogen for 10 minutes in a reaction tube before the tube was sealed and heated at 90° C. overnight. The reaction was then cooled to room temperature. The organic layer was removed from the tube and the residue was dissolved in water (10 mL). The aqueous layer was extracted with 5% of MeOH in DCM (30 mL×3). The combined organic layer was concentrated and purified by silica gel chromatography (25% to 50% of ethyl acetate in hexanes) to afford Compound 6e (0.43 g, 63%) as yellow powder. $^1$H NMR (300 MHz, CDCl$_3$) δ 12.09 (b, 1H), 10.65 (b, 1H), 9.35 (s, 1H), 9.20 (s, 1H), 8.80 (s, 1H), 8.64 (s, 1H), 8.10 (d, 1H, J=6.6 Hz), 7.86 (d, 1H, J=8.1 Hz), 7.71 (m, 2H), 7.49 (m, 1H), 7.23 (t, 1H, J=7.8 Hz), 7.23 (d, 1H, J=6.3 Hz), 5.13 (s, 2H), 0.97 (s, 9H), 0.15 (s, 6H); MS (ESI) m/z: 507 (M+H$^+$).

Compound 6e (0.5 g, 0.99 mmol) was dissolved in dry THF (50 mL) and TBAF (2 mL, 1M THF solution, 2 mmol) was added. The reaction was closely monitored via TLC. The solvent was removed after 30 minutes and the residue was purified on silica gel chromatography to yield Compound 3 (0.28 g, 72%) as light yellow powder. $^1$H NMR (300 MHz, MeOD) δ 9.61 (s, 1H), 9.12 (s, 1H), 9.08 (s, 1H), 8.82 (s, 1H), 8.40 (m, 2H), 8.03 (m, 3H), 7.49 (m, 2H), 5.03 (s, 2H); MS (ESI) m/z: 393 (M+H$^+$).

Example 7

4-[3-(4-pyrrolidin-1-ylmethyl-1H-benzoimidazol-2-yl)-1H-pyrazolo[3,4-b]pyridin-5-yl]-isoquinoline (Compound 7)

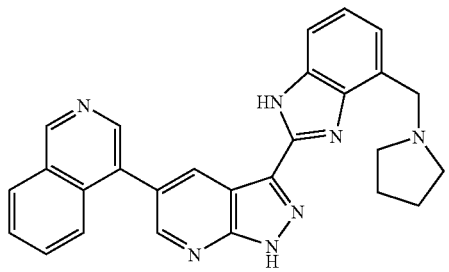

A suspension of Compound 3 (30 mg, 0.08 mmol) and DIPEA (28 μl, 0.36 mmol) in dry THF (1 mL) was cooled to 0° C. Methanesulfonyl chloride (18 μl, 0.23 mmol) was added dropwise and the mixture was stirred at 0° C. for 3 hours. Pyrrolidine (32 μl 0.39 mmol) was added and the suspension was gradually warmed to room temperature and stirred for 2 hours. The reaction was quenched with water (0.1 mL) and the solvent was removed in vacuo. The crude product was purified by silica gel chromatography to give Compound 7 (13 mg, 38%) as a yellow powder. $^1$H NMR (300 MHz MeOD) δ 9.36 (s, 1H), 9.10 (d, 1H, J=2.1 Hz), 8.78 (d, 1H, J=2.1 Hz), 8.55 (s, 1H), 8.27 (d, 1H, J=7.8 Hz), 7.95 (m, 1H), 7.83 (m, 2H), 7.72 (dd, 1H, J=1.8, 7.2 Hz), 7.39 (m, 2H), 4.75 (s, 2H), 3.38 (b, 4H), 2.01 (b, 4H); MS (ESI) m/z: 446 (M+H$^+$).

Using the procedure of Example 7, other compounds of the present invention were prepared:

| Cpd | Data |
|---|---|
| 8 | 4-[3-(4-piperidin-1-ylmethyl-1H-benzoimidazol-2-yl)-1H-pyrazolo[3,4-b]pyridin-5-yl]-isoquinoline<br>piperidine was used in place of pyrrolidine (34%).<br>$^1$H NMR (300 MHz, CD$_3$OD) δ 9.92 (s, 1H), 9.24 (d, 1H, J = 2.1 Hz), 8.92 (d, 1H, J = 2.1 Hz), 8.79 (s, 1H), 8.68 (d, 1H, J = 8.4 Hz), 8.25 (m, 2H), 8.15 (m, 1H), 7.82 (m, 1H), 7.49 (m, 2H), 4.75 (s, 2H), 3.55 (b, 2H), 3.06 (b, 2H), 1.88 (b, 2H), 1.69 (b, 2H), 1.40 (b, 2H),; MS (ESI) m/z: 460 (M + H$^+$). |
| 9 | 4-[3-(4-morpholin-4-ylmethyl-1H-benzoimidazol-2-yl)-1H-pyrazolo[3,4-b]pyridin-5-yl]-isoquinoline<br>morpholine was used in place of pyrrolidine (21%).<br>$^1$H NMR (300 MHz, CD$_3$OD) δ 9.35 (s, 1H), 9.08 (s, 1H), 8.78 (s, 1H), 8.56 (s, 1H), 8.26 (d, 1H, J = 7.8 Hz), 8.01 (m, 2H), 7.83 (m, 2H), 7.25 (m, 2H), 5.03 (s, 2H), 3.96 (b, 4H), 3.72 (b, 4H); MS (ESI) m/z: 462 (M + H$^+$). |
| 10 | 4-{3-[4-(4-ethyl-piperazin-1-ylmethyl)-1H-benzoimidazol-2-yl]-1H-pyrazolo[3,4-b]pyridin-5-yl}-isoquinoline<br>N-ethyl piperazine was used in place of pyrrolidine (48%).<br>$^1$H NMR (300 MHz, CD$_3$OD) δ 9.89 (s, 1H), 9.18 (s, 1H), 8.89 (s, 1H), 8.78 (s, 1H), 8.61 (d, 1H, J = 7.8 Hz), 8.25 (m, 2H), 8.12 (m, 1H), 7.79 (d, 1H, J = 7.2 Hz), 7.51 (m, 2H), 4.55 (s, 2H), 3.42 (b, 4H), 3.35 (b, 4H), 3.19 (q, 2H, J = 7.8 Hz), 1.25 (t, 3H, J = 7.8 Hz); MS (ESI) m/z: 489 (M + H$^+$). |
| 12 | 4-[3-(4-imidazol-1-ylmethyl-1H-benzoimidazol-2-yl)-1H-pyrazolo[3,4-b]pyridin-5-yl]-isoquinoline<br>imidazole was used in place of pyrrolidine (16%).<br>$^1$H NMR (300 MHz, CD$_3$OD) δ 9.79 (s, 1H), 9.13 (d, 1H, J = 2.1 Hz), 8.91 (s, 1H), 8.87 (d, 1H, J = 2.1 Hz), 8.78 (s, 1H), 8.72 (s, 1H), 7.59 (d, 1H, J = 8.1 Hz), 8.19 (m, 2H), 8.08 (m, 1H), 7.66 (d, 1H, J = 8.4 Hz), 7.59 (s, 1H), 7.39 (t, 1H, J = 8.4 Hz), 7.24 (m, 1H), 4.53 (s, 2H); MS (ESI) m/z: 443 (M + H$^+$). |
| 13 | isopropyl-[2-(5-isoquinolin-4-yl-1H-pyrazolo[3,4-b]pyridin-3-yl)-1H-benzoimidazol-4-ylmethyl]-amine<br>isopropyl amine was used in place of pyrrolidine (11%).<br>$^1$H NMR (300 MHz, CD$_3$OD) δ 9.69 (s, 1H), 9.18 (s, 1H), 8.89 (s, 1H), |

| Cpd | Data |
|---|---|
|  | 8.85 (s, 1H), 8.70 (d, 1H, J = 7.8 Hz), 8.51 (m, 1H), 8.11 (m, 2H), 7.72 (m, 1H), 7.41 (m, 2H), 4.62 (s, 2H), 3.54 (m, 1H), 1.80 (d, 6H, J = 4.8 Hz); MS (ESI) m/z: 434 (M + H$^+$). |
| 14 | 4-{3-[4-(2-methoxy-ethoxymethyl)-1H-benzoimidazol-2-yl]-1H-pyrazolo[3,4-b]pyridin-5-yl}-isoquinoline<br>2-methoxyethanol via sodium hydride was used in place of pyrrolidine (9%).<br>$^1$H NMR (400 MHz, CD$_3$OD) δ 9.84 (s, 1H), 9.22 (d, 1H, J = 2.4 Hz), 8.87 (d, 1H, J = 2.4 Hz), 8.76 (s, 1H), 8.62 (d, 1H, J = 8.0 Hz), 8.27 (m, 2H), 8.11 (m, 1H), 7.81 (d, 1H, J = 8.0 Hz), 7.52 (d, 1H, J = 8.0 Hz), 7.45 (t, 1H, J = 8.0 Hz), 5.25 (s, 2H), 3.76 (m, 2H), 3.62 (m, 2H), 3.39 (s, 3H); MS (ESI) m/z: 451 (M + H$^+$). |
| 15 | 4-{3-[4-(2-morpholin-4-yl-ethoxymethyl)-1H-benzoimidazol-2-yl]-1H-pyrazolo[3,4-b]pyridin-5-yl}-isoquinoline<br>2-morpholin-4-yl-ethanol via sodium hydride was used in place of pyrrolidine (17%).<br>$^1$H NMR (400 MHz, CD$_3$OD) δ 9.84 (s, 1H), 9.22 (d, 1H, J = 2.4 Hz), 8.89 (d, 1H, J = 2.4 Hz), 8.76 (s, 1H), 8.63 (d, 1H, J = 8.0 Hz), 8.26 (m, 2H), 8.11 (m, 1H), 7.81 (d, 1H, J = 8.0 Hz), 7.50 (m, 2H), 5.25 (s, 2H), 4.13 (b, 4H), 3.99 (m, 2H), 3.67 (b, 6H); MS (ESI) m/z: 506 (M + H$^+$). |
| 16 | 4-{3-[4-(2-ethoxy-ethoxymethyl)-1H-benzoimidazol-2-yl]-1H-pyrazolo[3,4-b]pyridin-5-yl}-isoquinoline<br>2-ethoxyethanol via sodium hydride was used in place of pyrrolidine. |
| 32 | 4-[3-(4-isopropoxymethyl-1H-benzoimidazol-2-yl)-1H-pyrazolo[3,4-b]pyridin-5-yl]-isoquinoline<br>isopropyl alcohol via sodium hydride was used in place of pyrrolidine (17%).<br>$^1$H NMR (300 MHz, CD$_3$OD) δ 9.80 (s, 1H), 9.07 (d, 1H, J = 2.1 Hz), 8.92 (d, 1H, J = 2.1 Hz), 8.73 (s, 1H), 8.59 (d, 1H, J = 8.1 Hz), 8.20 (m, 2H), 8.08 (m, 1H), 7.78 (d, 1H, J = 7.8 Hz), 7.59 (d, 1H, J = 7.8 Hz), 7.53 (t, 1H, J = 7.8 Hz), 5.05 (s, 2H), 3.96 (m, 1H), 1.84 (d, 6H, J = 4.8 Hz); MS (ESI) m/z: 435 (M + H$^+$). |

Example 8

2-(5-isoquinolin-4-yl-1H-pyrazolo[3,4-b]pyridin-3-yl)-1H-benzoimidazole-4-carboxylic acid methyl ester (Compound 108)

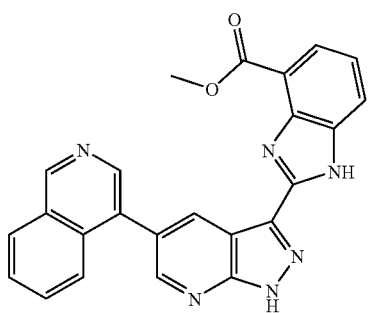

A mixture of 5-bromo-1H-pyrazolo[3,4-b]pyridine-3-carboxylic acid Compound 1c (0.3 g, 1.17 mmol), 2,3-diaminobenzoic acid methyl ester Compound 8a (3.43 g, 20.64 mmol), HATU (7.85 g, 20.66 mmol), DIPEA (8.64 mL, 62 mmol) in DMF (250 mL) was stirred at room temperature overnight. The solvent was removed and the residue was purified by silica gel chromatography (10% to 90% of ethyl acetate in hexanes) to yield 2-amino-3-[(5-bromo-1H-pyrazolo[3,4-b]pyridine-3-carbonyl)-amino]-benzoic acid methyl ester Compound 8b (5.1 g, 63% yield) as a colorless gel. $^1$H NMR (300 MHz, CD$_3$OD) δ 9.03 (d, 1H, J=2.1 Hz), 8.78 (d, 1H, J=2.1 Hz), 7.58 (d, 1H, J=7.8 Hz), 7.26 (d, 1H, J=7.8 Hz), 7.15 (t, 1H, J=7.8 Hz), 3.49 (s, 3H); MS (ESI) m/z: 391 (M+H$^+$).

A solution of Compound 8b (5.1 g, 13.08 mmol) in glacial acetic acid (70 mL) was heated in an oil-bath at 80° C. for 7 hrs; and evaporated to dryness in vacuo. The residue was purified by silica gel column chromatography (20% to 90% of ethyl acetate in hexanes) to give 2-(5-bromo-1H-pyrazolo[3,4-b]pyridin-3-yl)-1H-benzoimidazole-4-carboxylic acid methyl ester Compound 8c (3.7 g, 76%) as a grey gel. $^1$H NMR (300 MHz, CD$_3$OD) δ 9.06 (d, 1H, J=1.8 Hz), 8.96 (d, 1H, J=1.8 Hz), 8.74 (d, 1H, J=6.3 Hz), 8.52 (d, 1H, J=6.3 Hz), 7.41 (t, 1H, J=6.3 Hz), 3.99 (s, 3H); MS (ESI) m/z: 373 (M+H$^+$).

A mixture of Compound 8c (1.5 g, 4.04 mmol) was stirred with (BOC)$_2$O (2.2 mL, 9.57 mmoL), DMAP (0.1 g, 0.82 mmol) and TEA (1.69 mL, 12.13 mmol) in DCM (100 mL) at room temperature for one hour. The solution was diluted with additional DCM (100 mL) and washed with a saturated aqueous sodium bicarbonate solution. The organic phase was dried (MgSO$_4$) and evaporated to give the bis-Boc-protected 2-(5-bromo-1H-pyrazolo[3,4-b]pyridin-3-yl)-1H-benzoimidazole-4-carboxylic acid methyl ester Compound 8d (1.89 g, 99%) as white foam. MS (ESI) m/z: 573 (M+H$^+$).

A mixture of Compound 8d (2.31 g, 4.05 mmol), 4-isoquinoline boronic acid Compound 3a (0.84 g, 4.86 mmol), tetrakis(triphenylphosphine)palladium(0) (0.7 g, 0.61 mmol) and an aqueous sodium carbonate solution (5.06 mL, 2M, 10.12 mmol) in dioxane (120 mL) and MeOH (35 mL) was flushed with nitrogen for 10 minutes in a reaction tube before the tube was sealed and heated at 90° C. overnight. The reaction mixture was cooled to room temperature, the organic layer was removed from the tube and the residue was dissolved in water (50 mL). The aqueous layer was extracted with 5% of MeOH in DCM (100 mL×3). The combined organic layer was concentrated and purified with silica gel chromatography (25% to 90% of ethyl acetate in hexanes) to afford Compound 108 (1.5 g, 88%) as a yellow powder. $^1$H NMR (300 MHz, CD$_3$OD) δ 9.82 (s, 1H), 9.13 (s, 1H), 8.90 (s, 1H), 8.75 (s, 1H), 8.62 (d, 1H, J=8.4 Hz), 8.13 (m, 3H), 7.62 (d, 1H, J=7.8 Hz), 7.22 (d, 1H, J=7.8 Hz), 7.10 (t, 1H, J=7.8 Hz), 4.08 (s, 3H); MS (ESI) m/z: 421 (M+H$^+$).

Example 9

2-(5-isoquinolin-4-yl-1H-pyrazolo[3,4-b]pyridin-3-yl)-1H-benzoimidazole-4-carboxylic acid (Compound 17)

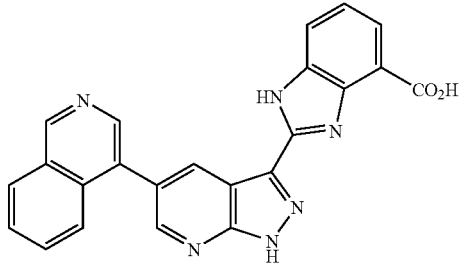

Compound 108 (1.5 g, 3.57 mmol) was suspended in a 10% aqueous sodium hydroxide solution (20 mL) and MeOH (10 mL). The suspension was heated to 80° C. for five hours. The reaction mixture was cooled to room temperature then acidified with 1M hydrochloric acid. The resulting precipitate was collected and the filtrate was concentrated to remove the residual MeOH. Additional precipitate was collected and combined with the previous portion and dried to afford Compound 17 (1.2 g, 83%) as a grey solid. $^1$H NMR (400 MHz, CD$_3$OD) δ 9.81 (s, 1H), 9.14 (s, 1H), 8.89 (m, 2H), 8.61 (d, 1H, J=8.4 Hz), 8.23 (m, 2H), 8.06 (m, 2H), 8.03 (d, 1H, J=8.0 Hz), 7.44 (t, 1H, J=8.0 Hz); MS (ESI) m/z: 407 (M+H$^+$).

Example 10

2-(5-isoquinolin-4-yl-1H-pyrazolo[3,4-b]pyridin-3-yl)-1H-benzoimidazole-4-carboxylic acid isopropylamide (Compound 18)

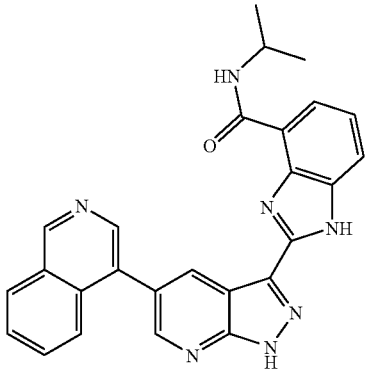

A mixture of Compound 17 (25 mg, 0.06 mmol), isopropylamine (11 μl, 0.12 mmol), HATU (23.4 mg, 0.06 mmol) and DIPEA (35 μl, 0.48 mmol) in DMSO (1 mL) was stirred at room temperature overnight. The solution was diluted with MeOH (0.4 mL) and purified by Gilson HPLC (10% to 90% of 0.1% TFA in ACN/0.1% TFA in H$_2$O) to yield Compound 18 (9 mg, 33%) as a pale yellow solid. $^1$H NMR (300 MHz, CD$_3$OD) δ 9.79 (s, 1H), 8.96 (s, 1H), 8.84 (s, 1H), 8.78 (s, 1H), 8.57 (d, 1H, J=8.4 Hz), 8.16 (m, 2H), 8.04 (m, 1H), 7.87 (d, 1H, J=7.8 Hz), 7.69 (d, 1H, J=6.9 Hz), 7.32 (t, 1H, J=7.8 Hz), 3.99 (m, 1H), 0.86 (d, 6H, J=6 Hz); MS (ESI) m/z: 448 (M+H$^+$).

Using the procedure of Example 10, other compounds of the present invention were prepared:

| Cpd | Data |
|---|---|
| 19 | 2-(5-isoquinolin-4-yl-1H-pyrazolo[3,4-b]pyridin-3-yl)-1H-benzoimidazole-4-carboxylic acid diethylamide<br>N,N-diethylamine was used in place of isopropylamine (46%).<br>$^1$H NMR (300 MHz, CD$_3$OD) δ 9.83 (s, 1H), 9.10 (d, 1H, J = 1.8 Hz), 8.85 (d, 1H, J = 1.8 Hz), 8.71 (s, 1H), 8.62 (d, 1H, J = 8.1 Hz), 8.22 (m, 2H), 8.11 (m, 1H), 7.34 (d, 1H, J = 8.1 Hz), 7.45 (dd, 1H, J = 7.2, 8.1 Hz), 7.34 (d, 1H, J = 7.2 Hz), 3.58 (b, 4H), 1.16 (b, 3H), 1.07 (b, 3H); MS (ESI) m/z: 462 (M + H$^+$). |
| 20 | 2-(5-isoquinolin-4-yl-1H-pyrazolo[3,4-b]pyridin-3-yl)-1H-benzoimidazole-4-carboxylic acid tert-butylamide<br>tert-butylamine was used in place of isopropylamine (31%).<br>$^1$H NMR (300 MHz, CD$_3$OD) δ 9.88 (s, 1H), 9.07 (d, 1H, J = 2.1 Hz), 8.87 (d, 1H, J = 2.1 Hz), 8.79 (s, 1H), 8.65 (d, 1H, J = 8.4 Hz), 8.24 (m, 2H), 8.13 (m, 1H), 7.92 (d, 1H, J = 7.5 Hz), 7.75 (d, 1H, J = 7.8 Hz), 7.38 (dd, 1H, J = 7.5, 7.8 Hz), 1.20 (s, 9H); MS (ESI) m/z: 462 (M + H$^+$). |
| 21 | [2-(5-isoquinolin-4-yl-1H-pyrazolo[3,4-b]pyridin-3-yl)-1H-benzoimidazole-4-yl]-pyrrolidin-1-yl-methanone<br>pyrrolidine was used in place of isopropylamine (44%).<br>$^1$H NMR (300 MHz, CD$_3$OD) δ 9.79 (s, 1H), 9.09 (d, 1H, J = 2.1 Hz), 8.84 (d, 1H, J = 2.1 Hz), 8.68 (s, 1H), 8.60 (d, 1H, J = 8.1 Hz), 8.18 (m, 2H), 8.07 (m, 1H), 7.77 (m, 1H), 7.46 (m, 2H), 3.62 (b, 2H), 3.46 (b, 2H), 2.00 (b, 2H), 1.83 (b, 2H); MS (ESI) m/z: 460 (M + H$^+$). |
| 22 | [2-(5-isoquinolin-4-yl-1H-pyrazolo[3,4-b]pyridin-3-yl)-1H-benzoimidazol-4-yl]-piperidin-1-yl-methanone<br>piperidine was used in place of isopropylamine (38%).<br>$^1$H NMR (300 MHz, CD$_3$OD) δ 9.83 (s, 1H), 9.12 (d, 1H, J = 2.1 Hz), 8.86 (d, 1H, J = 2.1 Hz), 8.72 (s, 1H), 8.62 (d, 1H, J = 7.8 Hz), 8.22 (m, 2H), 8.11 (m, 1H), 7.76 (d, 1H, J = 8.1 Hz), 7.45 (dd, 1H, J = 7.2, 8.1 Hz), 7.35 (d, 1H, J = 7.2 Hz), 3.73 (b, 2H), 3.33 (b, 2H), 1.56 (b, 6H); MS (ESI) m/z: 474 (M + H$^+$). |

| Cpd | Data |
|---|---|
| 23 | [2-(5-isoquinolin-4-yl-1H-pyrazolo[3,4-b]pyridin-3-yl)-1H-benzoimidazole-4-yl]-(4-methyl-piperazin-1-yl)-methanone<br>1-methyl-piperazine was used in place of isopropylamine (24%).<br>$^1$H NMR (300 MHz, CD$_3$OD) δ 9.84 (s, 1H), 9.10 (d, 1H, J = 2.1 Hz),<br>8.87 (d, 1H, J = 2.1 Hz), 8.73 (s, 1H), 8.63 (d, 1H, J = 8.1 Hz), 8.23 (m, 2H),<br>8.09 (m, 1H), 7.81 (d, 1H, J = 8.1 Hz), 7.46 (m, 2H), 3.22 (b, 4H), 2.98 (b, 4H),<br>2.81 (s, 3H); MS (ESI) m/z: 489 (M + H$^+$). |
| 24 | [2-(5-isoquinolin-4-yl-1H-pyrazolo[3,4-b]pyridin-3-yl)-1H-benzoimidazole-4-yl]-morpholin-4-yl-methanone<br>morpholine was used in place of isopropylamine (27%).<br>$^1$H NMR (300 MHz, CD$_3$OD) δ 9.84 (s, 1H), 9.14 (d, 1H, J = 2.1 Hz),<br>8.90 (d, 1H, J = 2.1 Hz), 8.72 (s, 1H), 8.61 (d, 1H, J = 6.9 Hz), 8.25 (m, 2H),<br>8.11 (m, 1H), 7.78 (d, 1H, J = 8.4 Hz), 7.47 (dd, 1H, J = 7.2, 8.4 Hz), 7.39 (d,<br>1H, J = 7.2 Hz), 3.77 (b, 4H), 3.42 (b, 4H); MS (ESI) m/z: 476 (M + H$^+$). |
| 25 | 2-(5-isoquinolin-4-yl-1H-pyrazolo[3,4-b]pyridin-3-yl)-1H-benzoimidazole-4-carboxylic acid (2-dimethylamino-ethyl)-amide<br>N,N-dimethyl-ethane-1,2-diamine was used in place of isopropylamine<br>(56%).<br>$^1$H NMR (300 MHz, CD$_3$OD) δ 9.84 (s, 1H), 9.14 (d, 1H, J = 2.1 Hz),<br>8.90 (d, 1H, J = 2.1 Hz), 8.72 (s, 1H), 8.61 (d, 1H, J = 8.4 Hz), 8.23 (m, 2H),<br>8.09 (m, 1H), 7.94 (d, 1H, J = 7.8 Hz), 7.83 (d, 1H, J = 7.8 Hz), 7.42 (t, 1H, J = 7.8 Hz),<br>3.78 (m, 2H), 3.46 (m, 2H), 2.97 (s, 6H); MS (ESI) m/z:<br>477 (M + H$^+$). |
| 26 | 2-(5-isoquinolin-4-yl-1H-pyrazolo[3,4-b]pyridin-3-yl)-1H-benzoimidazole-4-carboxylic acid (2-dimethylamino-ethyl)-methyl-amide<br>N,N,N'-trimethyl-ethane-1,2-diamine was used in place of isopropylamine<br>(50%).<br>$^1$H NMR (300 MHz, CD$_3$OD) δ 9.85 (s, 1H), 9.10 (d, 1H, J = 1.8 Hz),<br>8.87 (d, 1H, J = 1.8 Hz), 8.72 (s, 1H), 8.63 (d, 1H, J = 8.4 Hz), 8.21 (m, 2H),<br>8.10 (m, 1H), 7.81 (d, 1H, J = 7.8 Hz), 7.48 (m, 2H), 3.95 (m, 2H), 3.49 (m, 2H),<br>3.06 (s, 3H), 2.93 (s, 6H); MS (ESI) m/z: 491 (M + H$^+$). |
| 27 | 2-(5-isoquinolin-4-yl-1H-pyrazolo[3,4-b]pyridin-3-yl)-1H-benzoimidazole-4-carboxylic acid cyclopentylamide<br>cyclopentylamine was used in place of isopropylamine (50%).<br>$^1$H NMR (300 MHz, CD$_3$OD) δ 9.90 (s, 1H), 8.97 (d, 1H, J = 1.8 Hz),<br>8.85 (m, 2H), 8.67 (d, 1H, J = 8.4 Hz), 8.20 (m, 3H), 7.92 (d, 1H, J = 7.5 Hz),<br>7.74 (d, 1H, J = 7.8 Hz), 7.34 (dd, 1H, J = 7.5, 7.8 Hz), 4.19 (p, 1H, J = 6.3 Hz),<br>2.06 (m, 4H), 1.24 (m, 4H); MS (ESI) m/z: 474 (M + H$^+$). |
| 28 | 2-(5-isoquinolin-4-yl-1H-pyrazolo[3,4-b]pyridin-3-yl)-1H-benzoimidazole-4-carboxylic acid (1-methyl-piperidin-4-yl)-amide<br>1-methyl-piperidin-4-ylamine was used in place of isopropylamine (53%).<br>$^1$H NMR (300 MHz, CD$_3$OD) δ 9.83 (s, 1H), 8.81 (m, 3H), 8.62 (d, 1H, J = 7.5 Hz),<br>8.21 (m, 3H), 7.94 (d, 1H, J = 7.5 Hz), 7.82 (d, 1H, J = 7.8 Hz),<br>7.42 (dd, 1H, J = 7.5, 7.8 Hz), 4.09 (b, 1H), 3.61 (m, 4H), 2.87 (s, 3H),<br>1.52 (m, 4H); MS (ESI) m/z: 503 (M + H$^+$). |
| 29 | 2-(5-isoquinolin-4-yl-1H-pyrazolo[3,4-b]pyridin-3-yl)-1H-benzoimidazole-4-carboxylic acid (4-hydroxy-cyclohexyl)-amide<br>4-amino-cyclohexanol was used in place of isopropylamine (37%).<br>$^1$H NMR (300 MHz, CD$_3$OD) δ 9.90 (s, 1H), 9.00 (d, 1H, J = 7.5 Hz),<br>8.83 (m, 2H), 8.67 (d, 1H, J = 6.0 Hz), 8.26 (m, 2H), 8.13 (t, 1H, J = 5.1 Hz),<br>7.93 (d, 1H, J = 5.4 Hz), 7.75 (d, 1H, J = 6.0 Hz), 7.37 (dd, 1H, J = 5.4, 6.0 Hz),<br>3.80 (b, 1H), 3.56 (m, 1H), 1.84 (m, 4H), 1.30 (m, 4H); MS (ESI) m/z:<br>504 (M + H$^+$). |
| 45 | 2-(5-isoquinolin-4-yl-1H-pyrazolo[3,4-b]pyridin-3-yl)-1H-benzoimidazole-4-carboxylic acid (4-amino-cyclohexyl)-amide<br>cyclohexane-1,4-diamine was used in place of isopropylamine (15%).<br>$^1$H NMR (300 MHz, CD$_3$OD) δ 9.68 (s, 1H), 9.01 (d, 1H, J = 2.1 Hz),<br>8.84 (d, 1H, J = 2.1 Hz), 8.77 (s, 1H), 8.50 (d, 1H, J = 8.4 Hz), 8.12 (m, 2H),<br>8.02 (d, 1H, J = 6.6 Hz), 7.95 (d, 1H, J = 7.5 Hz), 7.80 (d, 1H, J = 7.8 Hz),<br>7.41 (dd, 1H, J = 7.5, 7.8 Hz), 3.81 (m, 1H), 2.59 (m, 1H), 2.05 (b, 2H), 1.67 (b,<br>2H), 1.40 (m, 2H), 1.15 (m, 2H); MS (ESI) m/z: 503 (M + H$^+$). |
| 46 | 2-(5-isoquinolin-4-yl-1H-pyrazolo[3,4-b]pyridin-3-yl)-1H-benzoimidazole-4-carboxylic acid o-tolylamide<br>o-toluidine was used in place of isopropylamine (20%).<br>$^1$H NMR (300 MHz, CD$_3$OD) δ 9.77 (s, 1H), 8.96 (d, 1H, J = 2.1 Hz),<br>8.82 (d, 1H, J = 2.1 Hz), 8.62 (s, 1H), 8.56 (m, 1H), 8.02 (m, 3H), 7.82 (d, 1H, J = 7.8 Hz),<br>7.38 (m, 3H), 6.93 (m, 2H), 6.77 (d, 1H, J = 7.2 Hz), 2.19 (s, 3H);<br>MS (ESI) m/z: 496 (M + H$^+$). |
| 47 | 2-(5-isoquinolin-4-yl-1H-pyrazolo[3,4-b]pyridin-3-yl)-1H-benzoimidazole-4-carboxylic acid cyclopropylamide<br>cyclopropylamine was used in place of isopropylamine (41%).<br>$^1$H NMR (300 MHz, CD$_3$OD) δ 9.91 (s, 1H), 9.01 (d, 1H, J = 2.4 Hz),<br>8.91 (d, 1H, J = 2.4 Hz), 8.81 (s, 1H), 8.68 (d, 1H, J = 8.4 Hz), 8.28 (m, 2H),<br>8.07 (d, 1H, J = 7.5 Hz), 8.00 (d, 1H, J = 7.5 Hz), 7.78 (d, 1H, J = 8.4 Hz),<br>7.41 (dd, 1H, J = 7.5, 8.4 Hz), 4.77 (b, 1H), 0.85 (m, 2H), 0.74 (m, 2H); MS<br>(ESI) m/z: 446 (M + H$^+$). |

-continued

| Cpd | Data |
|---|---|
| 48 | 2-(5-isoquinolin-4-yl-1H-pyrazolo[3,4-b]pyridin-3-yl)-1H-benzoimidazole-4-carboxylic acid pyridin-3-ylamide<br>pyridine-3-ylamine was used in place of isopropylamine (27%).<br>$^1$H NMR (300 MHz, CD$_3$OD) δ 9.85 (s, 1H), 9.65 (s, 1H), 9.21 (d, 1H, J = 2.1 Hz), 8.89 (d, 1H, J = 2.1 Hz), 8.82 (s, 1H), 8.64 (d, 1H, J = 8.4 Hz), 8.44 (d, 1H, J = 6.9 Hz), 8.25 (d, 2H, J = 8.7 Hz), 8.15 (m, 2H), 8.04 (m, 1H), 7.92 (m, 1H), 7.68 (m, 1H), 7.51 (dd, 1H, J = 7.5, 8.1 Hz); MS (ESI m/z: 483 (M + H$^+$). |
| 49 | 2-(5-isoquinolin-4-yl-1H-pyrazolo[3,4-b]pyridin-3-yl)-1H-benzoimidazole-4-carboxylic acid (4-dimethylamino-phenyl)-amide<br>N,N-dimethyl-benzene-1,4-diamine was used in place of isopropylamine. |
| 50 | 2-(5-isoquinolin-4-yl-1H-pyrazolo[3,4-b]pyridin-3-yl)-1H-benzoimidazole-4-carboxylic acid (4-diethylamino-2-methyl-phenyl)-amide<br>N$^4$,N$^4$-diethyl-2-methyl-benzene-1,4-diamine was used in place of isopropylamine (24%).<br>$^1$H NMR (300 MHz, CD$_3$OD) δ 9.73 (s, 1H), 8.98 (d, 1H, J = 2.1 Hz), 8.82 (d, 1H, J = 2.1 Hz), 8.69 (s, 1H), 8.53 (d, 1H, J = 8.1 Hz), 8.09 (m, 5H), 8.03 (m, 2H), 7.86 (d, 1H, J = 7.8 Hz), 7.47 (t, 1H, J = 7.8 Hz), 3.63 (q, 4H, J = 7.2 Hz), 2.39 (s, 3H), 1.09 (t, 6H, J = 7.2 Hz); MS (ESI) m/z: 567 (M + H$^+$). |

Example 11

4-[3-(4-methoxymethyl-1H-benzoimidazol-2-yl)-1-methyl-1H-pyrazolo[3,4-b]pyridin-5-yl]-isoquinoline (Compound 33)

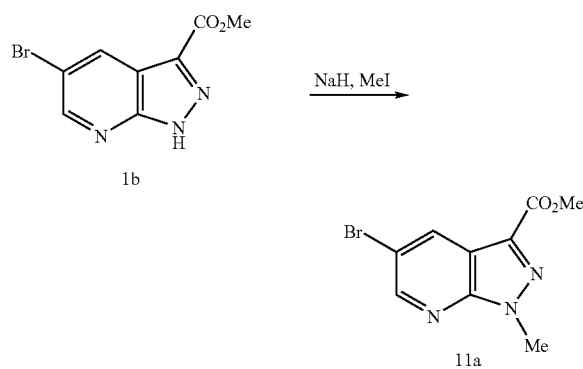

Sodium hydride (47 mg, 60% in mineral oil, 1.18 mmol) was added in portions to a solution of 5-bromo-1H-pyrazolo[3,4-b]pyridine-3-carboxylic acid methyl ester Compound 1b (0.3 g, 1.17 mmol) in dry THF (20 mL) at 0° C. The mixture was stirred at 0° C. for 15 minutes then methyl iodide (80 μl, 1.29 mmol) was added. The reaction was warmed to room temperature gradually and stirred overnight. the solvent was removed and the residue was purified by silica gel chromatography (10% to 50% of ethyl acetate in hexanes) to yield 5-bromo-1-methyl-1H-pyrazolo[3,4-b]pyridine-3-carboxylic acid methyl ester Compound 11a (0.31 g, 97% yield) as a white powder. $^1$H NMR (400 MHz, CDCl$_3$) δ 9.89 (s, 2H), 4.51 (s, 3H), 3.37 (s, 3H); MS (ESI) m/z: 271 (M+H$^+$).

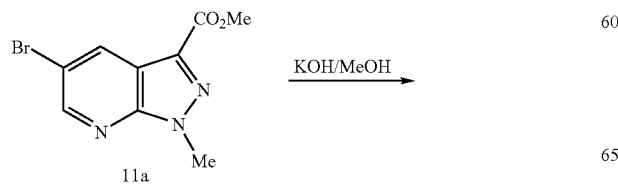

-continued

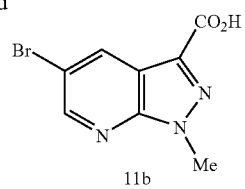

Compound 11a (0.31 g) was dissolved in MeOH (5 mL) and 10% aqueous sodium hydroxide solution (5 mL) and heated at 80° C. for two hours. The solution was cooled to room temperature before it was acidified by hydrochloric acid (1M solution) to pH 3 to 4. Precipitate was collected and washed with additional water and dried to afford 5-bromo-1-methyl-1H-pyrazolo[3,4-b]pyridine-3-carboxylic acid Compound 11b (0.26 g, 90%) as a white solid. MS (ESI) m/z: 257 (M+H$^+$).

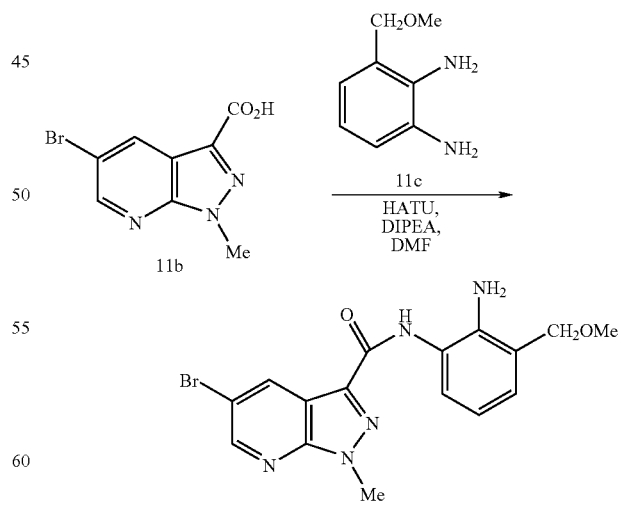

A mixture of Compound 11b (0.26 g, 1.0 mmol), 3-methoxymethyl-benzene-1,2-diamine Compound 11c (0.15 g, 1.0 mmol), HATU (0.38 g, 1.0 mmol) and DIPEA (0.42 mL, 3.0 mmol) in DMF (10 mL) was stirred at room temperature overnight. the solvent was removed and the residue was purified by silica gel chromatography (10% to 90% of ethyl acetate in hexanes) to yield 5-bromo-1-methyl-1H-pyrazolo [3,4-b]pyridine-3-carboxylic acid (2-amino-3-methoxymethyl-phenyl)-amide Compound 11d (0.19 g, 48% yield) as a yellow powder. $^1$H NMR (300 MHz, CDCl$_3$) δ 8.81 (d, 1H, J=2.1 Hz), 8.61 (d, 1H, J=2.1 Hz), 7.46 (d, 1H, J=8.1 Hz), 7.04 (d, 1H, J=8.1 Hz), 6.78 (t, 1H, J=8.1 Hz), 4.79 (s, 2H), 4.20 (s, 3H), 3.36 (s, 3H); MS (ESI) m/z: 391 (M+H$^+$).

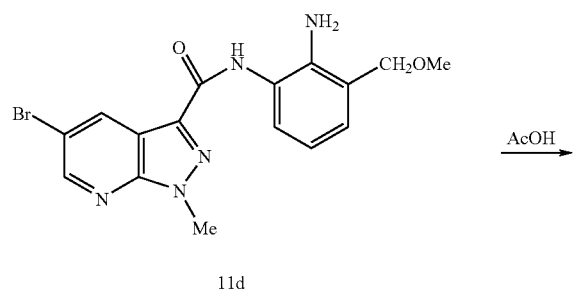

11d

-continued

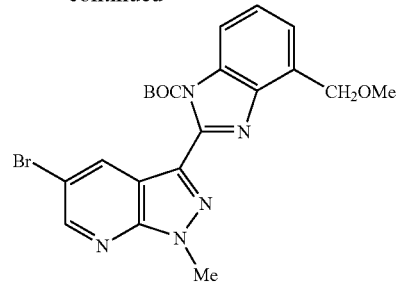

11f

A mixture of Compound 11e (0.16 g, 0.43 mmol) was stirred with (BOC)$_2$O (0.11 mL, 0.48 mmoL), DMAP (2 mg, 0.02 mmol), TEA (0.2 mL, 1.43 mmol) in DCM (5 mL) at room temperature for one hour. The solution was diluted with addition DCM (30 mL) and, washed with saturated aqueous sodium bicarbonate solution. The organic phase was dried (MgSO$_4$) and evaporated to give the Boc-protected 5-bromo-3-(4-methoxymethyl-1H-benzoimidazol-2-yl)-1-methyl-1H-pyrazolo[3,4-b]pyridine Compound 11f (0.2 g, 100%) as white foam. MS (ESI) m/z: 473 (M+H$^+$).

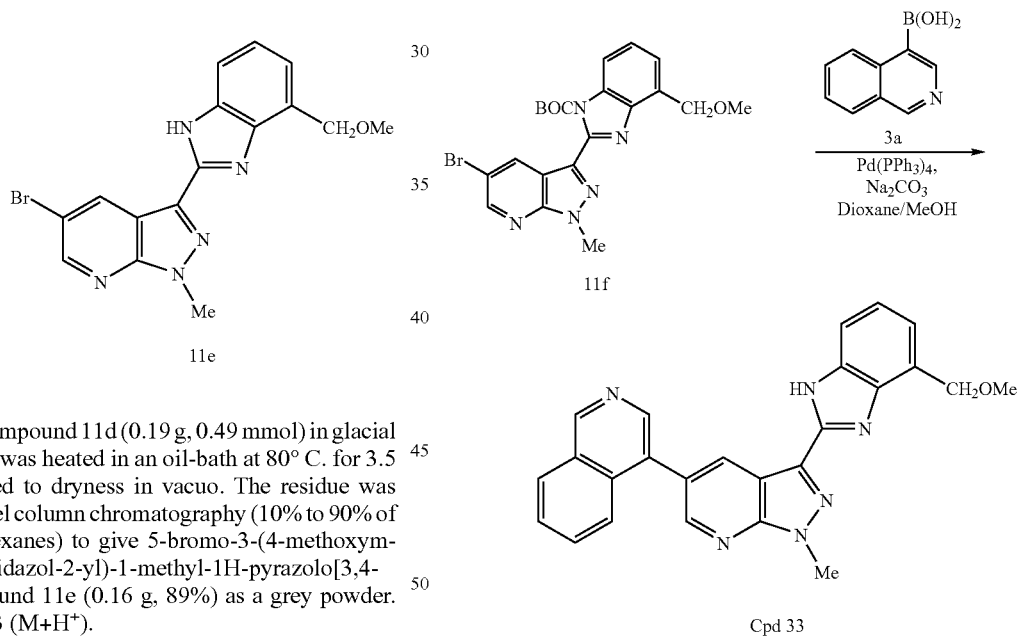

Cpd 33

A solution of Compound 11d (0.19 g, 0.49 mmol) in glacial acetic acid (5 mL) was heated in an oil-bath at 80° C. for 3.5 hrs; and evaporated to dryness in vacuo. The residue was purified by silica gel column chromatography (10% to 90% of ethyl acetate in hexanes) to give 5-bromo-3-(4-methoxymethyl-1H-benzoimidazol-2-yl)-1-methyl-1H-pyrazolo[3,4-b]pyridine Compound 11e (0.16 g, 89%) as a grey powder. MS (ESI) m/z: 373 (M+H$^+$).

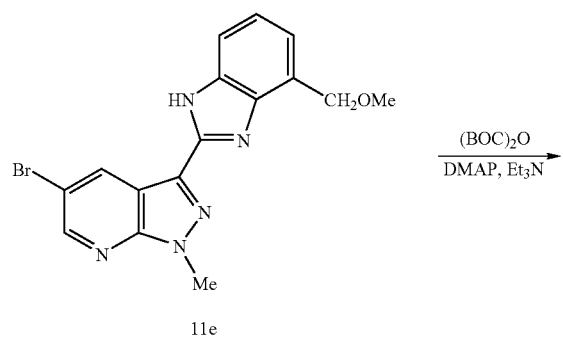

11e

A mixture of Compound 11f (0.2 g, 0.42 mmol), 4-isoquinoline boronic acid Compound 3a (0.1 g, 0.58 mmol), tetrakis(triphenylphosphine)palladium(0) (85 mg, 0.07 mmol) and an aqueous sodium carbonate solution (0.61 mL, 2M, 1.22 mmol) in dioxane (2 mL) and MeOH (0.5 mL) was flushed with nitrogen for 10 minutes in a reaction tube before the tube was sealed and heated at 90° C. overnight. The reaction mixture was cooled to room temperature, the organic layer was removed and the residue was dissolved in DMSO (1 mL) and MeOH (0.3 mL) and purified by Gilson HPLC (10% to 90% of 0.1% TFA in ACN/0.1% TFA in H$_2$O) to yield Compound 33 (85 mg, 48%) as a pale yellow solid. $^1$H NMR (300 MHz, CD$_3$OD) δ 9.86 (s, 1H), 9.10 (d, 1H, J=1.8 Hz), 8.90 (d, 1H, J=1.8 Hz), 8.71 (s, 1H), 8.61 (d, 1H, J=8.1 Hz), 8.20 (m, 2H), 8.07 (m, 1H), 7.71 (m, 1H), 7.48 (m, 2H), 4.85 (s, 2H), 4.46 (s, 3H), 3.43 (s, 3H); MS (ESI) m/z: 421 (M+H⁺).

Example 12 isopropyl-{5-[3-(4-methoxymethyl-1H-benzoimidazol-2-yl)-1H-pyrazolo[3,4-b]pyridin-5-yl]-4-methyl-pyridin-3-ylmethyl}-amine (Compound 58)

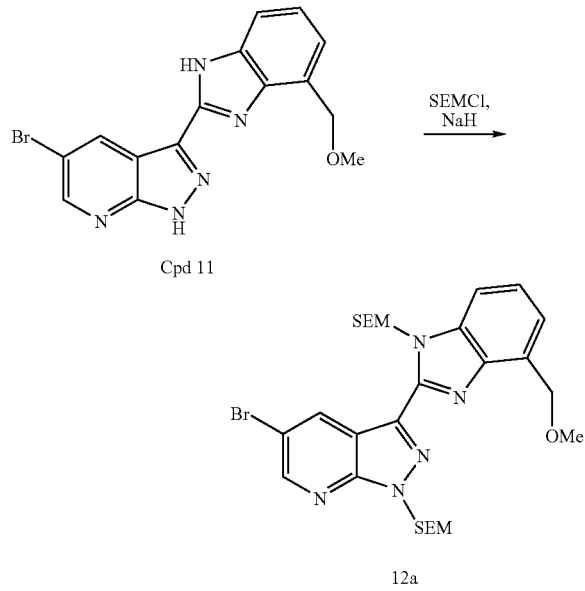

5-bromo-3-(4-methoxymethyl-1H-benzoimidazol-2-yl)-1H-pyrazolo[3,4-b]pyridine Compound 11 (1.2 g, 4.19 mmol) was dissolved in dry THF (20 mL). The solution was cooled to 0° C. before sodium hydride (0.37 g, 60% in mineral oil, 9.25 mmol) was added in portions. The suspension was stirred at 0° C. for additional 15 minutes before (trimethylsilyl)ethoxymethyl chloride (1.78 mL, 10.06 mmol) was added. The reaction was warmed to room temperature and stirred overnight. Solvent was removed and the residue was purified by silica gel chromatography (10% to 50% ethyl acetate in hexanes) to yield 5-bromo-3-[4-methoxymethyl-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 12a (1.59 g, 77%) as amber oil. ¹H NMR (300 MHz, CDCl₃) δ 9.35 (d, 1H, J=2.4 Hz), 8.84 (d, 1H, J=2.4 Hz), 7.74 (d, 1H, J=5.4 Hz), 7.57 (m, 2H), 6.45 (s, 2H), 6.09 (s, 2H), 5.26 (s, 2H), 3.86 (m, 4H), 3.77 (s, 3H), 1.13 (t, 2H, J=7.2 Hz), 1.05 (t, 2H, J=7.8 Hz), 0.14 (s, 9H), 0.03 (s, 9H); MS (ESI) m/z: 619 (M+H⁺).

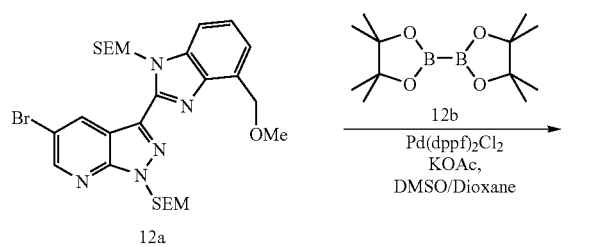

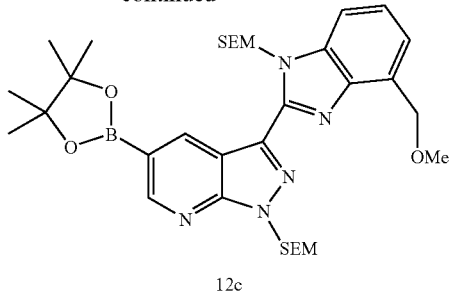

A mixture of Compound 12a (0.9 g, 1.46 mmol), 4,4,5,5,4',4',5',5'-octamethyl-[2,2']bi[[1,3,2]dioxaborolanyl] (also referred to as bis(pinacolato)diboron) Compound 12b (0.41 g, 1.61 mmol)), potassium acetate (0.71 g, 7.23 mmol) and 1,1'-bis(diphenylphosphino)ferrocenedichloropalladium(II) (60 mg, 0.07 mmol) in DMSO (5 mL) and dioxane (5 mL) were purged with nitrogen for 10 minutes and heated to 80° C. overnight. The reaction mixture was cooled, diluted with DCM (60 mL) and washed with water (30 mL). The aqueous layer was extracted with DCM (40 mL×2) and the organic layers were combined, dried over magnesium sulfate and concentrated. The crude product was purified by silica gel chromatography (10% to 50% ethyl acetate/hexanes) to afford 3-[4-methoxymethyl-1-(2-trimethylsilanyl-ethoxymethyl)-1H-benzoimidazol-2-yl]-5-(4,4,5,5-tetramethyl-[1,3,2]dioxaborolan-2-yl)-1-(2-trimethylsilanyl-ethoxymethyl)-1H-pyrazolo[3,4-b]pyridine Compound 12c (0.56 g, 58%) as a white solid. ¹H NMR (300 MHz, CDCl₃) δ 9.64 (d, 1H, J=1.5 Hz), 9.18 (d, 1H, J=1.5 Hz), 7.76 (dd, 1H, J=6, 1.5 Hz), 7.58 (m, 2H), 6.47 (s, 2H), 6.16 (s, 2H), 5.30 (s, 2H), 3.87 (m, 4H), 3.84 (s, 3H), 1.59 (s, 12H), 1.15 (t, 2H, J=8.1 Hz), 1.06 (t, 2H, J=8.1 Hz), 0.14 (s, 9H), 0.05 (s, 9H); MS (ESI) m/z: 666 (M+H⁺).

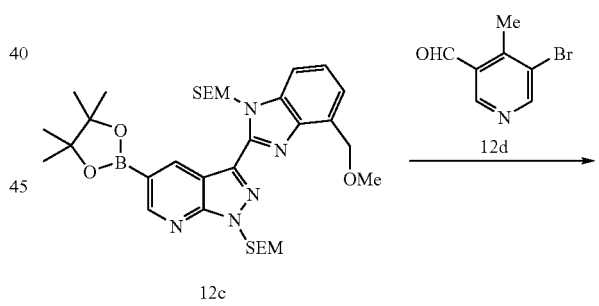

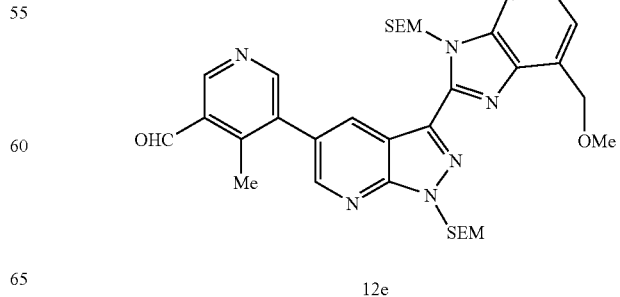

Aqueous sodium carbonate solution (2M, 1 mL) was added to a solution of Compound 12c (0.5 g, 0.75 mmol), 5-bromo-4-methyl-pyridine-3-carbaldehyde Compound 12d (0.15 g, 0.75 mmol), and tetrakis(triphenylphosphine)palladium(0) (0.13 g, 0.11 mmol) in 1,4-dioxane (30 mL) in a reaction tube. The reaction tube was sealed and heated to 90° C. overnight. After cooling to room temperature, the crude mixture was poured into water (30 mL) was extract with DCM (2×50 mL). The combined organic layer was dried over sodium sulfate and concentrated. Silica gel chromatography (10% to 50% ethyl acetate/hexanes) gave 5-[3-[4-methoxymethyl-1-(2-tri-methylsilanyl-ethoxymethyl)-1H-benzoimidazol-2-yl]-1-(2-trimethylsilanyl-ethoxymethyl)-1H-pyrazolo[3,4-b]pyridin-5-yl]-4-methyl-pyridine-3-carbaldehyde Compound 12e (0.34 g, 69%) as a white solid. $^1$H NMR (300 MHz, CD$_3$OD) δ 10.67 (s, 1H), 9.16 (d, 1H, J=2.1 Hz), 9.02 (s, 1H), 8.92 (d, 1H, J=2.1 Hz), 8.69 (s, 1H), 7.91 (d, 1H, J=6.9 Hz), 7.61 (m, 2H), 6.71 (s, 2H), 6.56 (s, 2H), 5.20 (s, 2H), 4.07 (t, 2H, J=8.4 Hz), 3.88 (t, 2H, J=7.8 Hz), 3.68 (s, 2H), 3.59 (s, 3H), 2.62 (s, 3H), 1.20 (t, 2H, J=7.8 Hz), 1.07 (t, 2H, J=8.4 Hz), 0.20 (s, 9H), 0.05 (s, 9H); MS (ESI) m/z: 659 (M+H$^+$).

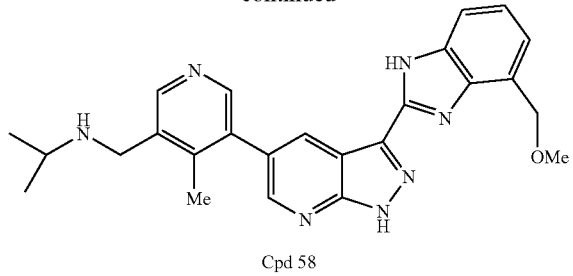

Cpd 58

Isopropylamine (25 μL, 0.29 mmol) was added to a solution of Compound 12e (60 mg, 0.09 mmol) in MeOH (2 mL). The solution was stirred for 30 mins at elevated temperature, then cooled to room temperature and sodium borohydride (40 mg, 1.06 mmol) was added in portion. The reaction mixture was stirred overnight. The solvent was removed, the residue was dissolved in ethanol (5 mL) and 5M hydrochloric acid (5 mL) was added. The mixture was heated at 70° C. for five hours, then the reaction mixture was cooled to room temperature and neutralized to pH 7 using an aqueous saturated sodium bicarbonate solution. The aqueous layer was extracted with 5% MeOH in DCM (30 mL×3). The combined organic layer was concentrated and the crude product was purified by Semi-prep Gilson HPLC (10% to 90% of 0.1% TFA in ACN/0.1% TFA in H$_2$O) to yield Compound 58 (24 mg, 60%) as a pale yellow solid. $^1$H NMR (300 MHz, CD$_3$OD) δ 8.91 (d, 1H, J=2.1 Hz), 8.84 (s, 1H), 8.74 (m, 2H), 7.81 (dd, 1H, J=8.1, 4.5 Hz), 7.59 (m, 2H), 4.54 (s, 2H), 3.47 (s, 3H), 3.31 (m, 3H), 2.55 (s, 3H), 1.5 (d, 6H, J=6.6 Hz); MS (ESI) m/z: 442 (M+H$^+$).

Using the procedure of Example 12, other compounds of the present invention were prepared:

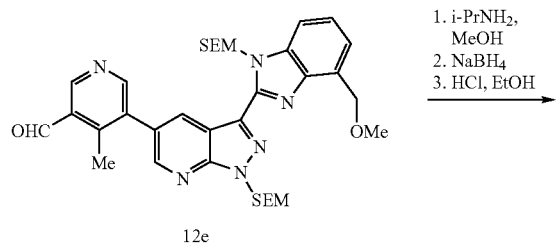

1. i-PrNH$_2$, MeOH
2. NaBH$_4$
3. HCl, EtOH

12e

| Cpd | Data |
|---|---|
| 59 | ethyl-{5-[3-(4-methoxymethyl-1H-benzoimidazol-2-yl)-1H-pyrazolo[3,4-b]pyridin-5-yl]-4-methyl-pyridin-3-ylmethyl}-amine<br>ethyl amine was used in place of i-propyl amine (44%).<br>$^1$H NMR (300 MHz, CD$_3$OD) δ 8.91 (d, 1H, J = 1.8 Hz), 8.83 (s, 1H), 8.75 (s, 1H), 8.74 (d, 1H, J = 1.8 Hz), 7.81 (dd, 1H, J = 4.2, 5.1 Hz), 7.59 (m, 2H), 4.42 (s, 2H), 3.46 (s, 3H), 3.31 (m, 4H), 2.49 (s, 3H), 1.43 (d, 3H, J = 1.5 Hz); MS (ESI) m/z: 428 (M + H$^+$). |
| 60 | 3-(4-methoxymethyl-1H-benzoimidazol-2-yl)-5-(4-methyl-5-morpholin-4-ylmethyl-pyridin-3-yl)-1H-pyrazolo[3,4-b]pyridine<br>morpholine and NaBH(OAc)$_3$ were used in place of i-propyl amine and NaBH$_4$ (48%).<br>$^1$H NMR (300 MHz, CD$_3$OD) δ 8.91 (d, 1H, J = 2.1 Hz), 8.88 (s, 1H), 8.77 (d, 1H, J = 2.1 Hz), 8.75 (s, 1H), 7.82 (d, 2H, J = 4.2 Hz), 7.59 (m, 3H), 4.64 (s, 2H), 3.95 (b, 4H), 3.45 (m, 7H), 3.31 (s, 2H), 2.52 (s, 3H); MS (ESI) m/z: 470 (M + H$^+$). |
| 61 | {5-[3-(4-methoxymethyl-1H-benzoimidazol-2-yl)-1H-pyrazolo[3,4-b]pyridin-5-yl]-4-methyl-pyridin-3-ylmethyl}-dimethyl-amine<br>N,N-dimethyl amine and NaBH(OAc)$_3$ were used in place of i-propyl amine and NaBH$_4$ (60%).<br>$^1$H NMR (300 MHz, CD$_3$OD) δ 8.91 (d, 1H, J = 1.8 Hz), 8.83 (s, 1H), 8.75 (s, 1H), 8.74 (d, 1H, J = 1.8 Hz), 7.81 (dd, 1H, J = 4.2, 5.1 Hz), 7.59 (m, 2H), 4.42 (s, 2H), 3.46 (s, 3H), 3.02 (s, 2H), 2.64 (br, 3H), 2.52 (br, 3H), 2.03 (s, 3H); MS (ESI) m/z: 428 (M + H$^+$). |
| 62 | {5-[3-(4-methoxymethyl-1H-benzoimidazol-2-yl)-1H-pyrazolo[3,4-b]pyridin-5-yl]-4-methyl-pyridin-3-ylmethyl}-methyl-amine<br>methyl amine was used in place of i-propyl amine (64%).<br>$^1$H NMR (300 MHz, CD$_3$OD) δ 8.88 (d, 1H, J = 1.8 Hz), 8.71 (m, 2H), 8.67 (s, 1H), 7.75 (dd, 1H, J = 9.3, 4.5 Hz), 7.50 (m, 2H), 4.49 (s, 2H), 3.46 (s, 3H), 3.31 (s, 2H), 2.29 (s, 3H), 2.49 (s, 3H); MS (ESI) m/z: 414 (M + H$^+$). |

Example 13
3-(4-methoxymethyl-1H-benzoimidazol-2-yl)-5-(4-methyl-pyridin-3-yl)-1H-pyrazolo[3,4-b]pyridine (Compound 57)

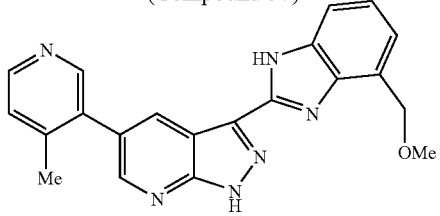

An aqueous 2M sodium carbonate solution (0.11 mL, 0.23 mmol) was added to a solution of 3-[4-methoxymethyl-1-(2-trimethylsilanyl-ethoxymethyl)-1H-benzoimidazol-2-yl]-5-(4,4,5,5-tetramethyl-[1,3,2]dioxaborolan-2-yl)-1-(2-trimethylsilanyl-ethoxymethyl)-1H-pyrazolo[3,4-b]pyridine Compound 12c (60 mg, 0.09 mmol), 3-bromo-4-methyl-pyridine Compound 13a (10 µl, 0.09 mmol) and tetrakis(triphenylphosphine)palladium(0) (16 mg, 0.01 mmol) in dioxane (1 mL) in a reaction tube. The reaction tube was sealed and heated to 90° C. overnight. After cooling to room temperature, the crude mixture was poured into water (30 mL) and was extract with DCM (2×25 mL). The combined organic layer was dried over sodium sulfate and concentrated. Silica gel chromatography (10% to 50% ethyl acetate/hexanes) gave 3-[4-methoxymethyl-1-(2-trimethylsilanyl-ethoxymethyl)-1H-benzoimidazol-2-yl]-5-(4-methyl-pyridin-3-yl)-1-(2-trimethylsilanyl-ethoxymethyl)-1H-pyrazolo[3,4-b]pyridine Compound 13b (54 mg, 95%) as a white solid. $^1$H NMR (300 MHz, CD$_3$OD) δ 9.17 (d, 1H, J=1.5 Hz), 8.92 (d, 1H, J=1.5 Hz), 8.71 (m, 2H), 7.87 (m, 2H), 7.61 (m, 2H), 6.50 (s, 2H), 6.23 (s, 2H), 5.17 (s, 2H), 4.04 (t, 2H, J=6 Hz), 3.86 (t, 2H, J=6 Hz), 3.66 (s, 3H), 2.62 (s, 3H), 1.18 (t, 2H, J=6 Hz); 1.05 (t, 2H, J=6 Hz), 0.18 (s, 9H), 0.05 (s, 9H); MS (ESI) m/z: 631 (M+H$^+$).

Compound 13b (54 mg) was dissolved in ethanol (5 mL) and 4M hydrochloric acid (5 mL and heated to 70° C. for five hours. The reaction mixture was cooled to room temperature, the solution was neutralized to pH 7 using saturated sodium bicarbonate aqueous solution and the aqueous layer was extracted with 5% MeOH in DCM (30 mL×3). The combined organic layer was concentrated and the crude product was purified by Semi-prep Gilson HPLC (10% to 90% of 0.1% TFA in ACN/0.1% TFA in H$_2$O) to yield Compound 57 (28 mg, 89%) as a white solid. $^1$H NMR (300 MHz, CD$_3$OD) δ 8.96 (d, 1H, J=2.1 Hz), 8.78 (s, 1H), 8.73 (d, 1H, J=2.1 Hz), 8.70 (d, 1H, J=5.7 Hz), 7.92 (d, 1H, J=6.0 Hz), 7.68 (m, 1H), 7.37 (m, 2H), 4.06 (s, 2H), 3.46 (s, 3H), 2.63 (s, 3H); MS (ESI) m/z: 371 (M+H$^+$).

Example 14
5-bromo-3-[5-(4-methyl-piperazin-1-yl)-1H-benzoimidazol-2-yl]-1H-pyrazolo[3,4-b]pyridine (Compound 30)
4-{3-[5-(4-methyl-piperazin-1-yl)-1H-benzoimidazol-2-yl]-1H-pyrazolo[3,4-b]pyridin-5-yl}-isoquinoline (Compound 31)

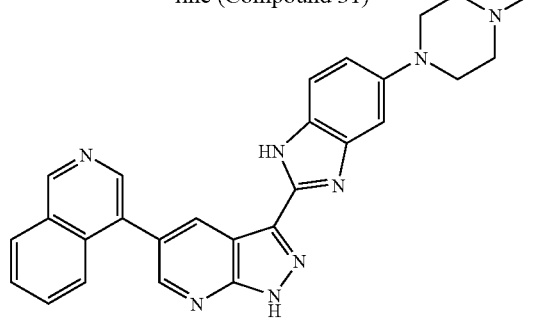

A mixture of 5-bromo-1H-pyrazolo[3,4-b]pyridine-3-carboxylic acid Compound 1c (2.095 g, 8.66 mmol), 4-(4-methyl-piperazin-1-yl)-benzene-1,2-diamine Compound 14a (1.79 g, 8.68 mmol), HATU (3.29 g, 8.66 mmol) and DIPEA (4 mL, 28.7 mmol) in DMF (70 mL) was stirred at room temperature overnight. The solvent was removed and the residue was purified by silica gel chromatography (10% to 90% of ethyl acetate in hexanes) to yield 5-bromo-1H-pyrazolo[3,4-b]pyridine-3-carboxylic acid [2-amino-4-(4-methyl-piperazin-1-yl)-phenyl]-amide Compound 14b (2 g, 54% yield) as a brown powder. $^1$H NMR (300 MHz, CD$_3$OD) δ 8.81 (d, 1H, J=2.1 Hz), 8.66 (d, 1H, J=2.1 Hz), 7.42 (d, 1H, J=8.7 Hz), 7.11 (dd, 1H, J=2.7, 8.7 Hz), 7.03 (d, 1H, J=2.7 Hz), 3.92 (b, 2H), 3.65 (b, 2H), 3.31 (b, 2H), 3.16 (b, 2H), 2.81 (s, 3H); MS (ESI) m/z: 431 (M+H$^+$).

A solution of Compound 14b (2 g, 4.65 mmol) in glacial acetic acid (20 mL) was heated in an oil-bath at 80° C. for 3.5 hrs then evaporated to dryness in vacuo. The residue was purified by silica gel column chromatography (10% to 90% of ethyl acetate in hexanes) to give 5-bromo-3-[5-(4-methyl-piperazin-1-yl)-1H-benzoimidazol-2-yl]-1H-pyrazolo[3,4-b]pyridine Compound 30 (1.7 g, 89%) as a dark red solid. MS (ESI) m/z: 413 (M+H$^+$).

Compound 30 (1.7 g, 4.13 mmol) was stirred with a mixture of (BOC)$_2$O (2.09 mL, 9.09 mmoL), DMAP (50 mg, 0.41 mmol) and TEA (1.73 mL, 12.41 mmol) in DCM (50 mL) at room temperature for one hour. The solution was diluted with additional DCM (200 mL) and washed with a saturated aqueous sodium bicarbonate solution. The organic phase was dried (MgSO$_4$) and evaporated to give the bis-Boc-protected 5-bromo-3-[5-(4-methyl-piperazin-1-yl)-1H-benzoimidazol-2-yl]-1H-pyrazolo[3,4-b]pyridine Compound 14c (2.53 g, 100%) as a red foam. $^1$H NMR (300 MHz, CDCl$_3$) δ 8.82 (d, 1H, J=2.4 Hz), 8.60 (d, 1H, J=2.4 Hz), 7.94 (d, 1H, J=9.0 Hz), 7.60 (d, 1H, J=2.4 Hz), 7.19 (dd, 1H, J=2.4, 9.0 Hz), 3.34 (b, 4H), 3.27 (b, 4H), 2.80 (s, 3H), 1.72 (s, 9H), 1.53 (s, 9H); MS (ESI) m/z: 613 (M+H$^+$).

A mixture of Compound 14c (2.53 g, 4.13 mmol), 4-isoquinoline boronic acid Compound 3a (0.86 g, 4.97 mmol), tetrakis(triphenylphosphine)palladium(0) (0.72 g, 0.62 mmol) an 4 an aqueous 2M sodium carbonate solution (5.16 mL, 10.32 mmol) in dioxane (120 mL) and MeOH (30 mL) was flushed with nitrogen for 10 minutes in a reaction tube before the tube was sealed and heated at 90° C. overnight. The reaction was cooled to room temperature and the organic layer was removed from the tube. The 15, residue was dissolved in water (50 mL) and the aqueous layer was extracted with 5% MeOH in DCM (100 mL×3). The combined organic layer was concentrated and purified by silica gel chromatography (10% to 20% MeOH in DCM) to yield Compound 31 (1.7 g, 89%) as dark red flakes. $^1$H NMR (400 MHz, CD$_3$OD) δ 9.94 (s, 1H), 9.30 (d, 1H, J=2.0 Hz), 8.98 (d, 1H, J=2.0 Hz), 8.83 (s, 1H), 8.69 (d, 1H, J=8.0 Hz), 8.29 (m, 2H), 8.17 (m, 1H), 7.80 (d, 1H, J=8.8 Hz), 7.47 (m, 2H), 3.99 (b, 4H), 3.67 (b, 4H), 3.06 (s, 3H); MS (ESI) m/z: 461 (M+H$^+$).

Using the procedure of Example 14, other compounds of the present invention were prepared:

| Cpd | Data |
|---|---|
| 51 | 4-[3-(5-morpholin-4-yl-1H-benzoimidazol-2-yl)-1H-pyrazolo[3,4-b]pyridin-5-yl]-isoquinoline<br>4-morpholin-4-yl-benzene-1,2-diamine was used in place of Compound 14a (25%).<br>$^1$H NMR (400 MHz, DMSO-d$_6$) δ 9.93 (s, 1H), 9.28 (d, 1H, J = 2.0 Hz), 8.95 (d, 1H, J = 2.0 Hz), 8.83 (s, 1H), 8.69 (d, 1H, J = 8.0 Hz), 8.29 (m, 2H), 8.17 (m, 1H), 7.79 (d, 1H, J = 8.8 Hz), 7.45 (m, 2H), 3.87 (t, 4H,, J = 5.4 Hz), 3.11 (b, 4H); MS (ESI) m/z: 448 (M + H$^+$). |

Example 15 methyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine (Compound 81)

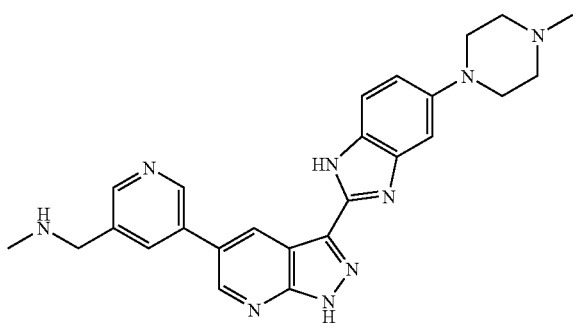

Using the procedure of Example 12, 5-bromo-3-[5-(4-methyl-piperazin-1-yl)-1H-benzoimidazol-2-yl]-1H-pyrazolo[3,4-b]pyridine Compound 30 was used in place of 5-bromo-3-(4-methoxymethyl-1H-benzoimidazol-2-yl)-1H-pyrazolo[3,4-b]pyridine Compound 11 to provide 5-bromo-3-[5-(4-methyl-piperazin-1-yl)-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 15a.

Using the procedure of Example 14, Compound 15a was used in place of bis-Boc-protected 5-bromo-3-[5-(4-methyl-piperazin-1-yl)-1H-benzoimidazol-2-yl]-1H-pyrazolo[3,4-b]pyridine Compound 14d and 5-(4,4,5,5-tetramethyl-[1,3,2]dioxaborolan-2-yl)-pyridine-3-carbaldehyde Compound 15b was used in place of 4-isoquinoline boronic acid Compound 3a to provide 5-[3-[5-(4-methyl-piperazin-1-yl)-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-pyridine-3-carbaldehyde Compound 15c.

Using the procedure of Example 12, Compound 15c was used in place of 5-[3-[4-methoxymethyl-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-4-methyl-pyridine-3-carbaldehyde Compound 12e and methyl amine was used in place of isopropylamine to provide Compound 81. $^1$H NMR (300 MHz, CD$_3$OD) δ 9.32 (d, 1H, J=1.8 Hz), 9.26 (s, 1H), 9.08 (d, 1H, J=1.8 Hz), 8.79 (s, 1H), 8.53 (s, 1H), 7.77 (d, 1H, J=9 Hz), 7.43 (d, 1H, J=9 Hz), 7.37 (m, 1H), 4.43 (s, 2H), 3.94 (b, 2H), 3.71 (b, 2H), 3.32 (b, 4H), 3.01 (s, 3H), 2.85 (s, 3H); MS (ESI) m/z: 454 (M+H$^+$).

Using the procedure of Example 15, other compounds of the present invention were prepared:

| Cpd | Data |
|---|---|
| 82 | ethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine<br>ethyl amine was used in place of methyl amine.<br>$^1$H NMR (300 MHz, CD$_3$OD) δ 9.26 (d, 1H, J = 1.8 Hz), 9.15 (s, 1H), 9.08 (d, 1H, J = 1.8 Hz), 8.80 (s, 1H), 8.55 (s, 1H), 7.77 (d, 1H, J = 9 Hz), 7.43 (d, 1H, J = 9 Hz), 7.37 (m, 1H), 4.40 (s, 2H), 3.96 (b, 2H), 3.70 (b, 2H), 3.32 (bm, 6H), 3.01 (s, 3H), 1.41 (t, 3H, J = 7.2 Hz); MS (ESI) m/z: 468 (M + H$^+$). |
| 83 | isopropyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine<br>isopropyl amine was used in place of methyl amine.<br>$^1$H NMR (300 MHz, CD$_3$OD) δ 9.21 (d, 1H, J = 2.1 Hz), 9.11 (s, 1H), 9.02 (d, 1H, J = 2.1 Hz), 8.77 (s, 1H), 8.48 (s, 1H), 7.71 (d, 1H, J = 9.6 Hz), 7.32 (m, 2H), 4.44 (s, 2H), 3.90 (b, 2H), 3.80 (b, 2H), 3.54 (m, 1H), 3.32 (b, 4H), 3.01 (s, 3H), 1.47 (d, 6H, J = 6.6 Hz); MS (ESI) m/z: 482 (M + H$^+$). |
| 84 | 3-[5-(4-methyl-piperazin-1-yl)-1H-benzoimidazol-2-yl]-5-(5-morpholin-4-ylmethyl-pyridin-3-yl)-1H-pyrazolo[3,4-b]pyridine<br>morpholine was used in place of methyl amine.<br>$^1$H NMR (300 MHz, CD$_3$OD) δ 9.23 (d, 1H, J = 2.4 Hz), 9.16 (s, 1H), 9.04 (d, 1H, J = 2.4 Hz), 8.77 (s, 1H), 8.49 (s, 1H), 7.71 (d, 1H, J = 9 Hz), 7.30 (m, 2H), 4.46 (s, 2H), 3.94 (m, 6H), 3.66 (b, 2H), 3.35 (m, 8H), 3.01 (s, 3H); MS (ESI) m/z: 510 (M + H$^+$). |
| 85 | (5-{3-[5-(4-methyl-piperazin-1-yl)-1H-benzoimidazol-2-yl]-1H-pyrazolo[3,4-b]pyridin-5-yl}-pyridin-3-ylmethyl)-propyl-amine<br>n-propyl amine was used in place of methyl amine.<br>$^1$H NMR (300 MHz, CD$_3$OD) δ 9.27 (d, 1H, J = 2.1 Hz), 9.17 (s, 1H), 9.09 (d, 1H, J = 2.1 Hz), 8.82 (s, 1H), 8.61 (s, 1H), 7.78 (d, 1H, J = 9.3 Hz), 7.44 (d, 1H, J = 9.3 Hz), 7.37 (m, 1H), 4.43 (s, 2H), 3.97 (b, 2H), 3.69 (b, 2H) 3.33 (b, 4H), 3.17 (t, 2H, J = 7.8 Hz), 3.01 (s, 3H), 1.82 (m, 2H), 1.07 (t, 3H, J = 7.5 Hz); MS (ESI) m/z: 482 (M + H$^+$). |
| 86 | (2-methoxy-ethyl)-(5-{3-[5-(4-methyl-piperazin-1-yl)-1H-benzoimidazol-2-yl]-1H-pyrazolo[3,4-b]pyridin-5-yl}-pyridin-3-ylmethyl)-amine<br>2-methoxy-ethyl amine was used in place of methyl amine.<br>$^1$H NMR (300 MHz, CD$_3$OD) δ 9.27 (d, 1H, J = 2.1 Hz), 9.16 (s, 1H), 9.09 (d, 1H, J = 2.1 Hz), 8.82 (s, 1H), 8.60 (s, 1H), 7.77 (d, 1H, J = 9.3 Hz), 7.43 (d, 1H, J = 9.3 Hz), 7.38 (m, 1H), 4.48 (s, 2H), 3.97 (b, 2H), 3.71 (m, 4H), 3.43 (s, 3H), 3.32 (m, 6H), 3.01 (s, 3H); MS (ESI) m/z: 498 (M + H$^+$). |
| 87 | 3-[5-(4-methyl-piperazin-1-yl)-1H-benzoimidazol-2-yl]-5-(5-pyrrolidin-1-ylmethyl-pyridin-3-yl)-1H-pyrazolo[3,4-b]pyridine<br>pyrrolidine was used in place of methyl amine.<br>$^1$H NMR (300 MHz, CD$_3$OD) δ 9.26 (d, 1H, J = 1.8 Hz), 9.18 (s, 1H), 9.12 (d, 1H, J = 1.8 Hz), 8.91 (s, 1H), 8.62 (s, 1H), 7.77 (d, 1H, J = 9.3 Hz), 7.43 (d, 1H, J = 9.3 Hz), 7.37 (b, 1H), 4.54 (s, 2H), 3.97 (b, 2H), 3.70 (b, 2H), 3.43 (m, 8H), 3.01 (s, 3H), 2.16 (b, 4H); MS (ESI) m/z: 494 (M + H$^+$). |

-continued

| Cpd | Data |
|---|---|
| 88 | dimethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine<br>dimethyl amine was used in place of methyl amine.<br>$^1$H NMR (300 MHz, CD$_3$OD) δ 9.27 (d, 1H, J = 1.8 Hz), 9.21 (s, 1H),<br>9.12 (d, 1H, J = 1.8 Hz), 8.85 (s, 1H), 8.65 (s, 1H), 7.77 (d, 1H, J = 9.0 Hz),<br>7.43 (dd, 1H, J = 1.8, 9.0 Hz), 7.37 (d, 1H, J = 1.8 Hz), 4.59 (s, 2H), 3.97 (b, 2H),<br>3.70 (b, 2H), 3.26 (m, 4H), 3.00 (m, 9H); MS (ESI) m/z: 468 (M + H$^+$). |
| 89 | 3-[5-(4-methyl-piperazin-1-yl)-1H-benzoimidazol-2-yl]-5-pyridin-3-yl-1H-pyrazolo[3,4-b]pyridine<br>3-(4,4,5,5-tetramethyl-[1,3,2]dioxaborolan-2-yl)-pyridine was used in place of Compound 15b.<br>$^1$H NMR (300 MHz, CD$_3$OD) δ 9.31 (d, 1H, J = 2.4 Hz), 9.29 (s, 1H),<br>9.12 (d, 1H, J = 2.4 Hz), 8.87 (m, 2H), 8.08 (dd, 1H, J = 7.2, 8.1 Hz), 7.78 (d,<br>1H, J = 9.0 Hz), 7.40 (m, 2H), 3.97 (b, 2H), 3.69 (b, 2H), 3.28 (m, 4H),<br>3.01 (s, 3H); MS (ESI) m/z: 411 (M + H$^+$). |

Example 16

5-pyridin-3-yl-3-(5-trifluoromethoxy-1H-benzoimidazol-2-yl)-1H-pyrazolo[3,4-b]pyridine (Compound 94)

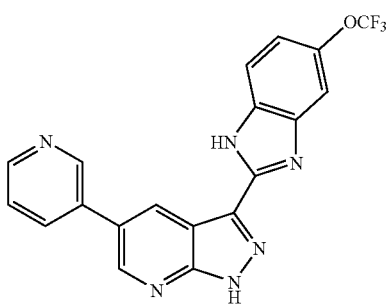

2-nitro-4-trifluoromethoxy-phenylamine Compound 16a (0.5 g, 2.25 mmol) was dissolved into EtOH (30 mL) and Raney Ni (~0.5 g, prewashed with EtOH) was added. The mixture was shaken in a Parr shaker under H$_2$ (50 psi) at room temperature overnight, filtered through Celite and the solvent was evaporated to dryness to provide 4-trifluoromethoxy-benzene-1,2-diamine Compound 16b (0.373 g, yield 86%) as a red-brown semi-solid.

A mixture of 5-bromo-1H-pyrazolo[3,4-b]pyridine-3-carboxylic acid Compound 1c (0.68 g, 1.93 mmol), Compound 16b (0.373 g, 1.93 mmol), HATU (0.73 g, 1.9 mmol) and DIPEA (1 mL, 5.8 mmol) in DMF (30 mL) was stirred at room temperature overnight. The solvent was removed under vacuum and the resulting yellow residue was mixed with AcOEt, sequentially washed with saturated aqueous NH$_4$Cl, 1M HCl, water and saturated aqueous NaHCO$_3$, then dried over Na$_2$SO$_4$. The solvent was evaporated to dryness to provide 5-bromo-1H-pyrazolo[3,4-b]pyridine-3-carboxylic acid (2-amino-4-trifluoromethoxy-phenyl)-amide Compound 16c (0.67 g, 83% yield) as a yellow solid. LC-MS major peak 3.03 min, MS (ESI) m/z 416.0 (M$^+$)/417.0 (M+H$^+$).

A solution of Compound 16c (0.67 g, 1.61 mmol) in glacial acetic acid (20 mL) was stirred in an oil-bath at 80° C. for 4 hrs. The solvent was evaporated to dryness to provide 5-bromo-3-(5-trifluoromethoxy-1H-benzoimidazol-2-yl)-1H-pyrazolo[3,4-b]pyridine Compound 16d (0.63 g, 98% yield) as an off-white solid. LC-MS major peak 3.13 min, MS (ESI) m/z 398.0 (M$^+$)/399.0 (M+H$^+$).

Compound 16d (0.63 g, 1.58 mmol) was treated with NaH (0.15 g, 3.96 mmol) in DMF (10 mL) for 0.5 hr at room temperature, followed by SEMCl (0.69 mL, 3.96 mmol). The solvent was removed under vacuum and the resulting yellow residue was mixed with AcOEt (80 mL), sequentially washed with water and saturated aqueous NH$_4$Cl, then dried over Na$_2$SO$_4$. The solvent was evaporated to dryness and the resulting brownish oil (1.03 g) was purified by flash column chromatography (10% AcOEt/Hexane, v/v) to provide 5-bromo-3-[5-trifluoromethoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 16e (0.579 g, yield 56%) as a colorless oil (solidified at room temperature). MS (ESI) m/z 658.2 (M$^+$)/660 (M$^+$+2).

Compound 16e (0.10 g, 0.15 mmol), 3-(4,4,5,5-tetramethyl-[1,3,2]dioxaborolan-2-yl)-pyridine Compound 16f (0.062 g, 0.3 mmol) and 2M Na$_2$CO$_3$ (2 drops) were mixed in DME (5 mL) in a reaction tube. The resulting yellowish clear solution was degassed with nitrogen for 15 minutes, then tetrakis(triphenylphosphine)palladium(0) (0.018 g, 0.015 mmol) was added and the reaction tube was sealed and heated at 100° C. overnight. The sealed tube was cooled and opened and the dark brown contents was diluted with DCM and H$_2$O, then filtered through Celite. The solvent was evaporated to dryness and the resulting black oil (0.254 g) was purified by preparative thin layer chromatography (20% AcOEt/DCM, v/v) to provide 5-pyridin-3-yl-3-[5-trifluoromethoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 16g (0.056 g, yield 56%) as a yellowish oil. MS (ESI) m/z 657.3 (M+H$^+$)/679.2 (M+Na$^+$).

Compound 16g (0.45 g, 0.07 mmol) was treated with 4M HCl (10 mL) in EtOH (10 mL) at −78° C. for about 18 hrs. The solvent was evaporated to dryness to provide a yellowish solid (0.041 g) LC-MS single peak, 2.315 min, MS (ESI) m/z 397.2 (M+H$^+$). The solid was purified by preparative HPLC to provide Compound 94 (0.025 g, 71%) as an off-white solid. $^1$H NMR (300 MHz, CD$_3$OD) δ 9.38 (s, 1 H), 9.34 (s, 1 H), 9.11 (s, 1 H), 9.05 (d, 1 H, J=8.4 Hz), 8.93 (d, 1 H, J=5.4 Hz), 8.22 (t, 1 H, J=5.7 Hz), 7.83 (d, 1 H, J=9.0 Hz), 7.69 (s, 1 H), 7.38 (d, 1 H, J=8.7 Hz).

Example 17 methyl-{5-[3-(5-trifluoromethoxy-1H-benzoimidazol-2-yl)-1H-pyrazolo[3,4-b]pyridin-5-yl]-pyridin-3-ylmethyl}-amine (Compound 96)

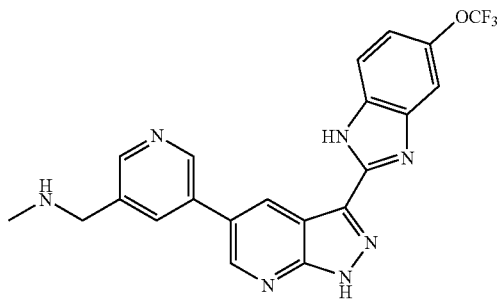

5-bromo-3-[5-trifluoromethoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 16e (0.12 g, 0.18 mmol), 5-(4,4,5,5-tetramethyl-[1,3,2]dioxaborolan-2-yl)-pyridine-3-carbaldehyde Compound 15b (0.063 g, 0.27 mmol) and 2M Na$_2$CO$_3$ (5 drops) were mixed in DME (10 mL) in a reaction tube. The resulting yellowish clear solution was degassed with nitrogen for 15 minutes, then tetrakis(triphenylphosphine)palladium(0) (0.021 g, 0.018 mmol) was added and the reaction tube was sealed and heated at 100° C. overnight. The sealed tube was cooled and opened and the contents was diluted with DCM and H$_2$O, then filtered through Celite. The solvent was evaporated to dryness to provide 5-[3-[5-trifluoromethoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-pyridine-3-carbaldehyde Compound 17a (0.241 g) as a brown semi-solid which was used directly in the next step without further purification. LCMS single peak, 4.614 min, MS (ESI) m/z 685.2 (M+H$^+$).

Compound 17a (0.062 g, 0.09 mmol) was treated with methylamine (1.0 mL of 2.0 M THF solution) and NaBH(OAc)$_3$ (0.057 g, 0.27 mmol) in DCM (20 mL) at room temperature overnight. The mixture was diluted with DCM, sequentially washed with H$_2$O, NaHCO$_3$ and brine, then dried over Na$_2$SO$_4$. The solvent was removed under vacuum and the resulting brown oil (0.14 g) was purified by preparative TLC separation (20% AcOEt/10% MeOH/DCM, v/v/v) to provide methyl-{5-[3-[5-trifluoromethoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-pyridin-3-ylmethyl}-amine Compound 17b (0.030 g, yield 47%) was obtained as yellowish oil by. MS (ESI) m/z 700.3 (M+H$^+$).

Compound 17b (0.25 g, 0.04 mmol) was treated with 4M HCl (6 mL) in EtOH (6 mL) at −78° C. for about 18 hrs. The solvent was evaporated to dryness and the resulting off-white solid (0.025 g) was purified by preparative HPLC to provide Compound 96 (0.0056 g, yield 28%) as a white solid. MS (ESI) m/z 440 (M+H$^+$); $^1$H NMR (300 MHz, CD$_3$OD) δ 9.26 (s, 1 H), 9.19 (s, 1 H), 9.05 (s, 1 H), 8.80 (s, 1 H), 8.52 (s, 1 H), 7.82 (d, 1 H, J=8.7 Hz), 7.68 (s, 1 H), 7.37 (d, 1 H, J=8.4 Hz), 4.45 (s, 2 H), 2.88 (s, 3 H).

Example 18

2-[2-(5-pyridin-3-yl-1H-pyrazolo[3,4-b]pyridine-3-yl)-1H-benzoimidazol-5-yloxyl]-ethanol (Compound 95)

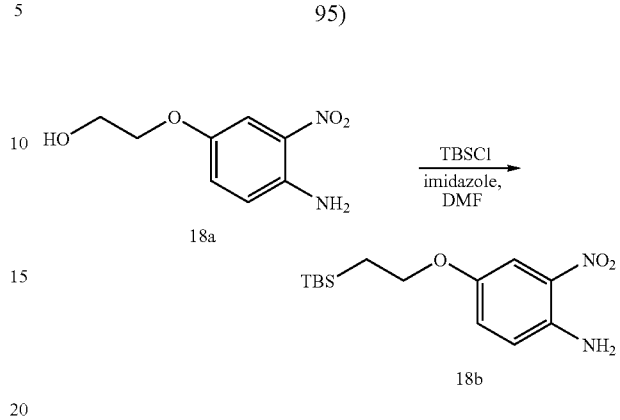

2-(4-amino-3-nitro-phenoxy)-ethanol Compound 18a (0.5 g, 2.52 mmol) was treated with TBSCl (0.42 g, 2.52 mmol) and imidazole (0.173 g, 2.52 mmol) in DMF (10 mL) at room temperature overnight. DMF was removed under vacuum and the residue was diluted with AcOEt, washed with H$_2$O and saturated aqueous NH$_4$Cl and dried over Na$_2$SO$_4$. The solvent was evaporated to dryness to provide 4-[2-(tert-butyl-dimethyl-silanyl)-ethoxy]-2-nitro-phenylamine Compound 18b (0.787 g) as a golden solid. LCMS single peak, 3.93 min, MS (ESI) m/z 313.2 (M+H$^+$). $^1$H NMR (300 MHz, CDCl$_3$) δ 7.46 (s, 1 H), 7.00 (d, 1 H, J=9.0 Hz), 6.66 (d, 1 H, J=9.0 Hz), 3.94-3.84 (m, 4 H), 0.81 (s, 9 H), −0.01 (s, 6 H).

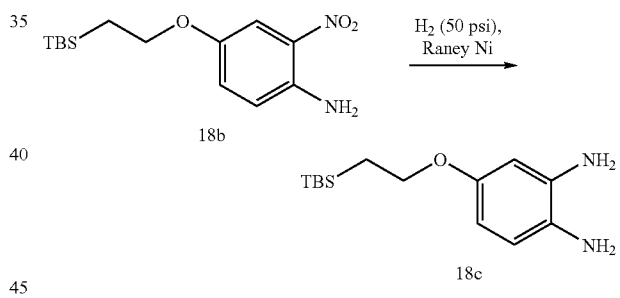

Compound 18b (0.787 g, 2.52 mmol) was dissolved in EtOH (30 mL) and Raney Ni (~0.5 g, pre-washed with EtOH) was added. The mixture was shaken in a Parr shaker under H$_2$ (50 psi) at room temperature overnight then filtered through Celite. The solvent was evaporated to dryness to provide 4-[2-(tert-butyl-dimethyl-silanyl)-ethoxy]-benzene-1,2-diamine Compound 18c (0.58 g, yield 82%) as a red-brown sticky oil. LCMS major peak, 2.817 min, MS (ESI) m/z 283.2 (M+H$^+$). $^1$H NMR (300 MHz, CDCl$_3$) δ 6.59 (d, 1 H, J=8.4 Hz), 6.30 (s, 1 H), 6.23 (d, 1 H, J=8.1 Hz), 3.93-3.89 (m, 4 H), 0.88 (s, 9 H), 0.06 (s, 6 H).

A mixture of 5-bromo-1H-pyrazolo[3,4-b]pyridine-3-carboxylic acid Compound 1c (0.72 g, 2.05 mmol), Compound 18c (0.58 g, 2.05 mmol), HATU (0.78 g, 2.05 mmol) and DIPEA (1.1 mL, 6.15 mmol) in DMF (30 mL) was stirred at room temperature overnight. The solvent was removed in vacuo and the resulting yellow residue was mixed with AcOEt, sequentially washed with saturated aqueous NH$_4$Cl, 1M HCl, H$_2$O and saturated aqueous NaHCO$_3$ and dried over Na$_2$SO$_4$. The solvent was evaporated to dryness to provide 5-bromo-1H-pyrazolo[3,4-b]pyridine-3-carboxylic acid {2-amino-4-[2-(tert-butyl-dimethyl-silanyl)-ethoxy]-phenyl}-amide Compound 18d (1.02 g, 98% yield) as a reddish solid. LCMS major peak, 3.523 min, MS (ESI) m/z 506.1 (M$^+$)/507.1 (M+H$^+$).

A solution of Compound 18d (1.02 g, 2.05 mmol) in glacial acetic acid (50 mL) was stirred in an oil-bath at 80-90° C. for 9 hrs. The solvent was evaporated to dryness to provide 5-bromo-3-{5-[2-(tert-butyl-dimethyl-silanyl)-ethoxy]-1H-benzoimidazol-2-yl}-1H-pyrazolo[3,4-b]pyridine Compound 18e (0.98 g, 98% yield) as a deep yellow solid. LCMS major peak, 3.509-3.595 min, MS (ESI) m/z 490.0 (M$^+$+2).

Compound 18e (0.98 g, 2 mmol) was treated with NaH (0.176 g, 4.4 mmol) in DMF (30 mL) for 0.5 hr. at room temperature, followed by SEMCl (1.05 mL, 6 mmol). The solvent was removed in vacuo and the resulting yellow residue was mixed with AcOEt (80 mL), washed with H$_2$O and saturated aqueous NH$_4$Cl and dried over Na$_2$SO$_4$. The solvent was evaporated to dryness to provide a brownish sticky oil (1.23 g, 82% yield) which was purified by flash column chromatography (10-25% AcOEt/Hexane, v/v) to provide 5-bromo-3-[5-[2-(tert-butyl-dimethyl-silanyl)-ethoxy]-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 18f as a colorless oil (solidified at room temperature). LCMS two peaks, 5.165 and 5.259 min, MS (ESI) m/z 766.2 (M$^+$+H$_2$O).

Compound 18f (0.10 g, 0.13 mmol), 3-(4,4,5,5-tetramethyl-[1,3,2]dioxaborolan-2-yl)-pyridine Compound 16f (0.055 g, 0.27 mmol) and 2M Na$_2$CO$_3$ (2 drops) were mixed in DME (5 mL) in a reaction tube and the resulting yellowish clear solution was degassed with nitrogen for 15 minutes. Tetrakis(triphenylphosphine)palladium(0) (0.015 g, 0.013 mmol) was added to the tube and the tube was heated at 100° C. overnight. The sealed tube was cooled and opened and the contents was diluted with DCM and H$_2$O, then filtered through Celite. The solvent was evaporated to dryness to provide a black oil (0.204 g) which was purified by preparative thin layer chromatography (20% AcOEt/DCM, v/v) to provide 3-[5-[2-(tert-butyl-dimethyl-silanyl)-ethoxy]-1-(2-trimethylsilanyl-ethoxymethyl)-1H-benzoimidazol-2-yl]-5-pyridin-3-yl-1-(2-trimethylsilanyl-ethoxymethyl)-1H-pyrazolo[3,4-b]pyridine Compound 18g (0.036 g, yield 36%) as a yellow oil. MS (ESI) m/z 765.3 (M$^+$+H$_2$O).

Compound 18g (0.026 g, 0.03 mmol) was treated with 4M HCl (10 mL) in EtOH (20 mL) at −78° C. for about 18 hrs. The solvent was evaporated to dryness and the resulting yellowish solid (0.025 g) was purified by preparative HPLC to provide Compound 95 (0.011 g) as a yellow solid. MS (ESI) m/z 373.2 (M+H$^+$); $^1$H NMR (300 MHz, CD$_3$OD) δ 9.26 (s, 2 H), 9.10 (s, 1 H), 8.85 (s, 2 H), 8.06 (d, 1 H, J=4.2 Hz), 8.73 (d, 1 H, J=9.3 Hz), 7.32 (s, 1 H), 7.25 (d, 1 H, J=8.7 Hz), 4.16 (m, 2 H), 3.95 (t, 2 H, J=4.2 Hz).

Using the procedure of Example 18, other compounds of the present invention were prepared:

| Cpd | Data |
|---|---|
| 93 | 2-(5-pyridin-3-yl-1H-pyrazolo[3,4-b]pyridin-3-yl)-1H-benzoimidazole-4-carboxylic acid methyl ester<br>2,3-diamino-benzoic acid methyl ester was used in place of Compound 18c.<br>$^1$H NMR (300 MHz, CD$_3$OD) δ 9.36 (s, 1H), 9.32 (d, 1H, J = 2.1 Hz), 9.10 (d, 1H, J = 1.8 Hz), 9.01 (d, 1H, J = 8.4 Hz), 8.90 (d, 1H, J = 6.3 Hz), 8.18 (t, 1H, J = 5.7 Hz), 8.08 (s, 1H), 8.05 (s, 1H), 7.49 (t, 1H, J = 8.1 Hz), 4.09 (s, 3H); MS (ESI) m/z: 371.1 (M + H$^+$). |
| 98 | 2,2-difluoro-6-(5-pyridin-3-yl-1H-pyrazolo[3,4-b]pyridin-3-yl)-5H-[1,3]dioxolo[4',5':4,5]benzo[1,2-d]imidazole<br>2,2-difluoro-benzo[1,3]dioxole-5,6-diamine was used in place of Compound 18c.<br>$^1$H NMR (400 MHz, DMSO-d$_6$) δ 9.34 (s, 1H), 9.27 (d, 1H, J = 1.8 Hz), 9.07 (d, 1H, J = 2.1 Hz), 9.05 (d, 1H, J = 8.1 Hz), 8.90 (d, 1H, J = 5.4 Hz), 8.25-8.14 (m, 1H), 7.53 (s, 2H); MS (ESI) m/z: 393 (M + H$^+$). |
| 99 | 6-(5-pyridin-3-yl-1H-pyrazolo[3,4-b]pyridin-3-yl)-5H-[1,3]dioxolo[4',5':4,5]benzo[1,2-d]imidazole<br>benzo[1,3]dioxole-5,6-diamine was used in place of Compound 18c.<br>$^1$H NMR (400 MHz, DMSO-d$_6$) δ 9.29 (s, 1H), 9.24 (s, 1H), 9.11 (s, 1H), 8.95-8.80 (m, 2H), 8.15-8.05 (m, 1H), 7.24 (s, 2H), 6.16 (s, 2H); MS (ESI) m/z: 357 (M + H$^+$). |
| 100 | {5-[3-(2,2-difluoro-5H-[1,3]dioxolo[4',5':4,5]benzo[1,2-d]imidazol-6-yl)-1H-pyrazolo[3,4-b]pyridin-5-yl]-pyridin-3-ylmethyl}-methyl-amine<br>2,2-difluoro-benzo[1,3]dioxole-5,6-diamine was used in place of Compound 18c, 5-(4,4,5,5-tetramethyl-[1,3,2]dioxaborolan-2-yl)-pyridine-3-carbaldehyde Compound 15b was used in place of 3-(4,4,5,5-tetramethyl-[1,3,2]dioxaborolan-2-yl)-pyridine Compound 16f to provide 5-[3-[2,2-difluoro-5-(2-trimethylsilanyl-ethoxymethyl)-5H-[1,3]dioxolo[4',5':4,5]benzo[1,2-d]imidazol-6-yl]-1-(2-trimethylsilanyl-ethoxymethyl)-1H-pyrazolo[3,4-b]pyridin-5-yl]-pyridine-3-carbaldehyde which was then reacted with methyl amine to provide {5-[3-[2,2-difluoro-5-(2-trimethylsilanyl-ethoxymethyl)-5H-[1,3]dioxolo[4',5':4,5]benzo[1,2-d]imidazol-6-yl]-1-(2-trimethylsilanyl-ethoxymethyl)-1H-pyrazolo[3,4-b]pyridin-5-yl]-pyridin-3-ylmethyl}-methyl-amine which was carried forward in place of 3-[5-[2-(tert-butyl-dimethyl-silanyl)-ethoxy]-1-(2-trimethylsilanyl-ethoxymethyl)-1H-benzoimidazol-2-yl]-5-pyridin-3-yl-1-(2-trimethylsilanyl-ethoxymethyl)-1H-pyrazolo[3,4-b]pyridine Compound 18g.<br>$^1$H NMR (400 MHz, DMSO-d$_6$) δ 9.21 (s, 1H), 9.19 (s, 1H), 9.03 (s, 1H), 8.82 (s, 1H), 8.59 (s, 1H), 7.59 (s, 2H), 4.46 (s, 2H), 2.876 (s, 3H); MS (ESI) m/z: 436 (M + H$^+$). |

Example 19

3-(6-methoxy-1H-benzoimidazol-2-yl)-5-pyridin-3-yl-1H-pyrazolo[3,4-b]pyridine (Compound 90)

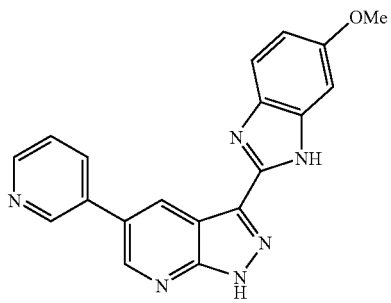

A mixture of 5-bromo-1H-pyrazolo[3,4-b]pyridine-3-carboxylic acid Compound 1c (200 mg, 0.826 mmol), 4-methoxy-benzene-1,2-diamine Compound 19a (114 mg, 0.826 mmol), HATU (314 mg, 0.826 mmol) and DIPEA (213 mg, 1.652 mmol) in DMF (10 mL) was stirred and heated to 45° C. overnight. The mixture was diluted with AcOEt (60 mL) and washed with water. The organic layer was separated, dried and evaporated to give a brown solid residue. The residue was recrystallized with AcOEt/hexane mixture to give 5-bromo-1H-pyrazolo[3,4-b]pyridine-3-carboxylic acid (2-amino-5-methoxy-phenyl)-amide Compound 19b (221 mg, 74% yield) as a light brown powder. MS m/z 362 (M+).

A solution of Compound 19b (221 mg, 0.610 mmol) in acetic acid (3 mL) was heated to 80° C. for 4.5 hrs. The solvent was evaporated to provide 5-bromo-3-(6-methoxy-1H-benzoimidazol-2-yl)-1H-pyrazolo[3,4-b]pyridine Compound 19c (HOAc salt, 230 mg, 93% yield) as a brown powder, which was used in the next step without further purifications. MS: m/z 345 (M+H+).

A solution of Compound 19c (70 mg, 0.173 mmol), (BOC)$_2$O (83 mg, 0.381 mmol), Et$_3$N (58 mg, 0.571 mmol) and DMAP (3 mg) in dichloromethane-(5 mL) was stirred at rt and monitored by TLC. After 3 hrs, the reaction mixture was sequentially washed with sat'd NaHCO$_3$ and water. The organic layer was separated, dried and evaporated to give 5-bromo-3-(1-tert-butoxycarbonyl-6-methoxy-1H-benzoimidazol-2-yl)-pyrazolo[3,4-b]pyridine-1-carboxylic acid tert-butyl ester Compound 19d as a crude product.

A mixture of Compound 19d in dioxane (5 mL), 3-(4,4,5,5-tetramethyl-[1,3,2]dioxaborolan-2-yl)-pyridine Compound 16f (39 mg, 0.190 mmol), tetrakis(triphenylphosphine)palladium(0) (40 mg, 0.034 mmol), 2M Na$_2$CO$_3$ (0.2 mL) and MeOH (2 mL) was put into a reaction tube and the tube was sealed and heated to 90° C. for 12 hrs. The reaction mixture was filtered and the filtrate solvents were evaporated to give an orange oil which was purified by preparative HPLC to give the TFA salt of Compound 90 (8.0 mg, 10% yield) as a yellowish powder. $^1$H NMR (400 MHz, DMSO-d$_6$) δ 3.84 (s, 3H), 6.98 (d, J=6.0 Hz, 1H), 7.17 (s, 1H), 7.63 (d, J=8.0 Hz, 1H), 7.7 (m, 1H), 8.45 (d, J=8.0 Hz, 1H), 8.80 (m, 1H), 9.0 (s, 1H), 9.1 (s, 1H), 9.20 (s, 1H), MS (ESI) m/z: 343 (M+H+).

Using the procedure of Example 19, other compounds of the present invention were prepared:

| Cpd | Data |
|---|---|
| 91 | 2-(5-pyridin-3-yl-1H-pyrazolo[3,4-b]pyridin-3-yl)-3H-benzoimidazole-5-carboxylic acid methyl ester (TFA salt)<br>3,4-diamino-benzoic acid methyl ester was used in place of Compound 19a.<br>$^1$H NMR (400 MHz, DMSO-d$_6$) δ 3.95 (s, 3H), 7.73 (d, J = 5.8 Hz, 1H), 8.02 (m, 2H), 8.44 (s, 1H), 8.79 (d, J = 5.7 Hz, 2H), 9.02 (s, 1H), 9.24 (s, 2H); MS (ESI) m/z: 371 (M + H+). |
| 92 | 3-(6-fluoro-1H-benzoimidazol-2-yl)-5-pyridin-3-yl-1H-pyrazolo[3,4-b]pyridine (TFA salt)<br>4-fluoro-benzene-1,2-diamine was used in place of Compound 19a.<br>$^1$H NMR (400 MHz, DMSO-d$_6$) δ 7.12 (m, 1H), 7.43 (d, J = 10 Hz, 1H), 7.63 (m, 1H), 7.70 (m, 1H), 8.49 (d, J = 10 Hz, 1H), 8.76 (m, 1H), 9.10 (s, 2H), 9.15 (m, 1H); MS (ESI) m/z: 331 (M + H+). |

Example 20

{5-[3-(6-methoxy-1H-benzoimidazol-2-yl)-1H-pyrazolo[3,4-b]pyridin-5-yl]-pyridin-3-ylmethyl}-methyl-amine (Compound 97)

5-bromo-3-(6-methoxy-1H-benzoimidazol-2-yl)-1H-pyrazolo[3,4-b]pyridine Compound 19c (HOAc salt, 50 mg, 0.145 mmol) was added to a suspension of NaH (60% in mineral oil, 23 mg, 0.581 mmol) in DMF (5 mL). The mixture was stirred at r.t. for 5 mins, then SEMCl (97 mg, 0.581 mmol) was added. The mixture was stirred at r.t. for 12 hrs, then diluted with AcOEt (60 mL) and washed with water. The solvent was evaporated to dryness and the residue was purified by chromatography to provide 5-bromo-3-[6-methoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridine Compound 20a (60 mg, 78% yield) as a sticky oil.

A mixture of Compound 20a (60 mg, 0.099 mmol), 5-(4,4,5,5-tetramethyl-[1,3,2]dioxaborolan-2-yl)-pyridine-3-carbaldehyde Compound 15b (25 mg, 0.109 mmol), tetrakis(triphenylphosphine)palladium(0) (23 mg, 0.0198 mmol) and 2M Na$_2$CO$_3$ (0.1 mL) in dioxane (5 mL) was heated to 90° C. in a sealed reaction tube for 12 hrs. The reaction mixture was filtered through Celite and the solvents were evaporated to dryness to provide 5-[3-[6-methoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-pyridine-3-carbaldehyde Compound 20b as an orange oil, which was used in the next step without further purification.

Compound 20b was dissolved in THF (1 mL) and MeOH (3 mL) and a solution of 2M MeNH$_2$ (0.5 mL) in THF was added. The mixture was stirred at r.t. for 1 hr and NaBH$_4$ (37 mg, 0.99 mmol) was added in portions. The mixture was stirred at r.t. for 12 hrs, then evaporated to dryness and the residue was purified in 2 steps via preparative TLC to provide {5-[3-[6-methoxy-1-(2-trimethylsilanyl-ethoxymethyl)-1H-benzoimidazol-2-yl]-1-(2-trimethylsilanyl-ethoxymethyl)-1H-pyrazolo[3,4-b]pyridin-5-yl]-pyridin-3-ylmethyl}-methyl-amine Compound 20c (18 mg, 28% yield) as a sticky oil.

4M HCl (2 mL) was added to a solution of Compound 20c in EtOH (1 mL), then additional EtOH was added to make a homogeneous solution. The solution was refluxed for 12 hrs, evaporated to dryness and the residue was recrystallized from MeOH/Et$_2$O to give Compound 97 (tri-HCl salt, 13 mg, 100% yield) as a yellow powder. $^1$H NMR (400 MHz, DMSO-d$_6$) δ 2.48 (s, 3H), 3.92 (s, 3H), 4.37 (m, 2H), 7.20 (d, J=7.2 Hz, 1H), 7.32 (s, 1H), 7.81 (d, J=7.2 Hz, 1H), 8.94 (s, 1H), 9.05 (s, 1H), 9.28 (s, 1H), 9.46 (s, 1H), 9.88 (s, 1H); MS (ESI) m/z: 386 (M+H$^+$).

Using the procedure of Example 20, other compounds of the present invention were prepared:

| Cpd | Data |
|---|---|
| 101 | ethyl-{5-[3-(5-methoxy-1H-benzoimidazol-2-yl)-1H-pyrazolo[3,4-b]pyridin-5-yl]-pyridin-3-ylmethyl}-amine<br>ethylamine was used in place of methylamine.<br>$^1$H NMR (400 MHz, DMSO-d$_6$) δ 1.08 (t, J = 7.6 Hz, 3H), 3.06 (m, 2H), 3.88 (s, 3H), 4.36 (m, 2H), 7.15 (d, J = 8.8 Hz, 1H), 7.28 (s, 1H), 7.78 (d, J = 8.8 Hz, 1H), 8.88 (s, 1H), 8.92 (s, 1H), 9.23 (s, 1H), 9.36 (s, 1H), 9.71 (s, 1H); MS (ESI) m/z: 400 (M + H$^+$). |
| 102 | isopropyl-{5-[3-(5-methoxy-1H-benzoimidazol-2-yl)-1H-pyrazolo[3,4-b]pyridin-5-yl]-pyridin-3-ylmethyl}-amine<br>isopropylamine was used in place of methylamine.<br>$^1$H NMR (400 MHz, DMSO-d$_6$) δ 1.31 (d, J = 6.5 Hz, 6H), 3.45 (m, 1H), 3.83 (s, 3H), 4.37 (t, J = 6.2 Hz, 2H), 6.91 (dd, J$_1$ = 8.7 Hz, J$_2$ = 2.1 Hz, 1H), 7.12 (s, 1H), 7.57 (d, J = 8.5 Hz, 1H), 8.45 (s, 1H), 8.78 (s, 1H), 9.05 (d, J = 1.9 Hz, 1H), 9.08 (d, J = 1.8 Hz, 1H), 9.12 (s, 1H); MS (ESI) m/z: 414 (M + H$^+$). |
| 103 | {5-[3-(5-methoxy-1H-benzoimidazol-2-yl)-1H-pyrazolo[3,4-b]pyridin-5-yl]-pyridin-3-ylmethyl}-propyl-amine<br>ethyl-propyl-amine was used in place of methylamine.<br>MS m/z: 414 (calc'd M + H$^+$). |
| 104 | butyl-{5-[3-(5-methoxy-1H-benzoimidazol-2-yl)-1H-pyrazolo[3,4-b]pyridin-5-yl]-pyridin-3-ylmethyl}-amine<br>butyl-ethyl-amine was used in place of methylamine.<br>MS m/z: 428 (calc'd M + H$^+$). |
| 105 | 2-[5-(5-methylaminomethyl-pyridin-3-yl)-1H-pyrazolo[3,4-b]pyridin-3-yl]-3H-benzoimidazole-5-carbonitrile<br>ethyl-methyl-amine was used in place of methylamine and 3,4-diamino-benzonitrile was used in place of Compound 19a.<br>MS m/z: 381 (calc'd M + H$^+$). |
| 106 | ethyl-{5-[3-(6-fluoro-1H-benzoimidazol-2-yl)-1H-pyrazolo[3,4-b]pyridin-5-yl]-pyridin-3-ylmethyl}-amine<br>diethyl-amine was used in place of methylamine and 4-fluoro-benzene-1,2-diamine was used in place of Compound 19a.<br>MS m/z: 388 (calc'd M + H$^+$). |
| 107 | {5-[3-(5,6-difluoro-1H-benzoimidazol-2-yl)-1H-pyrazolo[3,4-b]pyridin-5-yl]-pyridin-3-ylmethyl}-ethyl-amine<br>diethyl-amine was used in place of methylamine and 5,6-difluoro-benzene-1,2-diamine was used in place of Compound 19a.<br>MS m/z: 406 (calc'd M + H$^+$). |

BIOLOGICAL EXAMPLES

The ability of the compounds to treat or ameliorate protein kinase mediated disorders was determined using the following procedures.

Example 1

CDK-1, VEGF-R2, RET, Aurora-A and HER2 Screening Assays

A kinase reaction mixture was prepared containing 50 mM Tris-HCl pH=8, 10 mM $MgCl_2$, 0.1 mM $Na_3PO_4$, 1 mM DTT, 10 μM ATP, 0.025 μM biotinylated histone-H1 peptide substrate and 0.2 μCuries per well $^{33P}$-γ-ATP (2000-3000 Ci/mmol). 70 μL of the kinase reaction mixture was dispensed into the well of a streptavidin coated FlashPlate™ (Cat. # SMP103, NEN, Boston, Mass.).

Test compound stock in 100% DMSO (1 μL) was added to the wells resulting in a final concentration of 1% DMSO in the reaction with a 100 μL final reaction volume. Each enzyme was diluted in 50 mM Tris-HCl pH=8.0, 0.11% BSA and 30 μL was added to each well to initiate the reaction. The reaction was incubated for one hour at 30° C. At the end of the 1 hr incubation, the reaction was terminated by aspirating the mixture from the plate and washing the wells twice with PBS containing 100 mM EDTA. The biotinylated peptide substrate became immobilized on the Flashplate™ and the incorporation of $^{33}$P-γ-ATP was measured by reading the plate on a scintillation counter. Inhibition of the enzymatic activity was measured by observing a reduced amount of $^{33}$P-γ-ATP incorporated into the immobilized peptide.

The CDK1 enzyme was isolated from insect cells expressing both the human CDK1 catalytic subunit (Accession number NM_001786) and its positive regulatory subunit cyclin B (New England Biolabs, Beverly, Mass.; Cat. # 6020). The assay used 30 ng of the N-terminal biotinylated peptide biotin-KTPKKAKKPKTPKKAKKL-amide (Cyclin dependent kinase 1) per well.

The VEGF-R2 enzyme is a fusion protein containing a polyhistidine tag at the N terminus followed by amino acids 786 to 1343 of the rat VEGF-R2 kinase domain (Accession number U93306). The assay used 150 ng of the N-terminal biotinylated peptide biotin-AEPDYGALYEGRNPG-FYVEANP-amide (VEGF-R2) per well.

The HER2 construct consisted of a fusion of GST (Glutathione-S-Transferase), HIS6 Thrombin and the nucleotides encoding amino acids 679 to 1255 of HER-2 (Accession number M11730) (Proqinase, Freiburg, Germany). The assay used 200 ng of the N-terminal biotinylated peptide biotin-poly(GT) 4:1 (HER2) per well.

The RET enzyme is a fusion protein containing a polyhistidine tag at the N terminus followed by amino acids 405 to 860 of the human RET kinase domain (Accession number X12929) starting after the transmembrane domain and including the entire intracellular domain. The assay used 200 ng of the N-terminal biotinylated peptide biotin-AEPDYGA-LYEGRNPGFYVEANP-amide (RET) per well.

Aurora-A was a fusion protein containing a polyhistidine tag at the N terminus followed by the entire protein sequence of mouse Aurora-A (Accession number BC014711). The assay used 400 ng of the N-terminal biotinylated peptide biotin-GRTGRRNSI-amide (Aurora-A) per well.

A maximum and minimum signal for the assay was determined on each plate. The percent inhibition of a test compound was calculated according to the formula:

$$\left[ \frac{(\text{max signal- test compound})}{(\text{max signal- min signal})} \right] (100) = \% \text{ inhibition}$$

For a series of test concentrations, the $IC_{50}$ was derived by graphing percent inhibition against the log of the concentrations tested for a given compound with results shown in Table 1.

For those compounds without an $IC_{50}$, the inhibition values in percent are shown at a test concentration of 2 μM. For compounds with multiple values, each value represents a separate assay result.

TABLE 1

Kinase $IC_{50}$ (μM)

| Cpd | CDK1 $IC_{50}$ (μM) | VEGF-R2 $IC_{50}$ (μM) | HER2 $IC_{50}$ (μM) | Aurora-A $IC_{50}$ (μM) | RET $IC_{50}$ (μM) |
|---|---|---|---|---|---|
| 1 | 0.0233 | 1.463 | 0.1409 | ND | ND |
| 2 | 0.09672 | 10 | 1 | ND | ND |
| 3 | 0.04125 | >100 | 0.2451 | >10 | >100 |
| 4 | 0.00561 | 0.4607 | 0.08507 | 0.3241 | >10 |
| 5 | 0.00178 | 1.547 | 0.0893 | 1 | 1 |
| 6 | 0.07763 | 0.9522 | 0.08938 | 0.9751 | >10 |
| 7 | 0.004922 | 1.5710 | ND | 1.7180 | >10 |
| 8 | 0.008111 | 0.4032 | ND | 1.3700 | >10 |
| 9 | 0.00845 | 0.2103 | ND | ~10 | ~10 |
| 10 | 0.01585 | 0.1630 | ND | 6.7440 | >10 |
| 11 | 0.3584 | 0.9158 | ND | ~10 | ~10 |
| 12 | 0.0415 | ~10 | ND | ~10 | ~100 |
| 13 | 0.0128 | ~1 | >100 | 3.623 | >100 |
| 14 | 0.07206 | 4.5660 | >100 | >1 | ~100 |
| 15 | 0.033 | ~1 | ~100 | 2.2660 | 0.9286 |
| 16 | 0.06546 | 0.0607 | >100 | >1 | >1 |
| 17 | 0.5414 | >10 | >100 | >10 | >100 |
| 18 | 0.003953 | 0.3780 | >10 | >0.1 | 0.4135 |
| 19 | 0.0534 | ~10 | ~100 | >1 | >10 |
| 20 | 0.02856 | ~10 | >10 | ~1 | 1.2270 |
| 21 | 0.1623 | 2.7920 | >10 | 4.8320 | >10 |
| 22 | 0.1369 | 2.1220 | >10 | 1.9880 | ~100 |
| 23 | 1.633 | 6.9260 | >10 | 10.8600 | >100 |
| 24 | 0.04199 | 4.6170 | >10 | 2.7930 | ~100 |
| 25 | 0.1129 | ~100 | >10 | >1 | >100 |
| 26 | 0.2435 | >10 | >10 | 12.0800 | ~100 |
| 27 | 0.03173 | 1.0440 | >10 | >1 | >1 |
| 28 | 0.7237 | >100 | >10 | >10 | >100 |
| 29 | 0.01158 | 0.2317 | >100 | ~1 | ~1 |
| 30 | 0.425 | 0.2384 | >10 | ~1 | 1.0730 |
| 31 | 0.01363 | 1.0020 | 6.5130 | ~1 | ~1 |
| 32 | 0.09874 | ~0.1 | >100 | >1 | >100 |
| 33 | 0.1232 | >100 | >100 | ~100 | >100 |
| 34 | 1.362 | 0.1573 | >100 | >10 | ~10 |
| 35 | 0.02934 | 0.1603 | >100 | >1 | 1.0990 |
| 36 | 0.5459 | 0.4363 | >100 | >1 | >10 |
| 37 | 0.08747 | >.01 | >100 | 0.1913 | 0.1502 |
| 38 | >10 | >1 | >100 | ~100 | >100 |
| 39 | 1.215 | 0.2662 | >100 | >1 | >100 |
| 40 | 1.185 | 0.4617 | >100 | ~1 | 1.268 |
| 41 | 0.2307 | >1 | ~100 | 0.2483 | >100 |
| 42 | 0.0098 | ~1 | >10 | 4.4640 | 7.633 |
| 43 | 0.0291 | 0.6827 | >10 | 6.58 | 2.229 |
| 44 | 0.08894 | 0.3410 | >100 | >1 | ~10 |
| 45 | 0.03491 | >0.1 | 30.9900 | 0.0400 | >100 |
| 46 | 0.08056 | 0.7021 | ~100 | 0.2303 | ~10 |
| 47 | 0.001586 | 0.1487 | ~10 | 0.0572 | ~1 |
| 48 | 0.01855 | ~0.01 | >100 | ~1 | >10 |
| 49 | 0.06484 | >10 | >100 | 0.1542 | ~1 |
| 50 | 0.04061 | >100 | >100 | 0.1679 | >10 |
| 51 | 0.008548 | 1.0760 | >100 | 0.0415 | ~1 |
| 52 | 0.02456 | 1.0270 | >100 | 3.6250 | ~10 |
| 53 | 0.1039 | 0.0370 | >10 | 1.5230 | >1 |
| 54 | 0.1766; 0.3431 | 1.876; 1.570 | >100; >100 | 3.260; 4.639 | 2.99; >10 |
| 55 | 0.124 | 1.599 | >100 | 3.7540 | 3.2320 |
| 56 | 0.002538 | 0.6394 | >100 | >1 | ~1 |

TABLE 1-continued

| Cpd | CDK1 IC$_{50}$ (µM) | VEGF-R2 IC$_{50}$ (µM) | HER2 IC$_{50}$ (µM) | Aurora-A IC$_{50}$ (µM) | RET IC$_{50}$ (µM) |
|---|---|---|---|---|---|
| 57 | 0.06628 | >1 | >100 | >1 | >10 |
| 58 | 0.3388 | 3.8980 | >100 | 12.4300 | >10 |
| 59 | 0.1065 | 4.6730 | >100 | 8.0210 | >10 |
| 60 | 0.4708 | 3.0520 | ~100 | ~1 | >10 |
| 61 | 0.2835 | 4.1130 | >10 | 0.3209 | >10 |
| 62 | 0.06806 | 2.7900 | >100 | 1.7480 | ~10 |
| 63 | >10 | 0.3186 | >100 | ~100 | >100 |
| 64 | 0.08032 | 0.1598 | >100 | ~10 | >100 |
| 65 | >1 | 0.1149 | >100 | >1 | >100 |
| 66 | >100 | 0.1207 | >100 | >1 | >100 |
| 67 | >10 | >10 | >100 | >100 | >100 |
| 68 | 1.283 | 0.1146 | >100 | ~10 | >100 |
| 69 | >10 | ~1 | >100 | >1 | >100 |
| 70 | >100 | ~100 | >100 | ~100 | >100 |
| 71 | 0.3751 | ~1 | >100 | >10 | >100 |
| 72 | 0.02363 | >100 | >100 | >10 | >100 |
| 73 | 0.0427 | >10 | >10 | 4.7450 | >10 |
| 74 | 0.5509 | 0.2838 | ~100 | 6.8230 | ~100 |
| 75 | 0.06359 | 1.638 | >10 | 4.5010 | >10 |
| 76 | 0.5947 | 1.372 | >100 | 6.6020 | >100 |
| 77 | 0.01302 | 0.349 | >10 | 3.1850 | >10 |
| 78 | 0.007398 | ND | >10 | 3.9910 | >10 |
| 79 | 0.006814 | ~1 | >10 | 2.4480 | >10 |
| 80 | 0.8752 | 2.079 | >100 | >10 | >100 |
| 81 | 0.003044 | 0.03588 | 0.7153 | 0.1733 | 0.1106 |
| 82 | 0.003046 | 0.02498 | 1.0720 | 0.2830 | 0.1452 |
| 83 | 0.007669 | 0.0734 | 1.4910 | 0.2634 | 0.4107 |
| 84 | 0.03221 | ~0.1 | 1.8510 | 0.0873 | >1 |
| 85 | 0.001845 | 0.1604 | 1.8380 | 0.2799 | 0.3754 |
| 86 | 0.005171 | ~0.1 | 1.0460 | 0.4276 | 0.2139 |
| 87 | 0.02926 | 0.1128 | 12.1200 | 0.4451 | 0.4753 |
| 88 | 0.006144 | 0.1198 | 1.9190 | 0.2810 | 0.1036 |
| 89 | 0.006144 | 0.0475 | 31.8200 | 0.2249 | 0.1927 |
| 90 | 0.00274 | 0.3158 | 100 | 0.279 | 10 |
| 91 | 0.01121 | 100 | 100 | 100 | 100 |
| 92 | 0.00657 | 1 | 100 | 10 | 100 |
| 93 | 1 | 100 | 100 | 100 | 100 |
| 94 | 0.0060 | ND | >100 | >10 | >100 |
| 95 | 0.0034 | ND | >100 | 0.2293 | >1 |
| 96 | 0.0009-0.0013 | >0.1 | 3.8210 | ~1 | >100 |
| 97 | 0.0009 | | 1.4540 | 0.2041 | 0.2007 |
| 98 | 0.0066 | >0.1 | >100 | >10 | >100 |
| 99 | 0.0033 | ~1 | >100 | ~10 | >100 |
| 100 | 0.0016 | ~0.1 | 7.0600 | ~10 | 0.2175 |
| 101 | 0.0008 | >0.1 | 4.1700 | 0.3564 | ~1 |
| 102 | 0.0032 | 0.2689 | 10.6900 | 0.3587 | ~1 |
| 103 | 0.0004 | 0.0476 | 2.1600 | 0.2695 | 0.0355 |
| 104 | 0.0008 | 0.0179 | 1.8810 | 0.2448 | 0.0384 |
| 105 | 0.0017 | >.01 | >10 | >1 | >.01 |
| 106 | 0.0007 | 0.1538 | 5.1250 | 0.8032 | 0.1061 |
| 107 | 0.0011 | ~0.1 | 3.5990 | >1 | 0.0395 |
| 108 | ~10 | ~100 | >100 | ~100 | >100 |

Example 2 c-Src Kinase Assay

A mixture of a 10× kinase buffer (80 mM MOPS at pH 7.0, 2 mM EDTA and 100 mM Magnesium Chloride), ATP (5 µM final from a 10 mM stock), a Cdc2 peptide KVEKIGEG-TYGVVYK (100 µM final from a 2.5 mM stock), γ-$^{33}$P ATP (10 µCi/µL stock) and water (for a total of 20 µL/well) was added to each well of a Streptavidin Flashplate.

Test compound in 100% DMSO (0.5 µL) was added to the appropriate wells. Diluted c-Src kinase (human) (Accession Number SWISS-PROT P12931) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%), and 1 mg/mL bovine serum albumin) (2.5 µL) was added to the wells to initiate the reactions. The reaction plates were incubated at 30° C. for 40 min. The reaction was terminated by the addition of a 3% phosphoric acid solution (5 µL). The reaction product (10 µL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 µL scintillation fluid.

A maximum and minimum signal for the assay was determined on each plate. The percent inhibition of a test compound was calculated according to the formula:

$$\left[ \frac{(\text{max signal- test compound})}{(\text{max signal- min signal})} \right] (100) = \% \text{ inhibition}$$

For a series of test concentrations, the IC$_{50}$ was derived by graphing percent inhibition against the log of the concentrations tested for a given compound with results shown in Table 2

For those compounds without an IC$_{50}$, the inhibition values in percent are shown at a test concentration of 2 µM. For compounds with multiple values, each value represents a separate assay result.

TABLE 2

| Cpd | c-Src IC$_{50}$ (µM) |
|---|---|
| 31 | 0.004214 |
| 33 | 1.172 |
| 40 | 0.3269 |
| 41 | 0.09253 |
| 42 | 0.3582 |
| 43 | 0.8364 |
| 44 | 0.288 |
| 45 | 0.000653 |
| 46 | 0.001399 |
| 47 | 0.000635 |
| 48 | 0.004998 |
| 49 | 0.001126 |
| 50 | 0.001039 |
| 51 | 0.002825 |
| 52 | 0.5701 |
| 54 | 0.1428 |
| 55 | 0.1428 |
| 56 | 0.886 |
| 58 | 0.6526 |
| 64 | 0.6207 |
| 65 | 0.3154 |
| 69 | 0.5967 |
| 71 | 0.278 |
| 72 | 0.3753 |
| 73 | 0.8228 |
| 74 | 0.9536 |
| 75 | 0.3781 |
| 76 | 1.013 |
| 77 | 0.1827 |
| 80 | 0.2114 |
| 81 | 0.2254 |
| 82 | 0.712 |
| 83 | 0.006626 |
| 84 | 0.005183 |
| 90 | 0.05667 |
| 92 | 0.09792 |
| 94 | 0.756 |
| 95 | 0.07401 |
| 96 | 0.03116 |
| 97 | 0.01643 |
| 101 | 0.008852 |
| 102 | 0.01173 |

Example 3

Lyn Kinase Assay

A mixture of a 10× kinase buffer (500 mM MOPS at pH 7.5, 1 mM EGTA, 1 mM Sodium Vanadate, 1% β-mercaptoethanol and 100 mM Magnesium Acetate), ATP (5 μM final from a 10 mM stock), polyGluTyr (0.1 mg/mL final from a 1 mg/mL stock), γ-$^{33}$P ATP (10 μCi/μL stock) and water (for a total of 20 μL/well) was added to each well of a Streptavidin Flashplate.

Test compound in 100% DMSO (0.5 μL) was added to the appropriate wells. Diluted Lyn kinase (human) (Accession Number EMBL M16038) (Upstate Biotechnology, Lake Placid, N.Y.) (diluted in a buffer consisting of 50 mM Tris at pH 7.5, 0.1 mM EGTA, Sodium Vanadate (0.1 mM), β-mercaptoethanol (0.1%) and 1 mg/mL bovine serum albumin) (2.5 μL) was added to the wells to initiate the reactions.

The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

A maximum and minimum signal for the assay was determined on each plate. The percent inhibition of a test compound was calculated according to the formula:

$$\left[\frac{(\text{max signal-test compound})}{(\text{max signal-min signal})}\right](100) = \% \text{ inhibition}$$

For a series of test concentrations, the IC$_{50}$ was derived by graphing percent inhibition against the log of the concentrations tested for a given compound with results shown in Table 3

For those compounds without an IC$_{50}$, the inhibition values in percent are shown at a test concentration of 2 μM. For compounds with multiple values, each value represents a separate assay result.

TABLE 3

| Cpd | Lyn IC$_{50}$ (μM) |
|---|---|
| 31 | 0.003873 |
| 33 | 1.141 |
| 43 | 0.1323 |
| 44 | 0.3788 |
| 45 | 0.001328 |
| 46 | 0.006306 |
| 47 | 0.002276 |
| 48 | 0.02363 |
| 49 | 0.004349 |
| 50 | 0.005209 |
| 51 | 0.005 |
| 52 | 0.2989 |
| 54 | 0.5784 |
| 55 | 0.5784 |
| 56 | 1.076 |
| 58 | 0.5286 |
| 64 | 4.061 |
| 65 | 0.2771 |
| 69 | 2.889 |
| 71 | 9.012 |
| 72 | 1.055 |
| 80 | 0.1919 |
| 81 | 0.1697 |
| 82 | 0.4152 |
| 83 | 0.002426 |
| 84 | 0.009645 |
| 90 | 0.06941 |

TABLE 3-continued

| Cpd | Lyn IC$_{50}$ (μM) |
|---|---|
| 92 | >100 |
| 96 | 0.00838 |
| 97 | 0.00429 |
| 101 | 0.00254 |

Example 4

Cell Proliferation Inhibition Assay

The ability of a test compound to inhibit unregulated cell proliferation may be determined by measuring incorporation of $^{14}$C-labelled thymidine into newly synthesized DNA within cell lines derived from carcinomas originating from several tissues. Accordingly, the effect of a test compound on proliferation of cells with a variety of phenotypes may be determined.

Carcinoma cell lines used include the HeLa cervical adenocarcinoma from the American Type Culture Collection (ATCC Cat. #CCL2), A375 malignant melanoma (ATCC Cat. #CRL-1619) and HCT-116 colon carcinoma (ATCC Cat. #CCL-247).

The carcinoma cells are trypsinized and counted. The cells (3600-8000 count) are added to each well of a 96-well CytoStar tissue culture treated scintillating microplate (Amersham #RPNQ0160) in complete medium (100 μL) and the plate is then incubated in complete medium for 24 hrs at 37° C. in an inert atmosphere containing 5% $CO_2$.

Test compound (1 μL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) and complete medium (20 uL to provide 0.2 μCi/well) is then added to each well and the plate is incubated for a third 24 hr period at 37° C. in an atmosphere containing 5% $CO_2$.

The plate contents are then discarded, the plate is washed twice with PBS (200 μL) and then PBS (200 μL) is added to each well. The plate is sealed and the degree of methyl $^{14}$C-thymidine incorporation is quantified on a Packard Top Count.

TABLE 4

| Cpd | HELA IC$_{50}$ (μM) | HCT 116 IC$_{50}$ (μM) | A375 IC$_{50}$ (μM) |
|---|---|---|---|
| 1 | 2.758; 1.731; 0.5899 | 0.906; 0.5972; 0.14600 | 0.4201; 0.161; 2.028 |
| 2 | 3.093 | 1.637 | 1.717 |
| 3 | 1.756 | 0.8917 | 1.47 |
| 4 | 0.01478 | 0.01011 | 0.01011 |
| 5 | 0.02889 | 0.03055 | 0.04668 |
| 6 | 0.3539 | 0.2587 | 0.2549 |
| 7 | 0.1134 | 0.0648 | 0.0825 |
| 8 | 0.0486 | 0.0285 | 0.0292 |
| 9 | 0.0926 | 0.0647 | 0.0840 |
| 10 | 0.1267 | 0.1906 | 0.1176 |
| 11 | 1.8370 | 0.8657 | 0.8657 |
| 12 | 3.1970 | 1.8880 | 4.0940 |
| 13 | 0.1345 | 0.1091 | 0.1404 |
| 14 | 1.0040 | 0.3116 | 0.6494 |
| 15 | 8.5240 | 5.8190 | 7.6110 |
| 16 | 0.6318 | 0.2371 | 0.9095 |
| 17 | >10 | >10 | >10 |
| 18 | 0.0352 | 0.0415 | 0.0647 |
| 19 | 0.9746 | 1.8300 | 1.5710 |
| 20 | 0.1669 | 0.0550 | 0.0711 |
| 21 | 0.8045 | 0.8994 | 0.4721 |

TABLE 4-continued

| Cpd | HELA IC$_{50}$ (μM) | HCT 116 IC$_{50}$ (μM) | A375 IC$_{50}$ (μM) |
|---|---|---|---|
| 22 | 0.5944 | 0.5541 | 0.1876 |
| 23 | 6.5850 | 3.1690 | 2.7620 |
| 24 | 0.4602 | 0.7433 | 0.4895 |
| 25 | 3.7970 | 1.2220 | 2.0210 |
| 26 | 1.1640 | 0.8897 | 1.2080 |
| 27 | 0.1627 | 0.0787 | 0.0752 |
| 28 | 26.8900 | 4.9940 | 5.6240 |
| 29 | 0.2047 | 0.2549 | 0.0697 |
| 30 | 3.1020 | 2.4960 | 1.7030 |
| 31 | 0.4549 | 0.3554 | 0.1646 |
| 32 | 2.1370 | 2.8850 | 0.9053 |
| 33 | 1.1770 | 0.2029 | 0.2560 |
| 34 | 1.4640 | 0.0032 | 0.0107 |
| 35 | 0.6505 | 0.0188 | 0.0328 |
| 36 | 1.4280 | 0.0434 | 0.2124 |
| 37 | 1.8420 | 0.0050 | 0.0201 |
| 38 | 1.8970 | 0.0394 | 0.0568 |
| 39 | 1.6800 | 0.0260 | 0.0358 |
| 40 | 1.2250 | 0.0565 | 0.0737 |
| 41 | 1.2240 | 0.1608 | 0.2654 |
| 42 | 0.2981 | 0.2799 | 0.2390 |
| 43 | 0.1798 | 0.1313 | 0.1658 |
| 44 | 0.7707 | 0.1284 | 0.3568 |
| 45 | 7.5250 | >10 | 28.4900 |
| 46 | 0.1587 | 0.2251 | 0.1945 |
| 47 | 0.0122 | 0.0313 | 0.0129 |
| 48 | 0.3003 | 0.4876 | 0.1883 |
| 49 | 0.3344 | 0.4261 | 0.3019 |
| 50 | 0.2585 | 0.4554 | 0.2423 |
| 51 | 0.4009 | 0.3764 | 0.2969 |
| 52 | 0.4543 | 0.3448 | 0.2468 |
| 53 | 0.7092 | 0.3907 | 0.3277 |
| 54 | 0.402; 1.205 | 0.03355; 0.06349 | 0.02644; 0.1517 |
| 55 | 1.2260 | 0.1859 | 0.3303 |
| 56 | 0.4592 | 0.3131 | 0.2685 |
| 57 | 0.6852 | 0.0687 | 0.1194 |
| 58 | 2.7050 | 0.4589 | 0.1676 |
| 59 | 2.0740 | 0.4437 | 0.1234 |
| 60 | 1.5990 | 0.0395 | 0.0111 |
| 61 | 1.8340 | 0.0992 | 0.2192 |
| 62 | 1.1850 | 0.2286 | 0.0623 |
| 63 | 9.9650 | 0.1195 | 0.0763 |
| 64 | 1.5660 | 0.0261 | 0.0113 |
| 65 | 3.0860 | 0.0620 | 0.0226 |
| 66 | 1.0810 | 0.0204 | 0.0044 |
| 67 | 1.9810 | 0.0245 | 0.0109 |
| 68 | 9.9100 | 0.3254 | 0.1604 |
| 69 | 1.7290 | 0.0770 | 0.0185 |
| 70 | 1.9380 | 0.0554 | 0.0387 |
| 71 | 2.2610 | 0.2828 | 0.1495 |
| 72 | 0.6401 | 0.0292 | 0.0102 |
| 73 | 2.5540 | 0.4125 | 0.6777 |
| 74 | 4.7830 | 0.3855 | 0.4589 |
| 75 | 0.5936 | 0.1634 | 0.2047 |
| 76 | 10.0600 | 0.2553 | 0.1784 |
| 77 | 1.6190 | 0.6434 | 1.6130 |
| 78 | 0.2630 | 0.2722 | 0.2490 |
| 79 | 0.4173 | 0.2180 | 0.3434 |
| 80 | >10 | 2.3140 | 0.3969 |
| 81 | 0.4440 | 0.6000 | 0.7679 |
| 82 | 0.4738 | 0.5426 | 0.6269 |
| 83 | 1.4470 | 1.5000 | 1.0600 |
| 84 | 1.8850 | 0.7389 | 2.5300 |
| 85 | 0.6925 | 0.7740 | 0.4120 |
| 86 | 2.2880 | 2.3160 | 2.4860 |
| 87 | 2.1490 | 1.0460 | 0.8074 |
| 88 | 0.8609 | 0.4308 | 0.8850 |
| 89 | 0.6171 | 0.4227 | 0.5443 |
| 90 | 0.4181 | 0.299 | 0.3708 |
| 91 | 0.8262 | 0.3857 | 0.4284 |
| 92 | 0.6977 | 0.3483 | 0.4668 |
| 93 | 100 | 100 | 100 |
| 94 | 0.7987 | 0.5190 | 0.6451 |
| 95 | 1.9330 | 1.4070 | 2.648 |
| 96 | 0.0930 | 0.0555 | 0.04705 |
| 97 | 0.0614 | 0.0615 | 0.1644 |
| 98 | 1.6110 | 0.9426 | 1.08 |
| 99 | 0.4711 | 0.2712 | 0.4892 |
| 100 | 0.0551 | 0.2367 | 0.0525 |
| 101 | 0.0342 | 0.0487 | 0.1007 |
| 102 | 0.0472 | 0.1057 | 0.1199 |
| 103 | 0.0623 | 0.0335 | 0.0392 |
| 104 | 0.0850 | 0.0520 | 0.0395 |
| 105 | 0.12 | 0.685 | 0.526 |
| 106 | 0.0586 | 0.0937 | 0.0512 |
| 107 | 0.1377 | 0.0947 | 0.0461 |
| 108 | 10.5100 | 8.0100 | 7.3810 |

Example 5

In Vivo Models—Inhibition of Tumor Growth

The ability of test compounds to inhibit unregulated growth of human tumor cells in vivo was evaluated by implanting human tumor cells into the hindflank of athymic mice, administering a test compound and then quantifying any change in tumor size.

Certain compounds at particular doses produced adverse effects in this model. One skilled in the art would be able to establish the effective amount of compound required to achieve an effective therapeutic window.

The term "therapeutic window" means the range of dosage of a drug or of its concentration in a bodily system that provides safe effective therapy.

Human melanoma A375 cells were implanted subcutaneously into the hindflank of female athymic mice (Charles River) and allowed to grow for 6-10 days. After a measurable tumor was established (as determined by baseline caliper measurement), the animal was administered an intraperitoneal (i.p.) dose of the test compound daily at 25 mg/kg for the length of the study. Tumor size was measured at certain intervals as shown in Table 5 and the degree of inhibition for a test compound was determined by comparing the reduction in tumor volume for drug-treated animals to that of untreated and vehicle-treated animals. The vehicle used was 20% hydroxypropyl β-cyclodextran.

TABLE 5

Reduction in Tumor Volume (mm$^3$)

| Cpd | Day 1 | Day 4 | Day 8 | Day 11 | Day 14 |
|---|---|---|---|---|---|
| No treatment | 94.3 | 177.8 | 349.3 | 603.3 | 954.9 |
| Vehicle | 94.3 | 142.1 | 406.8 | 663.8 | 902.1 |
| 78 | 95.4 | 113.6 | 329.3 | 558 | 856.9 |
| 82 | 97.7 | 222 | 455.5 | 742.4 | 1323.6 |
| 96 | 95.4 | 68.3 | ND | ND | ND |
| 101 | 95.4 | 128 | 354.1 | 632.3 | 988.7 |
| 106 | 95.4 | 94.7 | 318.6 | 558.3 | 896.8 |
| 107 | 95.4 | ND | ND | ND | ND |

Variations of this method are intended to include oral administration or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of formula (I):

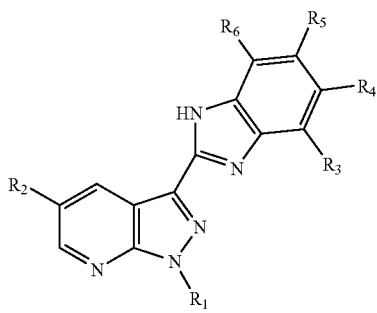

or a pharmaceutically acceptable form thereof, wherein $R_1$ is hydrogen or $C_{1-8}$alkyl, $R_2$ is hydrogen, halogen, $C_{3-12}$cycloalkyl-$R_7$, heterocyclyl-$R_8$, aryl-$R_9$, heteroaryl-$R_{10}$, $C_{1-8}$alkyl-$C_{3-12}$cycloalkyl-$R_7$, $C_{1-8}$alkyl-heterocyclyl-$R_8$, $C_{1-8}$alkyl-aryl-$R_9$, $C_{1-8}$alkyl-heteroaryl-$R_{10}$, $C_{1-8}$alkyl-O—$C_{1-8}$alkyl-$C_{3-12}$ cycloalkyl-$R_7$, $C_{1-8}$alkyl-O—$C_{1-8}$alkyl-heterocyclyl-$R_8$, $C_{1-8}$alkyl-O—$C_{1-8}$alkyl-aryl-$R_9$, $C_{1-8}$alkyl-O—$C_{1-8}$ alkyl-heteroaryl-$R_{10}$, C(O)—$C_{3-12}$cycloalkyl-$R_7$, C(O)-heterocyclyl-$R_8$, C(O)-aryl-$R_9$, C(O)-heteroaryl-$R_{10}$, C(O)NH—$C_{3-12}$cycloalkyl-$R_7$, C(O)NH-heterocyclyl-$R_8$, C(O)NH-aryl-$R_9$ or C(O)NH-heteroaryl-$R_{10}$, $R_3$, $R_4$, $R_5$ and $R_6$ is each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, $C_{1-8}$alkyl-O—$C_{1-8}$alkyl, $C_{1-8}$alkyl-O—$C_{1-8}$alkyl-O—$C_{1-8}$alkyl, OH, OC(O)$C_{1-8}$ alkyl, $C_{1-8}$alkyl-OH, $C_{1-8}$alkoxy-OH, C(O)H, C(O)$C_{1-8}$ alkyl, C(O)OH, C(O)O—$C_{1-8}$alkyl, $NH_2$, NH—$C_{1-8}$ alkyl, $N(C_{1-8}$alkyl)$_2$, NHC(O)$C_{1-8}$alkyl, NHC(O)NH$C_{1-8}$alkyl, $N(C_{1-8}$alkyl)C(O)C$_{1-8}$alkyl, $C_{1-8}$alkyl-$NH_2$, $C_{1-8}$alkyl-NH—$C_{1-8}$alkyl, $C_{1-8}$alkyl-N($C_{1-8}$alkyl)$_2$, $C_{1-8}$alkyl-NH(OH), $C_{1-8}$alkyl=N(OH), $C_{1-8}$alkyl-NH—$C_{1-8}$alkyl-$NH_2$, $C_{1-8}$alkyl-N($C_{1-8}$alkyl-$NH_2$)$_2$, $C_{1-8}$alkyl-N($C_{1-8}$alkyl)-$C_{1-8}$alkyl-$NH_2$, C(O)$NH_2$, C(O)NH—$C_{1-8}$alkyl, C(O)N($C_{1-8}$alkyl)$_2$, C(O)NH—$C_{1-8}$alkyl-$NH_2$, C(O)NH—$C_{1-8}$alkyl-NH—$C_{1-8}$ alkyl, C(O)NH—$C_{1-8}$alkyl-N($C_{1-8}$alkyl)$_2$, C(O)N($C_{1-8}$ alkyl-$NH_2$)$_2$, C(O)N($C_{1-8}$alkyl)-$C_{1-8}$alkyl-$NH_2$, C(O)N($C_{1-8}$ alkyl)-$C_{1-8}$alkyl-NH—$C_{1-8}$alkyl, C(O)N($C_{1-8}$ alkyl)-$C_{1-8}$alkyl-N($C_{1-8}$alkyl)$_2$, $C_{3-12}$cycloalkyl-$R_{11}$, heterocyclyl-$R_{12}$, aryl-$R_{13}$, heteroaryl-$R_{14}$, $C_{1-8}$alkyl-$C_{3-12}$cycloalkyl-$R_{11}$, $C_{1-8}$alkyl-heterocyclyl-$R_{12}$, $C_{1-8}$alkyl-aryl-$R_{13}$, $C_{1-8}$alkyl-heteroaryl-$R_{14}$, $C_{1-8}$alkyl-O—$C_{1-8}$alkyl-$C_{3-12}$cycloalkyl-$R_{11}$, $C_{1-8}$alkyl-O—$C_{1-8}$alkyl-heterocyclyl-$R_{12}$, $C_{1-8}$alkyl-O—$C_{1-8}$alkyl-aryl-$R_{13}$, $C_{1-8}$alkyl-O—$C_{1-8}$alkyl-heteroaryl-$R_{14}$, C(O)—$C_{3-12}$cycloalkyl-$R_{11}$, C(O)-heterocyclyl-$R_{12}$, C(O)-aryl-$R_{13}$, C(O)-heteroaryl-$R_{14}$, C(O) NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$, alternatively, one of each $R_3$ and $R_4$, $R_4$ and $R_5$ or $R_5$ and $R_6$ are taken together to form —O—$CH_2$—O— or —O—$(CH_2)_2$—O— which, together with the benzoimidazolyl ring of formula (I), form a 5H-[1,3]dioxolo[4',5':4,5]benzo[1,2-d]imidazol-6-yl, 6H-1,3-dioxa-6,8-diaza-as-indacen-7-yl, 8H-1,3-dioxa-6,8-diaza-as-indacen-7-yl, 6,7-dihydro-1H-5,8-dioxa-1,3-diaza-cyclopenta[b]naphthalen-2-yl, 7,8-dihydro-1H-6,9-dioxa-1,3-diaza-cyclopenta[a]naphthalen-2-yl or a 7,8-dihydro-3H-6,9-dioxa-1,3-diaza-cyclopenta[a]naphthalen-2-yl ring system, wherein the —O—$CH_2$—O— or —O—$(CH_2)_2$—O— portion is each optionally substituted on one or two carbon atoms with one or two substituents each selected from halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH or $C_{1-8}$alkyl-OH, $R_7$, $R_8$, $R_9$ and $R_{10}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-O—$C_{1-8}$alkyl, $C_{1-8}$alkoxy-OH, C(O)H, C(O)$C_{1-8}$alkyl, C(O)OH, C(O)O—$C_{1-8}$alkyl, $NH_2$, NH—$C_{1-8}$alkyl, $N(C_{1-8}$alkyl)$_2$, $C_{1-8}$alkyl-$NH_2$, $C_{1-8}$alkyl-NH—$C_{1-8}$alkyl, CH($C_{1-8}$alkyl)-NH—$C_{1-8}$ alkyl, C($C_{1-8}$alkyl)$_2$-NH—$C_{1-8}$alkyl, $C_{1-8}$alkyl-N($C_{1-8}$ alkyl)$_2$, $C_{1-8}$alkyl-NH—$C_{1-8}$alkyl-O—$C_{1-8}$alkyl, $C_{1-8}$alkyl-NH—$C_{1-8}$alkyl-$NH_2$, $C_{1-8}$alkyl-NH—C(O)$C_{1-8}$alkyl, $C_{1-8}$alkyl-NH—C(O)NH$C_{1-8}$alkyl, $C_{1-8}$alkyl-NH—$C_{1-8}$alkyl-NH—$C_{1-8}$alkyl, $C_{1-8}$alkyl-NH—$C_{1-8}$alkyl-N($C_{1-8}$alkyl)$_2$, $C_{1-8}$alkyl=N(OH), $C_{1-8}$alkyl-NH—$C_{1-8}$alkyl-OH, $SO_2NH_2$, $SO_2$NH—$C_{1-8}$ alkyl, $SO_2N(C_{1-8}$alkyl)$_2$, $C_{3-12}$cycloalkyl-$R_{15}$, heterocyclyl-$R_{16}$, aryl-$R_{17}$, heteroaryl-$R_{18}$, $C_{1-8}$alkyl-$C_{3-12}$ cycloalkyl-$R_{15}$, $C_{1-8}$alkyl-heterocyclyl-$R_{16}$, $C_{1-8}$alkyl-aryl-$R_{17}$, $C_{1-8}$alkyl-heteroaryl-$R_{18}$, $C_{1-8}$alkyl-NH—$C_{3-12}$ cycloalkyl-$R_{15}$, $C_{1-8}$alkyl-NH-heterocyclyl-$R_{16}$, $C_{1-8}$alkyl-NH-aryl-$R_{17}$, $C_{1-8}$alkyl-NH-heteroaryl-$R_{18}$, $C_{1-8}$alkyl-NH—$C_{1-8}$alkyl-$C_{3-12}$cycloalkyl-$R_{15}$, $C_{1-8}$alkyl-NH—$C_{1-8}$-alkyl-heterocyclyl-$R_{16}$, $C_{1-8}$alkyl-NH—$C_{1-8}$alkyl-aryl-$R_{17}$, $C_{1-8}$alkyl-NH—$C_{1-8}$alkyl-heteroaryl-$R_{18}$, $SO_2$—$C_{3-12}$cycloalkyl-$R_{15}$, $SO_2$-heterocyclyl-$R_{16}$, $SO_2$-aryl-$R_{17}$ or $SO_2$-heteroaryl-$R_{18}$, $R_{11}$, $R_{12}$, $R_{13}$ and $R_{14}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-OH, $NH_2$, NH—$C_{1-8}$alkyl or $N(C_{1-8}$ alkyl)$_2$, and $R_{15}$, $R_{16}$, $R_{17}$ and $R_{18}$ is each one, two, three, four or five substituents each selected from hydrogen, halogen, nitro, cyano, $C_{1-8}$alkyl, $C_{1-8}$alkoxy, $C_{1-8}$alkyl(halogen)$_{1-3}$, $C_{1-8}$alkoxy(halogen)$_{1-3}$, OH, $C_{1-8}$alkyl-OH, $C_{1-8}$alkoxy-OH, C(O)H, C(O)$C_{1-8}$alkyl, C(O)OH, C(O)O—$C_{1-8}$alkyl, $NH_2$, NH—$C_{1-8}$alkyl or $N(C_{1-8}$ alkyl)$_2$.

2. The compound of claim 1, wherein $R_1$ is hydrogen.

3. The compound of claim 1, wherein $R_2$ is hydrogen, halogen, $C_{3-12}$cycloalkyl-$R_7$, heterocyclyl-$R_8$, aryl-$R_9$ or heteroaryl-$R_{10}$.

4. The compound of claim 3, wherein $R_2$ is hydrogen, halogen, aryl-$R_9$ or heteroaryl-$R_{10}$.

5. The compound of claim 1, wherein $R_3$, $R_4$, $R_5$ and $R_6$ is each selected from hydrogen, halogen, cyano, $C_{1-4}$alkyl, $C_{1-4}$alkoxy, $C_{1-4}$alkyl(halogen)$_{1-3}$, $C_{1-4}$alkoxy(halogen)$_{1-3}$, $C_{1-4}$alkyl-O—$C_{1-4}$alkyl, $C_{1-4}$alkyl-O—$C_{1-4}$alkyl-O—$C_{1-4}$ alkyl, OH, $C_{1-4}$alkyl-OH, $C_{1-4}$alkoxy-OH, C(O)OH, C(O)O—$C_{1-4}$alkyl, $NH_2$, NH—$C_{1-4}$alkyl, $N(C_{1-4}$alkyl)$_2$, NHC(O)$C_{1-4}$alkyl, NHC(O)NH$C_{1-4}$alkyl, $N(C_{1-4}$alkyl)C(O)$C_{1-4}$ alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, C(O)$NH_2$, C(O)NH—$C_{1-4}$alkyl, C(O)N($C_{1-4}$ alkyl)$_2$, C(O)NH—$C_{1-4}$alkyl-$NH_2$, C(O)NH—$C_{1-4}$alkyl-NH—$C_{1-4}$alkyl, C(O)NH—$C_{1-4}$alkyl-N($C_{1-4}$alkyl)$_2$, C(O)N ($C_{1-4}$alkyl)-$C_{1-4}$alkyl-$NH_2$, C(O)N($C_{1-4}$alkyl)-$C_{1-4}$alkyl-NH—$C_{1-4}$alkyl, C(O)N($C_{1-4}$alkyl)-$C_{1-4}$alkyl-N($C_{1-4}$alkyl)$_2$, $C_{3-12}$cycloalkyl-$R_{11}$, heterocyclyl-$R_{12}$, aryl-$R_{13}$, heteroaryl-$R_{14}$, $C_{1-4}$alkyl-$C_{3-12}$cycloalkyl-$R_{11}$, $C_{1-4}$alkyl-heterocyclyl-$R_{12}$, $C_{1-4}$alkyl-aryl-$R_{13}$, $C_{1-4}$alkyl-heteroaryl-$R_{14}$, $C_{1-4}$alkyl-O—$C_{1-4}$alkyl-$C_{3-12}$cycloalkyl-$R_{11}$, $C_{1-4}$alkyl-O—$C_{1-4}$alkyl-heterocyclyl-$R_{12}$, $C_{1-4}$alkyl-O—$C_{1-4}$alkyl-aryl-$R_{13}$, $C_{1-4}$alkyl-O—$C_{1-4}$alkyl-heteroaryl-$R_{14}$, C(O)—$C_{3-12}$cycloalkyl-$R_{11}$, C(O)-heterocyclyl-$R_{12}$, C(O)-aryl-$R_{13}$, C(O)-heteroaryl-$R_{14}$, C(O)NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$.

6. The compound of claim 5, wherein $R_3$, $R_4$, $R_5$ and $R_6$ is each selected from hydrogen, halogen, cyano, $C_{1-4}$alkyl, $C_{1-4}$alkoxy, $C_{1-4}$alkoxy(halogen)$_{1-3}$, $C_{1-4}$alkyl-O—$C_{1-4}$alkyl, $C_{1-4}$alkyl-O—$C_{1-4}$alkyl-O—$C_{1-4}$alkyl, $C_{1-4}$alkyl-OH, $C_{1-4}$alkoxy-OH, C(O)OH, C(O)O—$C_{1-4}$alkyl, $C_{1-4}$alkyl-NH—$C_{1-4}$alkyl, $C_{1-4}$alkyl-N($C_{1-4}$alkyl)$_2$, C(O)NH—$C_{1-4}$alkyl, C(O)N($C_{1-4}$alkyl)$_2$, C(O)NH—$C_{1-4}$alkyl-N($C_{1-4}$alkyl)$_2$, C(O)N($C_{1-4}$alkyl)-$C_{1-4}$alkyl-N($C_{1-4}$alkyl)$_2$, heterocyclyl-$R_{12}$, $C_{1-4}$alkyl-heterocyclyl-$R_{12}$, $C_{1-4}$alkyl-O—$C_{1-4}$alkyl-heterocyclyl-$R_{12}$, C(O)-heterocyclyl-$R_{12}$, C(O)NH—$C_{3-12}$cycloalkyl-$R_{11}$, C(O)NH-heterocyclyl-$R_{12}$, C(O)NH-aryl-$R_{13}$ or C(O)NH-heteroaryl-$R_{14}$.

7. The compound of claim 1, wherein $R_4$ and $R_5$ are taken together to form —O—$CH_2$—O— or —O—$(CH_2)_2$—O— which, together with the benzoimidazolyl ring of formula (I), form a 5H-[1,3]dioxolo[4',5':4,5]benzo[1,2-d]imidazol-6-yl or a 6,7-dihydro-1H-5,8-dioxa-1,3-diaza-cyclopenta[b]naphthalen-2-yl ring system, wherein the —O—$CH_2$—O— or —O—$(CH_2)_2$—O— portion is each optionally substituted on one or two carbon atoms with one or two substituents each selected from halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH or $C_{1-4}$alkyl-OH.

8. The compound of claim 1, wherein $R_4$ and $R_5$ are taken together to form —O—$CH_2$—O— which, together with the benzoimidazolyl ring of formula (I), form a 5H-[1,3]dioxolo[4',5':4,5]benzo[1,2-d]imidazol-6-yl ring system, wherein the —O—$CH_2$—O— portion is optionally substituted on the carbon atom with one or two substituents each selected from halogen, $C_{1-4}$alkyl, $C_{1-4}$alkoxy, $C_{1-4}$alkyl(halogen)$_{1-3}$, $C_{1-4}$alkoxy(halogen)$_{1-3}$, OH or $C_{1-4}$alkyl-OH.

9. The compound of claim 1, wherein $R_7$, $R_8$, $R_9$ and $R_{10}$ is each one, two, three, four or five substituents each selected from hydrogen, halogen, nitro, cyano, $C_{1-4}$alkyl, $C_{1-4}$alkoxy, OH, $C_{1-4}$alkyl-OH, $C_{1-4}$alkoxy-O—$C_{1-4}$alkyl, $C_{1-4}$alkoxy-OH, C(O)H, C(O)$C_{1-4}$alkyl, C(O)OH, C(O)O—$C_{1-4}$alkyl, $C_{1-4}$alkyl-$NH_2$, $C_{1-4}$alkyl-NH—$C_{1-4}$alkyl, CH($C_{1-4}$alkyl)-NH—$C_{1-4}$alkyl, C($C_{1-4}$alkyl)$_2$-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-$NH_2$, $C_{1-4}$alkyl-NH—C(O)$C_{1-4}$alkyl, $C_{1-4}$alkyl-NH—C(O)NH$C_{1-4}$alkyl, $C_{1-4}$alkyl-NH—$C_{1-4}$alkyl-NH—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, $SO_2NH_2$, $C_{3-12}$cycloalkyl-$R_{15}$, heterocyclyl-$R_{16}$, aryl-$R_{17}$, heteroaryl-$R_{18}$, $C_{1-4}$alkyl-$C_{3-12}$cycloalkyl-$R_{15}$, $C_{1-4}$alkyl-heterocyclyl-$R_{16}$, $C_{1-4}$alkyl-aryl-$R_{17}$, $C_{1-4}$alkyl-heteroaryl-$R_{18}$, $C_{1-4}$alkyl-NH—$C_{3-12}$cycloalkyl-$R_{15}$, $C_{1-4}$alkyl-NH-heterocyclyl-$R_{16}$, $C_{1-4}$alkyl-NH-aryl-$R_{17}$, $C_{1-4}$alkyl-NH-heteroaryl-$R_{18}$, $C_{1-4}$alkyl-NH—$C_{1-4}$alkyl-$C_{3-12}$cycloalkyl-$R_{15}$, $C_{1-4}$alkyl-NH—$C_{1-4}$alkyl-heterocyclyl-$R_{16}$, $C_{1-4}$alkyl-NH—$C_{1-4}$alkyl-aryl-$R_{17}$, $C_{1-4}$alkyl-NH—$C_{1-4}$alkyl-heteroaryl-$R_{18}$, $SO_2$—$C_{3-12}$cycloalkyl-$R_{15}$, $SO_2$-heterocyclyl-$R_{16}$, $SO_2$-aryl-$R_{17}$ or $SO_2$-heteroaryl-$R_{18}$.

10. The compound of claim 9, wherein $R_7$ and $R_8$ is each hydrogen.

11. The compound of claim 9, wherein $R_9$ and $R_{10}$ is each one, two, three, four or five substituents each selected from hydrogen, halogen, $C_{1-4}$alkyl, $C_{1-4}$alkoxy, $C_{1-4}$alkyl-OH, C(O)H, C(O)O—$C_{1-4}$alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, $SO_2NH_2$, heterocyclyl-$R_{16}$, $C_{1-4}$alkyl-heterocyclyl-$R_{16}$, $C_{1-4}$alkyl-NH-heterocyclyl-$R_{16}$, $C_{1-4}$alkyl-NH—$C_{1-4}$alkyl-heterocyclyl-$R_{16}$ or $SO_2$-aryl-$R_{17}$.

12. The compound of claim 9, wherein $R_9$ is selected from hydrogen or $SO_2NH_2$.

13. The compound of claim 9, wherein $R_{10}$ is one, two, three, four or five substituents each selected from hydrogen, halogen, $C_{1-4}$alkyl, $C_{1-4}$alkoxy, $C_{1-4}$alkyl-OH, C(O)H, C(O)O—$C_{1-4}$alkyl, $C_{1-4}$alkyl-$NH_2$, $C_{1-4}$alkyl-NH—$C_{1-4}$alkyl, $C_{1-4}$alkyl-N($C_{1-4}$alkyl)$_2$, $C_{1-4}$alkyl-NH—$C_{1-4}$alkyl-O—$C_{1-4}$alkyl, $C_{1-4}$alkyl-NH—$C_{1-4}$alkyl-N($C_{1-4}$alkyl)$_2$, $C_{1-4}$alkyl=N(OH), $C_{1-4}$alkyl-NH—$C_{1-4}$alkyl-OH, heterocyclyl-$R_{16}$, $C_{1-4}$alkyl-heterocyclyl-$R_{16}$, $C_{1-4}$alkyl-NH-heterocyclyl-$R_{16}$, $C_{1-4}$alkyl-NH—$C_{1-4}$alkyl-heterocyclyl-$R_{16}$ or $SO_2$-aryl-$R_{17}$.

14. The compound of claim 1, wherein $R_{11}$, $R_{12}$, $R_{13}$ and $R_{14}$ is each one, two, three, four or five substituents each selected from hydrogen, $C_{1-4}$alkyl, OH, $NH_2$ or N($C_{1-4}$alkyl)$_2$.

15. The compound of claim 14, wherein $R_{11}$ is one, two, three, four or five substituents each selected from hydrogen, halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or N($C_{1-4}$alkyl)$_2$.

16. The compound of claim 15, wherein $R_{11}$ is one, two, three, four or five substituents each selected from hydrogen, OH or $NH_2$.

17. The compound of claim 14, wherein $R_{12}$ is one, two, three, four or five substituents each selected from hydrogen, halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or N($C_{1-4}$alkyl)$_2$.

18. The compound of claim 17, wherein $R_{12}$ is one, two, three, four or five substituents each selected from hydrogen or $C_{1-4}$alkyl.

19. The compound of claim 14, wherein $R_{13}$ is one, two, three, four or five substituents each selected from hydrogen, halogen, nitro, cyano, $C_{1-4}$alkyl, $C_{1-4}$alkoxy, $C_{1-4}$alkyl(halogen)$_{1-3}$, $C_{1-4}$alkoxy(halogen)$_{1-3}$, OH, $C_{1-4}$alkyl-OH, $C_{1-4}$alkoxy-OH, $NH_2$, NH—$C_{1-4}$alkyl or N($C_{1-4}$alkyl)$_2$.

20. The compound of claim 19, wherein $R_{13}$ is one, two, three, four or five substituents each selected from hydrogen, $C_{1-4}$alkyl or N($C_{1-4}$alkyl)$_2$.

21. The compound of claim 14, wherein $R_{14}$ is hydrogen.

22. The compound of claim 1, wherein $R_{15}$, $R_{16}$, $R_{17}$ and $R_{18}$ is each one, two, three, four or five substituents each selected from hydrogen, halogen, $C_{1-4}$alkyl, $C_{1-4}$alkoxy, $C_{1-4}$alkyl(halogen)$_{1-3}$, $C_4$alkoxy(halogen)$_{1-3}$, OH, $C_{1-4}$alkyl-OH, C(O)OH, C(O)O—$C_{1-4}$alkyl, $NH_2$, NH—$C_{1-4}$alkyl or N($C_{1-4}$alkyl)$_2$.

23. The compound of claim 22, wherein $R_{15}$ and $R_{16}$ is each hydrogen.

24. The compound of claim 23, wherein $R_{17}$ and $R_{18}$ is each one, two, three, four or five substituents each selected from hydrogen, halogen, $C_{1-4}$alkyl or $C(O)O$—$C_{1-4}$alkyl.

25. The compound of claim 1, wherein the compound is selected from a compound of formula (Ia):

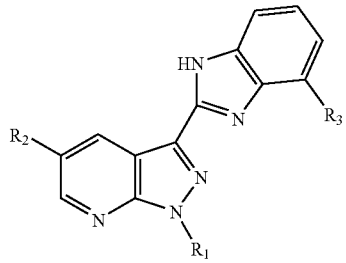

or a form thereof, wherein $R_1$ is selected from hydrogen or $CH_3$;

$R_2$ is selected from Br, isoquinolin-4-yl, pyridin-3-yl, 4-$SO_2NH_2$-phenyl, 7-aza-indol-3-yl, (1-$SO_2$-phenyl)-indol-3-yl, indol-3-yl, 1H-pyrrol-3-yl, 5-C(O)H-pyridin-3-yl, 5-$CH_2NHCH_2CH_3$-pyridin-3-yl, 5-$CH_2NHCH(CH_3)_2$-pyridin-3-yl, 5-$CH_2OH$-pyridin-3-yl, 5-$CH_2NHC(CH_3)_3$-pyridin-3-yl, 5-$CH_2$-morpholin-4-yl-pyridin-3-yl, 5-$CH_2N(CH_3)_2$-pyridin-3-yl, 5-$CH_2NHCH_3$-pyridin-3-yl, 4-$CH_3$-pyridin-3-yl, 4-$CH_3$-5-$CH_2NH$—$CH(CH_3)_2$-pyridin-3-yl, 4-$CH_3$-5-$CH_2NHCH_2CH_3$-pyridin-3-yl, 4-$CH_3$-5-$CH_2$-morpholin-4-yl-pyridin-3-yl, 4-$CH_3$-5-$CH_2N(CH_3)_2$-pyridin-3-yl, 4-$CH_3$-5-$CH_2NHCH_3$-pyridin-3-yl, 6-$OCH_3$-pyridin-3-yl, 5-$OCH_3$-pyridin-3-yl, pyridin-4-yl, 6-morpholin-4-yl-pyridin-3-yl, 6-[4-$C(O)OC(CH_3)_3$-piperazin-1-yl]-pyridin-3-yl, pyrimidin-5-yl, 6-piperazin-1-yl-pyridin-3-yl, 5-$C(O)OCH_2CH_3$-pyridin-3-yl, 6-F-pyridin-3-yl, 5-CH=N(OH)-pyridin-3-yl, 5-$CH_2NH_2$-pyridin-3-yl, 5-$CH_2NH(CH_2)_2$-Morpholin-4-yl-pyridin-3-yl, 5-$CH_2NH(CH_2)_2OCH_3$-pyridin-3-yl, 5-$CH_2NH(CH_2)_2N(CH_3)_2$-pyridin-3-yl, 5-$CH_2NH$ $(CH_2)_2OH$-pyridin-3-yl, 5-$CH_2NH(CH_2)_2CH_3$-pyridin-3-yl, 5-$CH_2NH(CH_2)_3CH_3$-pyridin-3-yl or 5-$CH_2NH$-(1-$CH_3$-piperidin-4-yl)-pyridin-3-yl; and $R_3$ is selected from hydrogen, $CH_3$, $CH_2OH$, $CH_2OCH_3$, $CH_2N(CH_2CH_3)_2$, $CH_2$-pyrrolidin-1-yl, $CH_2$-piperidin-1-yl, $CH_2$-morpholin-4-yl, $CH_2$-(4-$CH_2CH_3$-piperazin-1-yl), $CH_2$-imidazol-1-yl, $CH_2NHCH(CH_3)_2$, $CH_2O(CH_2)_2OCH_3$, $CH_2O(CH_2)_2$-morpholin-4-yl, $CH_2O(CH_2)_2OCH_2CH_3$, C(O)OH, C(O)NHCH($CH_3)_2$, C(O)N($CH_2CH_3)_2$, C(O)NHC($CH_3)_3$, C(O)-pyrrolidin-1-yl, C(O)-piperidin-1-yl, C(O)-(4-$CH_3$-piperazin-1-yl), C(O)-morpholin-4-yl, C(O)NH($CH_2)_2N(CH_3)_2$, C(O)N($CH_3$)($CH_2)_2N(CH_3)_2$, C(O)NH-cyclopentyl, C(O)NH-(1-$CH_3$-piperidin-4-yl), C(O)NH-(4-OH-cyclohexyl), $CH_2OCH(CH_3)_2$, C(O)NH-(4-$NH_2$-cyclohexyl), C(O)NH-(2-$CH_3$-phenyl), C(O)NH-cyclopropyl, C(O)NH-pyridin-3-yl, C(O)NH-[4-N($CH_3)_2$-phenyl], C(O)NH-[2-$CH_3$-4-N($CH_2CH_3)_2$-phenyl], $CH_2N(CH_2CH_3)_2$ or C(O)$OCH_3$.

26. The compound of claim 1, wherein the compound is selected from a compound of formula (Ib):

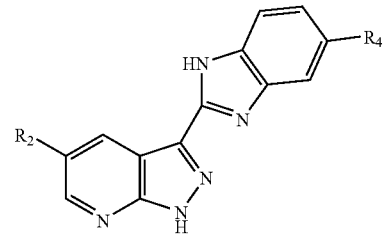

or a form thereof, wherein $R_2$ is selected from Br, isoquinolin-4-yl, 5-$CH_2NHCH_3$-pyridin-3-yl, 5-$CH_2NHCH_2CH_3$-pyridin-3-yl, 5-$CH_2NHCH(CH_3)_2$-pyridin-3-yl, 5-$CH_2$-morpholin-4-yl-pyridin-3-yl, 5-$CH_2NH(CH_2)_2CH_3$-pyridin-3-yl, 5-$CH_2NH(CH_2)_2OCH_3$-pyridin-3-yl, 5-$CH_2$-pyrrolidin-1-yl-pyridin-3-yl, 5-$CH_2N(CH_3)_2$-pyridin-3-yl, pyridin-3-yl or 5-$CH_2NH(CH_2)_3CH_3$-pyridin-3-yl; and $R_4$ is selected from 4-$CH_3$-piperazin-1-yl, morpholin-4-yl, C(O)$OCH_3$, F, $OCF_3$, O($CH_2)_2OH$, $OCH_3$ or CN.

27. The compound of claim 1, wherein the compound is selected from a compound of formula (Ic):

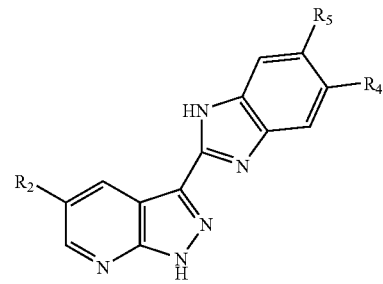

or a form thereof, wherein $R_2$ is selected from pyridin-3-yl, 5-$CH_2NHCH_3$-pyridin-3-yl or 5-$CH_2NHCH_2CH_3$-pyridin-3-yl; and $R_4$ is selected from hydrogen or F; and $R_5$ is selected from $OCH_3$ or F; or alternatively, $R_4$ and $R_5$ are taken together to form —O—$CH_2$—O— which, together with the benzoimidazolyl ring of formula (I), form a 5H-[1,3]dioxolo[4',5': 4,5]benzo[1,2-d]imidazol-6-yl ring system, wherein the —O—$CH_2$—O— portion is optionally substituted on the carbon atom with one or two substituents selected from F.

28. The compound of claim 1, wherein the compound is selected from the group consisting of:

4-[3-(1H-benzoimidazol-2-yl)-1H-pyrazolo[3,4-b]pyridin-5-yl]-isoquinoline,

4-[3-(4-methyl-1H-benzoimidazol-2-yl)-1H-pyrazolo[3,4-b]pyridin-5-yl]-isoquinoline,

[2-(5-isoquinolin-4-yl-1H-pyrazolo[3,4-b]pyridin-3-yl)-1H-benzoimidazol-4-yl]-methanol, 4-[3-(4-methoxymethyl-1H-benzoimidazol-2-yl)-1H-pyrazolo[3,4-b]pyridin-5-yl]-isoquinoline, diethyl-[2-(5-isoquinolin-4-yl-1H-pyrazolo[3,4-b]pyridin-3-yl)-1H-benzoimidazol-4-ylmethyl]-amine,

[2-(5-bromo-1H-pyrazolo[3,4-b]pyridin-3-yl)-1H-benzoimidazol-4-ylmethyl]-diethyl-amine, 4-[3-(4-pyrrolidin-1-ylmethyl-1H-benzoimidazol-2-yl)-1H-pyrazolo[3,4-b]pyridin-5-yl]-isoquinoline,
4-[3-(4-piperidin-1-ylmethyl-1H-benzoimidazol-2-yl)-1H-pyrazolo[3,4-b]pyridin-5-yl]-isoquinoline,
4-[3-(4-morpholin-4-ylmethyl-1H-benzoimidazol-2-yl)-1H-pyrazolo[3,4-b]pyridin-5-yl]-isoquinoline,
4-{3-[4-(4-ethyl-piperazin-1-ylmethyl)-1H-benzoimidazol-2-yl]-1H-pyrazolo[3,4-b]pyridin-5-yl}-isoquinoline,
4-[3-(4-imidazol-1-ylmethyl-1H-benzoimidazol-2-yl)-1H-pyrazolo[3,4-b]pyridin-5-yl]-isoquinoline,
isopropyl-[2-(5-isoquinolin-4-yl-1H-pyrazolo[3,4-b]pyridin-3-yl)-1H-benzoimidazol-4-ylmethyl]-amine,
4-{3-[4-(2-methoxy-ethoxymethyl)-1H-benzoimidazol-2-yl]-1H-pyrazolo[3,4-b]pyridin-5-yl}-isoquinoline,
4-{3-[4-(2-morpholin-4-yl-ethoxymethyl)-1H-benzoimidazol-2-yl]-1H-pyrazolo[3,4-b]pyridin-5-yl}-isoquinoline,
4-{3-[4-(2-ethoxy-ethoxymethyl)-1H-benzoimidazol-2-yl]-1H-pyrazolo[3,4-b]pyridin-5-yl}-isoquinoline,
2-(5-isoquinolin-4-yl-1H-pyrazolo[3,4-b]pyridin-3-yl)-1H-benzoimidazole-4-carboxylic acid isopropylamide,
2-(5-isoquinolin-4-yl-1H-pyrazolo[3,4-b]pyridin-3-yl)-1H-benzoimidazole-4-carboxylic acid diethylamide,
2-(5-isoquinolin-4-yl-1H-pyrazolo[3,4-b]pyridin-3-yl)-1H-benzoimidazole-4-carboxylic acid tert-butylamide,
[2-(5-isoquinolin-4-yl-1H-pyrazolo[3,4-b]pyridin-3-yl)-1H-benzoimidazole-4-yl]-morpholin-4-yl-methanone,
2-(5-isoquinolin-4-yl-1H-pyrazolo[3,4-b]pyridin-3-yl)-1H-benzoimidazole-4-carboxylic acid cyclopentylamide,
2-(5-isoquinolin-4-yl-1H-pyrazolo[3,4-b]pyridin-3-yl)-1H-benzoimidazole-4-carboxylic acid (4-hydroxy-cyclohexyl)-amide,
4-{3-[5-(4-methyl-piperazin-1-yl)-1H-benzoimidazol-2-yl]-1H-pyrazolo[3,4-b]pyridin-5-yl}-isoquinoline,
4-[3-(4-isopropoxymethyl-1H-benzoimidazol-2-yl)-1H-pyrazolo[3,4-b]pyridin-5-yl]-isoquinoline,
3-[3-(4-methoxymethyl-1H-benzoimidazol-2-yl)-1H-pyrazolo[3,4-b]pyridin-5-yl]-quinoline,
3-(4-methoxymethyl-1H-benzoimidazol-2-yl)-5-pyridin-3-yl-1H-pyrazolo[3,4-b]pyridine,
4-[3-(4-methoxymethyl-1H-benzoimidazol-2-yl)-1H-pyrazolo[3,4-b]pyridin-5-yl]benzenesulfonamide,
3-(4-methoxymethyl-1H-benzoimidazol-2-yl)-5-(1H-pyrrolo[2,3-b]pyridin-3-yl)-1H-pyrazolo[3,4-b]pyridine,
5-(1-benzenesulfonyl-1H-indol-3-yl)-3-(4-methoxymethyl-1H-benzoimidazol-2-yl)-1H-pyrazolo[3,4-b]pyridine,
5-(1H-indol-3-yl)-3-(4-methoxymethyl-1H-benzoimidazol-2-yl)-1H-pyrazolo[3,4-b]pyridine,
3-(4-methoxymethyl-1H-benzoimidazol-2-yl)-5-(1H-pyrrol-3-yl)-1H-pyrazolo[3,4-b]pyridine,
5-[3-(4-methoxymethyl-1H-benzoimidazol-2-yl)-1H-pyrazolo[3,4-b]pyridin-5-yl]-pyridine-3-carbaldehyde,
ethyl-{5-[3-(4-methoxymethyl-1H-benzoimidazol-2-yl)-1H-pyrazolo[3,4-b]pyridin-5-yl]-pyridin-3-ylmethyl}-amine,
isopropyl-{5-[3-(4-methoxymethyl-1H-benzoimidazol-2-yl)-1H-pyrazolo[3,4-b]pyridin-5-yl]-pyridin-3-ylmethyl}-amine,
{5-[3-(4-methoxymethyl-1H-benzoimidazol-2-yl)-1H-pyrazolo[3,4-b]pyridin-5-yl]-pyridin-3-yl}-methanol,
2-(5-isoquinolin-4-yl-1H-pyrazolo[3,4-b]pyridin-3-yl)-1H-benzoimidazole-4-carboxylic acid (4-amino-cyclohexyl)-amide,
2-(5-isoquinolin-4-yl-1H-pyrazolo[3,4-b]pyridin-3-yl)-1H-benzoimidazole-4-carboxylic acid o-tolylamide,
2-(5-isoquinolin-4-yl-1H-pyrazolo[3,4-b]pyridin-3-yl)-1H-benzoimidazole-4-carboxylic acid cyclopropylamide,
2-(5-isoquinolin-4-yl-1H-pyrazolo[3,4-b]pyridin-3-yl)-1H-benzoimidazole-4-carboxylic acid pyridin-3-ylamide,
2-(5-isoquinolin-4-yl-1H-pyrazolo[3,4-b]pyridin-3-yl)-1H-benzoimidazole-4-carboxylic acid (4-dimethylamino-phenyl)-amide,
2-(5-isoquinolin-4-yl-1H-pyrazolo[3,4-b]pyridin-3-yl)-1H-benzoimidazole-4-carboxylic acid (4-diethylamino-2-methyl-phenyl)-amide,
4-[3-(5-morpholin-4-yl-1H-benzoimidazol-2-yl)-1H-pyrazolo[3,4-b]pyridin-5-yl]-isoquinoline,
diethyl-[2-(5-pyridin-3-yl-1H-pyrazolo[3,4-b]pyridin-3-yl)-1H-benzoimidazol-4-ylmethyl]-amine,
3-(4-methoxymethyl-1H-benzoimidazol-2-yl)-5-(5-morpholin-4-ylmethyl-pyridin-3-yl)-1H-pyrazolo[3,4-b]pyridine,
{5-[3-(4-methoxymethyl-1H-benzoimidazol-2-yl)-1H-pyrazolo[3,4-b]pyridin-5-yl]-pyridin-3-ylmethyl}-methyl-amine,
3-(4-methoxymethyl-1H-benzoimidazol-2-yl)-5-(4-methyl-pyridin-3-yl)-1H-pyrazolo[3,4-b]pyridine,
isopropyl-{5-[3-(4-methoxymethyl-1H-benzoimidazol-2-yl)-1H-pyrazolo[3,4-b]pyridin-5-yl]-4-methyl-pyridin-3-ylmethyl}-amine,
ethyl-{5-[3-(4-methoxymethyl-1H-benzoimidazol-2-yl)-1H-pyrazolo[3,4-b]pyridin-5-yl]-4-methyl-pyridin-3-ylmethyl}-amine,
3-(4-methoxymethyl-1H-benzoimidazol-2-yl)-5-(4-methyl-5-morpholin-4-ylmethyl-pyridin-3-yl)-1H-pyrazolo[3,4-b]pyridine,
{5-[3-(4-methoxymethyl-1H-benzoimidazol-2-yl)-1H-pyrazolo[3,4-b]pyridin-5-yl]-4-methyl-pyridin-3-ylmethyl}-dimethyl-amine,
{5-[3-(4-methoxymethyl-1H-benzoimidazol-2-yl)-1H-pyrazolo[3,4-b]pyridin-5-yl]-4-methyl-pyridin-3-ylmethyl}-methyl-amine,
3-(4-methoxymethyl-1H-benzoimidazol-2-yl)-5-(6-methoxy-pyridin-3-yl)-1H-pyrazolo[3,4-b]pyridine,
3-(4-methoxymethyl-1H-benzoimidazol-2-yl)-5-(5-methoxy-pyridin-3-yl)-1H-pyrazolo[3,4-b]pyridine,
3-(4-methoxymethyl-1H-benzoimidazol-2-yl)-5-pyridin-4-yl-1H-pyrazolo[3,4-b]pyridine,
3-(4-methoxymethyl-1H-benzoimidazol-2-yl)-5-(6-morpholin-4-yl-pyridin-3-yl)-1H-pyrazolo[3,4-b]pyridine,
4-{5-[3-(4-methoxymethyl-1H-benzoimidazol-2-yl)-1H-pyrazolo[3,4-b]pyridin-5-yl]-pyridin-2-yl}-piperazine-1-carboxylic acid tert-butyl ester,
3-(4-methoxymethyl-1H-benzoimidazol-2-yl)-5-(6-piperazin-1-yl-pyridin-3-yl)-1H-pyrazolo[3,4-b]pyridine,
5-[3-(4-methoxymethyl-1H-benzoimidazol-2-yl)-1H-pyrazolo[3,4-b]pyridin-5-yl]-nicotinic acid ethyl ester,
5-(6-fluoro-pyridin-3-yl)-3-(4-methoxymethyl-1H-benzoimidazol-2-yl)-1H-pyrazolo[3,4-b]pyridine,
5-[3-(4-methoxymethyl-1H-benzoimidazol-2-yl)-1H-pyrazolo[3,4-b]pyridin-5-yl]-pyridine-3-carbaldehyde oxime,
C-{5-[3-(4-methoxymethyl-1H-benzoimidazol-2-yl)-1H-pyrazolo[3,4-b]pyridin-5-yl]-pyridin-3-yl}-methyl amine,
(2-methoxy-ethyl)-{5-[3-(4-methoxymethyl-1H-benzoimidazol-2-yl)-1H-pyrazolo[3,4-b]pyridin-5-yl]-pyridin-3-ylmethyl}-amine, N'-{5-[3-(4-methoxymethyl-1H-benzoimidazol-2-yl)-1H-pyrazolo[3,4-b]pyridin-5-yl]-pyridin-3-ylmethyl}-N,N-dimethyl-ethane-1,2-diamine,
2-({5-[3-(4-methoxymethyl-1H-benzoimidazol-2-yl)-1H-pyrazolo[3,4-b]pyridin-5-yl]-pyridin-3-ylmethyl}-amino)-ethanol,
{5-[3-(4-methoxymethyl-1H-benzoimidazol-2-yl)-1H-pyrazolo[3,4-b]pyridin-5-yl]-pyridin-3-ylmethyl}-propyl-amine,
butyl-{5-[3-(4-methoxymethyl-1H-benzoimidazol-2-yl)-1H-pyrazolo[3,4-b]pyridin-5-yl]-pyridin-3-ylmethyl}-amine,
{5-[3-(4-methoxymethyl-1H-benzoimidazol-2-yl)-1H-pyrazolo[3,4-b]pyridin-5-yl]-pyridin-3-ylmethyl}-(1-methyl-piperidin-4-yl)-amine,
methyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
ethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
isopropyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-(5-morpholin-4-ylmethyl-pyridin-3-yl)-1H-pyrazolo[3,4-b]pyridine,
(5-{3-[5-(4-methyl-piperazin-1-yl)-1H-benzoimidazol-2-yl]-1H-pyrazolo[3,4-b]pyridin-5-yl}-pyridin-3-ylmethyl)-propyl-amine,
(2-methoxy-ethyl)-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-(5-pyrrolidin-1-ylmethyl-pyridin-3-yl)-1H-pyrazolo[3,4-b]pyridine,
dimethyl-(5-{3-[5-(4-methyl-piperazin-1-yl)-1H-benzoimidazol-2-yl]-1H-pyrazolo[3,4-b]pyridin-5-yl}-pyridin-3-ylmethyl)-amine,
3-[5-(4-methyl-piperazin-1-yl)-1H-benzoimidazol-2-yl]-5-pyridin-3-yl-1H-pyrazolo[3,4-b]pyridine,
3-(6-methoxy-1H-benzoimidazol-2-yl)-5-pyridin-3-yl-1H-pyrazolo[3,4-b]pyridine,
2-(5-pyridin-3-yl-1H-pyrazolo[3,4-b]pyridin-3-yl)-3H-benzoimidazole-5-carboxylic acid methyl ester,
3-(6-fluoro-1H-benzoimidazol-2-yl)-5-pyridin-3-yl-1H-pyrazolo[3,4-b]pyridine,
5-pyridin-3-yl-3-(5-trifluoromethoxy-1H-benzoimidazol-2-yl)-1H-pyrazolo[3,4-b]pyridine,
2-[2-(5-pyridin-3-yl-1H-pyrazolo[3,4-b]pyridine-3-yl)-1H-benzoimidazol-5-yloxy]-ethanol,
methyl-{5-[3-(5-trifluoromethoxy-1H-benzoimidazol-2-yl)-1H-pyrazolo[3,4-b]pyridin-5-yl]-pyridin-3-ylmethyl}-amine,
{5-[3-(6-methoxy-1H-benzoimidazol-2-yl)-1H-pyrazolo[3,4-b]pyridin-5-yl]-pyridin-3-ylmethyl}-methyl-amine,
2,2-difluoro-6-(5-pyridin-3-yl-1H-pyrazolo[3,4-b]pyridin-3-yl)-5H-[1,3]dioxolo[4',5':4,5]benzo[1,2-d]imidazole,
6-(5-pyridin-3-yl-1H-pyrazolo[3,4-b]pyridin-3-yl)-5H-[1,3]dioxolo[4',5':4,5]benzo[1,2-d]imidazole,
{5-[3-(2,2-difluoro-5H-[1,3]dioxolo[4',5':4,5]benzo[1,2-d]imidazol-6-yl)-1H-pyrazolo[3,4-b]pyridin-5-yl]-pyridin-3-ylmethyl}-methyl-amine,
ethyl-{5-[3-(5-methoxy-1H-benzoimidazol-2-yl)-1H-pyrazolo[3,4-b]pyridin-5-yl]-pyridin-3-ylmethyl}-amine,
isopropyl-{5-[3-(5-methoxy-1H-benzoimidazol-2-yl)-1H-pyrazolo[3,4-b]pyridin-5-yl]-pyridin-3-ylmethyl}-amine,
{5-[3-(5-methoxy-1H-benzoimidazol-2-yl)-1H-pyrazolo[3,4-b]pyridin-5-yl]-pyridin-3-ylmethyl}-propyl-amine,
butyl-{5-[3-(5-methoxy-1H-benzoimidazol-2-yl)-1H-pyrazolo[3,4-b]pyridin-5-yl]-pyridin-3-ylmethyl}-amine,
2-[5-(5-methylaminomethyl-pyridin-3-yl)-1H-pyrazolo[3,4-b]pyridin-3-yl]-3H-benzoimidazole-5-carbonitrile,
ethyl-{5-[3-(6-fluoro-1H-benzoimidazol-2-yl)-1H-pyrazolo[3,4-b]pyridin-5-yl]-pyridin-3-ylmethyl}-amine, and
{5-[3-(5,6-difluoro-1H-benzoimidazol-2-yl)-1H-pyrazolo[3,4-b]pyridin-5-yl]-pyridin-3-methyl}-ethyl-amine.

29. The compound of claim 1, wherein the compound is an isolated form thereof.

30. A pharmaceutical composition comprising an effective amount of the compound of claim 1 and a pharmaceutically acceptable carrier.

31. The pharmaceutical composition of claim 30, wherein the effective amount of the compound is in a range of from about 0.001 mg/kg to about 300 mg/kg of body weight per day.

32. A process for preparing a compound of claim 1 comprising the steps of:
   a. reacting a compound of Formula E1 with a compound of Formula E2 to provide a compound of Formula E3:

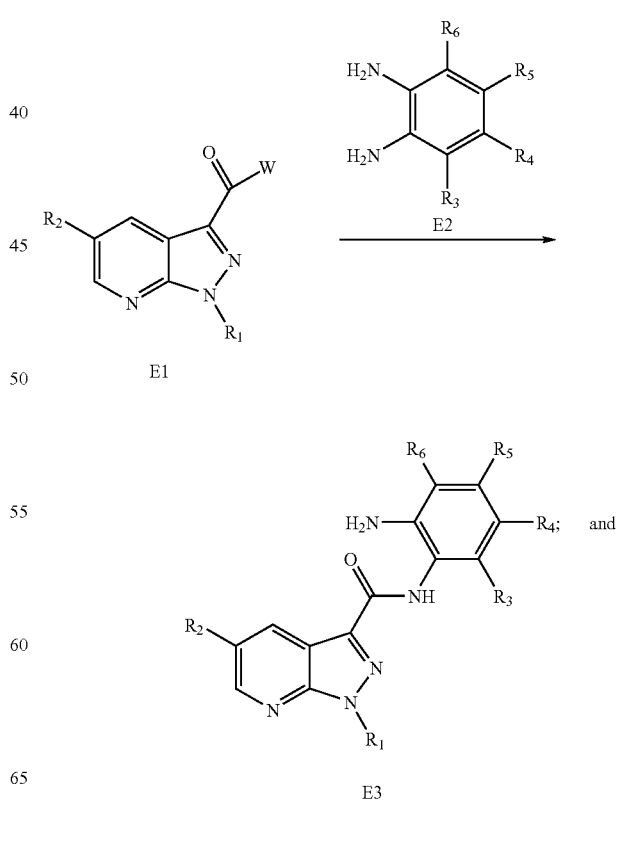

b. reacting a compound of Formula E3 in the presence of an acid to provide a compound of formula (I):

34. A process for preparing a compound of claim 1 comprising the step of reacting a compound of Formula E31 with a compound of Formula E2 in the presence of a sulfur solution to provide a compound of formula (I):

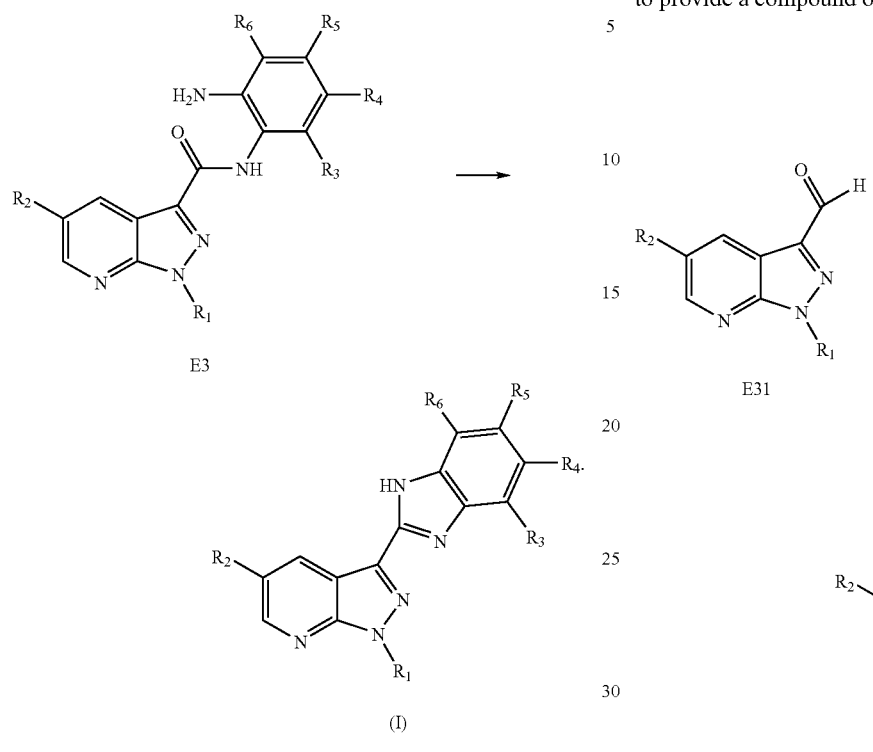

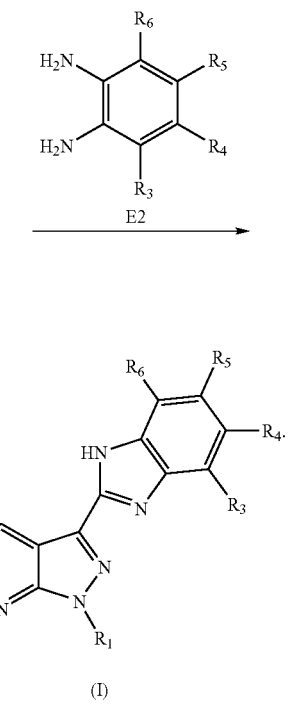

33. A process for preparing a compound of claim 1 comprising the step of reacting a compound of Formula C2 with a reagent to provide a compound of formula (I):

35. A process for preparing a compound of claim 1 comprising the steps of:
  a. reacting a compound of Formula F1 with a protecting group (wherein PG represents the protecting group) to provide a compound of Formula F2:

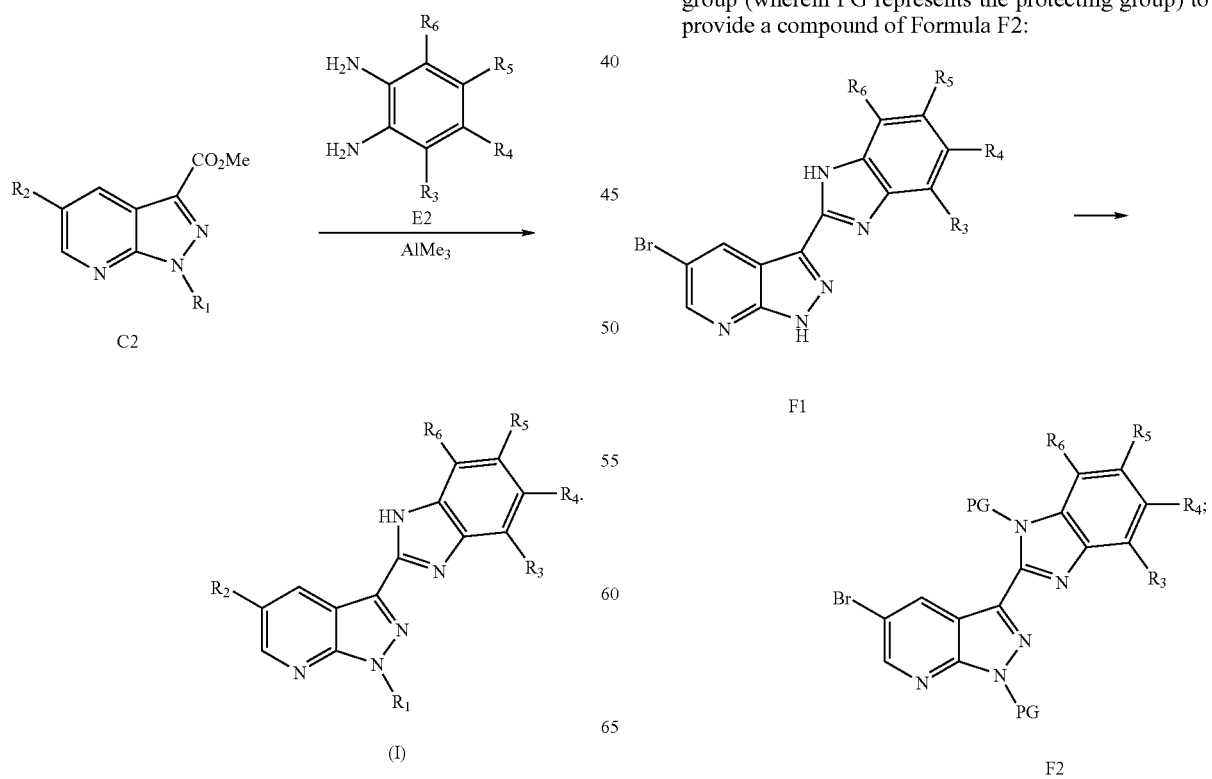

b. reacting the compound of Formula F2 with a suitable diboron species Compound F3 in the presence of a suitable catalyst to provide a compound of Formula F4:

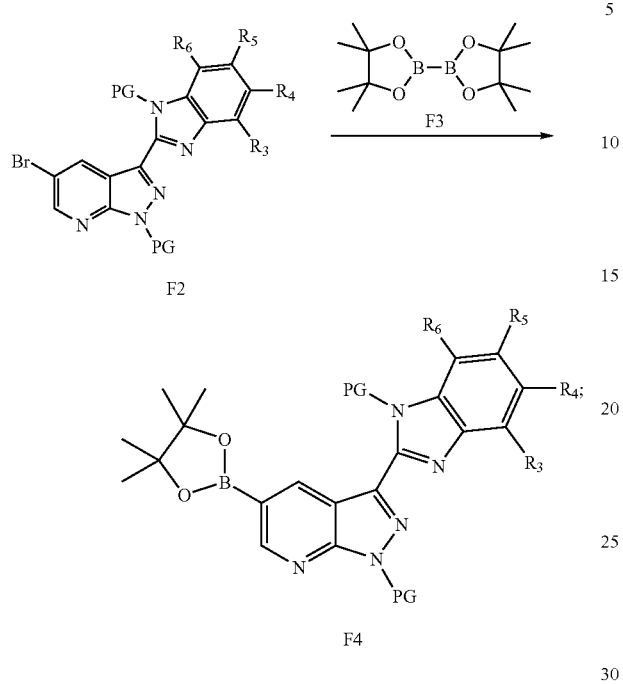

c. reacting the compound of Formula F4 with a Compound F5 (wherein $R_2$ is other than halogen and X is a halogen leaving group such as Cl, Br or I or a triflate leaving group such as OTf) in the presence of a suitable catalyst and a base to provide a compound of Formula F6:

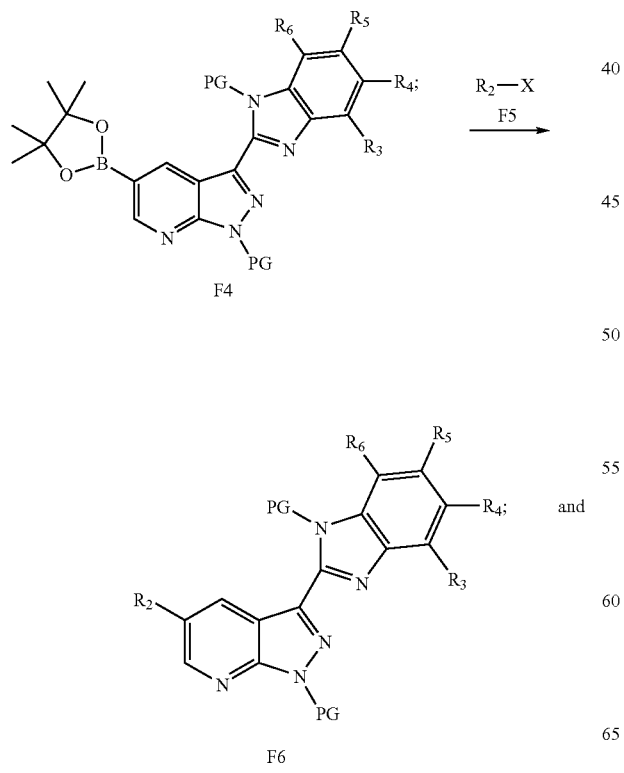

d. reacting the compound of Formula F6 with a suitable deprotection reagent to provide a compound of Formula F7, representative of the compound of claim 1:

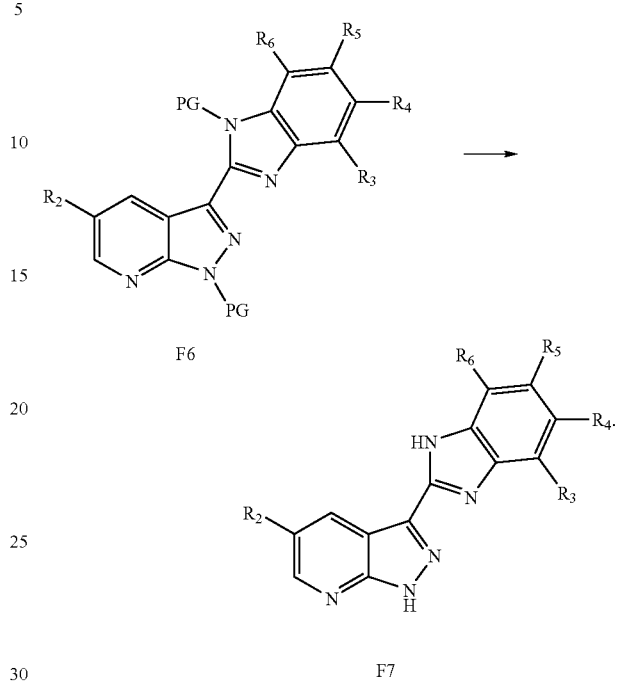

36. A process for preparing a compound of claim 1 comprising the steps of:

a. reacting the compound of Formula F2 with a suitable $R_2$ substituted boron Compound G1 (wherein $R_2$ is other than halogen and $R_a$ is hydrogen or $C_{1-4}$alkyl) in the presence of a suitable catalyst and a base to provide a compound of Formula F6:

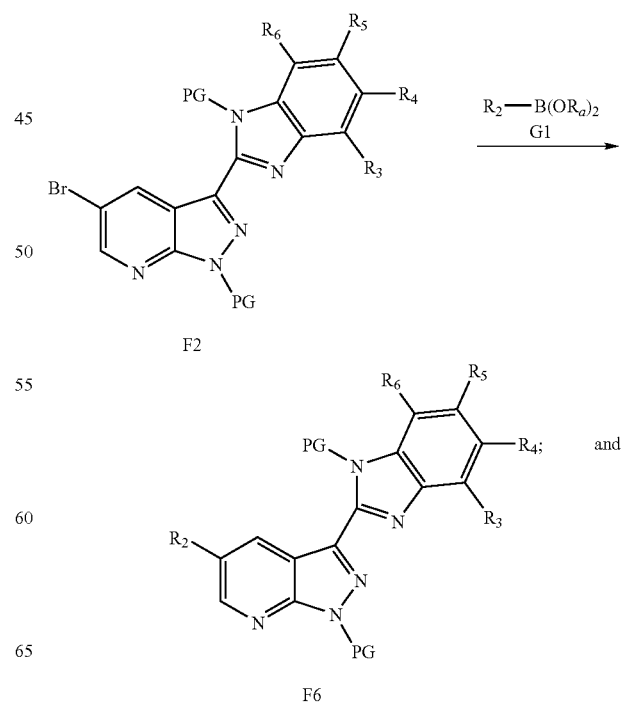

b. reacting a compound of Formula F6 with a suitable deprotection reagent to prepare a compound representative of the compound of claim 1.

37. A process for preparing a compound of claim 1 comprising the steps of:

a. reacting the compound of Formula F2 with a suitable $R_2$ substituted boron Compound G2 (wherein $R_2$ is other than halogen) in the presence of a suitable catalyst to provide a compound of Formula F6:

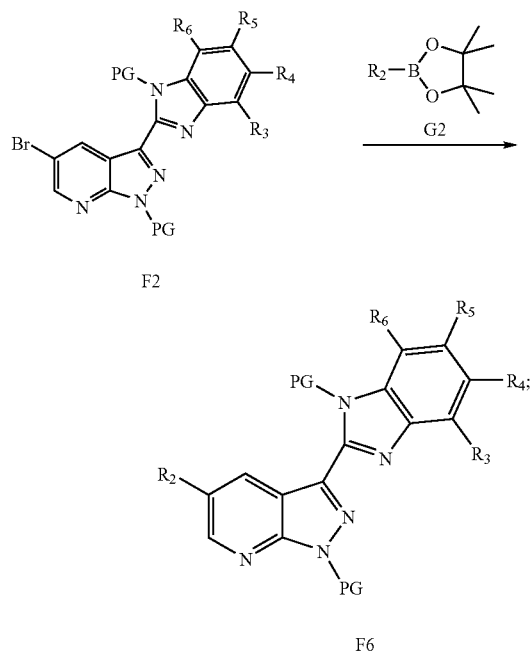

F2

F6 b. reacting a compound of Formula F6 with a suitable deprotection reagent to prepare a compound representative of the compound of claim 1.

38. A process for preparing a compound of claim 1 comprising the steps of:

a. reacting the compound of Formula F2 with a Compound C1 (wherein $R_2$ is other than halogen and Q is a suitable organometallic agent) in the presence of a suitable catalyst and a halogen-metallation agent to provide a compound of Formula F6:

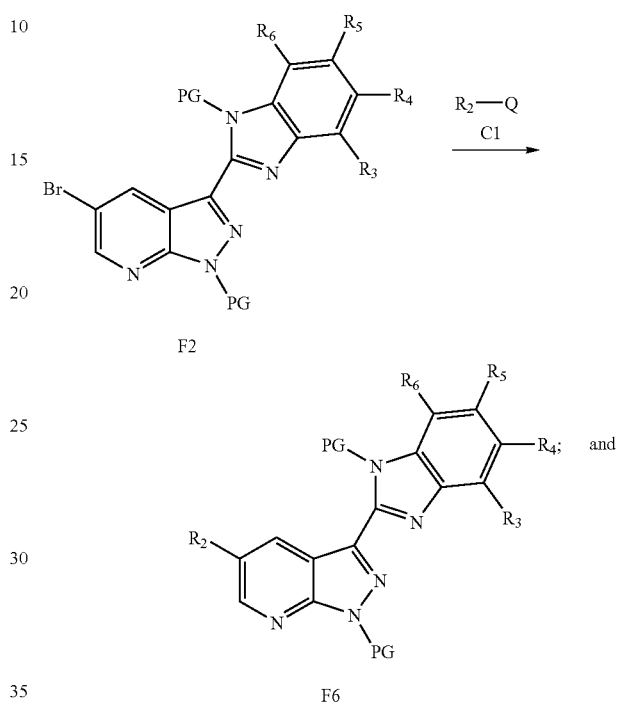

F2

F6 b. reacting a compound of Formula F6 with a suitable deprotection reagent to prepare a compound representative of the compound of claim 1.

* * * * *